US011154356B2

(12) United States Patent
Gertner

(10) Patent No.: US 11,154,356 B2
(45) Date of Patent: Oct. 26, 2021

(54) INTRAVASCULAR ENERGY DELIVERY

(71) Applicant: Otsuka Medical Devices Co., Ltd., Tokyo (JP)

(72) Inventor: Michael Gertner, Menlo Park, CA (US)

(73) Assignee: Otsuka Medical Devices Co., Ltd., Tokyo (JP)

( * ) Notice: Subject to any disclaimer, the term of this patent is extended or adjusted under 35 U.S.C. 154(b) by 241 days.

(21) Appl. No.: 16/412,379

(22) Filed: May 14, 2019

(65) Prior Publication Data

US 2019/0282298 A1    Sep. 19, 2019

Related U.S. Application Data

(63) Continuation of application No. 15/662,179, filed on Jul. 27, 2017, now Pat. No. 10,772,681, which is a
(Continued)

(51) Int. Cl.
*A61B 5/01* (2006.01)
*A61B 18/14* (2006.01)
(Continued)

(52) U.S. Cl.
CPC .............. *A61B 18/1492* (2013.01); *A61B 5/01* (2013.01); *A61B 5/055* (2013.01); *A61B 90/50* (2016.02);
(Continued)

(58) Field of Classification Search
CPC .......... A61B 2018/00434; A61B 2018/00511; A61B 2019/5276; A61B 6/506;
(Continued)

(56) References Cited

U.S. PATENT DOCUMENTS 385,256 A    6/1888   Eggers
3,274,437 A  9/1966   Mastrup
(Continued)

FOREIGN PATENT DOCUMENTS

EP    0225120 A2    6/1987
EP    0420758 A1    4/1991
(Continued)

OTHER PUBLICATIONS

U.S. Appl. No. 12/685,655 / U.S. Pat. No. 8,295,912, filed Jan. 11, 2010 / Oct. 23, 2012.
(Continued)

*Primary Examiner* — Mark D Remaly
(74) *Attorney, Agent, or Firm* — Eversheds Sutherland (US) LLP; Christopher C. Bolten; Nicola A. Pisano

(57) ABSTRACT

A method to apply a nerve inhibiting cloud surrounding a blood vessel includes creating a treatment plan, wherein the treatment plan prescribes application of the nerve inhibiting cloud towards at least a majority portion of a circumference of a blood vessel wall, and applying the nerve inhibiting cloud towards the majority portion of the circumference of the blood vessel wall for a time sufficient to inhibit a function of a nerve that surrounds the blood vessel wall.

33 Claims, 84 Drawing Sheets

Related U.S. Application Data continuation of application No. 14/939,670, filed on Nov. 12, 2015, now abandoned, which is a continuation of application No. 13/896,247, filed on May 16, 2013, now Pat. No. 9,199,097, which is a continuation of application No. 13/048,842, filed on Mar. 15, 2011, now Pat. No. 8,469,904, which is a continuation-in-part of application No. 12/902,133, filed on Oct. 11, 2010, now Pat. No. 9,174,065, and a continuation-in-part of application No. 12/725,450, filed on Mar. 16, 2010, now abandoned, which is a continuation-in-part of application No. 12/685,655, filed on Jan. 11, 2010, now Pat. No. 8,295,912.

(60) Provisional application No. 61/377,908, filed on Aug. 27, 2010, provisional application No. 61/347,375, filed on May 21, 2010, provisional application No. 61/256,983, filed on Oct. 31, 2009, provisional application No. 61/250,857, filed on Oct. 12, 2009, provisional application No. 61/261,741, filed on Nov. 16, 2009, provisional application No. 61/291,359, filed on Dec. 30, 2009, provisional application No. 61/303,307, filed on Feb. 10, 2010.

(51) Int. Cl.
*A61N 7/00* (2006.01)
*A61N 7/02* (2006.01)
*A61B 18/00* (2006.01)
*A61B 18/04* (2006.01)
*A61B 90/50* (2016.01)
*A61B 5/055* (2006.01)

(52) U.S. Cl.
CPC ........... *A61B 2018/00404* (2013.01); *A61B 2018/00434* (2013.01); *A61B 2018/00511* (2013.01); *A61B 2018/00577* (2013.01); *A61B 2018/048* (2013.01); *A61N 7/02* (2013.01); *A61N 7/022* (2013.01); *A61N 2007/0021* (2013.01); *A61N 2007/0078* (2013.01)

(58) Field of Classification Search
CPC ....... A61B 5/055; A61B 5/489; A61B 5/4893; A61B 18/14; A61N 7/02; A61N 7/00; A61N 2007/0026
See application file for complete search history.

(56) References Cited

U.S. PATENT DOCUMENTS

| | | |
|---|---|---|
| 3,499,437 A | 5/1970 | Balamuth |
| 3,552,382 A | 1/1971 | Mount |
| 3,847,016 A | 11/1974 | Ziedonis |
| 3,927,662 A | 12/1975 | Ziedonis |
| 4,059,098 A | 11/1977 | Murdock |
| 4,167,180 A | 9/1979 | Kossoff |
| 4,197,856 A | 4/1980 | Northrop |
| 4,206,763 A | 6/1980 | Pendersen |
| 1,423,790 A | 12/1980 | Taenzer |
| 4,273,127 A | 6/1981 | Auth et al. |
| 4,489,099 A | 9/1984 | McEwen |
| 4,479,404 A | 10/1984 | McEwen |
| 4,484,569 A | 11/1984 | Driller et al. |
| 4,545,386 A | 10/1985 | Hetz et al. |
| 4,601,296 A | 7/1986 | Yerushalmi |
| 4,605,010 A | 8/1986 | McEwen |
| 4,688,578 A | 8/1987 | Takano et al. |
| 4,702,732 A | 10/1987 | Powers et al. |
| 4,708,836 A | 11/1987 | Gain et al. |
| 4,748,985 A | 6/1988 | Nagasaki |
| 4,757,820 A | 7/1988 | Itoh |
| 4,770,175 A | 9/1988 | McEwen |
| 4,773,865 A | 9/1988 | Baldwin |
| 4,773,899 A | 9/1988 | Spears |
| 4,784,148 A | 11/1988 | Dow et al. |
| 4,841,979 A | 6/1989 | Dow et al. |
| 4,850,363 A | 7/1989 | Yanagawa |
| 4,858,613 A | 8/1989 | Fry et al. |
| 4,905,672 A | 3/1990 | Schwarze et al. |
| 4,913,155 A | 4/1990 | Dow et al. |
| 4,929,246 A | 5/1990 | Sinofsky |
| 4,931,047 A | 6/1990 | Broadwin et al. |
| 4,933,216 A | 7/1990 | Lele |
| 4,938,217 A | 7/1990 | Lele |
| 4,955,377 A | 9/1990 | Lennox et al. |
| 4,957,099 A | 9/1990 | Hassler |
| 4,957,481 A | 9/1990 | Gatenby |
| 5,005,579 A | 4/1991 | Wurster et al. |
| RE33,590 E | 5/1991 | Dory |
| 5,026,387 A | 6/1991 | Thomas |
| 5,036,855 A | 8/1991 | Fry et al. |
| 5,039,774 A | 8/1991 | Shikinami et al. |
| 5,042,486 A | 8/1991 | Pfeiler et al. |
| 5,065,742 A | 11/1991 | Belikan et al. |
| 5,080,101 A | 1/1992 | Dory |
| 5,080,102 A | 1/1992 | Dory |
| 5,150,712 A | 9/1992 | Dory |
| 5,170,790 A | 12/1992 | Lacoste et al. |
| 5,178,135 A | 1/1993 | Uchiyama et al. |
| 5,178,148 A | 1/1993 | Lacoste et al. |
| 5,181,522 A | 1/1993 | McEwen |
| 5,193,527 A | 3/1993 | Schaefer |
| 5,194,291 A | 3/1993 | D'Aoust et al. |
| 5,211,160 A | 5/1993 | Talish et al. |
| 5,215,680 A | 6/1993 | D'Arrigo |
| 5,219,401 A | 6/1993 | Cathignol et al. |
| 5,230,334 A | 7/1993 | Klopotek |
| 5,230,921 A | 7/1993 | Waltonen et al. |
| 5,233,994 A | 8/1993 | Shmulewitz |
| 5,243,988 A | 9/1993 | Sieben et al. |
| 5,254,087 A | 10/1993 | McEwen |
| 5,263,957 A | 11/1993 | Davison |
| 5,290,278 A | 3/1994 | Anderson |
| 5,311,869 A | 5/1994 | Okazaki |
| 5,312,431 A | 5/1994 | McEwen |
| 5,352,195 A | 10/1994 | McEwen |
| 5,364,389 A | 11/1994 | Anderson |
| 5,383,896 A | 1/1995 | Gershony et al. |
| 5,391,140 A | 2/1995 | Schaetzle et al. |
| 5,391,197 A | 2/1995 | Burdette et al. |
| 5,394,877 A | 3/1995 | Orr et al. |
| 5,413,550 A | 5/1995 | Castel |
| 5,415,657 A | 5/1995 | Taymor-Luria |
| 5,439,477 A | 8/1995 | McEwen |
| 5,445,608 A | 8/1995 | Chen et al. |
| 5,453,576 A | 9/1995 | Krivitski |
| 5,454,373 A | 10/1995 | Koger et al. |
| 5,454,831 A | 10/1995 | McEwen |
| 5,471,988 A | 12/1995 | Fujio et al. |
| 5,474,071 A | 12/1995 | Chapelon et al. |
| 5,492,126 A | 2/1996 | Hennige et al. |
| 5,501,655 A | 3/1996 | Rolt et al. |
| 5,503,152 A | 4/1996 | Oakley et al. |
| 5,507,744 A | 4/1996 | Tay et al. |
| 5,507,790 A | 4/1996 | Weiss |
| 5,515,853 A | 5/1996 | Smith et al. |
| 5,520,188 A | 5/1996 | Hennige et al. |
| 5,522,878 A | 6/1996 | Montecalvo et al. |
| 5,524,620 A | 6/1996 | Rosenschein |
| 5,526,815 A | 6/1996 | Granz et al. |
| 5,534,232 A | 7/1996 | Denes et al. |
| 5,536,489 A | 7/1996 | Lohrmann et al. |
| 5,553,618 A | 9/1996 | Suzuki et al. |
| 5,556,415 A | 9/1996 | McEwen et al. |
| 5,558,092 A | 9/1996 | Unger et al. |
| 5,573,497 A | 11/1996 | Chapelon |
| 5,578,055 A | 11/1996 | McEwen |
| 5,584,853 A | 12/1996 | McEwen |
| 5,598,845 A | 2/1997 | Chandraratna et al. |
| 5,601,526 A | 2/1997 | Chapelon et al. |
| 5,607,447 A | 3/1997 | McEwen et al. |

(56) References Cited

U.S. PATENT DOCUMENTS

| | | |
|---|---|---|
| 5,609,485 A | 3/1997 | Bergman et al. |
| 5,626,601 A | 5/1997 | Gershony et al. |
| 5,630,837 A | 5/1997 | Crowley |
| 5,638,823 A | 6/1997 | Akay et al. |
| 5,643,179 A | 7/1997 | Fujimoto |
| 5,649,954 A | 7/1997 | McEwen |
| 5,655,538 A | 8/1997 | Lorraine et al. |
| 5,657,760 A | 8/1997 | Ying et al. |
| 5,665,073 A | 9/1997 | Bulow et al. |
| 5,666,954 A | 9/1997 | Chapelon et al. |
| 5,681,339 A | 10/1997 | McEwen et al. |
| 5,685,307 A | 11/1997 | Holland et al. |
| 5,695,493 A | 12/1997 | Nakajima et al. |
| 5,697,897 A | 12/1997 | Buchholtz et al. |
| D389,574 S | 1/1998 | Emerson et al. |
| 5,711,058 A | 1/1998 | Frey et al. |
| 5,716,374 A | 2/1998 | Francese et al. |
| 5,720,286 A | 2/1998 | Chapelon et al. |
| 5,720,287 A | 2/1998 | Chapelon et al. |
| 5,722,411 A | 3/1998 | Suzuki |
| 5,726,066 A | 3/1998 | Choi |
| 5,735,796 A | 4/1998 | Granz et al. |
| 5,738,635 A | 4/1998 | Chapelon et al. |
| 5,741,295 A | 4/1998 | McEwen |
| 5,755,228 A | 5/1998 | Wilson et al. |
| 5,762,066 A | 6/1998 | Law et al. |
| 5,769,790 A | 6/1998 | Watkins et al. |
| 5,788,636 A | 8/1998 | Curley |
| 5,807,285 A | 9/1998 | Vaitekunas |
| 5,810,007 A | 9/1998 | Holupka et al. |
| 5,810,810 A | 9/1998 | Tay et al. |
| 5,817,021 A | 10/1998 | Reichenberger |
| 5,823,962 A | 10/1998 | Schaetzle et al. |
| 5,824,015 A | 10/1998 | Sawyer |
| 5,824,277 A | 10/1998 | Campos et al. |
| 5,827,204 A | 10/1998 | Grandia et al. |
| 5,827,268 A | 10/1998 | Laufer |
| 5,833,647 A | 11/1998 | Edwards |
| 5,840,028 A | 11/1998 | Chubachi et al. |
| 5,846,517 A | 12/1998 | Unger |
| 5,852,860 A | 12/1998 | Lorraine et al. |
| 5,853,752 A | 12/1998 | Unger et al. |
| 5,855,589 A | 1/1999 | McEwen et al. |
| 5,873,828 A | 2/1999 | Fujio et al. |
| 5,873,845 A | 2/1999 | Cline et al. |
| 5,879,314 A | 3/1999 | Peterson et al. |
| 5,882,302 A | 3/1999 | Driscoll, Jr. et al. |
| 5,882,328 A | 3/1999 | Levy et al. |
| 5,895,356 A | 4/1999 | Andrus et al. |
| 5,904,659 A | 5/1999 | Duarte et al. |
| 5,906,580 A | 5/1999 | Kline-Schoder et al. |
| 5,911,735 A | 6/1999 | McEwen |
| 5,919,139 A | 7/1999 | Lin |
| 5,921,994 A | 7/1999 | Andreas et al. |
| 5,922,945 A | 7/1999 | Allmaras et al. |
| 5,931,786 A | 8/1999 | Whitmore, III et al. |
| 5,931,853 A | 8/1999 | McEwen |
| 5,935,144 A | 8/1999 | Estabrook |
| 5,935,146 A | 8/1999 | McEwen |
| 5,935,339 A | 8/1999 | Henderson et al. |
| 5,938,600 A | 8/1999 | Van Vaals et al. |
| 5,951,476 A | 9/1999 | Beach |
| 5,957,849 A | 9/1999 | Munro |
| 5,964,782 A | 10/1999 | Lafontaine et al. |
| 5,976,092 A | 11/1999 | Chinn |
| 5,979,453 A | 11/1999 | Savage et al. |
| 5,993,389 A | 11/1999 | Driscoll, Jr. et al. |
| 5,997,481 A | 12/1999 | Adams et al. |
| 6,007,499 A | 12/1999 | Martin et al. |
| 6,014,473 A | 1/2000 | Hossack et al. |
| 6,033,506 A | 3/2000 | Klett |
| 6,036,650 A | 3/2000 | Wu et al. |
| 6,037,032 A | 3/2000 | Klett et al. |
| 6,039,694 A | 3/2000 | Larson et al. |
| 6,050,943 A | 4/2000 | Slayton et al. |
| 6,067,371 A | 5/2000 | Gouge et al. |
| 6,068,596 A | 5/2000 | Weth et al. |
| 6,071,239 A | 6/2000 | Cribbs et al. |
| 6,071,277 A | 6/2000 | Farley et al. |
| 6,078,831 A | 6/2000 | Belef et al. |
| 6,083,159 A | 7/2000 | Driscoll, Jr. et al. |
| 6,087,761 A | 7/2000 | Lorraine et al. |
| 6,102,860 A | 8/2000 | Mooney |
| 6,106,463 A | 8/2000 | Wilk |
| 6,117,101 A | 9/2000 | Diederich et al. |
| 6,120,453 A | 9/2000 | Sharp |
| 6,126,522 A | 10/2000 | Acker et al. |
| 6,179,831 B1 | 1/2001 | Bliweis |
| 6,182,341 B1 | 2/2001 | Talbot et al. |
| 6,200,539 B1 | 3/2001 | Sherman et al. |
| 6,206,843 B1 | 3/2001 | Iger et al. |
| 6,213,939 B1 | 4/2001 | McEwen |
| 6,217,530 B1 | 4/2001 | Martin et al. |
| 6,221,015 B1 | 4/2001 | Yock |
| 6,231,607 B1 | 5/2001 | Zikorus et al. |
| 6,233,477 B1 | 5/2001 | Chia et al. |
| 6,246,156 B1 | 6/2001 | Takeuchi et al. |
| 6,254,601 B1 | 7/2001 | Burbank et al. |
| 6,259,945 B1 | 7/2001 | Epstein et al. |
| 6,263,551 B1 | 7/2001 | Lorraine et al. |
| 6,267,734 B1 | 7/2001 | Ishibashi et al. |
| 6,270,458 B1 | 8/2001 | Barnea |
| 6,277,077 B1 | 8/2001 | Brisken et al. |
| 6,315,441 B2 | 11/2001 | King |
| 6,332,089 B1 | 12/2001 | Acker et al. |
| 6,361,496 B1 | 3/2002 | Zikorus et al. |
| 6,361,548 B1 | 3/2002 | McEwen |
| 6,399,149 B1 | 6/2002 | Klett et al. |
| 6,406,759 B1 | 6/2002 | Roth |
| 6,409,720 B1 | 6/2002 | Hissong et al. |
| 6,419,669 B1 | 7/2002 | Frazier et al. |
| 6,425,867 B1 | 7/2002 | Vaezy et al. |
| 6,425,876 B1 | 7/2002 | Frangi et al. |
| 6,432,067 B1 | 8/2002 | Martin et al. |
| 6,443,894 B1 | 9/2002 | Sumanaweera et al. |
| 6,453,526 B2 | 9/2002 | Lorraine et al. |
| 6,488,639 B1 | 12/2002 | Ribault et al. |
| 6,491,672 B2 | 12/2002 | Slepian et al. |
| 6,494,848 B1 | 12/2002 | Sommercorn et al. |
| 6,500,133 B2 | 12/2002 | Martin et al. |
| 6,506,171 B1 | 1/2003 | Vitek et al. |
| 6,514,221 B2 | 2/2003 | Hynynen et al. |
| 6,520,915 B1 | 2/2003 | Lin et al. |
| 6,522,926 B1 | 2/2003 | Kieval et al. |
| 6,543,047 B1 | 4/2003 | Unger |
| 6,551,576 B1 | 4/2003 | Unger et al. |
| 6,559,644 B2 | 5/2003 | Froundlich et al. |
| 6,562,037 B2 | 5/2003 | Paton et al. |
| 6,565,557 B1 | 5/2003 | Sporri et al. |
| 6,576,168 B2 | 6/2003 | Hardcastle et al. |
| 6,584,360 B2 | 6/2003 | Francischelli et al. |
| 6,595,934 B1 | 7/2003 | Hissong et al. |
| 6,599,256 B1 | 7/2003 | Acker et al. |
| 6,599,288 B2 | 7/2003 | Maguire |
| 6,602,251 B2 | 8/2003 | Burbank et al. |
| 6,612,988 B2 | 9/2003 | Maor et al. |
| 6,616,624 B1 | 9/2003 | Kieval |
| 6,626,855 B1 | 9/2003 | Weng et al. |
| 6,633,658 B1 | 10/2003 | Dabney et al. |
| 6,652,461 B1 | 11/2003 | Levkovitz |
| 6,656,131 B2 | 12/2003 | Alster et al. |
| 6,656,136 B1 | 12/2003 | Weng et al. |
| 6,676,601 B1 | 1/2004 | Lacoste et al. |
| 6,682,483 B1 | 1/2004 | Abend et al. |
| 6,685,639 B1 | 2/2004 | Wang et al. |
| 6,706,892 B1 | 3/2004 | Ezrin et al. |
| 6,709,392 B1 | 3/2004 | Salgo et al. |
| 6,709,407 B2 | 3/2004 | Fatemi |
| 6,716,184 B2 | 4/2004 | Vaezy et al. |
| 6,719,694 B2 | 4/2004 | Weng et al. |
| 6,719,699 B2 | 4/2004 | Smith |
| 6,726,627 B1 | 4/2004 | Lizzi et al. |
| 6,728,566 B1 | 4/2004 | Subramanyan et al. |
| 6,735,461 B2 | 5/2004 | Vitek et al. |

(56) References Cited

U.S. PATENT DOCUMENTS

| | | |
|---|---|---|
| 6,755,789 B2 | 6/2004 | Stringer et al. |
| 6,763,722 B2 | 7/2004 | Fjield et al. |
| 6,764,488 B1 | 7/2004 | Burbank et al. |
| 6,846,291 B2 | 1/2005 | Smith et al. |
| 6,875,176 B2 | 4/2005 | Mourad et al. |
| 6,875,420 B1 | 4/2005 | Quay |
| 6,905,498 B2 | 6/2005 | Hooven |
| 6,932,771 B2 | 8/2005 | Whitmore et al. |
| 6,955,648 B2 | 10/2005 | Mozayeni et al. |
| 6,978,174 B2 | 12/2005 | Gelfand et al. |
| 7,022,077 B2 | 4/2006 | Mourad et al. |
| 7,052,463 B2 | 5/2006 | Peszynski et al. |
| 7,063,666 B2 | 6/2006 | Weng et al. |
| 7,128,711 B2 | 10/2006 | Medan et al. |
| 7,149,564 B2 | 12/2006 | Vining et al. |
| 7,162,303 B2 | 1/2007 | Levin et al. |
| 7,211,060 B1 | 5/2007 | Talish et al. |
| 7,260,250 B2 | 8/2007 | Summers et al. |
| 7,285,093 B2 | 10/2007 | Anisimov et al. |
| 7,374,538 B2 | 5/2008 | Nightingale et al. |
| 7,445,599 B2 | 11/2008 | Kelly et al. |
| 7,470,241 B2 | 12/2008 | Weng et al. |
| 7,499,748 B2 | 3/2009 | Moffitt et al. |
| 7,510,536 B2 | 3/2009 | Foley et al. |
| 7,530,958 B2 | 5/2009 | Slayton et al. |
| 7,534,209 B2 | 5/2009 | Abend |
| 7,553,284 B2 | 6/2009 | Vaitekunas |
| 7,617,005 B2 | 11/2009 | Demarais et al. |
| 7,620,451 B2 | 11/2009 | Demarais et al. |
| 7,628,764 B2 | 12/2009 | Duarte et al. |
| 7,684,865 B2 | 3/2010 | Aldrich et al. |
| 7,697,972 B2 | 4/2010 | Verard et al. |
| 7,698,947 B2 | 4/2010 | Sarr |
| 7,766,833 B2 | 8/2010 | Lee |
| 7,783,358 B2 | 8/2010 | Aldrich et al. |
| 8,295,912 B2 | 10/2012 | Gertner |
| 8,347,891 B2 | 1/2013 | Demarais et al. |
| 8,383,671 B1 | 2/2013 | Consigny |
| 8,556,834 B2 | 10/2013 | Gertner |
| 8,715,209 B2 | 5/2014 | Gertner |
| 9,234,878 B2 | 1/2016 | Lavrentyev |
| 9,700,372 B2 | 7/2017 | Schaer |
| 9,707,034 B2 | 7/2017 | Schaer |
| 9,943,666 B2 | 4/2018 | Warnking |
| 9,981,108 B2 | 5/2018 | Warnking |
| 10,039,901 B2 | 8/2018 | Warnking |
| 10,230,041 B2 | 3/2019 | Taylor et al. |
| 10,350,440 B2 | 7/2019 | Taylor et al. |
| 10,368,944 B2 | 8/2019 | Schaer |
| 10,456,605 B2 | 10/2019 | Taylor et al. |
| 10,499,937 B2 | 12/2019 | Warnking |
| 2001/0014775 A1 | 8/2001 | Koger et al. |
| 2001/0014805 A1 | 8/2001 | Burbank et al. |
| 2001/0032382 A1 | 10/2001 | Lorraine et al. |
| 2001/0041910 A1 | 11/2001 | McEwen |
| 2001/0044636 A1 | 11/2001 | Pedros et al. |
| 2002/0055736 A1 | 5/2002 | Horn et al. |
| 2002/0072672 A1 | 6/2002 | Roundhill et al. |
| 2002/0095164 A1 | 7/2002 | Andreas et al. |
| 2002/0193831 A1 | 12/2002 | Smith, III |
| 2003/0009194 A1 | 1/2003 | Saker et al. |
| 2003/0018255 A1 | 1/2003 | Martin et al. |
| 2003/0036771 A1 | 2/2003 | McEwen |
| 2003/0050665 A1 | 3/2003 | Ginn |
| 2003/0060737 A1 | 3/2003 | Brisken |
| 2003/0069569 A1 | 4/2003 | Burdette et al. |
| 2003/0114756 A1 | 6/2003 | Li |
| 2003/0120204 A1 | 6/2003 | Unger et al. |
| 2003/0149366 A1 | 8/2003 | Stringer et al. |
| 2003/0153849 A1 | 8/2003 | Huckle et al. |
| 2003/0187371 A1 | 10/2003 | Vortman et al. |
| 2003/0195420 A1 | 10/2003 | Mendlein et al. |
| 2003/0208101 A1 | 11/2003 | Cecchi |
| 2003/0216792 A1 | 11/2003 | Levin et al. |
| 2003/0225331 A1 | 12/2003 | Diederich et al. |
| 2004/0002654 A1 | 1/2004 | Davidson et al. |
| 2004/0019349 A1 | 1/2004 | Fuimaono et al. |
| 2004/0030227 A1 | 2/2004 | Littrup et al. |
| 2004/0030268 A1 | 2/2004 | Weng et al. |
| 2004/0030269 A1 | 2/2004 | Horn et al. |
| 2004/0039280 A1 | 2/2004 | Wu et al. |
| 2004/0049105 A1 | 3/2004 | Crutchfield et al. |
| 2004/0054287 A1 | 3/2004 | Stephens |
| 2004/0054289 A1 | 3/2004 | Eberle et al. |
| 2004/0071664 A1 | 4/2004 | McHale et al. |
| 2004/0078034 A1 | 4/2004 | Acker et al. |
| 2004/0078219 A1 | 4/2004 | Kaylor et al. |
| 2004/0082859 A1 | 4/2004 | Schaer |
| 2004/0082978 A1 | 4/2004 | Harrison et al. |
| 2004/0097805 A1 | 5/2004 | Verard et al. |
| 2004/0097840 A1 | 5/2004 | Holmer |
| 2004/0106880 A1 | 6/2004 | Weng et al. |
| 2004/0113524 A1 | 6/2004 | Baumgartner et al. |
| 2004/0122493 A1 | 6/2004 | Ishibashi et al. |
| 2004/0127798 A1 | 7/2004 | Dala-Krishna et al. |
| 2004/0153126 A1 | 8/2004 | Okai |
| 2004/0158154 A1 | 8/2004 | Hanafy et al. |
| 2004/0220167 A1 | 11/2004 | Samly |
| 2004/0234456 A1 | 11/2004 | Smith |
| 2004/0254620 A1 | 12/2004 | Lacoste et al. |
| 2004/0267252 A1 | 12/2004 | Washington et al. |
| 2005/0038339 A1 | 2/2005 | Chauhan et al. |
| 2005/0038340 A1 | 2/2005 | Vaezy et al. |
| 2005/0043625 A1 | 2/2005 | Oliver et al. |
| 2005/0046311 A1 | 3/2005 | Baumgartner et al. |
| 2005/0054955 A1 | 3/2005 | Lidgren |
| 2005/0065436 A1 | 3/2005 | Ho et al. |
| 2005/0070790 A1 | 3/2005 | Niwa et al. |
| 2005/0085793 A1 | 4/2005 | Glossop |
| 2005/0090104 A1 | 4/2005 | Yang et al. |
| 2005/0096538 A1 | 5/2005 | Chomas et al. |
| 2005/0096542 A1 | 5/2005 | Weng et al. |
| 2005/0119704 A1 | 6/2005 | Peters et al. |
| 2005/0149126 A1 | 7/2005 | Libbuus |
| 2005/0154299 A1 | 7/2005 | Hoctor et al. |
| 2005/0165298 A1 | 7/2005 | Larson et al. |
| 2005/0182297 A1 | 8/2005 | Gravenstein et al. |
| 2005/0182319 A1 | 8/2005 | Glossop |
| 2005/0192638 A1 | 9/2005 | Gelfand et al. |
| 2005/0240102 A1 | 10/2005 | Rachlin et al. |
| 2005/0240103 A1 | 10/2005 | Byrd et al. |
| 2005/0240126 A1 | 10/2005 | Foley et al. |
| 2005/0240127 A1 | 10/2005 | Seip et al. |
| 2005/0240170 A1 | 10/2005 | Zhang et al. |
| 2005/0240241 A1 | 10/2005 | Yun et al. |
| 2005/0261672 A1 | 11/2005 | Deem et al. |
| 2005/0277853 A1 | 12/2005 | Mast et al. |
| 2005/0288730 A1 | 12/2005 | Deem et al. |
| 2006/0004417 A1 | 1/2006 | Rossing |
| 2006/0025756 A1 | 2/2006 | Francischelli et al. |
| 2006/0052701 A1 | 3/2006 | Carter et al. |
| 2006/0058678 A1 | 3/2006 | Vitek et al. |
| 2006/0058707 A1 | 3/2006 | Barthe et al. |
| 2006/0082771 A1 | 4/2006 | Doerrmann et al. |
| 2006/0084966 A1 | 4/2006 | Maguire et al. |
| 2006/0122514 A1 | 6/2006 | Byrd et al. |
| 2006/0184069 A1 | 8/2006 | Vaitekunas |
| 2006/0235300 A1 | 10/2006 | Weng et al. |
| 2006/0235303 A1 | 10/2006 | Vaezy et al. |
| 2006/0293712 A1 | 12/2006 | Kieval et al. |
| 2007/0004984 A1 | 1/2007 | Crum et al. |
| 2007/0016274 A1 | 1/2007 | Boveja et al. |
| 2007/0038115 A1 | 2/2007 | Quigley et al. |
| 2007/0055155 A1 | 3/2007 | Owen et al. |
| 2007/0055181 A1 | 3/2007 | Deem et al. |
| 2007/0066957 A1 | 3/2007 | Demarais et al. |
| 2007/0106339 A1 | 5/2007 | Errico et al. |
| 2007/0112327 A1 | 5/2007 | Yun et al. |
| 2007/0129720 A1 | 6/2007 | Demarais et al. |
| 2007/0129761 A1 | 6/2007 | Demarais et al. |
| 2007/0135875 A1 | 6/2007 | Demarais et al. |
| 2007/0142879 A1 | 6/2007 | Greenberg et al. |
| 2007/0149880 A1 | 6/2007 | Willis |
| 2007/0167806 A1 | 7/2007 | Wood et al. |

(56) References Cited

U.S. PATENT DOCUMENTS

| | | |
|---|---|---|
| 2007/0179379 A1 | 8/2007 | Weng et al. |
| 2007/0203527 A1 | 8/2007 | Ben-David et al. |
| 2007/0213616 A1 | 9/2007 | Anderson et al. |
| 2007/0233185 A1 | 10/2007 | Anderson et al. |
| 2007/0239000 A1 | 10/2007 | Emery et al. |
| 2007/0265687 A1 | 11/2007 | Deem et al. |
| 2007/0282407 A1 | 12/2007 | Demarais et al. |
| 2008/0030104 A1 | 2/2008 | Prus |
| 2008/0033292 A1 | 2/2008 | Shafran |
| 2008/0033420 A1 | 2/2008 | Nields et al. |
| 2008/0039746 A1 | 2/2008 | Hissong et al. |
| 2008/0045864 A1 | 2/2008 | Candy et al. |
| 2008/0045865 A1 | 2/2008 | Kislev |
| 2008/0046016 A1 | 2/2008 | Ben-David |
| 2008/0047325 A1 | 2/2008 | Bartlett |
| 2008/0051767 A1 | 2/2008 | Rossing et al. |
| 2008/0058683 A1 | 3/2008 | Gifford et al. |
| 2008/0194954 A1 | 8/2008 | Unger et al. |
| 2008/0200806 A1 | 8/2008 | Liu et al. |
| 2008/0200815 A1 | 8/2008 | Van Der Steen et al. |
| 2008/0234569 A1 | 9/2008 | Tidhar et al. |
| 2008/0255498 A1 | 10/2008 | Houle |
| 2008/0255642 A1 | 10/2008 | Zarins et al. |
| 2008/0288017 A1 | 11/2008 | Kieval |
| 2008/0312561 A1 | 12/2008 | Chauhan |
| 2008/0312562 A1 | 12/2008 | Routh et al. |
| 2008/0317204 A1 | 12/2008 | Sumanaweera et al. |
| 2008/0319375 A1 | 12/2008 | Hardy |
| 2009/0012098 A1 | 1/2009 | Jordan et al. |
| 2009/0036948 A1 | 2/2009 | Levin et al. |
| 2009/0054770 A1 | 2/2009 | Daigle |
| 2009/0062697 A1 | 3/2009 | Zhang et al. |
| 2009/0062873 A1 | 3/2009 | Wu et al. |
| 2009/0076409 A1 | 3/2009 | Wu et al. |
| 2009/0088623 A1 | 4/2009 | Vortman et al. |
| 2009/0112095 A1 | 4/2009 | Daigle |
| 2009/0112133 A1 | 4/2009 | Deisseroth et al. |
| 2009/0149782 A1 | 6/2009 | Cohen et al. |
| 2009/0163982 A1 | 6/2009 | Decharms |
| 2009/0198093 A1* | 8/2009 | Meissner ......... A61B 17/12136 600/2 |
| 2009/0221908 A1 | 9/2009 | Glossop |
| 2009/0221939 A1 | 9/2009 | Demarais et al. |
| 2009/0247911 A1 | 10/2009 | Novak et al. |
| 2009/0264755 A1 | 10/2009 | Chen et al. |
| 2009/0306644 A1 | 12/2009 | Mayse et al. |
| 2010/0010393 A1 | 1/2010 | Duffy et al. |
| 2010/0022921 A1 | 1/2010 | Seip et al. |
| 2010/0023088 A1 | 1/2010 | Stack et al. |
| 2010/0042020 A1 | 2/2010 | Ben-Ezra |
| 2010/0081971 A1 | 4/2010 | Allison |
| 2010/0092424 A1 | 4/2010 | Sanghvi et al. |
| 2010/0125269 A1 | 5/2010 | Emmons et al. |
| 2010/0160781 A1 | 6/2010 | Carter et al. |
| 2010/0174188 A1 | 7/2010 | Wang et al. |
| 2011/0021913 A1 | 1/2011 | Weng et al. |
| 2011/0028867 A1 | 2/2011 | Choo et al. |
| 2011/0060255 A1 | 3/2011 | Chen |
| 2011/0112400 A1 | 5/2011 | Emery et al. |
| 2011/0124976 A1 | 5/2011 | Sabczynski et al. |
| 2011/0251489 A1 | 10/2011 | Zhang et al. |
| 2011/0257561 A1 | 10/2011 | Gertner et al. |
| 2011/0319765 A1 | 12/2011 | Gartner et al. |
| 2012/0065492 A1 | 3/2012 | Gertner et al. |
| 2012/0109018 A1 | 5/2012 | Gertner et al. |
| 2012/0123243 A1 | 5/2012 | Hastings |
| 2014/0163540 A1 | 6/2014 | Iyer et al. |

FOREIGN PATENT DOCUMENTS

| | | |
|---|---|---|
| EP | 0679371 A1 | 11/1995 |
| EP | 1265223 A2 | 12/2002 |
| EP | 1579889 | 9/2005 |
| EP | 1847294 A1 | 10/2007 |
| JP | H05-220152 | 8/1993 |
| JP | 2007000218 | 1/2007 |
| WO | WO 9502361 | 1/1995 |
| WO | WO 1997031364 A1 | 8/1997 |
| WO | WO 1999048621 A2 | 9/1999 |
| WO | WO 2001034018 A2 | 5/2001 |
| WO | WO 2002069805 A2 | 9/2002 |
| WO | WO 2005030295 A2 | 4/2005 |
| WO | WO 2006003606 | 1/2006 |
| WO | WO 2006121447 A2 | 11/2006 |
| WO | WO 2006129099 | 12/2006 |
| WO | WO 2009003138 | 2/2008 |
| WO | WO 2008144274 | 11/2008 |
| WO | WO 2009018351 | 2/2009 |
| WO | WO 2009018394 A1 | 2/2009 |
| WO | WO 2009081339 | 7/2009 |
| WO | WO 2011053757 A1 | 5/2011 |
| WO | WO 2011053772 A1 | 5/2011 |

OTHER PUBLICATIONS

U.S. Appl. No. 12/725,450, filed Mar. 16, 2010.
U.S. Appl. No. 12/902,133 / U.S. Pat. No. 9,174,065, filed Oct. 11, 2010 / Nov. 3, 2015.
U.S. Appl. No. 12/902,135, filed Oct. 11, 2010.
U.S. Appl. No. 12/966,943, filed Dec. 13, 2010.
U.S. Appl. No. 12/966,954, filed Dec. 13, 2010.
U.S. Appl. No. 12/966,962, filed Dec. 13, 2010.
U.S. Appl. No. 13/019,273 / U.S. Pat. No. 8,374,674, filed Feb. 1, 2011 / Feb. 12, 2013.
U.S. Appl. No. 13/048,830 / U.S. Pat. No. 8,517,962, filed Mar. 15, 2011 / Aug. 27, 2013.
U.S. Appl. No. 13/048,837 / U.S. Pat. No. 8,986,231, filed Mar. 15, 2011 / Mar. 24, 2015.
U.S. Appl. No. 13/048,842 / U.S. Pat. No. 8,469,904, filed Mar. 15, 2011 / Jun. 25, 2013.
U.S. Appl. No. 13/048,844 / U.S. Pat. No. 8,986,211, filed Mar. 15, 2011 / Mar. 24, 2015.
U.S. Appl. No. 13/091,116 / U.S. Pat. No. 9,119,951, filed Apr. 20, 2011 / Sep. 1, 2015.
U.S. Appl. No. 13/111,837 / U.S. Pat. No. 9,005,143, filed May 16, 2011 / Apr. 14, 2015.
U.S. Appl. No. 13/228,366, filed Sep. 8, 2011.
U.S. Appl. No. 13/246,763, filed Sep. 27, 2011.
U.S. Appl. No. 13/246,775, filed Sep. 27, 2011.
U.S. Appl. No. 13/417,194 / U.S. Pat. No. 9,358,401, filed Mar. 9, 2012 / Jun. 7, 2016.
U.S. Appl. No. 13/445,903 / U.S. Pat. No. 8,715,209, filed Apr. 12, 2012 / May 6, 2014.
U.S. Appl. No. 13/487,118, filed Jun. 1, 2012.
U.S. Appl. No. 13/487,121, filed Jun. 1, 2012.
U.S. Appl. No. 13/487,135 / U.S. Pat. No. 9,579,518, filed Jun. 1, 2012 / Feb. 28, 2017.
U.S. Appl. No. 13/523,835 / U.S. Pat. No. 8,992,447, filed Jun. 12, 2012 / Mar. 31, 2015.
U.S. Appl. No. 13/535,070 / U.S. Pat. No. 8,512,262, filed Jun. 27, 2012 / Aug. 20, 2013.
U.S. Appl. No. 13/545,944, filed Jul. 10, 2012.
U.S. Appl. No. 13/657,725, filed Oct. 22, 2012.
U.S. Appl. No. 13/663,447 / U.S. Pat. No. 9,119,952, filed Oct. 29, 2012 / Sep. 1, 2015.
U.S. Appl. No. 13/717,401, filed Dec. 17, 2012.
U.S. Appl. No. 13/751,133 / U.S. Pat. No. 9,352,171, filed Jan. 27, 2013 / May 31, 2016.
U.S. Appl. No. 13/896,247 / U.S. Pat. No. 9,199,097, filed May 16, 2013 / Dec. 1, 2015.
U.S. Appl. No. 13/896,252, filed May 16, 2013.
U.S. Appl. No. 13/904,853, filed May 29, 2013.
U.S. Appl. No. 13/960,743, filed Aug. 6, 2013.
U.S. Appl. No. 13/966,212, filed Aug. 13, 2013.
U.S. Appl. No. 14/015,331, filed Aug. 30, 2013.
U.S. Appl. No. 14/099,834 / U.S. Pat. No. 9,125,642, filed Dec. 6, 2013 / Sep. 8, 2015.
U.S. Appl. No. 14/201,851, filed Mar. 8, 2014.

(56) References Cited

OTHER PUBLICATIONS

U.S. Appl. No. 14/207,511, filed Mar. 12, 2014.
U.S. Appl. No. 14/207,516, filed Mar. 12, 2014.
U.S. Appl. No. 14/207,526, filed Mar. 12, 2014.
U.S. Appl. No. 14/207,642, filed Mar. 13, 2014.
U.S. Appl. No. 14/562,477, filed Dec. 5, 2014.
U.S. Appl. No. 14/789,769, filed Jul. 1, 2015.
U.S. Appl. No. 14/939,670, filed Nov. 12, 2015.
Accord et al., "The issue of Transmurality in Surgical Ablation for Atrial Fibrillation." *Cardiothoracic Surgery Network*: 3pp, Aug. 8, 2005.
Amenta et al., "A New Voronoi-Based Surface Reconstruction Algorithm." *Computer Graphics*: 7pp, 1998.
American Red Cross:, "Blood 101." 4pp., Dec. 11, 2007.
Anand et al., "Monitoring format of high intensity focused ultrasound (HIFU) induced lesions using backscattered ultrasound," *Acoustical Society of America*; Mar. 10, 2004.
Anand et al., "Using the ATL 1000 to Collect. Demodulated RF Data for Monitoring HIFU Lesion Formation." *Presented at SPIE Medical Imaging 2003*. 11pp, 2003.
Aurenhammer, F. "Voronoi diagrams—A Survey of a Fundamental Geometric Data Structure." *ACM Computing Surveys*, vol. 23, No. 3: 345-405, Sep. 1991.
Bachmann, et al. "Targeting Mucosal Addressin Cellular Adhesion Molecule (MAdCAM)-1 to Noninvasively Image Experimental Crohn's Disease." Gastroenterology 2006; 130: 8-16.
Barthe et al. "Efficient Wideband Linear Arrays for Imaging and Therapy" IEEE Ultrasonics Symposium. pp. 1249-1252 (1999).
Bauer et al., "Ultrasound imaging with SonoVue: Low Mechanical Index Real-Time Imaging." *Acad. Radiol.*; vol. 9, Suppl. 2: S282-S284, 2002.
Beard et al., "An Annular Focus Ultrasonic Lens for Local Hyperthermia Treatment of Small Tumors:" *Ultrasound in Medicine & Biology*. vol. 8, No. 2: 177-184, 1982.
Bokarewe et al., "Tissue factor as a proinflammatory agent." *Arthritis Research*, vol. 4: 190-195, Jan. 10, 2002.
Bots et al., "Intima Media Thickness as a Surrogate Marker for Generalised Atherosclerosis." *Cardiovascular Drugs and Therapy*, ProQuest Medical Library; vol. 16, No. 4: 341-351, Jul. 2002.
Brayman et al., "Erosion of Artificial Endothelia In Vitro by Pulsed Ultrasound: Acoustic Pressure, Frequency, Membrane Orientation and Microbubble Contrast Agent Dependence." *Ultrasound in Medicine & Biology*; vol. 25, No. 8: 1305-1320, 1999.
Buller et al., "Accurate Three-dimensional Wall Thickness Measurement From Multi-Slice Short-Axis MR Imaging." *Computers in Cardiology*, 245-248, 1995.
Byram et al., "3-D Phantom and In Vivo Cardiac Speckle Tracking Using a Matrix Array and Raw Echo Data." IEEE Transactions on Ultrasonics, Ferroelectrics, and Frequency Controi, vol. 57, No. 4; 839-854, Apr. 2010.
Campese, V., Krol, E. Neurogenic Factors in Renal Hypertension. Current Hypertension Reports 2002, 4:256-260.
Canadian Examination Report dated Nov. 14, 2007 in CA Patent Application 2,387,127, filed Oct. 25, 2000.
Chao et al., "Aspheric lens design." *Ultrasonics Symposium, 2000 IEEE*, vol. 2: Abstract Only, Oct. 2000.
Chelule, K. et al., Fabrication of medical models from scan data via rapid prototyping techniques, Proceedings of the 2000 Conference on Time Compression Technologies, Cardiff International Arena, UK; 2000.
Chen et al., "A comparison of the fragmentation thresholds and inertial cavitation doses of different ultrasound contrast agents." *Journal of the Acoustical Society of America*, vol. 113, No. 1: 643-665, Jan. 2003.
Chen et al., "Inertial Cavitation Dose and Hemolysis Produced In Vitro With or Without Optison," *Ultrasound in Medicine & Biology*, vol. 29, No. 5: 725-737, 2003.
Chong et al., "Tissue Factor and Thrombin Mediate Myocardial Ischemia-Reperfusion Injury." *The Society of Thoracic Surgeons*, vol. 75: S649-655, 2003.

Dayton et al., "The magnitude of radiation force on ultrasound contrast agents." *Journal of the Acoustical Society of America*, vol. 112, No. 5, Part 1: 2183-2192, Nov. 2002.
Dempsey et al., "Thickness of Carotid Artery Atherosclerotic Plaque and Ischemic Risk." *Neurosurgery*, vol. 27, No. 3: 343-348, 1990.
Dibona, G. F., "Neural control of the kidney: functionally specific renal sympathetic nerve fibers." Am J Physiol Regulatory Integrative Comp Physiol. pp. 1517-1524, 2000.
Dibona, G, F., et al., Chaotic behavior of renal sympathetic nerve activity: effect of baroreceptor denervation and cardiac failure, Am J Physiol Renal Physiol, 279:F491-501, 2000.
Dibona, GF. Functionally Specific Renal Sympathetic Nerve Fibers: Role in Cardiovascular Regulation. American Journal of Hypertension, 2001 vol. 14(6) 163S-170S.
Advisory Action dated Jul. 9, 2012 for U.S. Appl. No. 12/685,655.
Final Office Action dated Jun. 26, 2012 for U.S. Appl. No. 12/685,655.
Notice of Allowance dated Aug. 27, 2012 for U.S. Appl. No. 12/685,655.
Final Office Action dated Feb. 15, 2013 for U.S. Appl. No. 13/445,903.
Non-Final Office Action dated Jul. 30, 2012 for U.S. Appl. No. 13/445,903.
Final Office Action dated Apr. 19, 2013 for U.S. 2013 for U.S. Appl. No. 13/545,944.
Non-Final Office Action dated Jan. 2, 2013 for U.S. Appl. No. 13/545,944.
Advisory Action dated Aug. 15, 2012 for U.S. Appl. No. 12/725,450.
Final Office Action dated Jun. 6, 2012 for U.S. Appl. No. 12/725,450.
Final Office Action dated Mar. 15, 2013 for U.S. Appl. No. 13/111,837.
Non-Final Office Action dated Sep. 25, 2012 for U.S. Appl. No. 13/111,837.
Extended European Search Report dated Oct. 22, 2012 for European Appln. No. 10823909.6.
Non-Final Office Action dated Jul. 3, 2012 for U.S. Appl. No. 12/902,133.
Final Office Action dated Dec. 5, 2012 for U.S Appl. No. 12/966,943.
Final Office Action dated Jun. 22, 2012 for U.S. Appl. No. 12/966,943.
Final Office Action dated Aug. 29, 2012 for U.S. Appl. No. 12/966,954.
Non-Final Office Action dated Jun. 18, 2012 for U.S. Appl. No. 12/966,954.
Final Office Action dated Dec. 10, 2012 for U.S. Appl. No. 12/966,962.
Non-Final Office Action dated Jun. 18, 2012 for U.S. Appl. No. 12/966,962.
Advisory Action dated Dec. 28, 2012 for U.S. Appl. No. 13/246,775.
Final Office Action dated Oct. 16, 2012 for U.S. Appl. No. 13/246,775.
Non-Final Office Action dated Apr. 15, 2013 for U.S. Appl. No. 13/246,775.
Non-Final Office Action dated Mar. 20, 2012 for U.S. Appl. No. 13/246,775.
Final Office Action dated Jan. 17, 2013 for U.S. Appl. No. 13/487,118.
Non-Final Office Action dated Aug. 29, 2012 for U.S. Appl. No. 13/487,118.
Final Office Action dated Jan. 15, 2013 for U.S. Appl. No. 13/487,121.
Non-Final Office Action dated Aug. 29, 2012 for U.S. Appl. No. 13/437,121.
Advisory Action dated Feb. 25, 2013 for U.S. Appl. No. 13/487,135.
Final Office Action dated Dec. 4, 2012 for U.S. Appl. No. 13/487,135.
Non-Final Office Action dated Jul. 27, 2012 for U.S. Appl. No. 13/487,135.
Final Office Action dated Jan. 31, 2013 for U.S. Appl. No. 13/535,070.
Final Office Action dated Sep. 21, 2012 for U.S. Appl. No. 13/535,070.
Final Office Action dated Feb. 15, 2013 for U.S. Appl. No. 13/048,830.
Non-Final Office Action dated Sep. 24, 2012 for U.S. Appl. No. 13/048,330.
Notice of Allowance dated Apr. 29, 2013 for U.S. Appl. No. 13/048,830.
Advisory Action dated Apr. 11, 2013 for U.S. Appl. No. 13/048,837.
Final Office Action dated Jan. 29, 2013 for U.S. Appl. No. 13/048,837.
Non-Final Office Action dated Sep. 7, 2012 for U.S. Appl. No. 13/048,837.
Final Office Action dated Feb. 25, 2013 for U.S. Appl. No. 13/048,842.

(56) References Cited

OTHER PUBLICATIONS

Non-Final Office Action dated Oct. 15, 2012 for U.S. Appl. No. 13/048,842.
Notice of Allowanced dated Apr. 30, 2013 for U.S. Appl. No. 13/048,842.
Final Office Action dated Apr. 29, 2013 for U.S. Appl. No. 13/048,844.
Non-Final Office Action dated Oct. 10, 2012 for U.S. Appl. No. 13/048,844.
Final Office Action dated Mar. 14, 2013 for U.S. Appl. No. 13/091,116.
Non-Final Office Action dated Oct. 4, 2012 for U.S. Appl. No. 13/091,116.
Advisory Action dated Jun. 29, 2012 for U.S. Appl. No. 13/246,763.
Non-Final Office Action dated Sep. 24, 2012 for U.S. Appl. No. 13/246,783.
Final Office Action dated Feb. 1, 2013 for U.S. Appl. No. 13/523,835.
Non-Final Office Action dated Sep. 10, 2012 for U.S. Appl. No. 13/523,835.
European Search Report & Search Opinion dated Dec. 7, 2012 for European Application No. 11758075.3.
European Examination Report dated Oct. 22, 2012 for EP Appln. No. 10810835.8.
Final Office Action dated Oct. 23, 2012 for U.S. Appl. No. 13/019,273.
Non-Final Office Action dated Jun. 8, 2012 for U.S. Appl. No. 13/019,273.
Notice of Allowance dated Nov. 9, 2012 for U.S. Appl. No. 13/019,273.
Doumas, M., et al., Renal Sympathetic Denervation; The Jury is Still Out, The Lancet, Nov. 2010, vol. 376, Issue 9756, pp. 1878-1880.
Ebbini at al., "Image-guided noninvasive surgery with ultrasound phased arrays." *SPIE*, vol. 3249: 230-239; Apr. 2, 1998.
Edelsbrunner, Herbert, "Geometry and Topology for Mesh Generation." *Cambridge University Press*: 68pp, 2001.
Esler, et al,. "Renal sympathetic denervation in patients with treatment-resistant hypertension (The Symplicity HTN-2 Trials): a randomised controlled trial," The Lancet: vol. 376, Issue 9755, pp. 1903-1909. Dec. 4, 2010.
European Examination Report dated Mar. 7, 2008 in EP Patent Application 989717.4; filed Oct. 25, 2000.
European Search Report & Search Opinion dated Nov. 25, 2011 for European Application No. 10810835.8.
Everbach et al., "Cavitational Mechanisms in Ultrasound-Accelerated Thrombolysis at 1 MHz." *Ultrasound in Medicine & Biology*, vol. 26, No. 7: 1153-1160, 2000.
Ewert, et al. "Anti-myeloperoxidase antibodies stimulate neutrophils to damage human endothelial cells." Kidney International, vol. 4, pp. 375-383. 1992.
Final Office Action dated Apr. 25, 2012 for U.S. Appl. No. 13/246,763.
Fjield, T., et al., A parametric study of the concentric-ring transducer design for MRI guided ultrasound surgery, J. Acoust. Soc. Am. vol. 100, Issue 2, pp. 1220-1230 (1996); (11 pages).
Ganapathy et al., "A New General Triangulation Method for Planar Contours." *Computer Graphics* vol. 16, No. 3:69-75, 1982.
Grassi, G. "Role of the sympathetic nervous system in human hypertension," Journals of Hypertension 1998, vol. 16. No. 12.
Gray, Henry. "The Skull," *Anatomy of the Human Body*: 7pp., 1918.
Guzman et al., "Ultrasound-Mediated Disruption of Cell Membranes: I. Quantification of Molecular uptake and Cell Viability. / II. Heterogeneous effects on cells." *Journal of the Acoustical Society of America*, vol. 110; No. 1: 588-606, Jul. 2001.
Hachimine, et al. "Sonoynamic therapy of cancer using a novel porphyrin deriative, DCPH-P-Na(I), which is devoid of photosensitivity." Japanese Cancer Association pp. 916-920. Apr. 4, 2007.
Hadimioglu et al., "High-Efficiency Fresnel Acoustic Lenses." *Ultrasonics Symposium 1993 IEEE*: 579-582, 1993.
Han et al., "A Fast Minimal Path Active Contour Model." IEEE Transactions on Image Processing, vol. 10, No. 6: 865-873, Jun. 2001.

Hatangadi, Ram. "A Novel Dual Axis Multiplanar Transesophageal Ultrasound Probe for Three-Dimensional Echocardiograph." *University of Washington, Department of Sciences and Engineering*, vol. 55-11B: Abstract 1 pg, 1994.
Holt et al., "Bubbles and Hifu: the Good, the Bad and the Ugly." *Boston University, Department of Aerospace and Mechanical Engineering*: 120-131, 2002.
Hubka at al., "Three-dimensional echocardiographic measurement of left ventricular wall thickness: In vitro and in vivo validation," *Journal of the American Society of Echocardiography*, vol. 15, No. 2: 129-135, 2002.
Hutchinson et al. "Intracavitary Ultrasound Phased Arrays for Noninvasive Prostate Surgery." IEEE Transactions on Ultrasonics. Ferroelectrics, and Frequency Control. 43(6):1032-1042 (1996).
Hwang et al., "Vascular Effects Induced by Combined 1-MHz Ultrasound and Microbubble Contrast Agent Treatments in Vivo." *Ultrasound in Medicine & Biology*, vol. 31, No. 4: 553-564, 2005.
Hynynen et al., "Potential Adverse Effects of High-Intensity Focused Ultrasound Exposure on Blood Vessels In Vivo." *Ultrasound in Medicine & Biology*, vol. 22, No. 2: 193-201, 1996.
Iannuzzi, et al. "Ultrasonographic Correlates of Carotid Atherosclerosis in Transient Ischemic Attack and Stroke." The American Heart Association. 1995; 26: 614-619.
Idell et al., "Fibrin Turnover in Lung Inflammation and Neoplasia." *American Journal of Respiratory and Critical Care Medicine*, vol. 163: 578-584, 2001.
Indman, P. "Advanced Gynecology Solutions," Dec. 10, 2010. <http://www.gynalternatives.com/hsc.htm>.
International Preliminary Report on Patentability dated Apr. 17, 2012 for PCT Appln. No. PCT/US10/52193.
International Preliminary Report on Patentability dated Apr. 17, 2012 for PCT Appln. No. PCT/US10/52197.
International Search Report and Written Opinion dated Dec. 6, 2010 for PCT Application No. PCT/US2010/052193.
International Search Report Written Opinion dated Jul. 27, 2011 for PCT/US2011/033337.
International Search Report and Written Opinion dated Jun. 6, 2011 for PCT/US2010/052197.
International Search Report and Written Opinion dated May 18, 2001 in PCT/US2000/041606.
Janssen, et al. "Renal Nerves in Hypertension." S.Karger AG, Basell, 1989.
Jolesz, F. MRI-Guided Focused Ultrasound Surgery. Annual Review of Medicine, 2009 60: 417-30.
Kaczkowski at al., "Development of a High Intensity Focused Ultrasound System for Image-Guided Ultrasonic Surgery." *Ultrasound for Surgery*, 2001. http://cimu.apl.washington.edu/hifusurgerysystem.html>.
Kang at al,, "Analysis of the Measurement Precision of Arterial Lumen and Wall Areas Using High-Resolution MRI," *Magnetic Resonance in Medicine*, vol. 44: 988-972, 2000.
Klibanov et al., "Detection of Individual Microbubbles of an Ultrasound contrast Agent: Fundamental and Pulse Inversion Imagine." *Academy of Radiology*, vol. 9, Suppl. 2: S279-S281, 2002.
Kojima, T., Matrix Array Transducer and Flexible Matrix Arry Transducer,Proceedings of the Ultrasonics Symposium, vol. 2:649-653 (1986).
Krum, et al. "Pharmacologic Mangement of the Cardiorenal Syndrome in Heart Failure." Current heart Failure Reports pp. 105-111, 2009.
Krum, H et. al., "Catheter-Based Renal Sympathetic Denervation for Resistant Hypertension: a Multicentre Safety and Proof-of-Principle Cohort Study," Lancet 2009 373; 1275-1281.
Kudo et al., "Study on Mechanism of Cell Damage Caused by Microbubbles Exposed to Ultrasound." *Ultrasound in Medicine & Biology*, vol. 29, Supplement: 4pp, 2003.
Lalonde at al., "Field conjugate acoustic lenses for ultrasound hyperthermia." *Ultrasonics, Ferroelectrics and Frequency Control, IEEE Transactions*, vol. 40, Issue 5: Abstract 1pg., Sep. 1993.
Martin et al., Hemostasis of Punctured Vessels Using Doppler-Guided High Intensity Ultrasound, Ultrasound in Med & Biol., vol. 25, pp. 965-990, 1999, USA.

(56) References Cited

OTHER PUBLICATIONS

Mde et al., Renal sympathetic denervation in patients with treatment resistant hypertension (The Symplicity HTN-2 Trial): a randomised controlled trial, Nov. 2010, The Lancet, vol. 376, Issue 9756, pp. 1903-1909.
Meyers, D. "Multiresolution tiling." *Computer Graphics*, No. 5: 325-340, 1994.
Miller et al., "A Review of In Vitro Bioeffects of Inertial Ultrasonic Cavitation From a Mechanistic Perspective." *Ultrasound in Medicine & Biology*, vol. 22, No. 9: 1131-1154, 1996.
Miller, et al. "Diagnostic ultrasound activation of contrastagent bodies induces capillary rupture in mice." National Academy of Sciences, vol. 97 No. 18: 10179-10184, 2000.
Moss, N. G. Renal Function and Renal Afferent and Efferent Nerve Activity. American Journal Physiology. 243 (Renal Fluid Electrolyte Physiology) 12: F425-F433, 1982.
N.a., "Breast Cancer—Insightec: focused ultrasound for non invasive treatment." FAQ, 2000. <http://www.exablate2000.com/physicians_faq.html>.
N.a., "Cavitation." Ultrasound Tip—U.S. Database: Dec. 12, 2007.
N.a., "Mechanical Bioeffects in the Presence of Gas-Carrier Ultrasound Contrast Agents." *Journal of Ultrasound & Medicine*, vol. 19: 120-142, 2000.
Ng et al., "Therapeutic Ultrasound: Its Application in Drug Delivery." *Medicinal Research Reviews*, vol. 22, No. 2: 204-233, 2002.
Non-Final Office Action dated Apr. 10, 2012 for U.S. Appl. No. 12/725,450.
Non-Final Office Action dated Apr. 6, 2012 for U.S. Appl. No. 12/685,655.
Non-Final Office Action dated Nov. 28, 2011 for U.S. Appl. No. 13/245,763.
Notice of Allowance dated Mar. 25, 2003 from U.S. Appl. No. 09/696,076, filed Oct. 25, 2000.
Office Action dated Aug. 17, 2006 from U.S. Appl. No. 10/671,417, filed Sep. 24, 2003.
Office Action dated Jul. 31, 2007 from U.S. Appl. No. 10/671,417, filed Sep. 24, 2003.
Office Action dated Jul. 5, 2006 from U.S. Appl. No. 10/616;831, filed Jul. 10, 2003.
Office Action dated Nov. 29, 2002 from U.S. Appl. No. 09/696,076, filed Oct. 25, 2000.
O'Leary, et al. "Carotid-Artery Intima and Media Thickness as a Risk Factor for Myocardial Infarction and Stroke in Older Adults." Cardiovascular Health Study Collaborative Research Group. New England Journal of Medicine; vol. 340, No. 1: 14-22, Jan. 7, 1999.
Ostensen et al., "Characterization and Use of Ultrasound Contrast Agents." *Academy of Radiology*, vol. 9, Suppl. 2: S275-S278, 2002.
Owaki et al., "The Ultrasonic Coagulating and Cutting System injuries Nerve Function." *Endoscopy*, vol. 34, No. 7: 575-579, 2002.
Pignoli, P., et al., Intimal plus medial thickness of the arterial wall: a direct measurement with ultrasound imaging, Circulation 1986;74;1399-1406.
Poliachik et al., "Activation, Aggregation and Adhesion of Platelets Exposed to High-Intensity Focused Ultrasound," *Ultrasound in Medicine & Biology*, vol. 27, No. 11: 1567-1576, 2001.
Poliachik et al., "Effect of High-Intensity Focused Ultrasound on Whole Blood With or Without Microbubble Contrast Agent." *Ultrasound in Medicine & Biology*, vol. 25, No, 6: 991-998, 1999.
Porter et al., "Ultrasound, Microbubbles and Thrombolysis." *Progress in Cardiovascular Diseases*, vol. 44. No, 2: 101-110, Oct. 2001.
Rivens at al., "Vascular Occlusion Using Focused Ultrasound Surgery for Use in Fetal Medicine." *European Journal of Ultrasound*, vol. 9: 89-97, 1999.
Rosen et al., "Vascular Occlusive Diseases." 37pp., revised 2002.
Rosenschein et al., "Shock-Wave Thrombus Ablation, A New Method for Noninvasive Mechanical Thrombolysis." *The American Journal of Cardiology*, vol. 70, Issue 15: Abstract, Nov. 15, 1992.
Rosenschein, U., et al., Ultrasound Imaging—Guided Noninvasive Ultrasound Thrombolysis : Preclinical Results, *Circulation*, 2000;102;238-245.
Sanghvi et al. "High-Intensity Focused Ultrasounds." Experimental and Investigational Endoscopy. 4(2):383-395 (1994).
Schlaich, et al. "Sympathetic Activation in Chronic Renal Failure." J Am Soc Nephrol. pp. 933-939, 2009.
Schulte-Altedorneburg, et al. "Accuracy of In Vivo Carotid B-Mode Ultrasound Compared with Pathological Analysis: Intima-Media Thickening, Lumen Diameter, and Cross-Sectional Area." American Stroke Association, vol. 32, No. 7: 1520-1524, 2001.
Tachibana et al. "Albumin Microbubble Echo-Contrast Material as Enhancer for Ultrasound Accelerated Thrombolysis." American Heart Association, vol. 92: 1148-1150, 1995.
Tachibana et al., "The Use of Ultra for Drug Delivery," *Echocardiography* vol. 18, No. 4: 323-328, May 2001.
Tardy et al., "In Vivo Ultrasound Imaging of Thrombi Using a Target-specific Contrast Agent." *Academy of Radiology*, vol. 9, Suppl. 2: S294-S296, 2002.
ter Haar. G. Ultrasound Focal Beam Surgery. Ultrasound in Medicine and Biology. 21(9):1089-1100 (1995).
Vaezy et al, "Acoustic surgery." *Physics World*: 35-39, Aug. 2001.
Vaezy et al., "Hemostasis and Tumor Treatment using High Intensity Focused Ultrasound: Experimental Investigations and Device Development." *First International Workshop on the Application of HIFU in Medicine*: 46-49, 2001.
Vaezy et al, "Hernostasis using high intensity focused ultrasound." *European Journal of Ultrasound*, vol. 9: 79-87, 1999.
Vaezy et al., "Intra-operative acoustic hemostasis of liver: production of a homogenate for effective treatment," *Ultrasonics*, vol. 43: 265-269, 2005.
Vaezy, S. et al., Hemostasis of Punctured Blood Vessels Using High-Intensity Focused Ultrasound, Ultrasound in Medicine and Biology, 1998, vol. 24; No. 6, pp. 903-910.
Valente, et al. "Laparoscopic renal denervation for intractable ADPKD-related pain," Nephrol Dial Transplant. pp. 163. 2001.
Von Land et al., "Development of an Improved Centreline Wail Motion Model." *IEEE*: 687-690, 1991.
Watkin et al., "Multi-Modal Contrast Agents: A First Step." *Academy of Radiology*, vol. 9, Suppl. 2: S285-S287, 2002.
Wickline et al., "Blood Contrast Enhancement with a Novel, Non-Gaseous Nanoparticle Contrast Agent." *Academy of Radiology*, vol. 9, Suppl. 2: S290-S293, 2002.
Williamson et al., "Color Doppler Ultrasound Imaging of the Eye and Orbit." *Survey of Ophthalmology*, vol. 40, No. 4: 255-257, 1996.
Yu et al., "A microbubble agent improves the therapeutic efficiency of high intensity focused ultrasound: a rabbit kidney study," *Urological Research*, PubMed: Abstract, 2004.
Advisory Action dated Jul. 25, 2013 for U.S. Appl. No. 13/545,944.
Non-Final Office Action dated Aug. 20, 2013 for U.S. Appl. No. 13/545,944.
Non-Final Office Action dated Oct. 10, 2013 for U.S. Appl. No. 13/657,725.
Advisory Action dated Sep. 3, 2013 for U.S. Appl. No. 13/111,837.
Notice of Allowance dated Sep. 13, 2013 for U.S. Appl. No. 13/111,837.
Examination Report dated Jun. 24, 2013 for EP Appln. No. 10823909.6.
Office Action dated Aug. 20, 2013 for Russian Appln. No. 2012119540.
Advisory Action dated Jun. 18, 2013 for U.S. Appl. No. 12/902,133.
Notice of Allowance dated Jun. 24, 2013 for U.S. Appl. No. 12/966,962.
Final Office Action dated Jan. 13, 2014 for U.S. Appl. No. 13/246,775.
Notice of Allowance dated May 15, 2013 for U.S. Appl. No. 13/535,070.
Advisory Action dated Aug. 15, 2013 for U.S. Appl. No. 13/048,844.
Final Office Action dated Jul. 1, 2013 for U.S. Appl. No. 13/246,763.
Advisory Action dated Jun. 18, 2013 for U.S. Appl. No. 13/523,835.
Notice of Allowance dated Oct. 8, 2013 for U.S. Appl. No. 13/523,835.
European Examination Report dated Jun. 24, 2013 for EP Appln. No. 10810835.8.
International Search Report and Written Opinion dated Nov. 26, 2013 for PCT Appln. No. PCT/US2013/057624.

(56) References Cited

OTHER PUBLICATIONS

M. William Apoutou N'dijin; "Transducteur torique a Ultrasons Focalises de Haute Intensite pour generer des ablations volumineuses", Dec. 17, 2008, XP055009820, URL: http://u556.lyon.inserm.fr/theses/pdf/ndjin.pdf.
Foreign Office Action dated Feb. 14, 2013 for Australian Appln. No. 2010307029.
Final Office Action dated Dec. 27, 2013 for U.S. Appl. No. 13/545,944.
Foreign Office Action for CN Patent Application No. 201110378545.2 dated Jan. 13, 2014.
Notice of Allowance dated Jan. 14, 2014 for U.S. Appl. No. 13/445,903.
Foreign Office Action dated Feb. 26, 2014 for Korean Application No. 10-2012-701259.
Notice of Allowance dated Mar. 6, 2014 for U.S. Appl. No. 13/523,835.
Foreign Office Action dated Mar. 14, 2014 for Australian Appln. No. 2010307029.
Non-Final Office Action dated Apr. 1, 2014 for U.S. Appl. No. 12/902,135.
Foreign Office Action dated Apr. 8, 2014 for Japanese Patent Appln. No. 2012-533385.
Advisory Action dated Apr. 21, 2014 for U.S. Appl. No. 13/246,775.
Foreign Office Action dated May 6, 2014 for Canadian Patent Appln. No. 2777228.
Non-Final Office Action dated Jun. 9, 2014 for U.S. Appl. No. 12/725,450.
Examination Report dated May 16, 2014 for European Application No. 11758075.3.
Foreign Office Action dated Jun. 17, 2014 for European Appln. No. 10823909.6.
European Examination Report dated Jun. 18, 2014 for EP Appln. No. 10810835.8.
Non-Final Office Action dated Jun. 26, 2014 for U.S. Appl. No. 12/966,954.
International Search Report and Written Opinion for PCT/US14/22141 dated Jul. 9, 2014.
Foreign Office Action dated Jul. 21, 2014 for Israeli Application No. 219083.
Non-Final Office Action dated Aug. 1, 2014 for U.S. Appl. No. 12/902,133.
Notice of Allowance dated Aug. 19, 2014 for U.S. Appl. No. 13/048,837.
Non-Final Office Action dated Sep. 11, 2014 for U.S. Appl. No. 12/966,943.
Non-Final Office Action dated Sep. 11, 2014 for U.S. Appl. No. 13/487,121.
Non-Final Office Action dated Sep. 12, 2014 for U.S. Appl. No. 13/487,135.
Non-Final Office Action dated Sep. 17, 2014 for U.S. Appl. No. 13/246,775.
Non-Final Office Action dated Oct. 3, 2014 for U.S. Appl. No. 14/207,511.
Non-Final Office Action dated Oct. 3, 2014 for U.S. Appl. No. 14/207,516.
Rabkin et al. "Biology and Physical Mechanisms of HIFU-Induced Hyperecho in Ultrasound Images" 2006 Ultrasound in Med. & Bioi. 32:1721-1729.
Singh et al. "Ultrasonic Hyperthermia for Cancer Treatment" 1993 Defence Science J. 43:235-241.
Vaezy et al. "Hemorrhage control using high intensity focused ultrasound" 2007 Int.J.Hyperthermia 23:203-211.
Non-Final Office Action dated Oct. 8, 2014 for U.S. Appl. No. 13/487,118.
Notice of Allowance dated Oct. 27, 2014 for U.S. Appl. No. 13/523,835.
Non-Final Office Action dated Nov. 6, 2014.
Notice of Allowance dated Nov. 7, 2014 for U.S. Appl. No. 13/048,837.
Notice of Allowance dated Nov. 7, 2014 for U.S. Appl. No. 13/523,835.
Foreign Office Action dated Nov. 20, 2014 for Korean Application No. 10-2012-701259.
Non-Final Office Action dated Nov. 24, 2014 or U.S. Appl. No. 13/091,116.
Notice Allowance dated Nov. 26, 2014 for U.S. Appl. No. 13/048,844.
Foreign Office Action dated Nov. 27, 2014 for Indonesian Appln. No. W00201201713.
Notice of Allowance dated Nov. 28, 2014 for U.S. Appl. No. 13/111,837.
Foreign Office Action dated Dec. 16, 2014 for Japanese Patent Appln. No. 2012-533385.
Non-Final Office Action dated Dec. 23, 2014 for U.S. Appl. No. 13/545,944.
Final Office Action dated Jan. 12, 2015 for U.S. Appl. No. 12/725,450.
Final Office Action dated Jan. 13, 2015 or U.S. Appl. No. 12/966,943.
Final Office Action dated Jan. 14, 2015 for U.S. Appl. No. 13/487,121.
Final Office Action dated Jan. 15, 2015 for U.S. Appl. No. 12/966,954.
Notice of Allowance dated Jan. 20, 2015 for U.S. Appl. No. 12/902,133.
Advisory Action dated Jan. 22, 2015 for U.S. Appl. No. 13/487,121.
Final Office Action dated Jan. 26, 2015 for U.S. Appl. No. 12/902,135.
Non-Final Office Action dated Jan. 28, 2015 for U.S. Appl. No. 13/246,763.
Final Office Action dated Feb. 24, 2015 for U.S. Appl. No. 13/487,135.
Non-Final Office Action dated Mar. 12, 2015 for U.S. Appl. No. 13/228,366.
Non-Final Office Action dated Mar. 23, 2015 for U.S. Appl. No. 14/015,331.
Foreign Office Action dated Apr. 17, 2015 for Canadian Appln. No. 2,777,228.
Non-Final Office Action dated Apr. 20, 2015 for U.S. Appl. No. 13/960,743.
Eckberg Physiological basis for human autonomic rhythms. 2000 Ann.Med, 32:341-349.
Liedtke et al. Total systemic autoregulation in the dog and its inhibition by baroreceptor reflexes. 1973 Cir. Res. 32:673-677.
Lohmeier et al. Prolonged activation of the baroreflex abolishes obesity-induced hypertension. 2007 Hypertension 49:1307-1314.
Lohmeier et al. Prolonged Activation of the Baroreflex Produces Sustained Hypotension, 2004 Hypertension 43:306-311.
Non-Final Office Action dated Apr. 22, 2015 for U.S. Appl. No. 13/717,401.
Non-Final Office Action dated Apr. 24, 2015 for U.S. Appl. No. 14/207,526.
Non-Final Office Action dated Apr. 28, 2015 for U.S. Appl. No. 14/207,642.
Final Office Action dated May 22, 2015 for U.S. Appl. No. 13/487,118.
Final Office Action dated Jun. 5, 2015 for U.S. Appl. No. 14/207,511.
Final Office Action dated Jun. 5, 2015 for U.S. Appl. No. 14/207,516.
Notice of Allowance dated Jun. 5, 2015 for U.S. Appl. No. 13/091,118.
Ebbini et al. A spherical-section ultrasound phased array applicator for deep localized hyperthermia. 1991 IEEE Trans. Biom. Eng. 38:634-643.
Karmakar. Thoracic paravertebral block, 2001 Anesth. 95:771-780.
Kostreva et al, Reflex effects of hepatic baroreceptors on renal and cardiac sympathetic nerve activity. 1980 Am, J. Physiol. 238:R390-R394.
Liu et al. a fast and conformal heating scheme for producing large thermal lesions using a 20 ultrasound phased array, 2007 Int. J. Hyperthermia 23:69-82.
Pernot et al. 3-D Real-time motion correction in high-intensity focused ultrasound therapy, 2004 Ultrasound Med. Biol. 30:1239-1249.
Rails, Color doppler sonography of the hepatic artery and portal venous system. 1990 Am. J. Roentgenology 155:517-525.
Shanta, Unilateral bronchospasm after interpleural analgesia. 1992 Anesth. Analg. 74;291-293.
Final Office Action dated Jun. 8, 2015 for U.S. Appl. No. 13/657,725.
Non-Final Office Action dated Jun. 19, 2015 for U.S. Appl. No. 13/896,252.

(56) References Cited

OTHER PUBLICATIONS

Notice of Allowance dated Jun. 29, 2015 for U.S. Appl. No. 13/663,447.
Notice of Allowance dated Jul. 8, 2015 for U.S. Appl. No. 14/099,834.
Final Office Action dated Jul. 16, 2015 for U.S. Appl. No. 13/545,944.
Non-Final Office Action dated Jul. 20, 2015 for U.S. Appl. No. 13/966,212.
Notice of Allowance dated Jul. 20, 2015 for U.S. Appl. No. 13/896,247.
Non-Final Office Action dated Jul. 31, 2015 for U.S. Appl. No. 13/417,194.
Final Office Action dated Aug. 14, 2015 for U.S. Appl. No. 13/487,121.
Final Office Action dated Aug. 18, 2015 for U.S. Appl. No. 12/966,943.
Non-Final Office Action dated Sep. 29, 2015 for U.S. Appl. No. 14/562,477.
Final Office Action dated Jan. 4, 2016 for U.S. Appl. No. 14/015,331.
Bouthier et al. 1985 J. Cardiovasc. Pharmacol. 7:S99-S104.
Final Office Action dated Jan. 15, 2016 for U.S. Appl. No. 13/960,743.
Final Office Action dated Feb. 11, 2016 for U.S. Appl. No. 13/966,212.
Foreign Office Action dated Feb. 22, 2016 for Israeli Appln. No. 238653.
Search Report dated Mar. 10, 2016 for EP Appln. No. 15196135.6.
Search Report dated Mar. 29, 2016 for EP Appln. No. 13832046.0.
Foreign Office Action dated Jan. 29, 2016 for Malaysian Appln. No. PI 2012001623.
"The Journal of Allergy and Clinical Immunology" vol. 63, No. 3, 1979.
Chen, Jie, and T. R. Gururaja. "DC-biased eleotrostrictive materials and transducers for medical imaging." Ultrasonics Symposium, 1997. Proceedings., 1997 IEEE. vol. 2. IEEE, 1997.
Damianou, C., K. Hynynen, and X. Fan, "Application of the thermal dose concept for predicting the necrosed tissue volume during ultrasound surgery." Ultrasonics Symposium, 1993. Proceedings., IEEE 1993. IEEE, 1993.
Dewhisrt et al., "Basic principles of thermal dosimetry and thermal threshold for tissue damage from hyperthermia" 2003.
Fowlkes, J. Brian, and Christy K. Holland. "Mechanical bioeffects from diagnostic ultrasound: AIUM consensus statements. American Institute of Ultrasound in Medicine." Journal of ultrasound in medicine: official journal of the American Institute of Ultrasound in Medicine 19.2 (2000): 69-72.
Henry Gray, "The Skull" 1918.
Janssen, B, J., and J, F. Smits. "Renal nerves in hypertension." Mineral and electrolyte metabolism 15.1-2 (1988): 74-82.
Kirk Shung, K., et al. "Ultrasonic characterization of blood during coagulation." Journal of clinical ultrasound 12.3 (1984): 147-153.
N. F. Sheehan et al., "Observing the brachial artery through a pressure cuff", 1993.
Raul D. Indman, "What is Hysteroscopy" http://www.gynalternatives.com/hsc.htm, accessed on 2010.
Pernot, Mathieu, et al. "Temperature estimation using ultrasonic spatial compound imaging." Ultrasonics, Ferroelectrics and Frequency Control, IEEE Transactions on 51.5 (2004): 606-615.
Recchia et al., "Ultrasonic tissue characterization of blood during stasis and thrombosis with a real-time linear-array backscatter imaging system", Coronary Artery Disease, 1993.
Rose. J.L., "Ultrasonic Waves in Solid Media", 1999.
Sherrit, S., G. Catoiu, and B. K. Mukherjee. "The characterisation and modelling of electrostrictive ceramics for transducers." Ferroeleotrics 228.1 (1999): 167-196.
Shrout, T. R., et al. "Classification of Electrostrictive Based Materials for Transducers." Proceedings of the 6th US-Japan Seminar on Dielectric and Piezoelectric Ceramics. 1993.
Simon, Claudia, Philip VanBaren, and Emad S. Ebbini. "Two-dimensional temperature estimation using diagnostic ultrasound." Ultrasonics, Ferroelectrics and Frequency Control, IEEE Transactions on 45.4 (1998): 1088-1099.
Foreign Office Action dated Mar. 1, 2016 for Japanese Appln. No. 2015-082029.
Non-Final Office Action dated Apr. 20, 2016 for U.S. Appl. No. 14/201,851.
Office Action dated Apr. 18, 2016 for Canadian Appln. No. 2777228.
Office Action dated Jun. 22, 2017 for Indian Appln. No. 855/KOLNP/2012.
Non-Final Office Action dated Apr. 11, 2016 for U.S. Appl. No. 14/939,670.
Final Office Action dated Jul. 25, 2017 for U.S. Appl. No. 14/939,670.

\* cited by examiner

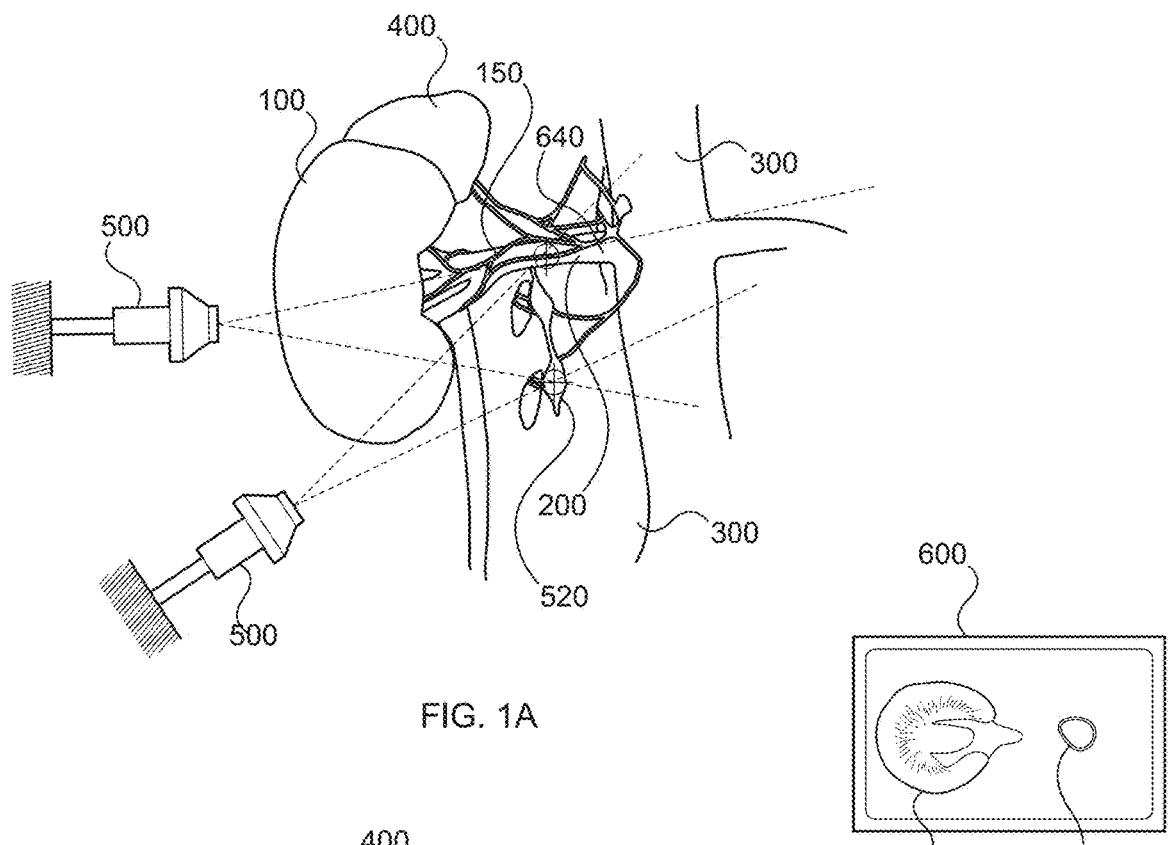
FIG. 1A
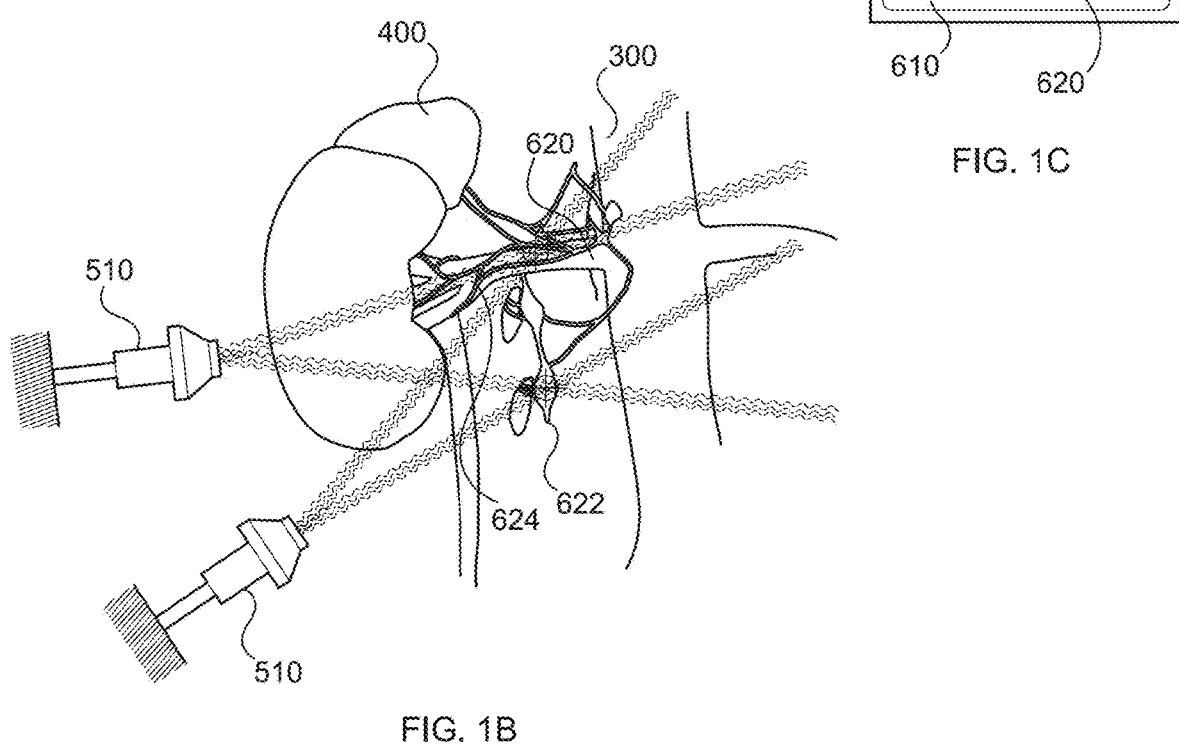
FIG. 1B
FIG. 1C

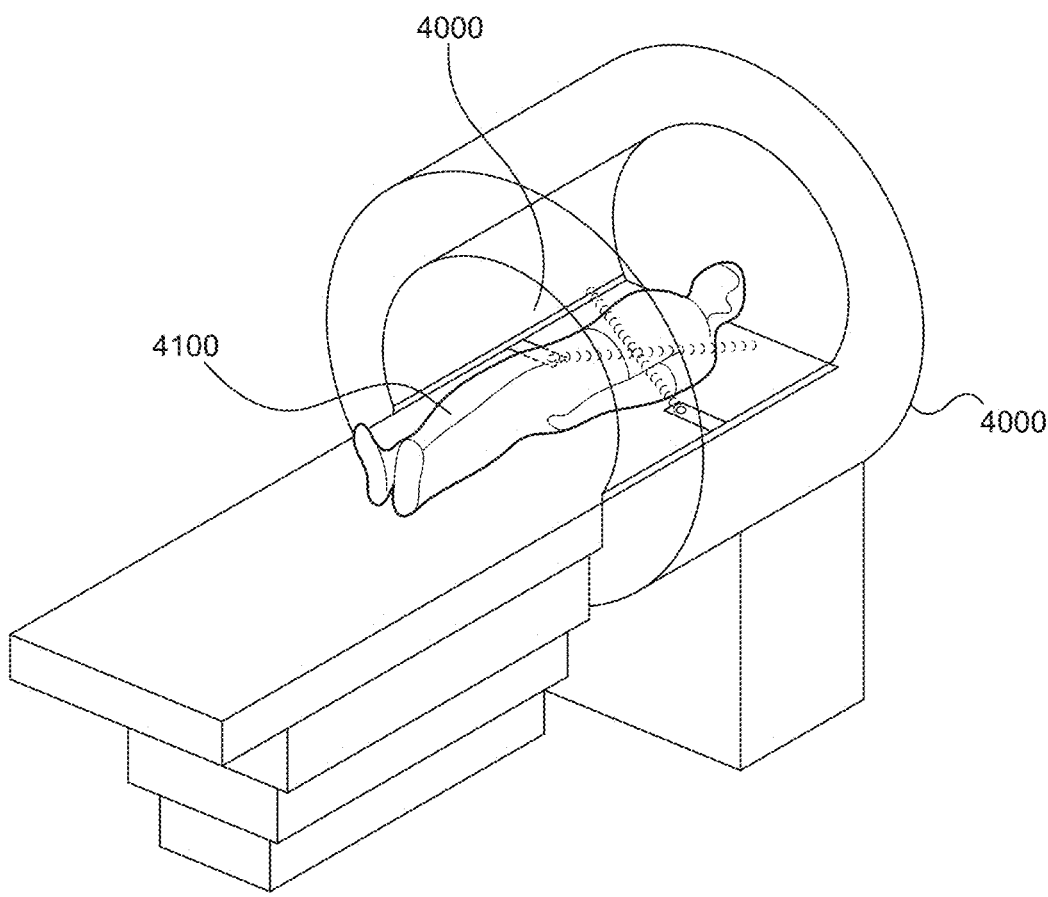
FIG. 7A
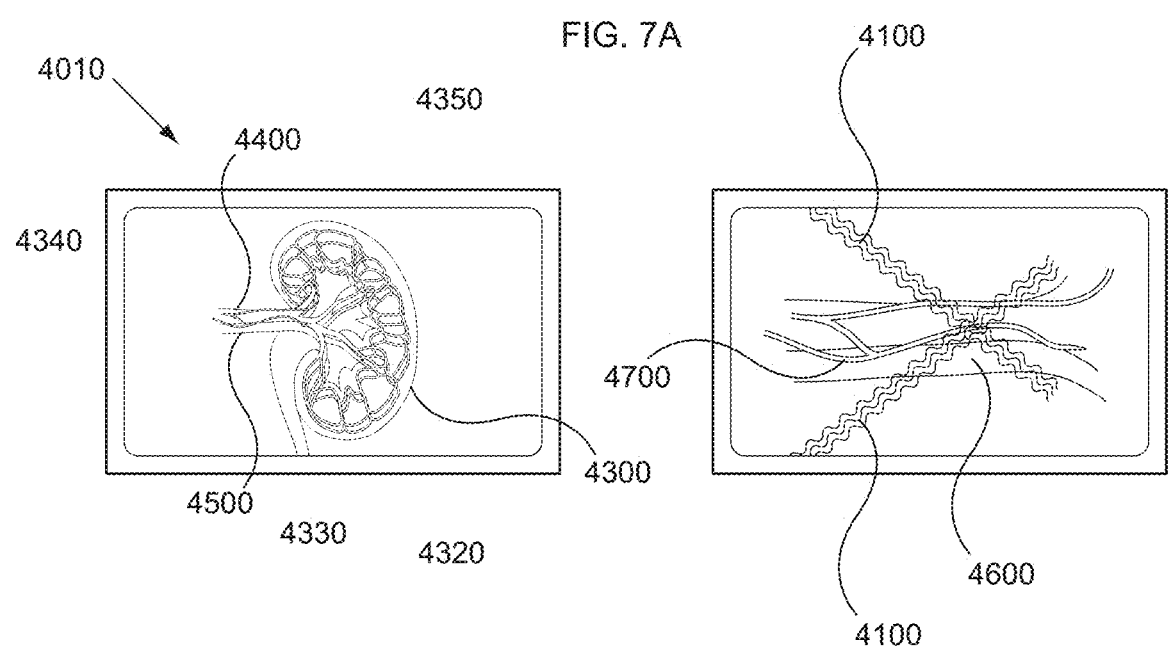
FIG. 7B
FIG. 7C

Parameters - Standard Position — 4730

| STRUCTURE | DISTANCE |
|---|---|
| Renal artery | 7.0 - 17 cm |
| Kidney hilum | 4 cm - 8 cm |
| Angle of approach | -10°(-48°) |

FIG. 7G

| | Prone Position | |
|---|---|---|
| | STRUCTURE | DISTANCE |
| 4770 | Renal artery | 6.0 - 10.0 cm |
| 4780 | Kidney hilum | 4.0 cm - 8.0 cm |
| 4790 | Angle of approach | 5 - 20° |

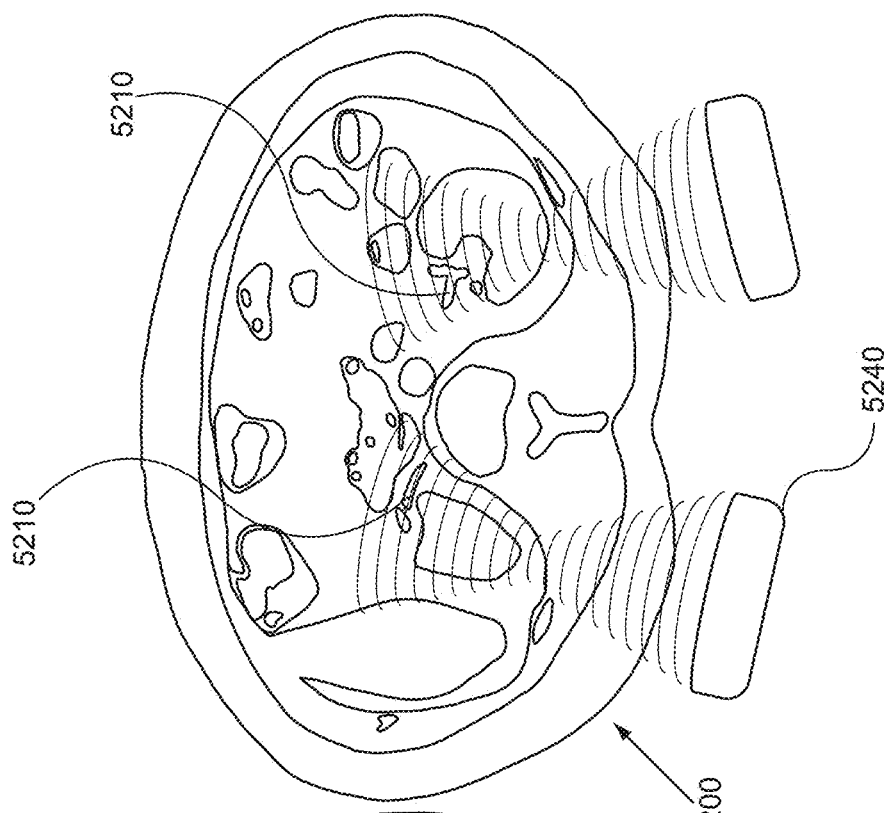
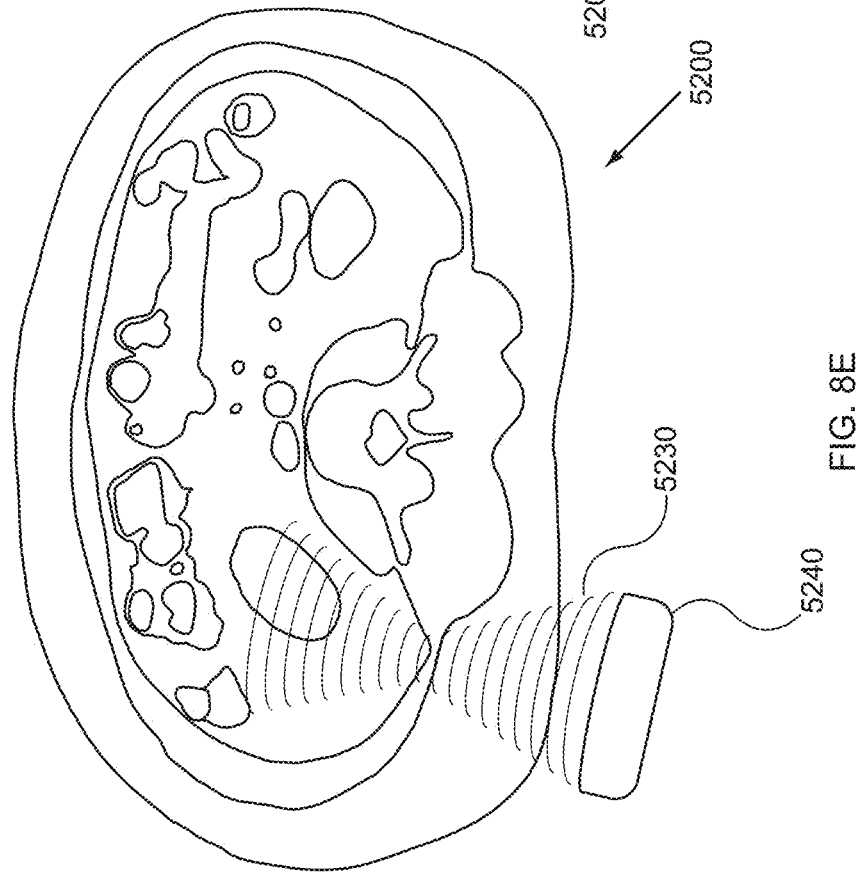

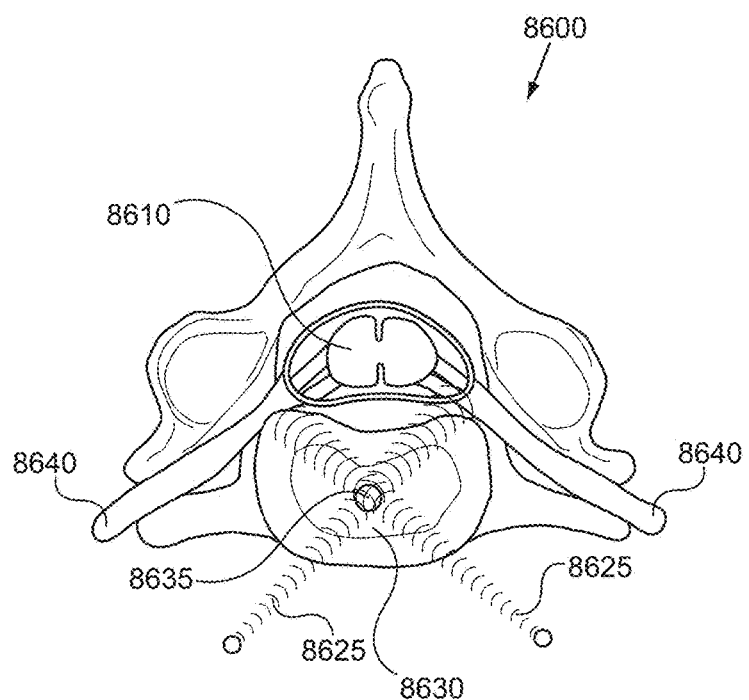
FIG. 15A
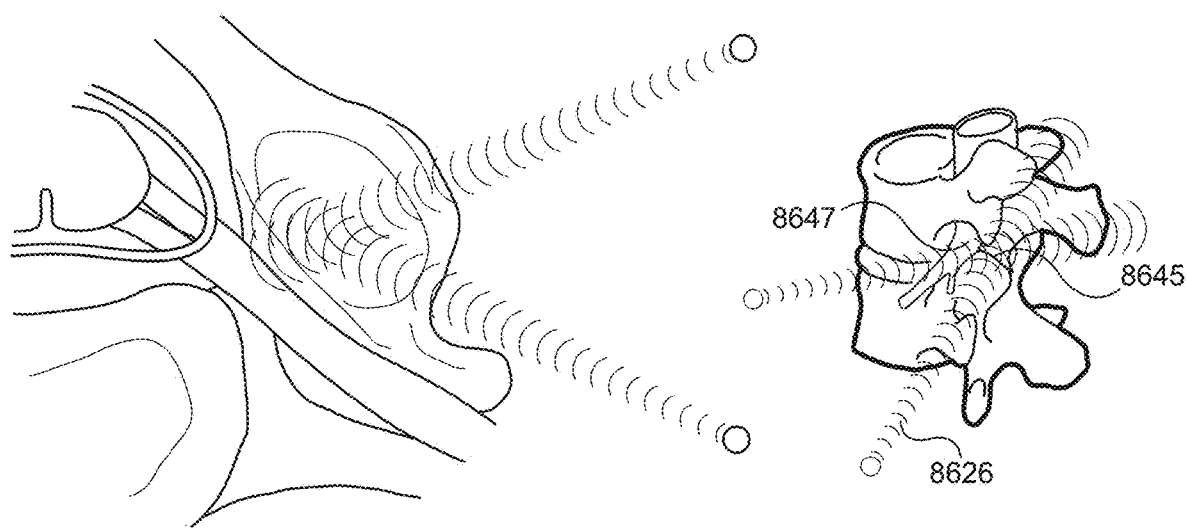
FIG. 15B
FIG. 15C

| Cat Results (pg/ml) | Cortex NE Conc. (ng/g) | Avg. Cortex NE (ng/g) | Procedure |
|---|---|---|---|
| 456 | 5 | 5 | HIFU |
| 543 | 5 | | HIFU |
| 28,135 | 281 | 347 | Control |
| 41,280 | 413 | | Control |
| 328 | 3 | 2 | HIFU |
| 96 | 1 | | HIFU |
| 30,480 | 305 | 352 | Control |
| 39,840 | 398 | | Control |

FIG. 16C

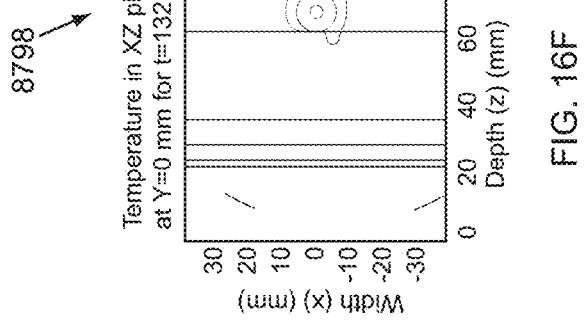
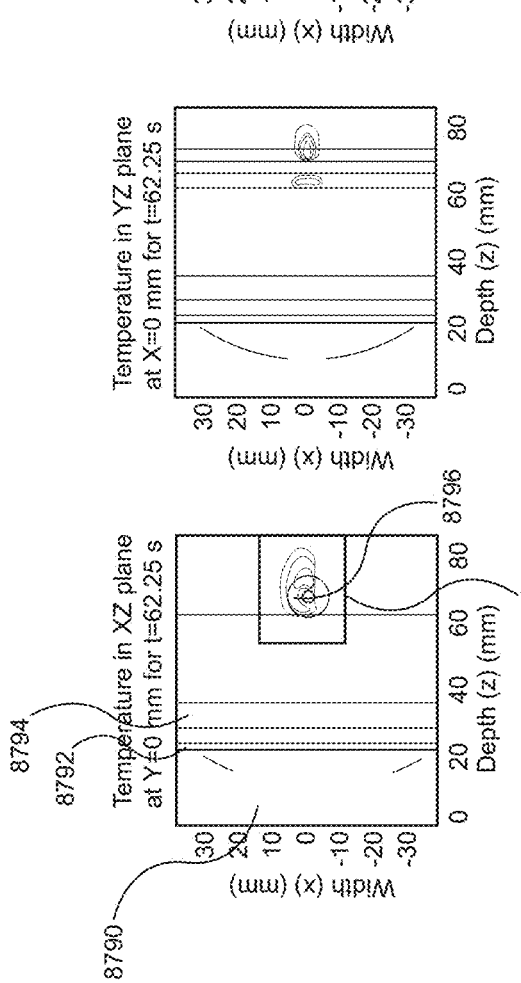
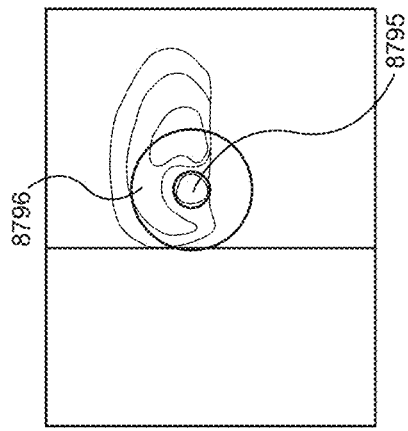
FIG. 16G
FIG. 16F
FIG. 16E
FIG. 16D
FIG. 16H

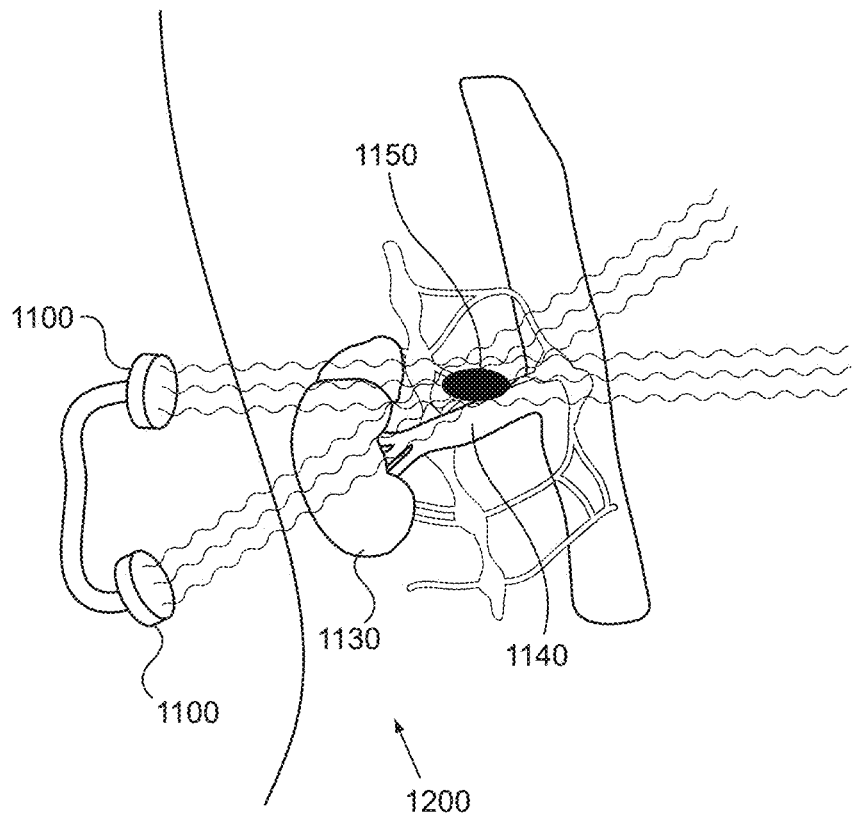
FIG. 17A
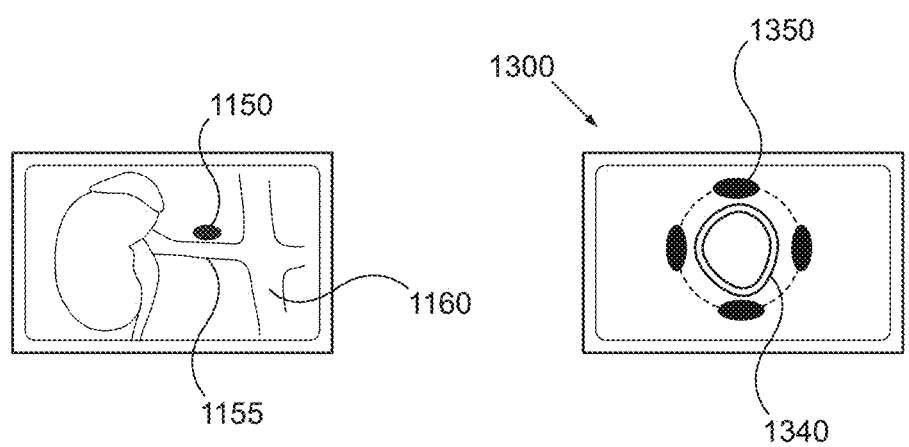
FIG. 17B
FIG. 17C

Target skin region
003
Left 8760  Right
007 (obese subject)
Left 8760  Right 8760
| Surface area (cm^2) | 214 | 202 | 386 | 367 |
|---|---|---|---|---|
| Shortest ray (cm) | 10 | 10 | 12 | 13 |
| Longest ray (cm) | 20 | 19 | 20 | 22 |
FIG. 29E

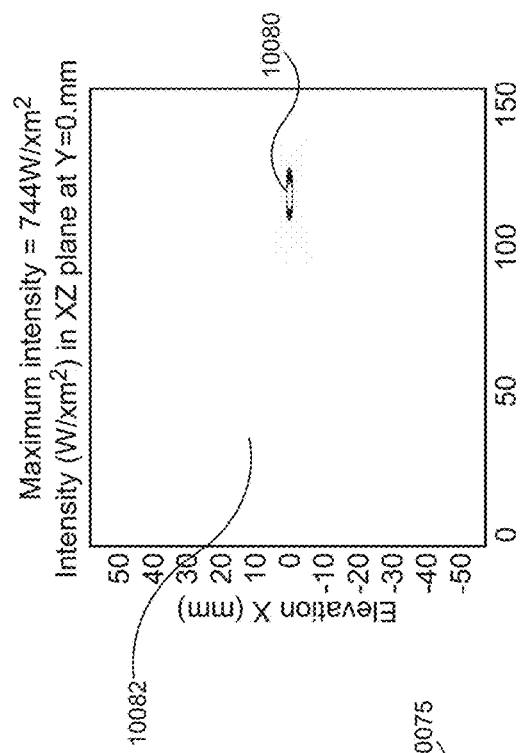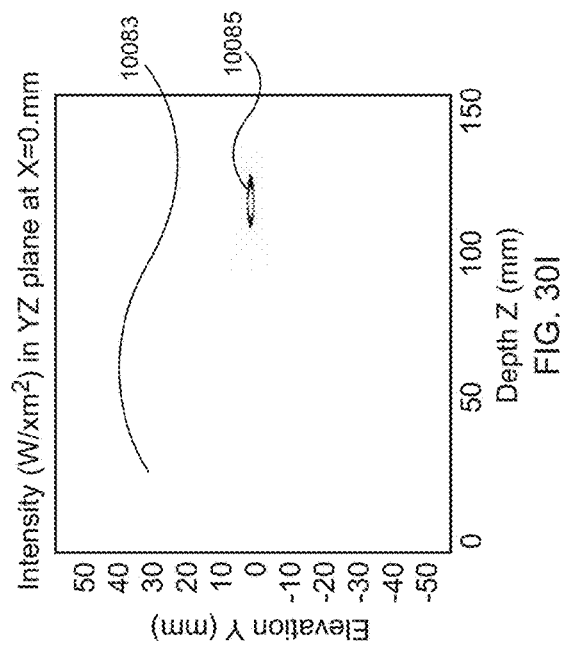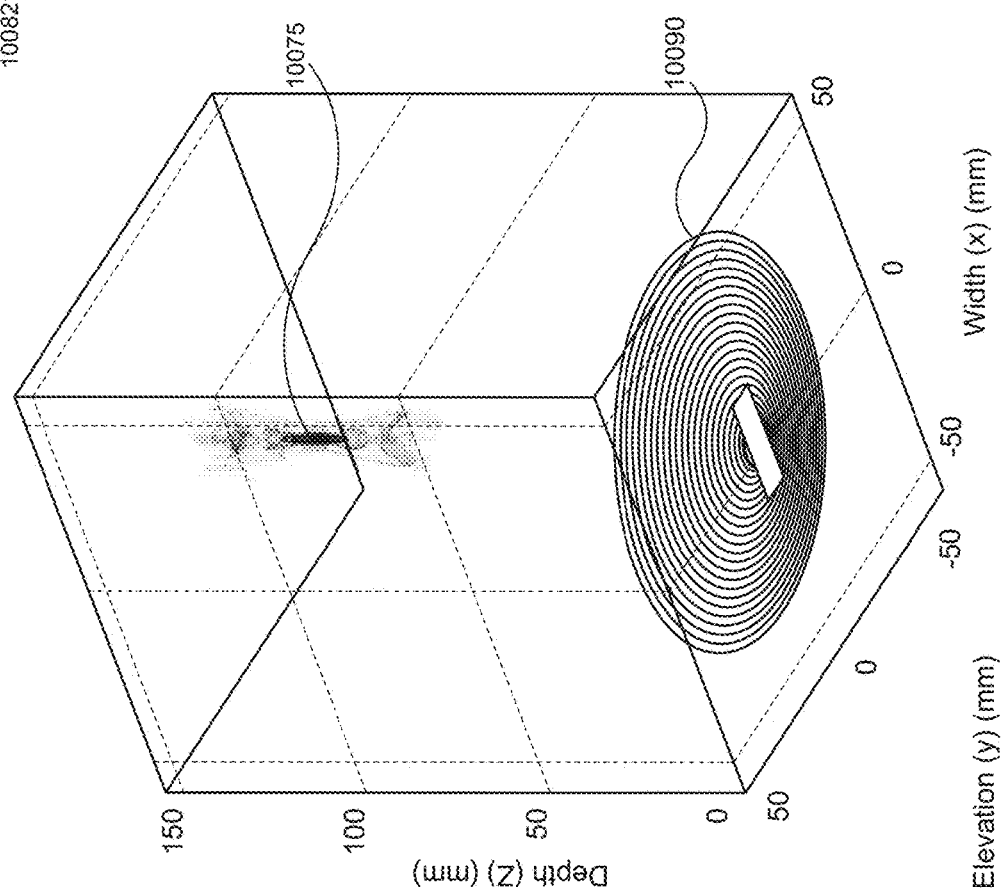

INTRAVASCULAR ENERGY DELIVERY

RELATED APPLICATION DATA

This application is a continuation of U.S. patent application Ser. No. 15/662,179, filed on Jul. 27, 2017, which is a continuation of U.S. patent application Ser. No. 14/939,670, filed on Nov. 12, 2015, abandoned, which is a continuation of U.S. patent application Ser. No. 13/896,247, filed on May 16, 2013, now U.S. Pat. No. 9,199,097, which is a continuation of U.S. patent application Ser. No. 13/048,842, filed on Mar. 15, 2011, now U.S. Pat. No. 8,469,904, which is a continuation-in-part of U.S. patent application Ser. No. 12/902,133 filed Oct. 11, 2010, now U.S. Pat. No. 9,174,065, which claims priority to and the benefit of U.S. Provisional patent application 61/377,908 filed Aug. 27, 2010, now lapsed, and U.S. Provisional patent application 61/347,375 filed May 21, 2010, now lapsed, and wherein U.S. patent application Ser. No. 13/048,842 is also a continuation-in-part of U.S. patent application Ser. No. 12/725,450 filed Mar. 16, 2010, now abandoned, which is a continuation-in-part of U.S. patent application Ser. No. 12/685,655, filed on Jan. 11, 2010, now issued as U.S. Pat. No. 8,295,912 on Oct. 23, 2012, which claims priority to and the benefit of U.S. Provisional Patent Application No. 61/256,983 filed Oct. 31, 2009, now lapsed, U.S. Provisional Patent Application No. 61/250,857 filed Oct. 12, 2009, now lapsed, U.S. Provisional Patent Application No. 61/261,741 filed Nov. 16, 2009, now lapsed, and U.S. Provisional Patent Application No. 61/291,359 filed Dec. 30, 2009, now lapsed.

U.S. patent application Ser. No. 12/725,450 also claims priority to, and the benefit of U.S. Provisional Patent Application No. 61/303,307 filed Feb. 10, 2010, now lapsed, U.S. Provisional Patent Application No. 61/256,983 filed Oct. 31, 2009, now lapsed, U.S. Provisional Patent Application No. 61/250,857 filed Oct. 12, 2009, now lapsed, U.S. Provisional Patent Application No. 61/261,741 filed Nov. 16, 2009, now lapsed, and U.S. Provisional Patent Application No. 61/291,359 filed Dec. 30, 2009, now lapsed.

The disclosures of all of the above referenced applications are expressly incorporated by reference herein.

This application is related to U.S. patent application Ser. Nos. 13/048,830, 13/048,837, and 13/048,844.

The following patent applications are also expressly incorporated by reference herein.

U.S. patent application Ser. Nos. 11/583,569, 12/762,938, 11/583,656, 12/247,969, 10/633,726, 09/721,526, 10/780,405, 09/747,310, 12/202,195, 11/619,996, 09/696,076, 11/016,701, 12/887,178, 12/390,975, 12/887,178, 12/887,211, 12/887,232, 11/583,656.

It should be noted that the subject matters of the above applications and any other applications referenced herein are expressly incorporated into this application as if they are expressly recited in this application. Thus, in the instance where the references are not specifically labeled as "incorporated by reference" in this application, they are in fact deemed described in this application.

BACKGROUND

Energy delivery from a distance involves transmission of energy waves to affect a target at a distance. It allows for more efficient delivery of energy to targets and a greater cost efficiency and technologic flexibility on the generating side. For example, cellular phones receive targets from towers close to the user and the towers communicate with one another over a long range; this way, the cell phones can be low powered and communicate over a relatively small range yet the network can quickly communicate across the world. Similarly, electricity distribution from large generation stations to the users is more efficient than the users themselves looking for solutions.

In terms of treating a patient, delivering energy over a distance affords great advantages as far as targeting accuracy, technologic flexibility, and importantly, limited invasiveness into the patient. In a simple form, laparoscopic surgery has replaced much of the previous open surgical procedures and lead to creation of new procedures and devices as well as a more efficient procedural flow for disease treatment. Laparoscopic tools deliver the surgeon's energy to the tissues of the patient from a distance and results in improved imaging of the region being treated as well as the ability for many surgeons to visualize the region at the same time.

Perhaps the most important aspect is the fact that patients have much less pain, fewer complications, and the overall costs of the procedures are lower. Visualization is improved as is the ability to perform tasks relative to the visualization.

Continued advances in computing, miniaturization and economization of energy delivery technologies, and improved imaging will lead to still greater opportunities to apply energy from a distance into the patient and treat disease.

SUMMARY

In some embodiments, procedures and devices are provided, which advance the art of medical procedures involving transmitted energy to treat disease. The procedures and devices follow along the lines of: 1) transmitting energy to produce an effect in a patient from a distance; 2) allowing for improved imaging or targeting at the site of treatment; 3) creating efficiencies through utilization of larger and more powerful devices from a position of distance from or within the patient as opposed to attempting to be directly in contact with the target as a surgeon, interventional cardiologist or radiologist might do. In many cases, advanced visualization and localization tools are utilized as well.

In accordance with some embodiments, a system for treatment includes a focused ultrasound energy source for placement outside a patient, wherein the focused ultrasound energy source is configured to deliver ultrasound energy towards a blood vessel with a surrounding nerve that is a part of an autonomic nervous system inside the patient, and wherein the focused ultrasound energy source is configured to deliver the ultrasound energy from outside the patient to the nerve located inside the patient to treat the nerve.

In any of the embodiments described herein, the focused ultrasound energy source comprises a transducer, and a angle of the focused ultrasound source is anywhere between 30 degrees to 80 degrees with respect to a line traveling down a center of the transducer relative to a line connecting the transducer to the blood vessel.

In any of the embodiments described herein, the focused ultrasound energy source is configured to provide the ultrasound energy to achieve partial ablation of the nerve.

In any of the embodiments described herein, the focused ultrasound energy source is configured to deliver the ultrasound energy to the nerve from multiple directions outside the patient while the focused ultrasound energy source is stationary relative to the patient.

In any of the embodiments described herein, the system further includes an imaging processor for determining a position of the blood vessel.

In any of the embodiments described herein, the imaging processor comprises a CT device, a MRI device, a thermography device, an infrared imaging device, an optical coherence tomography device, a photoacoustic imaging device, a PET imaging device, a SPECT imaging device, or an ultrasound device.

In any of the embodiments described herein, the processor is configured to operate the focused ultrasound energy source to target the nerve that surrounds the blood vessel during the ultrasound energy delivery based on the determined position.

In any of the embodiments described herein, the processor is configured to determine the position using a Doppler triangulation technique.

In any of the embodiments described herein, the focused ultrasound energy source is configured to deliver the ultrasound energy having an energy level sufficient to decrease a sympathetic stimulus to the kidney, decrease an afferent signal from the kidney to an autonomic nervous system, or both.

In any of the embodiments described herein, the focused ultrasound energy source has an orientation so that the focused ultrasound energy source aims at a direction that aligns with the vessel that is next to the nerve.

In any of the embodiments described herein, the focused ultrasound energy source is configured to track a movement of the nerve.

In any of the embodiments described herein, the focused ultrasound energy source is configured to track the movement of the nerve by tracking a movement of the blood vessel next to the nerve.

In any of the embodiments described herein, the focused ultrasound energy source is configured to aim towards the nerve by aiming towards the blood vessel that is surrounded by the nerve.

In any of the embodiments described herein, the system further includes a device for placement inside the patient, and a processor for determining a position using the device, wherein the focused ultrasound energy source is configured to deliver the ultrasound energy based at least in part on the determined position.

In any of the embodiments described herein, the device is sized for insertion into the blood vessel that is surrounded by the nerve.

In any of the embodiments described herein, the focused ultrasound energy source is configured to deliver the ultrasound energy towards the blood vessel at an angle anywhere between −10 degrees and −48 degrees relative to a horizontal line connecting transverse processes of a spinal column, the angle directed from a lower torso to an upper torso of the patient.

In accordance with some embodiments, a system for treatment of a nerve surrounding a blood vessel traveling to a kidney includes an ultrasound energy source for placement outside a patient wherein the ultrasound energy source comprises an array of ultrasound transducers, and a programmable interface, configured to control the ultrasound energy source to deliver focused ultrasound to a region surrounding a blood vessel leading to the kidney through energizing one or more elements of the array in one or more phases, at an angle and offset to a central axis of the array to a tissue depth anywhere from 6 cm to 15 cm.

In any of the embodiments described herein, the focused ultrasound energy source comprises a transducer, and an angle of the focused ultrasound source is anywhere between 30 degrees to 80 degrees with respect to a line traveling down a center of the transducer relative to a line connecting from the transducer to the blood vessel.

In any of the embodiments described herein, the focused ultrasound energy source is configured to provide the ultrasound energy to achieve partial ablation of the nerve.

In any of the embodiments described herein, the focused ultrasound energy source is configured to deliver the ultrasound energy to the nerve from multiple directions outside the patient while the focused ultrasound energy source is stationary relative to the patient.

In any of the embodiments described herein, the system further includes an imaging processor for determining a position of the blood vessel.

In any of the embodiments described herein, the imaging processor comprises a CT device, a MRI device, a thermography device, an infrared imaging device, an optical coherence tomography device, a photoacoustic imaging device, a PET imaging device, a SPECT imaging device, or an ultrasound device.

In any of the embodiments described herein, the processor is configured to operate the focused ultrasound energy source to target the nerve that surrounds the blood vessel during the ultrasound energy delivery based on the determined position.

In any of the embodiments described herein, the processor is configured to determine the position using a Doppler triangulation technique.

In any of the embodiments described herein, the focused ultrasound energy source is configured to deliver the ultrasound energy having an energy level sufficient to decrease a sympathetic stimulus to the kidney, decrease an afferent signal from the kidney to an autonomic nervous system, or both.

In any of the embodiments described herein, the focused ultrasound energy source has an orientation so that the focused ultrasound energy source aims at a direction that aligns with the vessel that is next to the nerve.

In any of the embodiments described herein, the focused ultrasound energy source is configured to track a movement of the nerve.

In any of the embodiments described herein, the focused ultrasound energy source is configured to track the movement of the nerve by tracking a movement of the blood vessel next to the nerve.

In any of the embodiments described herein, the focused ultrasound energy source is configured to aim towards the nerve by aiming towards the blood vessel that is surrounded by the nerve.

In any of the embodiments described herein, the system further includes a device for placement inside the patient, and a processor for determining a position using the device, wherein the focused ultrasound energy source is configured to deliver the ultrasound energy based at least in part on the determined position.

In any of the embodiments described herein, the device is sized for insertion into the blood vessel that is surrounded by the nerve.

In any of the embodiments described herein, the focused ultrasound energy source is configured to deliver the ultrasound energy towards the blood vessel at an angle anywhere between −10 degrees and −48 degrees relative to a horizontal line connecting transverse processes of a spinal column, the angle directed from a lower torso to an upper torso of the patient.

In accordance with some embodiments, a system for treatment of an autonomic nervous system of a patient includes a focused ultrasound energy source for placement outside the patient, wherein the focused ultrasound energy source is configured to deliver ultrasound energy towards a blood vessel with a surrounding nerve that is a part of the autonomic nervous system inside the patient, and wherein the focused ultrasound energy source is configured to deliver the ultrasound energy based on a position of an indwelling vascular catheter.

In any of the embodiments described herein, the focused ultrasound energy source comprises a transducer, and a angle of the focused ultrasound source is anywhere between 30 degrees to 80 degrees with respect to a line traveling down a center of the transducer relative to a line connecting from the transducer to the blood vessel.

In any of the embodiments described herein, the focused ultrasound energy source is configured to provide the ultrasound energy to achieve partial ablation of the nerve.

In any of the embodiments described herein, the focused ultrasound energy source is configured to deliver the ultrasound energy to the nerve from multiple directions outside the patient while the focused ultrasound energy source is stationary relative to the patient.

In any of the embodiments described herein, the system further includes an imaging processor for determining a position of the blood vessel.

In any of the embodiments described herein, the imaging processor comprises a CT device, a MRI device, a thermography device, an infrared imaging device, an optical coherence tomography device, a photoacoustic imaging device, a PET imaging device, a SPECT imaging device, or an ultrasound device.

In any of the embodiments described herein, the processor is configured to operate the focused ultrasound energy source to target the nerve that surrounds the blood vessel during the ultrasound energy delivery based on the determined position.

In any of the embodiments described herein, the processor is configured to determine the position using a Doppler triangulation technique.

In any of the embodiments described herein, the focused ultrasound energy source is configured to deliver the ultrasound energy having an energy level sufficient to decrease a sympathetic stimulus to the kidney, decrease an afferent signal from the kidney to an autonomic nervous system, or both.

In any of the embodiments described herein, the focused ultrasound energy source has an orientation so that the focused ultrasound energy source aims at a direction that aligns with the vessel that is next to the nerve.

In any of the embodiments described herein, the focused ultrasound energy source is configured to track a movement of the nerve.

In any of the embodiments described herein, the focused ultrasound energy source is configured to track the movement of the nerve by tracking a movement of the blood vessel next to the nerve.

In any of the embodiments described herein, the focused ultrasound energy source is configured to aim towards the nerve by aiming towards the blood vessel that is surrounded by the nerve.

In any of the embodiments described herein, the focused ultrasound energy source is configured to deliver the ultrasound energy towards the blood vessel at an angle anywhere between −10 degrees and −48 degrees relative to a horizontal line connecting transverse processes of a spinal column, the angle directed from a lower torso to an upper torso of the patient.

In accordance with some embodiments, a system for treatment includes a focused ultrasound energy source for placement outside a patient, wherein the focused ultrasound energy source is configured to deliver ultrasound energy towards a blood vessel with a surrounding nerve that is a part of an autonomic nervous system inside the patient, and wherein the focused ultrasound energy source is configured to deliver the ultrasound energy towards the blood vessel at an angle anywhere between −10 degrees and −48 degrees relative to a horizontal line connecting transverse processes of a spinal column, the angle directed from a lower torso to an upper torso of the patient.

In any of the embodiments described herein, the focused ultrasound energy source comprises a transducer, and a angle of the focused ultrasound source is anywhere between 30 degrees to 80 degrees with respect to a line traveling down a center of the transducer relative to a line connecting from the transducer to the blood vessel.

In any of the embodiments described herein, the focused ultrasound energy source is configured to provide the ultrasound energy to achieve partial ablation of the nerve.

In any of the embodiments described herein, the focused ultrasound energy source is configured to deliver the ultrasound energy to the nerve from multiple directions outside the patient while the focused ultrasound energy source is stationary relative to the patient.

In any of the embodiments described herein, the system further includes an imaging processor for determining a position of the blood vessel.

In any of the embodiments described herein, the imaging processor comprises a CT device, a MRI device, a thermography device, an infrared imaging device, an optical coherence tomography device, a photoacoustic imaging device, a PET imaging device, a SPECT imaging device, or an ultrasound device.

In any of the embodiments described herein, the processor is configured to operate the focused ultrasound energy source to target the nerve that surrounds the blood vessel during the ultrasound energy delivery based on the determined position.

In any of the embodiments described herein, the processor is configured to determine the position using a Doppler triangulation technique.

In any of the embodiments described herein, the focused ultrasound energy source is configured to deliver the ultrasound energy having an energy level sufficient to decrease a sympathetic stimulus to the kidney, decrease an afferent signal from the kidney to an autonomic nervous system, or both.

In any of the embodiments described herein, the focused ultrasound energy source has an orientation so that the focused ultrasound energy source aims at a direction that aligns with the vessel that is next to the nerve.

In any of the embodiments described herein, the focused ultrasound energy source is configured to track a movement of the nerve.

In any of the embodiments described herein, the focused ultrasound energy source is configured to track the movement of the nerve by tracking a movement of the blood vessel next to the nerve.

In any of the embodiments described herein, the focused ultrasound energy source is configured to aim towards the nerve by aiming towards the blood vessel that is surrounded by the nerve.

In any of the embodiments described herein, the system further includes a device for placement inside the patient, and a processor for determining a position using the device, wherein the focused ultrasound energy source is configured to deliver the ultrasound energy based at least in part on the determined position.

In any of the embodiments described herein, the device is sized for insertion into the blood vessel that is surrounded by the nerve.

In accordance with some embodiments, a method to apply a nerve inhibiting cloud surrounding a blood vessel includes creating a treatment plan, wherein the treatment plan prescribes application of the nerve inhibiting cloud towards at least a majority portion of a circumference of a blood vessel wall, and applying the nerve inhibiting cloud towards the majority portion of the circumference of the blood vessel wall for a time sufficient to inhibit a function of a nerve that surrounds the blood vessel wall.

In any of the embodiments described herein, the nerve inhibiting cloud comprises a cloud of light.

In any of the embodiments described herein, the nerve inhibiting cloud comprises a gaseous cloud.

In any of the embodiments described herein, the nerve inhibiting cloud comprises a heat cloud.

In any of the embodiments described herein, the nerve inhibiting cloud is applied using a transcutaneous energy source.

In any of the embodiments described herein, the nerve inhibiting cloud is applied using a transcutaneous energy source that is configured to deliver a focused ultrasound.

In any of the embodiments described herein, the nerve inhibiting cloud is applied using ionizing radiation.

In any of the embodiments described herein, the nerve inhibiting cloud is applied by delivering focused ultrasound, and the imaging device comprises an MRI device.

In any of the embodiments described herein, the method further includes obtaining an image of the blood vessel using an imaging device, wherein the treatment plan is created using the image.

In accordance with some embodiments, a system to deliver a nerve inhibiting cloud to a region surrounding a blood vessel includes a catheter comprising a plurality of electrodes configured to apply a cloud of heat, a processor storing a treatment plan that prescribes an application of the cloud of heat towards at least a majority of a circumference of a blood vessel wall surrounded by nerve, and an external detector configured for measuring temperature associated with the application of the cloud of heat.

In any of the embodiments described herein, the external detector comprises an ultrasound device.

In any of the embodiments described herein, the external detector comprises an MRI device.

In any of the embodiments described herein, the catheter is configured to be placed in a vein.

In any of the embodiments described herein, the catheter is configured to be placed into a visceral artery.

In accordance with some embodiments, a system to deliver a nerve inhibiting treatment to a nerve region surrounding a blood vessel includes a catheter comprising a component which is configured to be heated in response to an externally applied electromagnetic field, and a device configured for applying the electromagnetic field through a skin of a patient to heat the component of the catheter, wherein the heated component provides a heat cloud to the nerve region surrounding the blood vessel.

In any of the embodiments described herein, the catheter comprises an expandable member for pressing up against a wall of the blood vessel when the expandable member is expanded.

In any of the embodiments described herein, the device is further configured for measuring a temperature using the electromagnetic field.

In any of the embodiments described herein, the device comprises a magnetic resonance imaging device.

In any of the embodiments described herein, the device comprises an ultrasound detection device.

In accordance with some embodiments, a method to deliver focused ultrasound energy from a position outside a skin of a patient to a nerve surrounding a blood vessel includes placing the patient on a table in a substantially flat position, moving a transducer into a position inferior to ribs, superior to an iliac crest, and lateral to a spine of the patient, maintaining the transducer at the position relative to the patient, and delivering focused ultrasound energy through the skin of the patient without traversing bone, wherein the direction of the focused ultrasound is directed from a lower torso to an upper torso of the patient.

In any of the embodiments described herein, the method further includes detecting signals emanating from within the patient.

In any of the embodiments described herein, the method further includes detecting signals emanating from an intravascular device inside the patient.

In any of the embodiments described herein, the focused ultrasound energy is delivered to treat nerves inside the patient.

In any of the embodiments described herein, the nerves surrounds a vessel, and the focused ultrasound energy is delivered to the nerves by targeting the vessel.

In accordance with some embodiments, a system to deliver a nerve inhibiting treatment to a nerve region surrounding a blood vessel includes a catheter comprising a component which is configured to be heated in response to an externally applied electromagnetic field, and a magnetic resonance device configured for applying the electromagnetic field through a skin of a patient to heat the component of the catheter to a level that is sufficient to treat the nerve region surrounding the blood vessel, and a temperature detection system configured to limit a temperature of the nerve region surrounding the blood vessel.

In any of the embodiments described herein, the magnetic resonance device includes the temperature detection system.

In any of the embodiments described herein, the temperature detection system is inside the catheter.

In any of the embodiments described herein, the catheter is configured to be steered based at least in part on a signal provided by the magnetic resonance system.

In any of the embodiments described herein, the magnetic resonance system is configured to move the catheter towards a wall of the blood vessel.

In accordance with some embodiments, a system for treatment of a nerve surrounding a blood vessel traveling to a kidney includes an ultrasound energy source for placement outside a patient, wherein the ultrasound energy source comprises an array of ultrasound transducers, a programmable interface, configured to control the ultrasound energy source to deliver focused ultrasound to a region surrounding the blood vessel leading to the kidney through energizing one or more elements of the array in one or more phases, and a magnetic resonance imaging system comprising a permanent magnet, wherein the magnetic resonance imaging system is operatively coupled to the programmable interface.

In any of the embodiments described herein, the system further includes an intravascular catheter device for placement into the vessel.

In any of the embodiments described herein, the system further includes a radiofrequency coil for placement around an abdomen of the patient.

In any of the embodiments described herein, the system further includes a positioning device for delivering focused ultrasound energy to the region surrounding the blood vessel leading to the kidney.

In any of the embodiments described herein, the ultrasound energy source is configured to deliver the focused ultrasound at an angle and offset to a central axis of the array to a tissue depth anywhere from 6 cm to 15 cm.

In accordance with some embodiments, a system for treatment of a nerve surrounding a blood vessel traveling to a kidney includes an ultrasound energy source for placement outside a patient wherein the ultrasound energy source comprises an array of ultrasound transducers, a programmable interface, configured to control the ultrasound energy source to deliver focused ultrasound to a region surrounding the blood vessel leading to the kidney through energizing one or more elements of the array in one or more phases, and a processor configured to determine a quality factor based at least on an amount of time the focused ultrasound is within a pre-determined distance from a target.

In any of the embodiments described herein, the pre-determined distance is 500 microns.

In any of the embodiments described herein, the pre-determined distance is 2 mm.

In any of the embodiments described herein, the processor is further configured to operate the ultrasound energy source based at least in part on the quality factor.

In any of the embodiments described herein, the system further includes an intravascular catheter for placement into the vessel.

In any of the embodiments described herein, the intravascular catheter is configured to provide a signal related to movement of the region being treated, and the processor is configured to operate the ultrasound energy source based at least in part on the signal.

In any of the embodiments described herein, the system further includes a motion tracking system coupled to the processor.

In any of the embodiments described herein, the ultrasound energy source is configured to deliver the focused ultrasound at an angle and offset to a central axis of the array to a tissue depth anywhere from 6 cm to 15 cm.

In accordance with some embodiments, a device to apply focused ultrasound to a patient includes a transducer configured to deliver focused ultrasound to a blood vessel leading to a kidney, wherein the transducer comprises a plurality of individually phaseable elements, and a membrane for coupling the ultrasound to the patient, a first mechanical mover for positioning the transducer, wherein the first mechanical mover is configured to operate with the phaseable elements simultaneously to change a position of a focus of the transducer, and a second mechanical mover for maintaining a pressure between the membrane of the transducer and a skin of the patient.

In any of the embodiments described herein, the membrane contains fluid, and pressure and temperature of the fluid is maintained at a constant level.

In any of the embodiments described herein, the device further includes an imaging system operatively coupled to the first mechanical mover.

In any of the embodiments described herein, the imaging system is an MRI system.

In any of the embodiments described herein, the imaging system is an ultrasound system.

In any of the embodiments described herein, the imaging system is configured to detect an intravascular catheter.

In any of the embodiments described herein, the imaging system is configured to determine a three dimensional coordinate, and the transducer is configured to deliver the ultrasound based at least in part on the determined three dimensional coordinate.

Other and further aspects and features will be evident from reading the following detailed description of the embodiments.

DESCRIPTION OF FIGURES

FIGS. 1A-1B depict the focusing of energy sources on nerves of the autonomic nervous system.

FIG. 1C depicts an imaging system to help direct the energy sources.

FIG. 7A depicts a patient in an imaging system receiving treatment with focused energy waves.

FIG. 7B depicts visualization of a kidney being treated.

FIG. 7C depicts a close up view of the renal nerve region of the kidney being treated.

FIG. 7G depicts the results of measurements from a series of cross sectional image reconstructions.

FIG. 7H depicts the results of measurements from a series of cross-sectional images from a patient in a more optimized position.

FIG. 7I depicts an algorithmic methodology to apply treatment to the hilum of the kidney and apply energy to the renal blood vessels.

FIGS. 8E-8F depict cross sectional images with focused energy traveling from a posterior direction.

FIGS. 15A-15C depict the application of focused energy to the vertebral column to treat various spinal pathologies including therapy of the spinal or intravertebral nerves.

FIG. 16C depicts data from ultrasound energy applied to the renal blood vessels and the resultant change in norepinephrine levels.

FIGS. 16D-16H depict a simulation of multiple treatment spots along a blood vessel.

FIG. 17A depicts the application of multiple transducers to treat regions of the autonomic nervous system at the renal hilum.

FIGS. 17B-17C depict methods for using imaging to direct treatment of a specific region surrounding an artery as well as display the predicted lesion morphology.

FIG. 29E depicts the results of design processes in which the angle, length, and surface area from CT scans is quantified.

FIGS. 30A-30I depict results of simulations to apply focused ultrasound to the region of a renal artery with a prototype device design based on simulations.

DETAILED DESCRIPTION

Figure 1D:
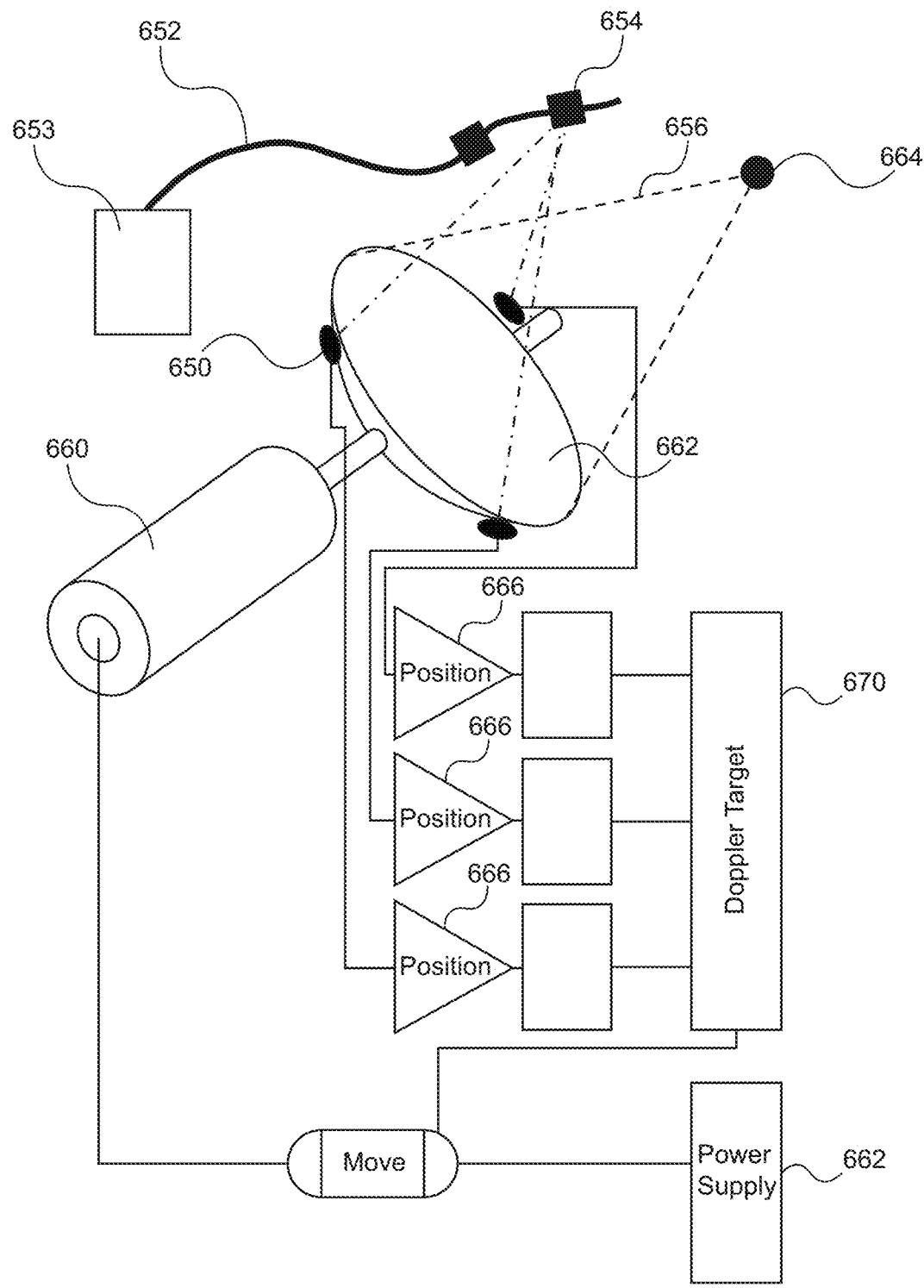
FIG. 1D depicts a system integration schematic.

Hypertension is a disease of extreme national and international importance. There are 80 million patients in the US alone who have hypertension and over 200 million in developed countries worldwide. In the United States, there are 60 million patients who have uncontrolled hypertension, meaning that they are either non-compliant or cannot take the medications because of the side effect profile. Up to 10 million people might have completely resistant hypertension in which they do not reach target levels no matter what the medication regimen. The morbidities associated with uncontrolled hypertension are profound, including stroke, heart attack, kidney failure, peripheral arterial disease, etc. A convenient and straightforward minimally invasive procedure to treat hypertension would be a very welcome advance in the treatment of this disease.

Congestive Heart Failure ("CHF") is a condition which occurs when the heart becomes damaged and blood flow is reduced to the organs of the body. If blood flow decreases sufficiently, kidney function becomes altered, which results in fluid retention, abnormal hormone secretions and increased constriction of blood vessels. These results increase the workload of the heart and further decrease the capacity of the heart to pump blood through the kidneys and circulatory system.

It is believed that progressively decreasing perfusion of the kidneys is a principal non-cardiac cause perpetuating the downward spiral of CHF. For example, as the heart struggles to pump blood, the cardiac output is maintained or decreased and the kidneys conserve fluid and electrolytes to maintain the stroke volume of the heart. The resulting increase in pressure further overloads the cardiac muscle such that the cardiac muscle has to work harder to pump against a higher pressure. The already damaged cardiac muscle is then further stressed and damaged by the increased pressure. Moreover, the fluid overload and associated clinical symptoms resulting from these physiologic changes result in additional hospital admissions, poor quality of life, and additional costs to the health care system. In addition to exacerbating heart failure, kidney failure can lead to a downward spiral and further worsening kidney function. For example, in the forward flow heart failure described above, (systolic heart failure) the kidney becomes ischemic. In backward heart failure (diastolic heart failure), the kidneys become congested vis-à-vis renal vein hypertension. Therefore, the kidney can contribute to its own worsening failure.

The functions of the kidneys can be summarized under three broad categories: filtering blood and excreting waste products generated by the body's metabolism; regulating salt, water, electrolyte and acid-base balance; and secreting hormones to maintain vital organ blood flow. Without properly functioning kidneys, a patient will suffer water retention, reduced urine flow and an accumulation of waste toxins in the blood and body. These conditions result from reduced renal function or renal failure (kidney failure) and are believed to increase the workload of the heart. In a CHF patient, renal failure will cause the heart to further deteriorate as fluids are retained and blood toxins accumulate due to the poorly functioning kidneys. The resulting hypertension also has dramatic influence on the progression of cerebrovascular disease and stroke.

The autonomic nervous system is a network of nerves which affect almost every organ and physiologic system to a variable degree. Generally, the system is composed of sympathetic and parasympathetic nerves. For example, the sympathetic nerves to the kidney traverse the sympathetic chain along the spine and synapse within the ganglia of the chain or within the celiac ganglia, then proceeding to innervate the kidney via post-ganglionic fibers inside the "renal nerves." Within the renal nerves, which travel along the renal hila (artery and to some extent the vein), are the post-ganglionic sympathetic nerves and the afferent nerves from the kidney. The afferent nerves from the kidney travel within the dorsal root (if they are pain fibers) and into the anterior root if they are sensory fibers, then into the spinal cord and ultimately to specialized regions of the brain. The afferent nerves, baroreceptors and chemoreceptors, deliver information from the kidneys back to the sympathetic nervous system via the brain; their ablation or inhibition is at least partially responsible for the improvement seen in blood pressure after renal nerve ablation, or dennervation, or partial disruption. It has also been suggested and partially proven experimentally that the baroreceptor response at the level of the carotid sinus is mediated by the renal artery afferent nerves such that loss of the renal artery afferent nerve response blunts the response of the carotid baroreceptors to changes in arterial blood pressure (American J. Physioogy and Renal Physiology 279:F491-F501, 2000).

It has been established in animal models that the heart failure condition results in abnormally high sympathetic activation of the kidneys. An increase in renal sympathetic nerve activity leads to decreased removal of water and sodium from the body, as well as increased renin secretion which stimulates aldosterone secretion from the adrenal gland. Increased renin secretion can lead to an increase in angiotensin II levels which leads to vasoconstriction of blood vessels supplying the kidneys as well as systemic vasoconstriction, all of which lead to a decrease in renal blood flow and hypertension. Reduction in sympathetic renal nerve activity, e.g., via de-innervation, may reverse these processes and in fact has been shown to in the clinic. Similarly, in obese patients, the sympathetic drive is intrinsically very high and is felt to be one of the causes of hypertension in obese patients.

Recent clinical work has shown that de-innervation of the renal sympathetic chain and other nerves which enter the kidney through the hilum can lead to profound systemic effects in patients (rats, dogs, pig, sheep, humans) with hypertension, heart failure, and other organ system diseases. Such treatment can lead to long term reduction in the need for blood pressure medications and improvements in blood pressure (O'Brien Lancet 2009 373; 9681). The devices used in this trial were highly localized radiofrequency (RF) ablation to ablate the renal artery adventitia with the presumption that the nerves surrounding the renal artery are being inhibited in the heating zone as well. The procedure is performed in essentially a blind fashion in that the exact location of the nerve plexus is not known prior to, during, or after the procedure. In addition, the wall of the renal artery is invariably damaged by the RF probe and patients whose vessels have a great deal of atherosclerosis cannot be treated safely. In addition, depending on the distance of the nerves from the vessel wall, the energy may not consistently lead to ablation or interruption. Finally, the use of internal catheters may not allow for treatment inside the kidney or inside the aorta if more selective. In many cases, it is required to create a spiral along the length and inside the blood vessel to avoid circumferential damage to the vessel.

Cross-sectional imaging can be utilized to visualize the internal anatomy of patients via radiation (CT) or magnetic fields (MRI). Ultrasound can also be utilized to obtain cross-sections of specific regions but only at high frequencies; therefore, ultrasound is typically limited to imaging superficial body regions. CT and MRI are often more amenable to cross sectional imaging because the radiation penetrates well into tissues. In addition, the scale of the body regions is maintained such that the anatomy within the coordinate references remains intact relative to one another; that is, distances between structures can be measured.

With ultrasound, scaling can be more difficult because of unequal penetration as the waves propagate deeper through the tissue. CT scans and MRIs and even ultrasound devices can be utilized to create three dimensional representations and reconstructed cross-sectional images of patients; anatomy can be placed in a coordinate reference frame using a three dimensional representation. Once in the reference frame, energy devices (transducers) can be placed in position and energy emitting devices directed such that specific regions of the body are targeted. Once knowledge of the transducer position is known relative to the position of the target in the patient body, energy can be delivered to the target.

Ultrasound is a cyclically generated sound pressure wave with a frequency greater than the upper limit of human hearing . . . 20 kilohertz (kHz). In medicine, ultrasound is widely utilized because of its ability to penetrate tissues. Reflection of the sound waves reveals a signature of the underlying tissues and as such, ultrasound can be used extensively for diagnostics and potentially therapeutics as well in the medical field. As a therapy, ultrasound has the ability to both penetrate tissues and can be focused to create ablation zones. Because of its simultaneous ability to image, ultrasound can be utilized for precise targeting of lesions inside the body. Ultrasound intensity is measured by the power per $cm^2$ (for example, $W/cm^2$ at the therapeutic target region). Generally, high intensity refers to intensities over 0.1-5 $kW/cm^2$. Low intensity ultrasound encompasses the range up to 0.01-0.10 $kW/cm^2$ from about 1 or 10 Watts per $cm^2$.

Ultrasound can be utilized for its forward propagating waves and resulting reflected waves or where energy deposition in the tissue and either heating or slight disruption of the tissues is desired. For example, rather than relying on reflections for imaging, lower frequency ultrasonic beams (e.g. <1 MHz) can be focused at a depth within tissue, creating a heating zone or a defined region of cavitation in which micro-bubbles are created, cell membranes are opened to admit bioactive molecules, or damage is otherwise created in the tissue. These features of ultrasound generally utilize frequencies in the 0.25 Megahertz (MHz) to 10 MHz range depending on the depth required for effect. Focusing is, or may be, required so that the surface of the tissue is not excessively injured or heated by single beams. In other words, many single beams can be propagated through the tissue at different angles to decrease the energy deposition along any single path yet allow the beams to converge at a focal spot deep within the tissue. In addition, reflected beams from multiple angles may be utilized in order to create a three dimensional representation of the region to be treated in a coordinate space.

It is important when planning an ultrasound therapy that sharp, discontinuous interfaces be avoided. For example, bowel, lung, bone which contain air and/or bone interfaces constitute sharp boundaries with soft tissues. These interfaces make the planning and therapy more difficult. If however, the interfaces can be avoided, then treatment can be greatly simplified versus what has to be done for the brain (e.g. MR-guided HIFU) where complex modeling is required to overcome the very high attenuation of the cranium. Data provided below reveals a discovery through extensive experimentation as to how to achieve this treatment simplicity for treatment of specific structures such as nerves surrounding blood vessels.

Time of flight measurements with ultrasound can be used to range find, or find distances between objects in tissues. Such measurements can be utilized to place objects such as vessels into three dimensional coordinate reference frames so that energy can be utilized to target the tissues. SONAR is the acronym for sound navigation and ranging and is a method of acoustic localization. Sound waves are transmitted through a medium and the time for the sound to reflect back to the transmitter is indicative of the position of the object of interest. Doppler signals are generated by a moving object. The change in the forward and reflected wave results in a velocity for the object.

The concept of speckle tracking is one in which the reflections of specific tissues is defined and tracked over time (IEEE Transactions on Ultrasonics, Ferroelectrics, AND Frequency Control, Vol. 57, no. 4, April 2010). With defined points in space, a three dimensional coordinate reference can be created through which energy can be applied to specific and well-defined regions. To track a speckle, an ultrasound image is obtained from a tissue. Light and dark spots are defined in the image, these light and dark spots representing inhomgeneities in the tissues. The inhomegeneities are relatively constant, being essentially properties of the tissue. With relatively constant markers in the tissue, tracking can be accomplished using real time imaging of the markers. With more than one plane of ultrasound, the markers can be related in three dimensions relative to the ultrasound transducer and a therapeutic energy delivered to a defined position within the three dimensional field.

At the time one or more of these imaging modalities is utilized to determine the position of the target in three dimensions, then a therapy can be both planned and applied to a specific region within the three dimensional volume.

Lithotripsy was introduced in the early part of the 1980's. Lithotripsy utilizes shockwaves to treat stones in the kidney. The Dornier lithotripsy system was the first system produced for this purpose. The lithotripsy system sends ultrasonic waves through the patient's body to the kidney to selectively heat and vibrate the kidney stones; that is, selectively over the adjacent tissue. At the present time, lithotripsy systems do not utilize direct targeting and imaging of the kidney stone region. A tremendous advance in the technology would be to image the stone region and target the specific region in which the stone resides so as to minimize damage to surrounding structures such as the kidney. In the case of a kidney stone, the kidney is in fact the speckle, allowing for three dimensional targeting and tracking off its image with subsequent application of ultrasound waves to break up the stone. In the embodiments which follow below, many of the techniques and imaging results described can be applied to clinical lithotripsy. For example, imaging of the stone region and tracking of the stone region can lead to an improved targeting system for breaking up kidney stones. Rather than wasting energy on regions which don't contain stones and destroying healthy kidney, energy can be concentrated on the portions of the kidney which contain the stones.

Histotripsy is a term given to a technique in which tissue is essentially vaporized using cavitation rather than heating (transcutaneous non-thermal mechanical tissue fractionation). These mini explosions do not require high temperature and can occur in less than a second. The generated pressure wave is in the range of megapascals (MPa) and even up to or exceeding 100 MPa. To treat small regions of tissue very quickly, this technique can be very effective. The border of the viable and non-viable tissue is typically very sharp and the mechanism of action has been shown to be cellular disruption.

In one embodiment, ultrasound is focused on the region of the renal arteries and/or veins from outside the patient; the ultrasound is delivered from multiple angles to the target, thereby overcoming many of the deficiencies in previous methods and devices put forward to ablate renal sympathetic nerves which surround the renal arteries.

Specifically, one embodiment allows for precise visualization of the ablation zone so that the operator can be confident that the correct region is ablated and that the incorrect region is not ablated. Because some embodiments do not require a puncture in the skin, they are considerably less invasive, which is more palatable and safer from the patient standpoint. Moreover, unusual anatomies and atherosclerotic vessels can be treated using external energy triangulated on the renal arteries to affect the sympathetic and afferent nerves to and from the kidney respectively.

With reference to FIG. 1A, the human renal anatomy includes the kidneys 100 which are supplied with oxygenated blood by the renal arteries 200 and are connected to the heart via the abdominal aorta 300. Deoxygenated blood flows from the kidneys to the heart via the renal veins (not shown) and thence the inferior vena cava (not shown). The renal anatomy includes the cortex, the medulla, and the hilum. Blood is delivered to the cortex where it filters through the glomeruli and is then delivered to the medulla where it is further filtered through a series of reabsorption and filtration steps in the loops of henle and individual nephrons; the ultrafiltrate then percolates to the ureteral collecting system and is delivered to the ureters and bladder for ultimate excretion.

The hila is the region where the major vessels (renal artery and renal vein) and nerves 150 (efferent sympathetic, afferent sensory, and parasympathetic nerves) travel to and from the kidneys. The renal nerves 150 contain post-ganglionic efferent nerves which supply sympathetic innervation to the kidneys. Afferent sensory nerves travel from the kidney to the central nervous system and are postganglionic afferent nerves with nerve bodies in the central nervous system. These nerves deliver sensory information to the central nervous system and are thought to regulate much of the sympathetic outflow from the central nervous system to all organs including the skin, heart, kidneys, brain, etc.

In one method, energy is delivered from outside a patient, through the skin, and to the renal afferent and/or renal efferent nerves. Microwave, light, vibratory (e.g. acoustic), ionizing radiation might be utilized in some or many of the embodiments.

Energy transducers 500 (FIG. 1A) deliver energy transcutaneously to the region of the sympathetic ganglia 520 or the post-ganglionic renal nerves 150 or the nerves leading to the adrenal gland 400. The energy is generated from outside the patient, from multiple directions, and through the skin to the region of the renal nerves 624 which surround the renal artery 620 or the sympathetic ganglion 622 which house the nerves. The energy can be focused or non-focused but in one preferred embodiment, the energy is focused with high intensity focused ultrasound (HIFU) or low intensity focused ultrasound.

Focusing with low intensity focused ultrasound (LIFU) may also occur intentionally as a component of the HIFU (penumbra regions) or unintentionally. The mechanism of nerve inhibition is variable depending on the "low" or "high" of focused ultrasound. Low energy might include energy levels of 25 W/cm$^2$–200 W/cm$^2$. Higher intensity includes energy levels from 200 W/cm$^2$ to 1 MW/cm$^2$. Focusing occurs by delivering energy from at least two different angles through the skin to meet at a focal point where the highest energy intensity and density occurs. At this spot, a therapy is delivered and the therapy can be sub-threshold nerve interruption (partial ablation), ablation (complete interruption) of the nerves, controlled interruption of the nerve conduction apparatus, partial ablation, or targeted drug delivery. The region can be heated to a temperature of less than 60 degrees Celsius for non-ablative therapy or can be heated greater than 60 degrees Celsius for heat based destruction (ablation). To ablate the nerves, even temperatures in the 40 degree Celsius range can be used and if generated for a time period greater than several minutes, will result in ablation. For temperatures at about 50 degrees Celsius, the time might be under one minute. Heating aside, a vibratory effect for a much shorter period of time at temperatures below 60 degrees Celsius can result in partial or complete paralysis or destruction of the nerves. If the temperature is increased beyond 50-60 degrees Celsius, the time required for heating is decreased considerably to affect the nerve via the sole mechanism of heating. In some embodiments, an imaging modality is included as well in the system. The imaging modality can be ultrasound based, MRI based, or CT (X-Ray) based. The imaging modality can be utilized to target the region of ablation and determined the distances to the target.

The delivered energy can be ionizing or non-ionizing energy in some embodiments. Forms of non-ionizing energy can include electromagnetic energy such as a magnetic field, light, an electric field, radiofrequency energy, and light based energy. Forms of ionizing energy include x-ray, proton beam, gamma rays, electron beams, and alpha rays. In some embodiments, the energy modalities are combined. For example, heat ablation of the nerves is performed and then ionizing radiation is delivered to the region to prevent re-growth of the nerves.

Alternatively, ionizing radiation is applied first as an ablation modality and then heat applied afterward in the case of re-growth of the tissue as re-radiation may not be possible (complement or multimodality energy utilization). Ionizing radiation may prevent or inhibit the re-growth of the nervous tissue around the vessel if there is indeed re-growth of the nervous tissue. Therefore, another method of treating the nerves is to first heat the nerves and then apply ionizing radiation to prevent re-growth.

Other techniques such as photodynamic therapy including a photosensitizer and light source to activate the photosensitizer can be utilized as a manner to combine modalities. Most of these photosensitizing agents are also sensitive to ultrasound energy yielding the same photoreactive species as if it were activated by light. A photoreactive or photosensitive agent can be introduced into the target area prior to the apparatus being introduced into the blood vessel; for example, through an intravenous injection, a subcutaneous injection, etc. However, it will be understood that if desired, the apparatus can optionally include a lumen for delivering a photoreactive agent into the target area. The resulting embodiments are likely to be particularly beneficial where uptake of the photoreactive agent into the target tissues is relatively rapid, so that the apparatus does not need to remain in the blood vessel for an extended period of time while the photoreactive agent is distributed into and absorbed by the target tissue.

Light source arrays can include light sources that provide more than one wavelength or waveband of light. Linear light source arrays are particularly useful to treat elongate portions of tissue. Light source arrays can also include reflective elements to enhance the transmission of light in a preferred direction. For example, devices can beneficially include expandable members such as inflatable balloons to occlude blood flow (which can interfere with the transmission of light from the light source to the intended target tissue) and to enable the apparatus to be centered in a blood vessel.

Another preferred embodiment contemplates a transcutaneous PDT method where the photosensitizing agent delivery system comprises a liposome delivery system consisting essentially of the photosensitizing agent. Light sources may be directed at a focus from within a blood vessel to a position outside a blood vessel. Infrared, Red, Blue, Green, and ultraviolet light may be used from within a blood vessel to affect nervous tissue outside the blood vessel. Light emitting diodes may be introduced via catheter to the vein, the artery, the aorta, etc. After introduction of the photoreactive agent (e.g. via intravenous, subcutaneous, transarterial, transvenous injection), the light is applied through the blood vessel wall in a cloud of energy which activates the photoreactive agents.

Yet another embodiment is drawn to a method for transcutaneous ultrasonic therapy of a target lesion in a mammalian subject utilizing a sensitizer agent. In this embodiment, the biochemical compound is activated by ultrasound through the following method:

1) administering to the subject a therapeutically effective amount of an ultrasonic sensitizing agent or a ultrasonic sensitizing agent delivery system or a prodrug, where the ultrasonic sensitizing agent or ultrasonic sensitizing agent delivery system or prodrug selectively binds to the thick or thin neointimas, nerve cells, nerve sheaths, nerve nuclei, arterial plaques, vascular smooth muscle cells and/or the abnormal extracellular matrix of the site to be treated. Nerve components can also be targeted, for example, the nerve sheath, myelin, S-100 protein. This step is followed by irradiating at least a portion of the subject with ultrasonic energy at a frequency that activates the ultrasonic sensitizing agent or if a prodrug, by a prodrug product thereof, where the ultrasonic energy is provided by an ultrasonic energy emitting source. This embodiment further provides, optionally, that the ultrasonic therapy drug is cleared from non-target tissues of the subject prior to irradiation.

A preferred embodiment contemplates a method for transcutaneous ultrasonic therapy of a target tissue, where the target tissue is close to a blood vessel. Other preferred embodiments contemplate that the ultrasonic energy emitting source is external to the patient's intact skin layer or is inserted underneath the patient's intact skin layer, but is external to the blood vessel to be treated. An additional preferred embodiment provides that the ultrasonic sensitizing agent is conjugated to a ligand and more preferably, where the ligand is selected from the group consisting of: a target lesion specific antibody; a target lesion specific peptide and a target lesion specific polymer. Other preferred embodiments contemplate that the ultrasonic sensitizing agent is selected from the group consisting of: indocyanine green (ICG); methylene blue; toluidine blue; aminolevulinic acid (ALA); chlorin compounds; phthalocyanines; porphyrins; purpurins; texaphyrins; and any other agent that absorbs light in a range of 500 nm-1100 nm. A preferred embodiment contemplates that the photosensitizing agent is indocyanine green (ICG).

Other embodiments are drawn to the presently disclosed methods of transcutaneous PDT, where the light source is positioned in proximity to the target tissue of the subject and is selected from the group consisting of: an LED light source; an electroluminesent light source; an incandescent light source; a cold cathode fluorescent light source; organic polymer light source; and inorganic light source. A preferred embodiment includes the use of an LED light source.

Yet other embodiments of the presently disclosed methods are drawn to use of light of a wavelength that is from about 500 nm to about 1100 nm, preferably greater than about 650 nm and more preferably greater than about 700 nm. A preferable embodiment of the present method is drawn to the use of light that results in a single photon absorption mode by the photosensitizing agent.

Additional embodiments include compositions of photosensitizer targeted delivery system comprising: a photosensitizing agent and a ligand that binds a receptor on the target tissue with specificity. Preferably, the photosensitizing agent of the targeted delivery system is conjugated to the ligand that binds a receptor on the target (nerve or adventitial wall of blood vessel) with specificity. More preferably, the ligand comprises an antibody that binds to a receptor. Most preferably, the receptor is an antigen on thick or thin neointimas, intimas, adventitia of arteries, arterial plaques, vascular smooth muscle cells and/or the extracellular matrix of the site to be treated.

A further preferred embodiment contemplates that the photosensitizing agent is selected from the group consisting of: indocyanine green (ICG); methylene blue; toluidine blue; aminolevulinic acid (ALA); chlorin compounds; phthalocyanines; porphyrins; purpurins; texaphyrins; and any other agent that absorbs light in a range of 500 nm-1100 nm.

Other photosensitizers that may be used with embodiments described herein are known in the art, including, photofrin. RTM, synthetic diporphyrins and dichlorins, phthalocyanines with or without metal substituents, chloroaluminum phthalocyanine with or without varying substituents, chloroaluminum sulfonated phthalocyanine, O-substituted tetraphenyl porphyrins, 3,1-meso tetrakis (o-propionamido phenyl) porphyrin, verdins, purpurins, tin and zinc derivatives of octaethylpurpurin, etiopurpurin, hydroporphyrins, bacteriochlorins of the tetra(hydroxyphenyl) porphyrin series, chlorins, chlorin e6, mono-l-aspartyl derivative of chlorin e6, di-l-aspartyl derivative of chlorin e6, tin(IV) chlorin e6, meta-tetrahydroxphenylchlorin, benzoporphyrin derivatives, benzoporphyrin monoacid derivatives, tetracyanoethylene adducts of benzoporphyrin, dimethyl acetylenedicarboxylate adducts of benzoporphyrin, Diels-Adler adducts, monoacid ring "a" derivative of benzoporphyrin, sulfonated aluminum PC, sulfonated AlPc, disulfonated, tetrasulfonated derivative, sulfonated aluminum naphthalocyanines, naphthalocyanines with or without metal substituents and with or without varying substituents, zinc naphthalocyanine, anthracenediones, anthrapyrazoles, aminoanthraquinone, phenoxazine dyes, phenothiazine derivatives, chalcogenapyrylium dyes, cationic selena and tellurapyrylium derivatives, ring-substituted cationic PC, pheophorbide derivative, pheophorbide alpha and ether or ester derivatives, pyropheophorbides and ether or ester derivatives, naturally occurring porphyrins, hematoporphyrin, hematoporphyrin derivatives, hematoporphyrin esters or ethers, protoporphyrin, ALA-induced protoporphyrin IX, endogenous metabolic precursors, 5-aminolevulinic acid benzonaphthoporphyrazines, cationic imminium salts, tetracyclines, lutetium texaphyrin, tin-etiopurpurin, porphycenes, benzophenothiazinium, pentaphyrins, texaphyrins and hexaphyrins, 5-amino levulinic acid, hypericin, pseudohypericin, hypocrellin, terthiophenes, azaporphyrins, azachlorins, rose bengal, phloxine B, erythrosine, iodinated or brominated derivatives of fluorescein, merocyanines, nile blue derivatives, pheophytin and chlorophyll derivatives, bacteriochlorin and bacteriochlorophyll derivatives, porphocyanines, benzochlorins and oxobenzochlorins, sapphyrins, oxasapphyrins, cercosporins and related fungal metabolites and combinations thereof.

Several photosensitizers known in the art are FDA approved and commercially available. In a preferred embodiment, the photosensitizer is a benzoporphyrin derivative ("BPD"), such as BPD-MA, also commercially known as BPD Verteporfin or "BPD" (available from QLT). U.S. Pat. No. 4,883,790 describes BPD compositions. BPD is a second-generation compound, which lacks the prolonged cutaneous phototoxicity of Photofrin® (Levy (1994) Semin Oncol 21: 4-10). BPD has been thoroughly characterized (Richter et al., (1987) JNCI 79:1327-1331), (Aveline et al. (1994) Photochem Photobiol 59:328-35), and it has been found to be a highly potent photosensitizer for PDT.

In a preferred embodiment, the photosensitizer is tin ethyl etiopurpurin, commercially known as purlytin (available from Miravant).

In some embodiments, external neuromodulation is performed in which low energy ultrasound is applied to the nerve region to modulate the nerves. For example, it has been shown in the past that low intensity (e.g. non-thermal) ultrasound can affect nerves at powers which range from 30-500 W/Cm$^2$ whereas HIFU (thermal modulation), which by definition generates heat at a focus point, requires power levels exceeding 1000 W/Cm$^2$. The actual power flux to the region to be ablated is dependent on the environment including surrounding blood flow and other structures. With low intensity ultrasound, the energy does not have to be so strictly focused to the target because it's a non-ablative energy; that is, the vibration or mechanical pressure may be the effector energy and the target may have a different threshold for effect depending on the tissue. However, even low energy ultrasound may require focusing if excessive heat to the skin is a worry or if there are other susceptible structures in the path and only a pinpoint region of therapy is desired. Nonetheless, transducers 500 in FIG. 1a provide the ability to apply a range of different energy and power levels as well as modeling capability to target different regions and predict the response.

In FIG. 1a, and in one embodiment, a renal artery 640 is detected with the assistance of imaging devices 600 such as Doppler ultrasound, infrared imaging, thermal imaging, B-mode ultrasound, MRI, or a CT scan. With an image of the region to be treated, measurements in multiple directions on a series of slices can be performed so as to create a three-dimensional representation of the area of interest. By detecting the position of the renal arteries from more than one angle via Doppler triangulation (for example) or another triangulation technique, a three dimensional positional map can be created and the renal artery can be mapped into a coordinate reference frame. In this respect, given that the renal nerves surround the renal blood vessels in the hilum, locating the direction and lengths of the blood vessels in three dimensional coordinate reference is the predominant component of the procedure to target these sympathetic nerves. Within the three dimensional reference frame, a pattern of energy can be applied to the vicinity of the renal artery from a device well outside the vicinity (and outside of the patient altogether) based on knowledge of the coordinate reference frame.

For example, once the renal artery is placed in the coordinate reference frame with the origin of the energy delivery device, an algorithm is utilized to localize the delivery of focused ultrasound to heat or apply mechanical energy to the adventitia and surrounding regions of the artery which contain sympathetic nerves to the kidney and afferent nerves from the kidney, thereby decreasing the sympathetic stimulus to the kidney and decreasing its afferent signaling back to the autonomic nervous system; affecting these targets will modulate the propensity toward hypertension which would otherwise occur. The ultrasonic energy delivery can be modeled mathematically by predicting the acoustic wave dissipation using the distances and measurements taken with the imaging modalities of the tissues and path lengths. Furthermore, a system such as acoustic time of flight can be utilized to quantitatively determine the distance from a position on the therapeutic transducer to the region of the blood vessel to the kidney. Such a system allows for detection of a distance using an ultrasound pulse. The distance obtained as such is then utilized for the therapeutic ultrasound treatment because the tissues and structures which are interrogated are the same ones through which the therapeutic ultrasound will travel, thereby allowing essentially auto-calibration of the therapeutic ultrasound pulse.

For example, FIG. 1D depicts a system with an integral catheter 652 and one or more transducers 654 on the catheter. Electrical impulses are sent from a generator 653 to the catheter 652 and to the transducers 654 which may be piezoelectric crystals. Detectors 650 detect the distance 656 from the piezoelectric transducers as well as the 3-dimensional orientation and exact position of the transducers 654. With positional information in three dimensional space, focused ultrasound transducer 662 can be directed toward the target under the direction of motion controllers/transducer(s) 660. In some embodiments, a single transducer (internal) is detected. In other embodiments, multiple transducers 654 are detected. In the embodiment in which multiple transducers are utilized, more detail around the three dimensional position and orientation of the vessel is available allowing for a redundant approach to position detection. In either case, by pulling back the catheter within the blood vessel while applying electrical signals to the piezoelectric crystal so that they may be detected outside the patient, the three dimensional anatomy of the vessel can be mapped and determined quantitatively so that treatment can be applied at an exact location along the blood vessel.

In this method, a guidewire is placed at the site of treatment and then moved to different positions close to the treatment site (e.g. within a blood vessel). During the movement along the blood vessel, the detectors outside the patient are mapping the movement and the region of treatment. The map of the blood vessel (for example) is then used to perform the treatment in the exact region planned with a high degree of accuracy due to the mapping of the region. Signal generator 653 may create signals with frequencies ranging from 0.5 MHz up to 3 MHz (or any frequency value in this range), or even a wider range of frequencies to ensure detection of the orientation.

In one embodiment of an algorithm, the Doppler signal from the artery is identified from at least two different directions and the direction of the artery is reconstructed in three dimensional space. In this example, acoustic time of flight may be utilized via the Doppler ultrasound of the flow signal, or via a piezoelectric transducer (internal) and receiver (external) 650 set up. With two points in space, a line is created and with knowledge of the thickness of the vessel, a tube, or cylinder, can be created to represent the blood vessel as a virtual model. The tube is represented in three dimensional space over time and its coordinates are known relative to the therapeutic transducers outside of the skin of the patient. Therapeutic energy can be applied from more than one direction as well and can focus on the cylinder (blood anterior vessel wall, central axis, or posterior wall). With a third point, the position of the target can be precisely localized in the 3D space and targeted with a HIFU transducer 660. Position detection algorithm 666 can be utilized to compare the baseline position of the catheter to a position after a period of time so as to detect respiratory and patient movement. In one embodiment, the therapeutic HIFU array 662 is also used to send a signal out for imaging (diagnostic pulse). For example, any number of elements can be activated from the HIFU array to deposit energy into the tissue. Such energy deposition can be advantageous because it is by definition focused on the region 664 that will ultimately be treated. In this respect, the exact region of treatment can be interrogated with the focused ultrasound pulse from the therapeutic array 662. Parameters in addition to imagining include Doppler flow, tissue elastography, stress strain curves, ultrasound spectroscopy, and targeting of therapeutics to the region. The therapeutic array 662 can be utilized as a receiver for the diagnostic signal or a separate detector can be utilized as the receiver. In some embodiments, the catheter may be adapted to deliver pharmaceuticals to the region as well as to assist in beam focusing. A Doppler targeting algorithm may complement the catheter 652 based targeting. Power supply is configured to apply the proper power to the HIFU transducer to treat a blood vessel deep within a patient. For example, the power input into the HIFU transducer might be 150 W, 200 W, 500 W 750 W, or 1000 W to achieve output suitable for deep treatment in a patient. Pulsing frequency may be as fast as 10 Hz or even 1 KHz. The piezoelectric signal may be detected from more than one direction outside the body of the patient. One or more modes of ultrasound may be utilized and detected from different directions outside the skin of the patient. Very large impulses may be generated in the first few microseconds of the piezoelectric impulse delivery. For example, in some embodiments, 8 W/Cm2 may be generated for a few microseconds and then the voltage may be quickly decreased to zero until the next cycle (<1% duty cycle).

Focused energy (e.g. ultrasound) can be applied to the center of the vessel (within the flow), on the posterior wall of the vessel, in between (e.g. when there is a back to back artery and vein next to one another) the artery vessel and a venous vessel, etc. Mover 660 directs the ultrasound focus based on position 666 of the catheter 652 relative to the ultrasound array 660. In some embodiments, a Doppler signal 670 is used with/combined in the system.

Imaging 600 (FIG. 1C) of the sympathetic nerves or the sympathetic region (the target) is also utilized so as to assess the direction and orientation of the transducers relative to the target 620; the target is an internal fiducial, which in one embodiment is the kidney 610 and associated renal artery 620 because they can be localized via their blood flow, a model then produced around it, and then they both can be used as a target for the energy. Continuous feedback of the position of the transducers 500, 510 relative to the target 620 is provided by the imaging system, wherein the position may be in the coordinate space of the imaging system, for example. The imaging may be a cross-sectional imaging technology such as CT or MRI or it may be an ultrasound imaging technology which yields faster real time imaging. In some embodiments, the imaging may be a combination of technologies such as the fusion of MRI/CT and ultrasound. The imaging system can detect the position of the target in real time at frequencies ranging from 1 Hz to thousands and tens of thousands of images per second.

In the example of fusion, cross-sectional imaging (e.g. MRI/CT) is utilized to place the body of the patient in a three dimensional coordinate frame and then ultrasound is linked to the three dimensional reference frame and utilized to track the patient's body in real time under the ultrasound linked to the cross-sectional imaging. The lack of resolution provided by the ultrasound is made up for by the cross-sectional imaging since only a few consistent anatomic landmarks are required for an ultrasound image to be linked to the MRI image. As the body moves under the ultrasound, the progressively new ultrasound images are linked to the MRI images and therefore MRI "movement" can be seen at a frequency not otherwise available to an MRI series.

In one embodiment, ultrasound is the energy used to inhibit nerve conduction in the sympathetic nerves. In one embodiment, focused ultrasound (HIFU) from outside the body through the skin is the energy used to inhibit sympathetic stimulation of the kidney by delivering waves from a position external to the body of a patient and focusing the waves on the sympathetic nerves on the inside of the patient and which surround the renal artery of the patient. MRI may be used to visualize the region of treatment either before, during, or after application of the ultrasound. MRI may also be used to heat a targeting catheter in the region of the sympathetic nerves. For example, a ferromagnetic element on the tip of a catheter will absorb energy in the presence of a magnetic field and heat itself, thereby enabling heat to be applied to the nerves surrounding the blood vessels leading to the kidney.

Figure 1E:
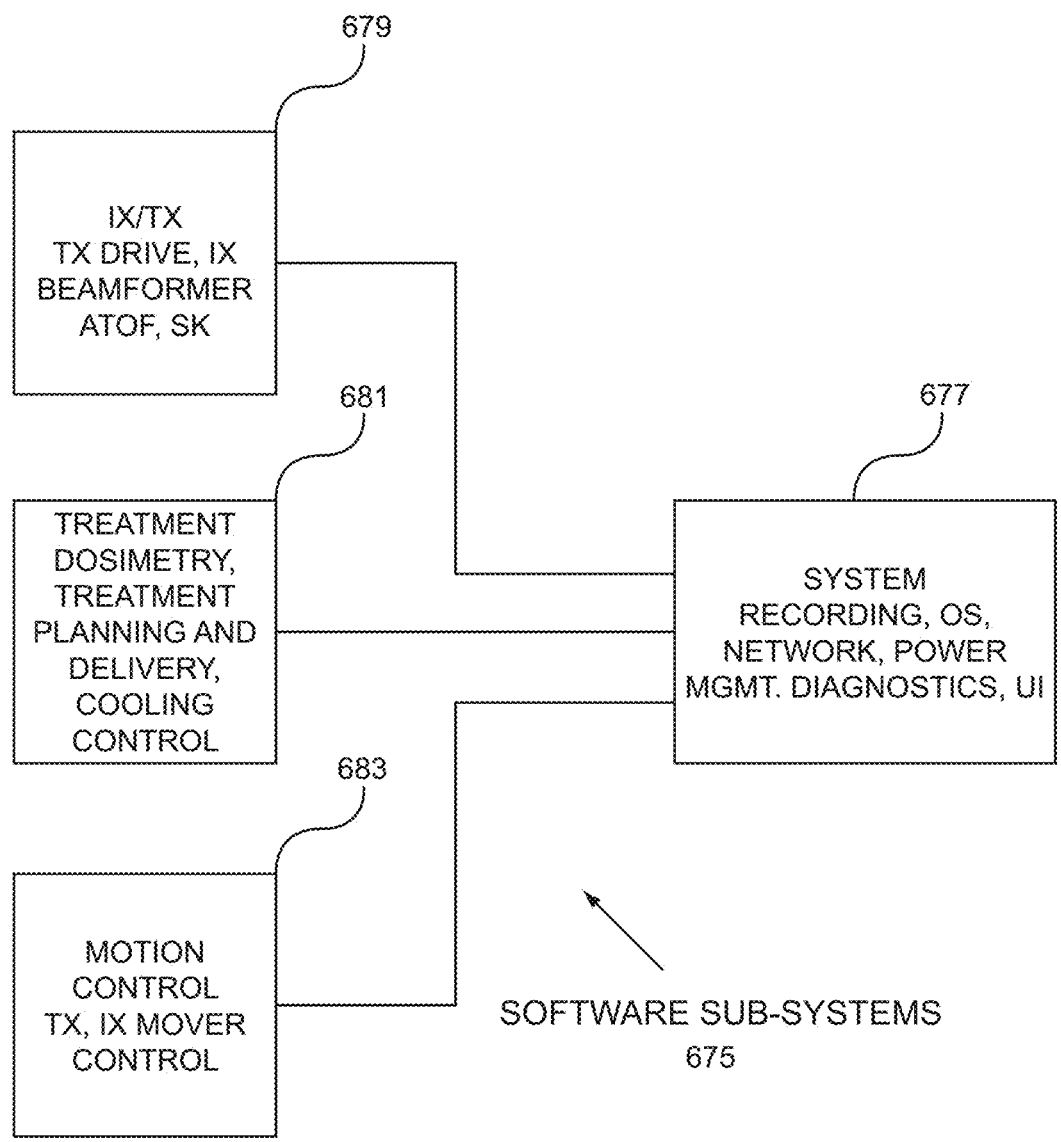
FIG. 1E depicts a box diagram of an integrated system schematic.

FIG. 1E depicts an overview of the software subsystems 675 to deliver a safe treatment to a patient. An executive control system 677 contains an operating system, a recording of the system functions, a network connection, and other diagnostic equipment. Communication with treatment dosimetry plan 681 may be accomplished via modeling and previously obtained empirical data. The software within the dosimetry plan allows for further communication with the acoustic time of flight transducer (ATOF) 679 and the motion controller for the diagnostic and therapeutic arrays. Target localization based on acoustic time of flight (ATOF) can provide accurate and robust position sensing of target location relative to the therapeutic ultrasound transducer. Direct X, Y and Z (i.e. three-dimensional) coordinate locations of the target can be provided without the need for image interpretation. Three-dimensional targeting information facilitates the use of an explicit user interface to guide operator actions. ATOF is less sensitive to variations in patient anatomy as compared to imaging techniques. ATOF can be accomplished with a relatively simple and inexpensive system compared to the complex imaging systems used by alternate techniques. In some embodiments, continuous tracking of the target in the presence of movement between the target and the external transducer may be provided. In some embodiments, ATOF allows use of system architectures that utilize a larger fraction of the patient contact area to generate therapeutic power (as contrasted with imaging based alternatives which occupy some space within the therapeutic transducer for diagnostic power)—thus reducing the power density applied to the patient's skin.

Figure 3A:
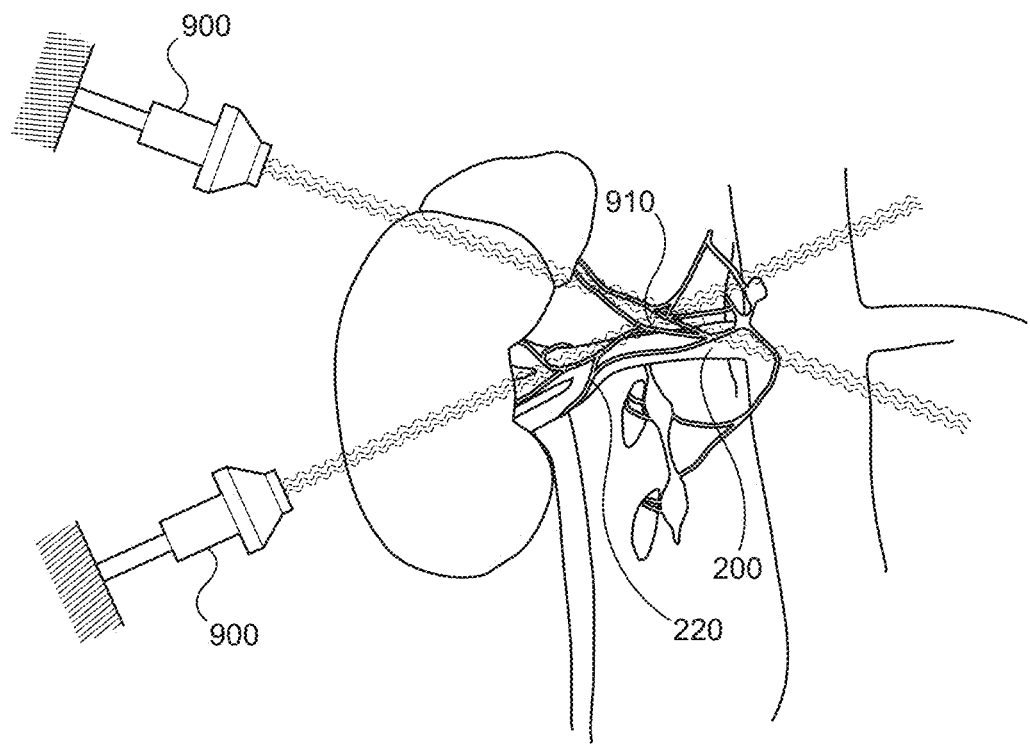
FIG. 3A depicts focusing of energy waves on the renal nerves.
Figure 3B:
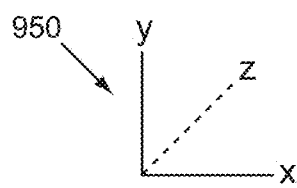
FIG. 3B depicts a coordinate reference frame for the treatment.

As is depicted in FIG. 3*a-b*, transducers 900 can emit ultrasound energy from a position outside the patient to the region of the renal sympathetic nerves at the renal pedicle 200. As shown in FIG. 1*a*, an image of the renal artery 620 using an ultrasound, MRI, or CT scan can be utilized to determine the position of the kidney 610 and the renal artery 620 target. Doppler ultrasound can be used to determine the location and direction of a Doppler signal from an artery and place the vessel into a three dimensional reference frame 950, thereby enabling the arteries 200 and hence the sympathetic nerves 220 (FIG. 3*a*) around the artery to be much more visible so as to process the images and then utilize focused external energy to pinpoint the location and therapy of the sympathetic nerves. In this embodiment, ultrasound is likely the most appropriate imaging modality. Ultrasound can refer to simple single dimensional pulse echos, or devices which scan a region and integrate pulse echos into an image (termed B-mode).

FIG. 1A also depicts the delivery of focused energy to the sympathetic nerve trunks and ganglia 622 which run along the vertebral column and aorta 300; the renal artery efferent nerves travel in these trunks and synapse to ganglia within the trunks. In another embodiment, ablation of the dorsal and ventral roots at the level of the ganglia or dorsal root nerves at T9-111 (through which the afferent renal nerves travel) would produce the same or similar effect to ablation at the level of the renal arteries.

In another embodiment, FIG. 1B illustrates the application of ionizing energy to the region of the sympathetic nerves on the renal arteries 620 and/or renal veins. In general, energy levels of greater than 20 Gy (Gray) are required for linear accelerators or low energy x-ray machines to ablate nervous tissue using ionizing energy; however, lower energy is required to stun, inhibit nervous tissue, or prevent re-growth of nervous tissue; in some embodiment, ionizing energy levels as low as 2-5 Gy or 5-10 Gy or 10-15 Gy are delivered in a single or fractionated doses. Ionizing energy can be applied using an orthovoltage X-ray generator, a linear accelerator, brachytherapy, and/or an intravascular X-ray radiator which delivers electronic brachytherapy. X-rays such as from a linear accelerator or from an orthovoltage x-ray generator can be delivered through the skin from multiple directions to target nerves surrounding a blood vessel. In one example, the blood vessel might be a renal artery or renal vein with nerves running around it. By targeting the blood vessel, ionizing energy can be applied to the nerves surrounding the blood vessel. Ultrasound, Doppler imaging, angiograms, fluoroscopy, CT scans, thermography imaging, and MRIs can be utilized to direct the ionizing energy.

Combinations of ionizing energy and other forms of energy can be utilized in this embodiment as well so as to prevent re-growth of the nervous tissue. For example, a combination of heat and/or vibration and/or cavitation and/or ionizing radiation might be utilized to prevent re-growth of nervous tissue after the partial or full ablation of the nervous tissue surrounding the renal artery. Combinations of pharmaceutical agents can be combined with one another or with device and physical means to prevent or initially inhibit nerve tissue and/or regrowth of nerve tissue.

Figure 2:
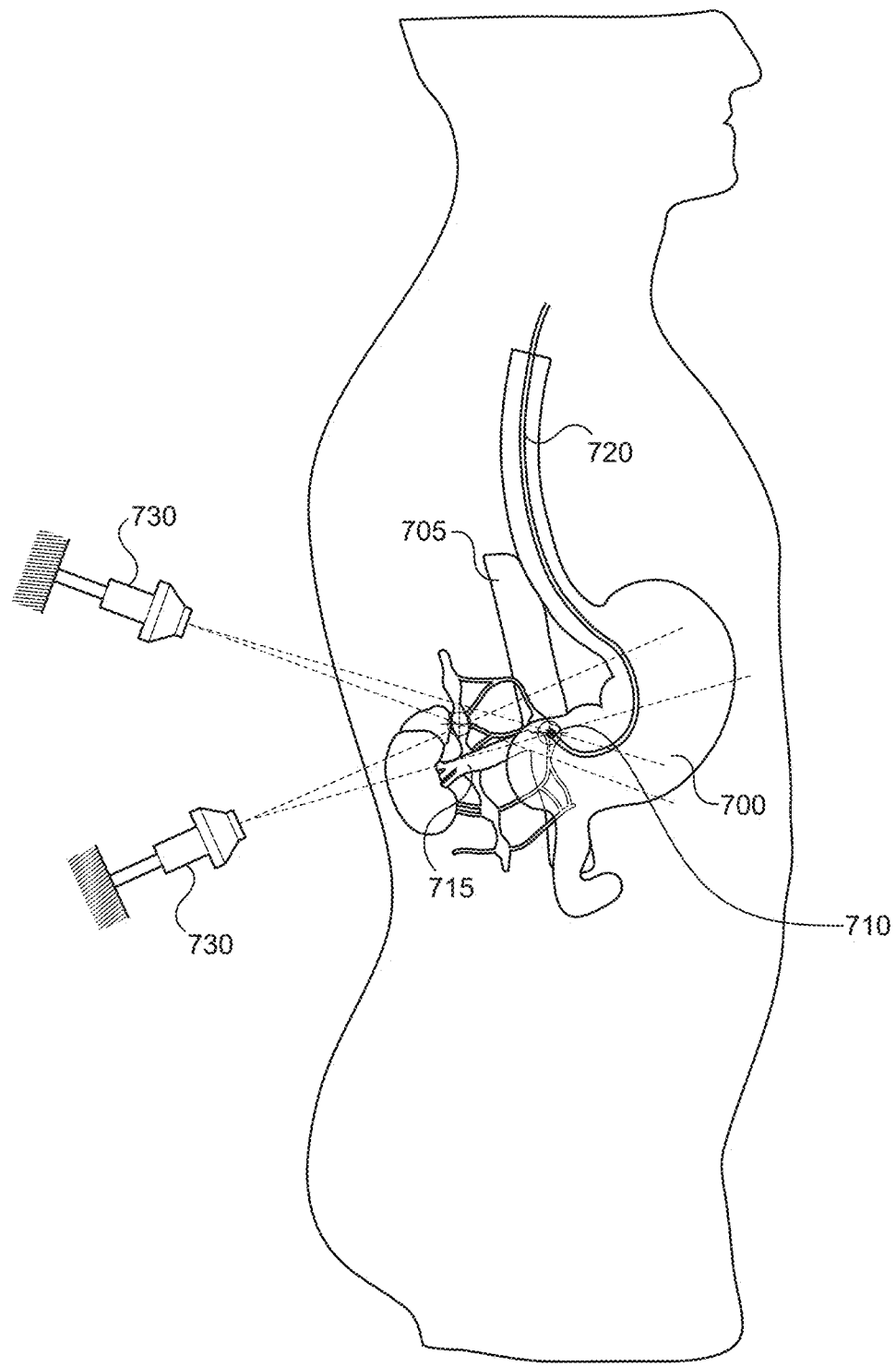
FIG. 2 depicts targeting and/or therapeutic ultrasound delivered through the stomach to the autonomic nervous system posterior to the stomach.

FIG. 2 illustrates the renal anatomy and surrounding anatomy with greater detail in that organs such as the stomach 700 are shown in its anatomic position overlying the abdominal aorta 705 and renal arteries 715. In this embodiment, energy is delivered through the stomach to reach an area behind the stomach. In this embodiment, the stomach is utilized as a conduit to access the celiac ganglion 710, a region which would otherwise be difficult to reach. The aorta 705 is shown underneath the stomach and the celiac ganglion 710 is depicted surrounding the superior mesenteric artery and aorta. A transorally placed tube 720 is placed through the esophagus and into the stomach. The tube overlies the celiac ganglion when placed in the stomach and can therefore be used to deliver sympatholytic devices or pharmaceuticals which inhibit or stimulate the autonomic celiac ganglia behind the stomach; these therapies would be delivered via transabdominal ultrasound or fluoroscopic guidance (for imaging) through the stomach. Similar therapies can be delivered to the inferior mesenteric ganglion, renal nerves, or sympathetic nerves traveling along the aorta through the stomach or other portion of the gastrointestinal tract. The energy delivery transducers 730 are depicted external to the patient and can be utilized to augment the therapy being delivered through the stomach to the celiac ganglion. Alternatively, the energy delivery transducers can be utilized for imaging the region of therapy. For example, an ultrasound transducer can be utilized to image the aorta and celiac ganglion and subsequently to apply ultrasound energy to the region to inhibit the nerves in the region. In some cases, ablation is utilized and in other cases, vibration is utilized to inhibit the nerves from functioning.

In one embodiment, energy is applied to the region of the celiac ganglion from a region outside the patient. In this embodiment, fluid is placed into the gastrointestinal system, such as for example, in the stomach or small intestine. Ultrasound can then be transmitted through the gastrointestinal organs to the ganglia of interest behind the stomach.

Temporary neurostimulators can also be placed through the tube placed into the esophagus and into the stomach, such as, for example, in an ICU setting where temporary blockage of the autonomic ganglia may be required. Temporary neurostimulators can be used to over pace the celiac ganglion nerve fibers and inhibit their function as a nerve synapse. Inhibition of the celiac ganglion may achieve a similar function as ablation or modulation of the sympathetic nerves around the renal arteries. That is, the decrease in the sympathetic activity to the kidneys (now obtained with a more proximal inhibition) leads to the lowering of blood pressure in the patient by decreasing the degree of sympathetic outflow from the sympathetic nerve terminals. In the celiac ganglia, the blood pressure lowering effect is more profound given that the celiac ganglia are pre-ganglionic and have more nerve fibers to a greater number of regions than each renal nerve. The effect is also likely more permanent than the effect on the post-ganglionic nerve fibers.

FIG. 3A illustrates the renal anatomy more specifically in that the renal nerves 220 extending longitudinally along the renal artery 200, are located generally within, or just outside the adventitia, of the outer portion of the artery. Arteries are typically composed of three layers: the first is the intimal, the second is the media, and the third is the adventitia. The outer layer, the adventitia, is a fibrous tissue which contains blood vessels and nerves. The renal nerves are generally postganglionic sympathetic nerves although there are some ganglia which exist distal to the takeoff from the aorta such that some of the nerve fibers along the renal artery are in fact pre-ganglionic. By the time the fibers reach the kidney, the majority of the fibers are post-ganglionic. The afferent nerves on the other hand leave the kidney and are postganglionic up to the level of the brain. These fibers do not re-grow as quickly as the efferent fibers, if at all.

Energy generators 900 deliver energy to the renal nerves accompanying the renal artery, depositing energy from multiple directions to target inhibition of the renal nerve complex. The energy generators can deliver ultrasound energy, ionizing radiation, light (photon) therapy, or microwave energy to the region. The energy can be non-focused in the case where a pharmaceutical agent is targeted to the region to be ablated or modulated. Preferably, however, the energy is focused, being applied from multiple angles from outside the body of the patient to reach the region of interest (e.g. sympathetic nerves surrounding blood vessels). The energy transducers 900 are placed in an X-Y-Z coordinate reference frame 950, as are the organs such as the kidneys. The x-y-z coordinate frame is a real space coordinate frame. For example, real space means that the coordinate reference is identifiable in the physical world; like a GPS (global positioning system), with the physical coordinates, a physical object can be located. Once in the x-y-z coordinate reference frame, cross-sectional imaging using MRI, CT scan, and/or ultrasound is utilized to couple the internal anatomy to the energy transducers. These same transducers may be utilized for the determination of the reference point as well as the therapy. The transducers 900 in this embodiment are focused on the region of the renal nerves at the level of the renal blood vessels, the arteries and veins 200. The focus of the beams can be inside the artery, inside the vein, on the adventitia of the artery or adventitia of the vein.

When applying ultrasonic energy across the skin to the renal artery region, energy densities of potentially over 1 $MW/cm^2$ might be required at region of interest in the adventitia of the blood vessel. Typically, however, power densities of 100 $W/cm^2$ to 3 $kW/cm^2$ would be expected to create the heating required to inhibit these nerves (see Foley et. al. Image-Guided HIFU Neurolysis of Peripheral Nerves To Treat Spasticity And Pain; Ultrasound in Med & Biol. Vol 30 (9) p 1199-1207). The energy may be pulsed across the skin in an unfocused manner; however, for application of heat, the transducers must be focused otherwise the skin and underlying tissues will receive too much heat. Under imaging with MRI, temperature can be measured with the MRI image. When low energy ultrasound is applied to the region, energy (power) densities in the range of 50 $mW/cm^2$ to 500 $mW/cm^2$ may be applied. Low energy ultrasound may be enough to stun or partially inhibit the renal nerves particularly when pulsed and depending on the desired clinical result. High intensity ultrasound applied to the region with only a few degrees of temperature rise may have the same effect and this energy range may be in the 0.1 kW/cm2 to the 500 kW/cm2 range. A train of pulses also might be utilized to augment the effect on nervous tissue. For example, a train of 100 short pulses, each less than a second and applying energy densities of 1 $W/cm^2$ to 500 $W/cm^2$. In some of the embodiments, cooling may be applied to the skin if the temperature rise is deemed too large to be acceptable. In some embodiments, infrared thermography is utilized to determine the temperature of the skin and subcutaneous tissues, or if detected from deeper within, from the kidneys and even renal blood vessels themselves. Alternatively, the ultrasound transducers can be pulsed or can be alternated with another set of transducers to effectively spread the heat across the surface of the skin. In some embodiments, the energy is delivered in a pulsed fashion to further decrease the risk to the intervening tissues between the target and the transducer. The pulses can be as close as millisecond, as described, or as long as hours, days or years.

In one method of altering the physiologic process of renal sympathetic excitation, the region around the renal arteries is imaged using CT scan, MRI, thermography, infrared imaging, optical coherence tomography (OCT), photoacoustic imaging, pet imaging, SPECT imaging, or ultrasound, and the images are placed into a three dimensional coordinate reference frame 950. The coordinate reference frame 950 refers to the knowledge of the relationship between anatomic structures, both two dimensional and three dimensional, the structures placed into a physical coordinate reference. Imaging devices determine the coordinate frame. Once the coordinate frame is established, the imaging and therapy transducers 900 can be coupled such that the information from the imaging system is utilized by the therapeutic transducers to position the energy. Blood vessels may provide a useful reference frame for deposition of energy as they have a unique imaging signature. An ultrasound pulse echo can provide a Doppler shift signature to identify the blood vessel from the surrounding tissue. In an MRI, CT scan, and even an ultrasound exam, intravenous contrast agents can be utilized to identify flow patterns useful to determine a coordinate reference for energy deposition. Energy transducers 900 which can deliver ultrasound, light, radiation, ionizing radiation, or microwave energy are placed in the same three-dimensional reference frame as the renal arteries, at which time a processor (e.g. using an algorithm) can determine how to direct the transducers to deliver energy to the region 220 of the nerves 910. The algorithm consists of a targeting feature (planning feature) which allows for prediction of the position and energy deposition of the energy leaving the transducers 900.

Once the three dimensional coordinate reference frames 950 are linked or coupled, the planning and prediction algorithm can be used to precisely position the energy beams at a target in the body.

The original imaging modality can be utilized to locate the renal sympathetic region, and/or can be used to track the motion of the region during treatment. For example, the imaging technology used at time zero is taken as the baseline scan and subsequent scans at time t1 are compared to the baseline scan, t0 (start). The frequency of updates can range from a single scan every few seconds to many scans per second. With ultrasound as the imaging technology, the location might be updated at a frame rate greater than 50 Hz and up to several hundred Hz or thousand Hz. With MRI as the imaging modality, the imaging refresh rate might be closer to 30 Hz. In other embodiments, internally placed fiducials transmit positional information at a high frequency and this information is utilized to fuse the target with an initial external imaging apparatus. Internal fiducials might include one or more imageable elements including doppler signals, regions of blood vessels, ribs, kidneys, and blood vessels and organs other than the target (e.g. vena cava, adrenal gland, ureter). These fiducials can be used to track the region being treated and/or to triangulate to the region to be treated. The fiducials can be placed externally to an internal position or might be intrinsic fiducials such as anatomic features and/or imageable features.

Figure 3C:
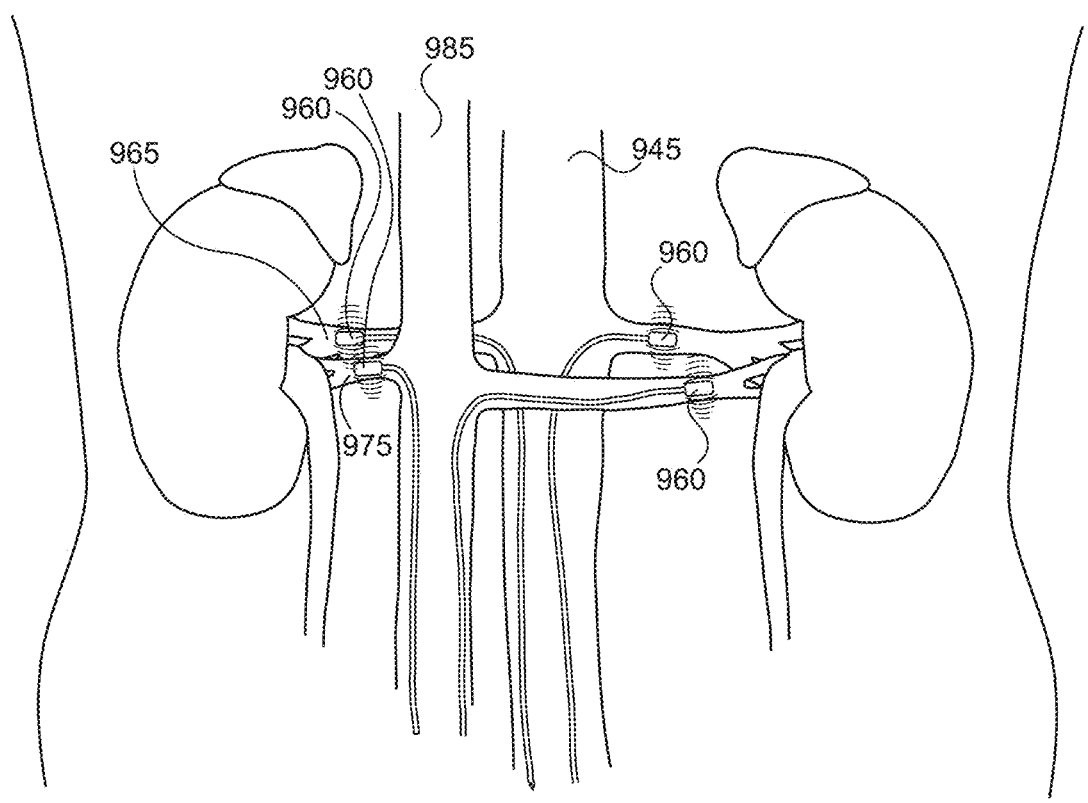
FIG. 3C depicts targeting catheters or energy delivery catheters placed in any of the renal vessels.

In some embodiments (FIG. 3C), a temporary fiducial 960 is placed in the region, such as in the artery 965, renal vein 975, aorta 945, and/or vena cava 985; such a fiducial is easily imageable from outside the patient. In one embodiment, the temporary fiducial may enhance imaging such as a balloon fillable with gas or bubbles. In another embodiment, the temporary fiducial may be a material imageable via MRI or ultrasound.

Figure 3D:
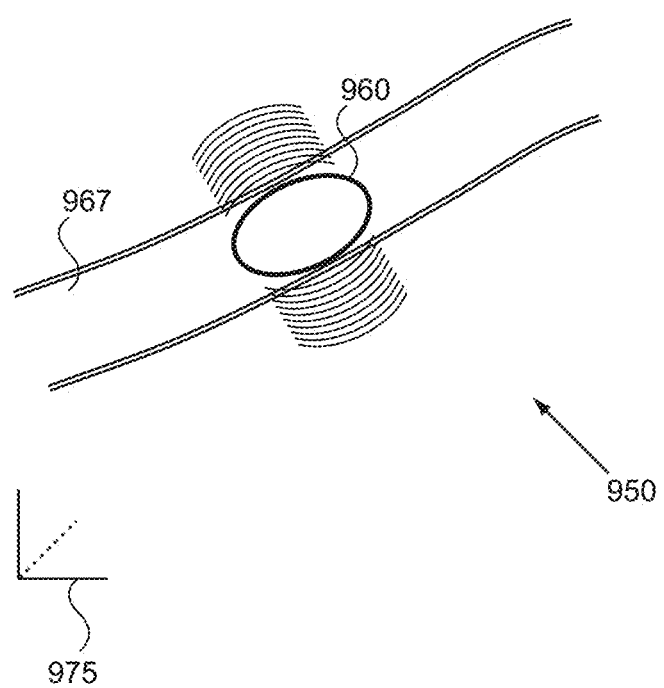
FIG. 3D depicts an image detection system of a blood vessel with a temporary fiducial placed inside the blood vessel, wherein the fiducial provides positional information with respect to a reference frame.

FIG. 3D depicts an imageable transducer 960 in a blood vessel 967 within a coordinate reference 975 on a monitor system 950. Alternatively, the temporary fiducial 960 is a transducer which further improves the ability to image and track the region to deliver therapy. The transducer may be a piezoelectric crystal which is stimulated to emit energy which can be detected by one or more detectors to determine a three dimensional position. The transducer may release radiofrequency energy which can be detected by one or more detectors to pinpoint a three dimensional position. The transducer may emit an audible sound or an optical signal. The temporary fiducial might be a mechanical, optical, electromechanical, a radiofrequency radiotransmitter, an ultrasound generator, a global positioning tracking (GPS) device, or ultrasound responsive technology. Similar devices that may be used to assist in performing the treatment described herein might be found in U.S. Pat. Nos. 6,656,131 and 7,470,241 which are incorporated by reference herein.

Internal reflections (e.g. speckles) can be tracked as well. These speckles are inherent characteristics of tissue as imaged with ultrasound. They can be tracked and incorporated into treatment planning algorithm and then linked to the therapeutic transducers. In some embodiments, cavitation is detected, in which vapor bubbles are detected to determine temperature or degree of heating.

In some embodiments, a test dose of energy can be applied to the renal sympathetic region and then a test performed to determine if an effect was created. For example, a small amount of heat or vibratory energy can be delivered to the region of the sympathetic nerves and then a test of sympathetic activity such as microneurography (detection of sympathetic nerve activity around muscles and nerves which correlate with the beating heart) can be performed. Past research and current clinical data have shown that the sympathetic nerves to the peripheral muscles are affected by interruption of the renal afferent nerves. The degree of temperature rise with the small degree of heat can be determined through the use of MRI thermometry or an ultrasound technique and the temperature rise can be determined or limited to an amount which is reversible.

In another embodiment, a stimulus is applied to a region such as the skin and an output downstream from the skin is detected. For example, a vibratory energy might be applied to the skin and a sympathetic outflow such as the heart rate might be detected. In another embodiment, heat or cold might be applied to the skin and heart rate, blood pressure; vasoconstriction might be detected as an output.

Alternatively, ultrasonic imaging can be utilized to determine the approximate temperature rise of the tissue region. The speed of ultrasonic waves is dependent on temperature and therefore the relative speed of the ultrasound transmission from a region being heated will depend on the temperature, therefore providing measureable variables to monitor. In some embodiments, microbubbles are utilized to determine the rise in temperature. Microbubbles expand and then degrade when exposed to increasing temperature so that they can then predict the temperature of the region being heated. The microbubbles can be injected into the vein or artery of a patient or the microbubbles can be injected locally into the aorta, renal artery, renal vein, etc. A technique called ultrasound elastography can also be utilized. In this embodiment, the elastic properties of tissue are dependent on temperature and therefore the elastography may be utilized to track features of temperature change. The microbubbles can also be utilized to augment the therapeutic effect of the region being targeted. For example, the microbubbles can be utilized to release a pharmaceutical when the ultrasound reaches them. Alternatively, the microbubble structure can be utilized to enhance imaging of the treatment region to improve targeting or tracking of the treatment region.

In some embodiments, only the temperature determination is utilized. That is, the temperature sensing embodiments and algorithms described herein are utilized with any procedure in which heating is being performed. For example, in a case where heating of the renal nerve region is performed using radiofrequency ablation through the renal artery, imaging of the region from a position external to the patient can be performed while the renal artery region is being heated via radiofrequency methods. Imaging can be accomplished utilizing MRI, ultrasound, infrared, or OCT methods. Imaging can be utilized to determine temperature or an effect of temperature on the regions surrounding the blood vessel and/or nerves. For example, a radiofrequency catheter can be utilized to apply energy to the wall of a blood vessel and then ultrasound imaging can be applied during or after the treatment with the radiofrequency catheter, at which point temperature, coagulation status, and nerve damage can be determined around the blood vessel with the nerve. In addition or alternatively, MRI can be utilized to determine temperature or map effect on the nerve structures surrounding the blood vessels.

Such imaging of the treatment can assist in the directing precise treatment to the region around the blood vessel, and allow for safe application of heat to the blood vessel wall. For example, in one embodiment, energy is applied to the wall of the blood vessel and the heat is detected during the treatment. The temperature in such an embodiment can be limited with a specified level (e.g. 55 degrees, 60 degrees, 65 degrees) for a specific amount of time (e.g. 30 seconds, 60 seconds, 120 seconds). MRI or ultrasound or both can be used for this treatment. In this method the localization of the heat about the wall of the blood vessel can be determined.

In another embodiment, a test may be performed on the baroreceptor complex at the region of the carotid artery bifurcation. After the test dose of energy is applied to the renal artery complex, pressure can be applied to the carotid artery complex; typically, with an intact baroreceptor complex, the systemic blood pressure would decrease after application of pressure to the carotid artery. However, with renal afferent nerves which have been inhibited, the baroreceptors will not be sensitive to changes in blood pressure and therefore the efficacy of the application of the energy to the renal nerves can be determined. Other tests include attaining indices of autonomic function such as microneurography, autonomic function variability, etc.

In another embodiment, stimulation of the baroreceptor complex is accomplished non-invasively via ultrasound pulses applied externally to the region of the carotid body. The ultrasound pulses are sufficient to stimulate the sinus to affect a blood pressure change, a change which will be affected when an afferent nerve such as the renal afferents have been altered.

Figure 3E:
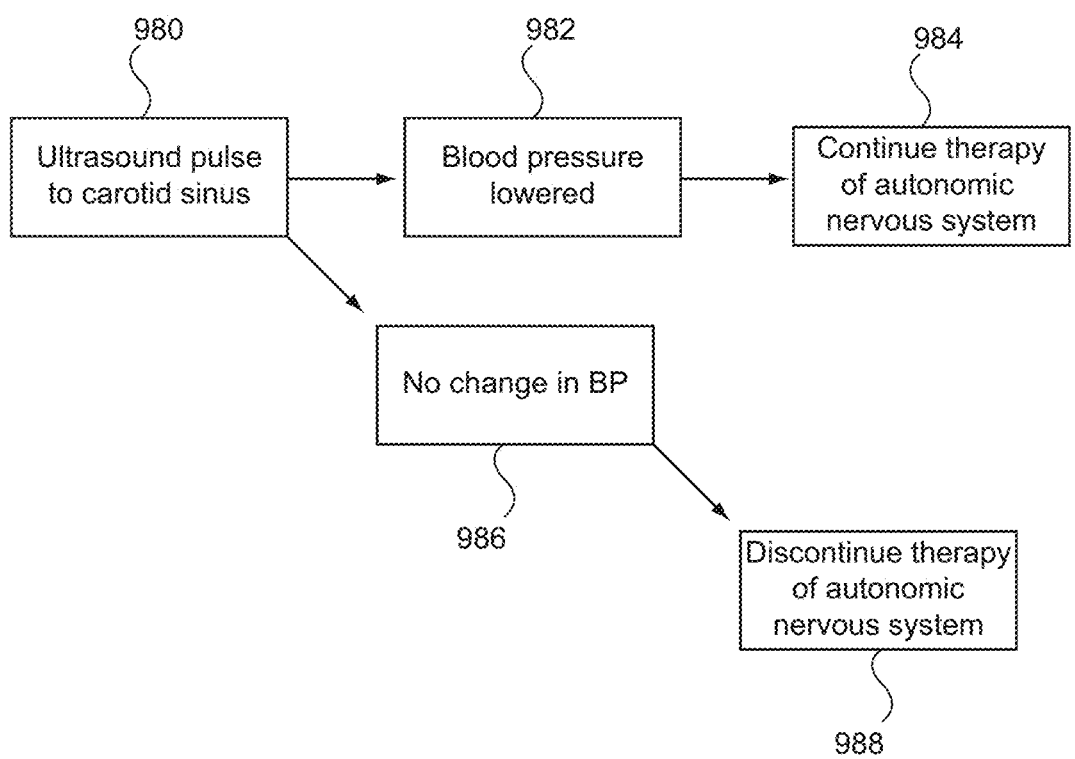
FIG. 3E depicts a therapy paradigm for the treatment and assessment of hypertension.

More specifically, this methodology is depicted in FIG. 3E. An ultrasound pulse 980 is utilized to stimulate the carotid sinus which will lower blood pressure transiently 982 by activating the baroreceptor complex; activation of the carotid sinus 980 simulates the effect of an increase in blood pressure which leads to a compensatory outflow of parasympathetic activity and decreased sympathetic outflow, subsequently lowering blood pressure. In the instance when the afferent system (e.g. from the kidney) has been inhibited, the pressure will not be modifiable as quickly if at all. In this case, stimulating the baroreceptor complex does not result in a lowering of blood pressure 986, then the treatment was successful. This diagnostic technique can therefore be utilized to determine the effect of a therapy on a system such as the renal nerve complex. If therapy is successful, then the modifying effect of the ultrasound pulse on the carotid sinus and blood pressure is less dramatic and the therapeutic (treatment of afferent nerves) successful; therefore, therapy can be discontinued 988 temporarily or permanently. If the blood pressure continues to decrease 982 with the baroreceptor stimulation, then the therapeutic effect has not been reached with the therapeutic treatment and it needs to be continued 984 and/or the dose increased. Other methods to stimulate the baroreceptor complex are to apply pressure in the vicinity with hands, compression balloons, electrical stimulators, and the like.

Figure 4A:
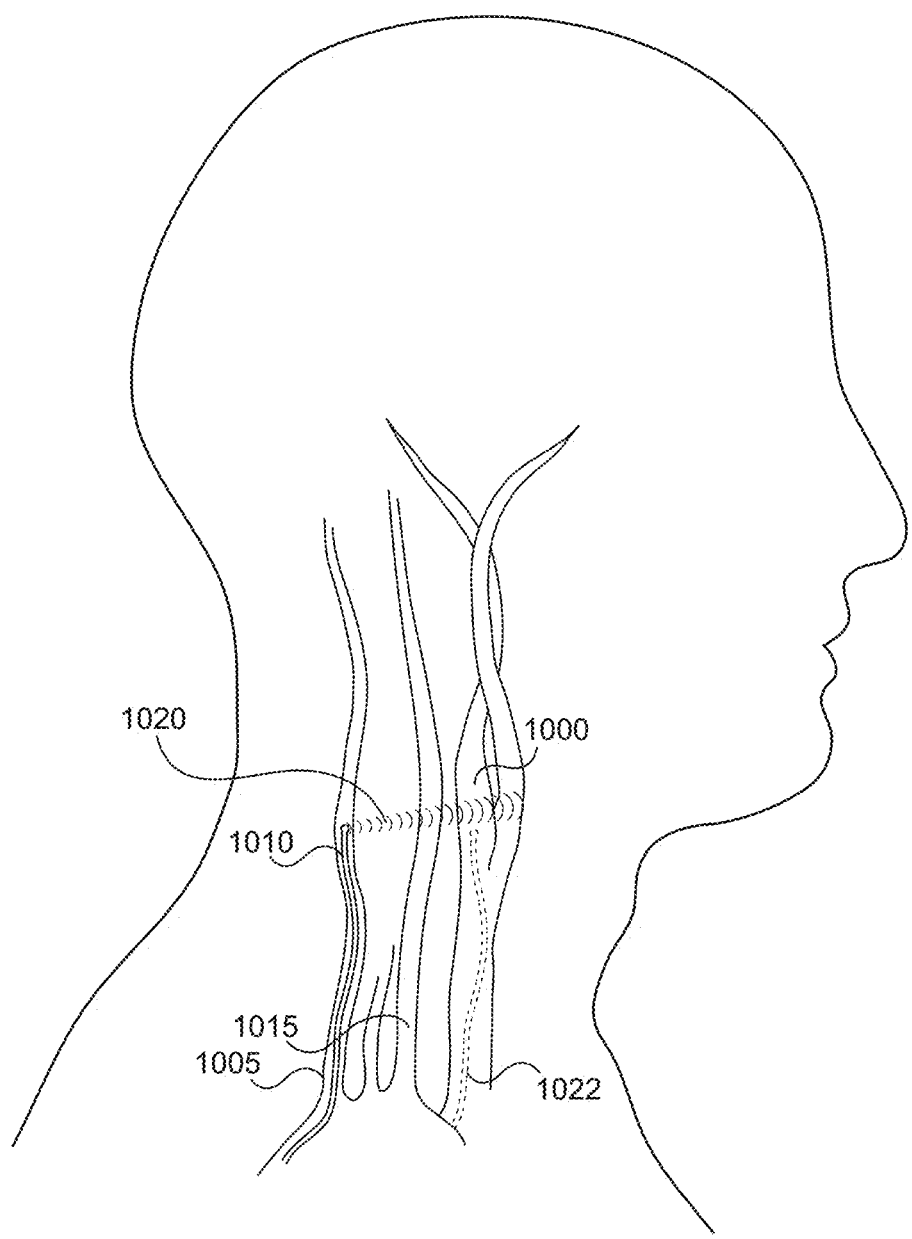
FIG. 4A depicts the application of energy to the autonomic nervous system surrounding the carotid arteries.

Other regions of the autonomic nervous system can also be affected directly by the technology described herein by applying energy from one region and transmitted through tissue to another region. For example, FIG. 4A illustrates a system in which energy external to the internal carotid artery is applied to a portion of the autonomic nervous system, the carotid body complex 1000, through the internal jugular vein 1005, and to the carotid body 1000 and/or vagus nerve region 1022, and/or vertebral artery 1015. Ablative energy, vibratory, or electrical stimulation energy can be utilized to affect the transmission of signals to and from these nerves. The transmission in this complex can be augmented, interrupted, inhibited with over-stimulation, or a combination of these effects via energy (e.g. ultrasound, electrical stimulation, etc.).

In addition, or in place of, in other embodiments, energy may be applied to peripheral nerves typically known as motor nerves but which contain autonomic fibers. Such nerves include the saphenous nerve, femoral nerves, lumbar nerves, median nerves, ulnar nerves, and radial nerves. In some embodiments, energy is applied to the nerves and specific autonomic fibers are affected rather than the other neural fibers (e.g. motor or somatic sensory fibers or efferent or afferent autonomic nerves). In some embodiments, other types of autonomic fibers are affected with energy applied internally or externally. For example, nerves surrounding the superior mesenteric artery, the inferior mesenteric artery, the femoral artery, the pelvic arteries, the portal vein, hepatic artery, pulmonary arteries, pulmonary veins, aorta, vena cava, etc. can be affected by the energy in a specific manner so as to create changes in the autonomic responses of the blood vessels themselves or organs related to the blood vessels, the nerves running through and along the vessels to the organs.

In another embodiment, in FIG. 4a, a catheter 1010 is advanced into the internal jugular vein 1005 and when in position, stimulation or ablative energy 1020 is directed toward the autonomic nerves, e.g. the vagus nerve and the carotid sinus/body 1000, from the catheter positioned in the venous system 1005.

In a similar type of embodiment 1100, a catheter based therapeutic energy source 1110 can be inserted into the region of the renal arteries or renal veins (FIG. 4B) to stimulate or inhibit the renal nerves from the inside of the vessel, either the renal artery 1105 or renal vein 1106. Energy is transferred through the vessel (e.g. renal vein) to reach the nerves around another vessel (e.g. renal artery). For example, a catheter delivering unfocused ultrasound energy with powers in the range of 50 mW/cm$^2$ to 50 kW/cm$^2$ can be placed into the renal artery and the energy transmitted radially around the artery or vein to the surrounding nerves. As discussed below, the 500 mW-2500 W/cm$^2$ is appropriate to create the specific nerve dysfunction to affect the norepinephrine levels in the kidney, a surrogate of nerve function which has been shown to lead to decreases in blood pressure over time. Pulsed ultrasound, for example, 100 pulse trains with each lasting less than 1 second each, can be applied to the region.

In an exemplary embodiment, the tubular body 1105 is elongate and flexible, and comprises an outer sheath that is positioned over an inner core. For example, in embodiments particularly well-suited for the renal blood vessels, the outer sheath 108 can comprise extruded polytetrafluoroethylene ("PTFE"), polyetheretherketone ("PEEK"), polyethylene ("PE"), polyamides, braided polyamides and/or other similar materials. In such embodiments, the outer sheath 108 has an outer diameter of approximately 0.039 inch (0.039 inch±0.01 inch) at its proximal end and between approximately 0.033 inch (0.033 inch±0.01 inch) and approximately 0.039 inch (0.039 inch±0.01 inch) at its distal end. In such embodiments, the outer sheath 108 has an axial length of approximately 150 centimeters (150 cm±20 cm). In other embodiments, the outer sheath 108 can be formed from a braided tubing comprising high or low density polyethylenes, urethanes, nylons, and so forth. Such configurations enhance the flexibility of the tubular body 1105. In still other embodiments, the outer sheath can include a stiffening member (not shown) at the tubular body proximal end.

The inner core at least partially defines a central lumen, or "guidewire lumen," which preferably extends through the length of the catheter. The central lumen has a distal exit port and a proximal access port. In some embodiments, the proximal portion of the catheter is defined by a therapeutic compound inlet port on a back end hub, which is attached proximally. In the exemplary embodiment the back end hub is attached to a control box connector, which is described in greater detail below.

In an exemplary embodiment, the central lumen is configured to receive a guidewire (not shown) having a diameter of between approximately 0.010 inch (0.01 inch±0.005 inch) to approximately 0.012 inch (0.012 inch±0.005 inch). In an exemplary embodiment, the inner core is formed from polymide or a similar material, which can optionally be braided to increase the flexibility of the tubular body 1105.

Figure 4B:
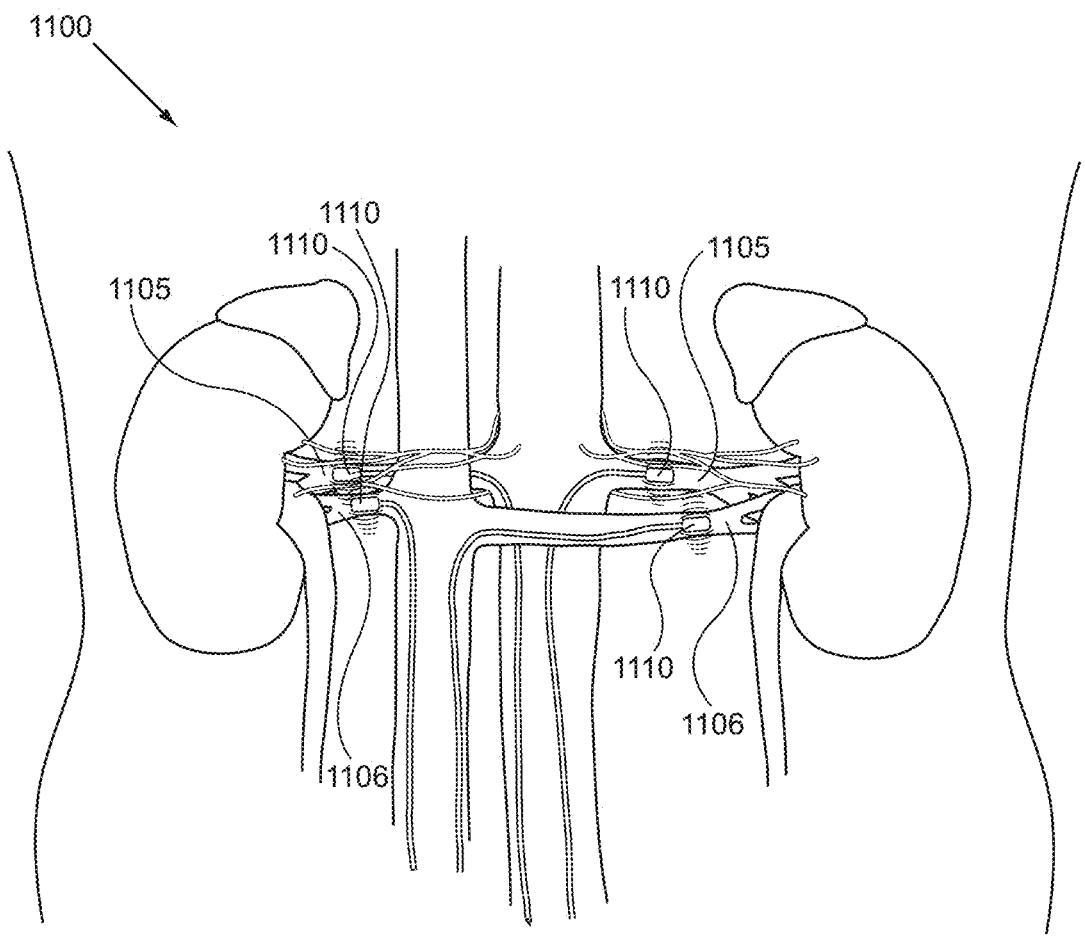
FIG. 4B depicts the application of energy to through the vessels of the renal hilum.

Referring now to an exemplary embodiment illustrated in FIG. 4B, the distal end of the tubular body includes an ultrasound radiating member 1110. In the illustrated embodiment, the ultrasound radiating member 1110 comprises an ultrasonic transducer, which converts, for example, electrical energy into ultrasonic energy.

An inner core extends through the ultrasound radiating member, which is positioned over the inner core. The ultrasound radiating member can be secured to the inner core in a suitable manner, such as with an adhesive. Extending the core through the member advantageously provides enhanced cooling of the ultrasound radiating member. A therapeutic compound can be injected through a central lumen, thereby providing a heat sink for heat generated by the ultrasound radiating member. The therapeutic compound can enhance the effect of the ultrasound on the nerves surrounding the blood vessel.

Suitable operating frequencies for the ultrasound radiating member include, but are not limited to, from about 20 kHz (20 kHz±2 kHz) to less than about 20 MHz (20 MHz±2 MHz). In one embodiment, the frequency is between 500 kHz and about 20 MHz (20 MHz±2 MHz), and in another embodiment the frequency is between about 1 MHz (1 MHz±0.1 MHz) and about 3 MHz (3 MHz±0.3 MHz). In yet another embodiment, the ultrasonic energy has a frequency of about 3 MHz (3 MHz±0.3 MHz).

In another embodiment, light is applied through the vessel from within the blood vessel. Infrared, red, blue, and near infrared can all be utilized to affect the function of nerves surrounding blood vessels. For example, a light source is introduced into the renal artery or renal vein 1105, 1106 and the light transmitted to the region surrounding the blood vessels. In a preferred embodiment, a photosensitizing agent is utilized to hasten the inhibition or destruction of the nerve bundles with this technique. Photosensitizing agents can be applied systemically to infiltrate the region around the blood vessels. Light is then applied from inside the vessel to the region of the nerves outside the vessel. For example, the light source is placed inside the renal vein and then light is transmitted through the vein wall to the adventitial region around the wall activating the photosensitizer and injuring or inhibiting the nerves in the adventitia through an apoptosis pathway. The light source may provide light that is visible, or light that is non-visible. In another embodiment, the light is applied to the region without photosensitizer. The light generates heat in the region through absorption of the light. Wavelengths such as those in the red, near-infrared, and infrared region are absorbed by the tissues around the artery and leads to destruction of the nerves in the region.

In one embodiment, a string of light emitting diodes (LEDs) is fed into the blood vessel and the vessel illuminated with light from inside the vessel. Lights that are near infrared and infrared have good penetration in blood and through tissues and can be utilized to heat or activate pharmaceuticals in the region surrounding the blood vessel leading to the kidney. These light frequency devices and energies can be utilized to visualize the inside and/or outside of the blood vessel. Intravascular OCT might be utilized to visualize damage to the nerves surrounding the blood vessels.

The therapies in FIGS. 4A-B can be delivered on an acute basis such as for example in an ICU or critical care setting. In such a case, the therapy would be acute and intermittent, with the source outside the patient and the catheter within the patient as shown in FIGS. 4*a-b*. The therapy can be utilized during times of stress for the patient such that the sympathetic system is slowed down. After the intensive care admission is nearing a close, the catheter and unit can be removed from the patient. In one embodiment, a method is described in which a catheter is placed within a patient to deliver energy to a region of the body sufficient to partially or fully inhibit an autonomic nerve complex during a state of profound sympathetic activation such as shock, sepsis, myocardial infarction, pancreatitis, post-surgical. After the acute phase of implantation during which the sympathetic system is modulated, the device is removed entirely.

Figure 5A:
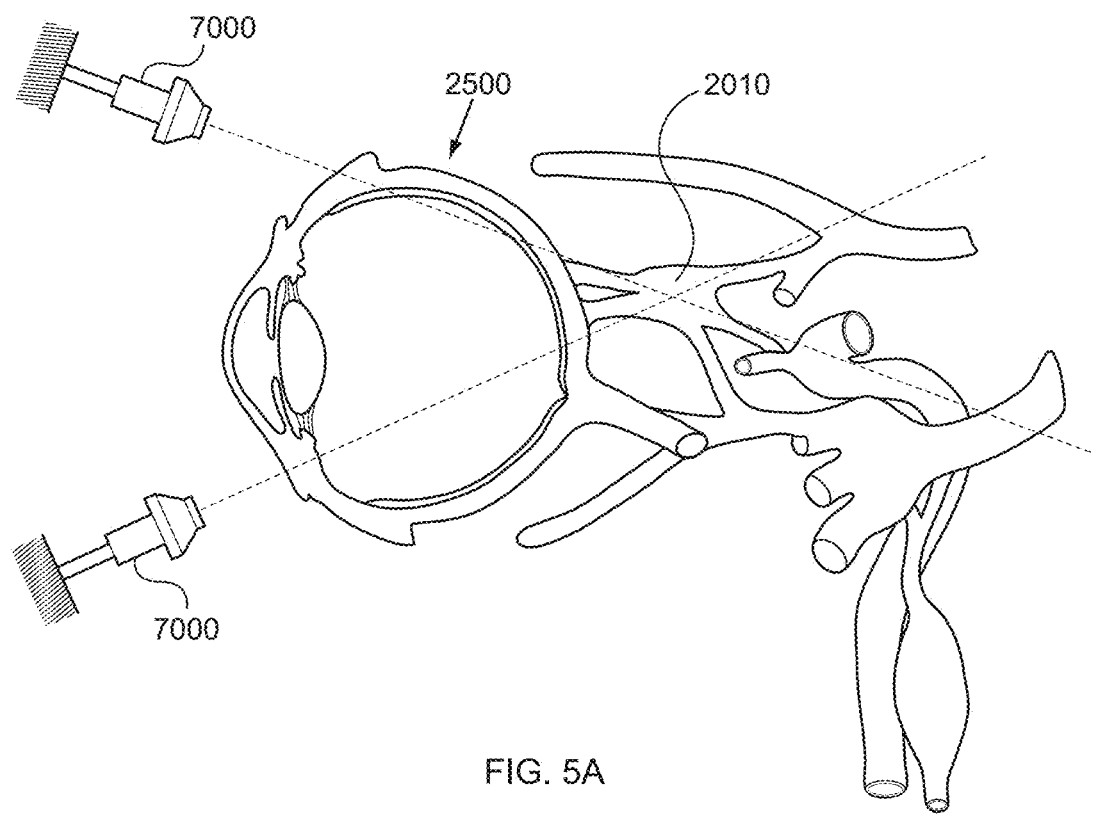
FIGS. 5A-5B depict the application of focused energy to the autonomic nervous system of the eye.
Figure 5B:
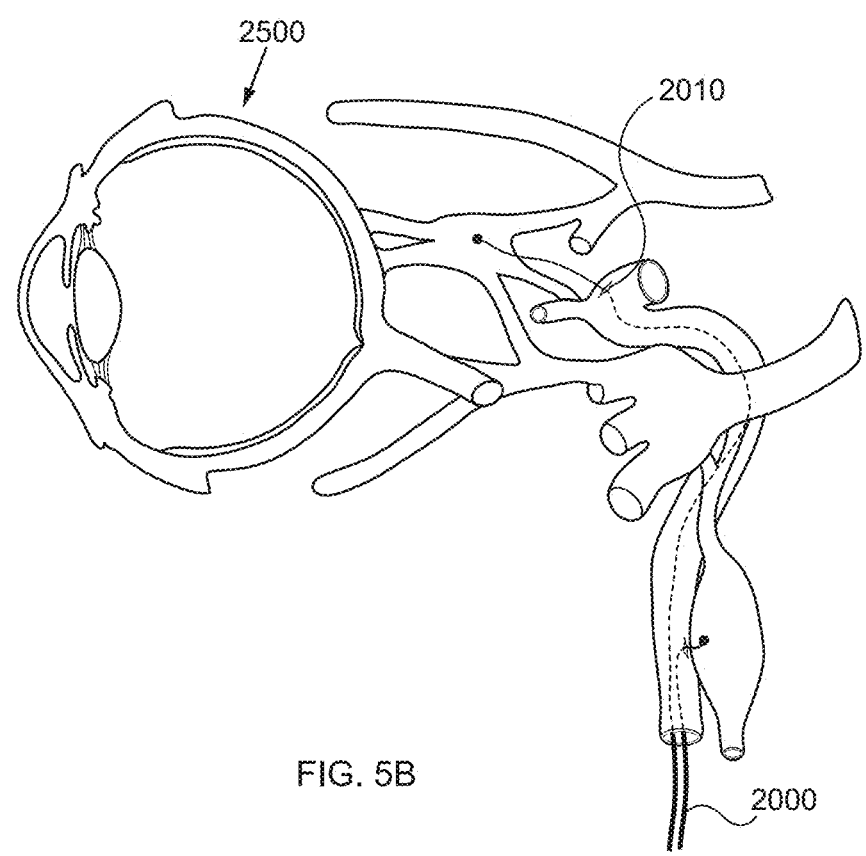

FIGS. 5A-B illustrates the eye in close up detail with sympathetic nerves surrounding the posterior of the eye. In the eye, glaucoma is a problem of world-wide importance. The most commonly prescribed medication to treat glaucoma is timoptic, which is a non-selective $\beta 1$ and $\beta 2$ (adrenergic) antagonist. Compliance with this pharmaceutical is a major problem and limits its effectiveness in preventing the complications of glaucoma, the major complication being progression of visual dysfunction.

Ultrasound, or other energy transducers 7000, can be applied to focus energy from an external region (e.g. a distance from the eye in an external location) anterior to the eye or to a region posteriorly behind the eye 2500 on the sympathetic 2010 or parasympathetic ganglia, all of which will affect lowering of intra-ocular pressure. The energy transducers 7000 apply ablative or near ablative energy to the adventitia of the blood vessels. In some embodiments, the energy is not ablative but vibratory at frequencies (e.g. 1-5 Mhz) and penetration depths (e.g. 0.5 mm to 0.5 cm) sufficient to inhibit the function of the nerves which are responsible for intra-ocular pressure. Lower energy (e.g. sub-ablative) can be applied to the eye to assist in drug delivery or to stimulate tissue healing type of tissue responses.

FIG. 5B depicts the anatomy of the nerves which travel behind the eye 2500. In this illustration, a catheter 2000 is tunneled through the vasculature to the region of the sympathetic nerves surrounding the arteries of the eye 2010 and utilized to ablate, stun, or otherwise modulate the efferent and/or afferent nerves through the wall of the vasculature leading to the eye.

Figure 6:
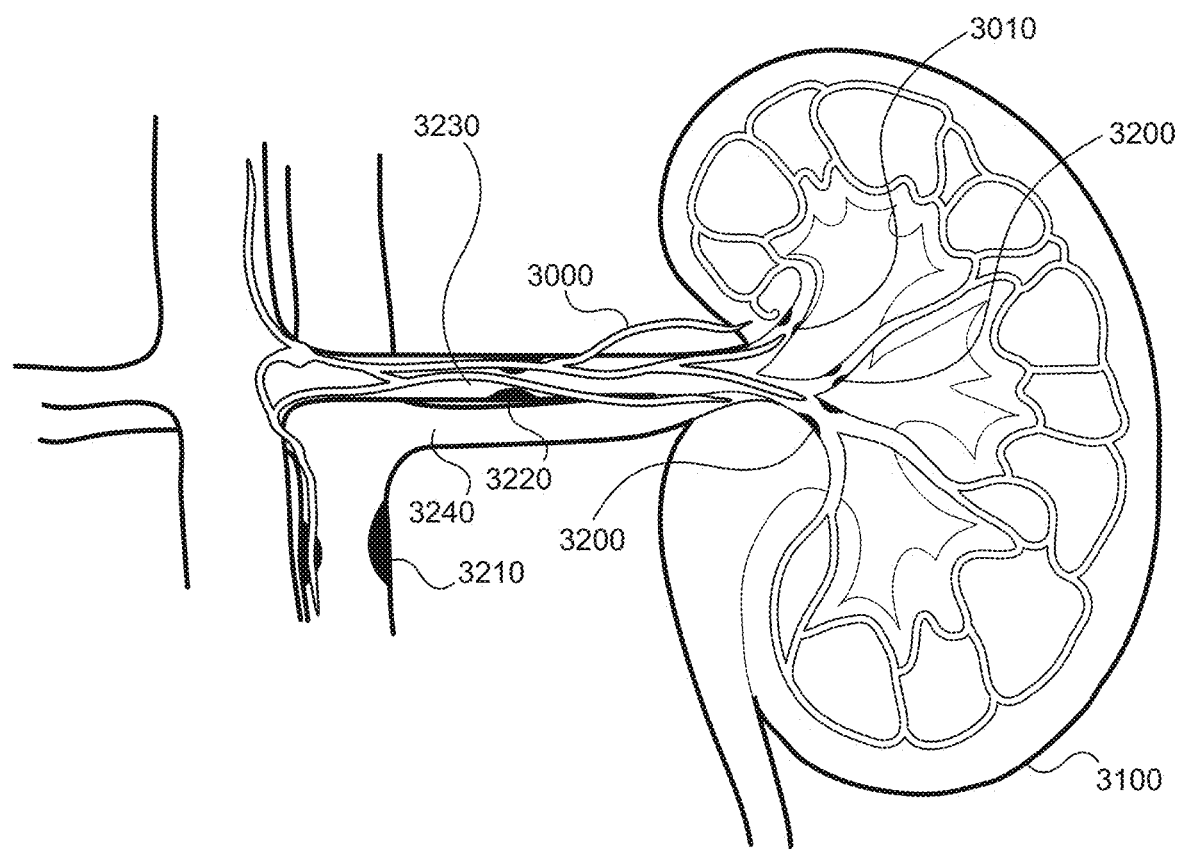
FIG. 6 depicts the application of constricting lesions to the kidney deep inside the calyces of the kidney.

FIG. 6 illustrates an overall schematic of the renal artery, renal vein, the collecting system, and the more distal vessels and collecting system within the renal parenchyma. The individual nerves of the autonomic nervous system typically follow the body vasculature and they are shown in close proximity 3000 to the renal artery as the artery enters the kidney 3100 proper. The hilum of the kidney contains pressure sensors and chemical sensors which influence the inputs to the efferent sympathetic system via afferent nerves traveling from the kidney to the central nervous system and then to the efferent nervous system. Any one or multiple of these structures can influence the function of the kidney. Ablative or non-ablative energy can be applied to the renal vein, the renal artery, the aorta, and/or the vena cava, the renal hilum, the renal parenchyma, the renal medulla, the renal cortex, etc.

In another embodiment, selective lesions, constrictions or implants 3200 are placed in the calyces of the kidney to control or impede blood flow to specific regions of the kidney. Such lesions or implants can be placed on the arterial 3010 or venous sides 3220 of the kidney. In some embodiments, the lesions/implants are created so as to selectively block certain portions of the sympathetic nerves within the kidney. The lesions also may be positioned so as to ablate regions of the kidney which produce hormones, such as renin, which can be detrimental to a patient in excess. The implants or constrictions can be placed in the aorta 3210 or the renal vein 3230. The implants can be active implants, generating stimulating energy chronically or multiple ablative or inhibitory doses discretely over time.

In the renal vein 3230, the implants 3220, 3200 might cause an increase in the pressure within the kidney (by allowing blood flow to back up into the kidney and increase the pressure) which will prevent the downward spiral of systolic heart failure described above because the kidney will act as if it is experiencing a high pressure head. That is, once the pressure in the kidney is restored or artificially elevated by increased venous pressure, the relative renal hypotension signaling to retain electrolytes and water will not be present any longer and the kidney will "feel" full and the renal sympathetic stimulation will be turned off. In one embodiment, a stent which creates a stenosis is implanted using a catheter delivery system. In another embodiment, a stricture 3220 is created using heat delivered either externally or internally. Externally delivered heat is delivered via direct heating via a percutaneous procedure (through the skin to the region of the kidney) or transmitted through the skin (e.g. with HIFU focused through the skin). In one embodiment, an implant is placed between girota's fascia and the cortex of the kidney. The implant can stimulate or inhibit nerves surrounding the renal blood vessels, or even release pharmaceuticals in a drug delivery system.

FIG. 7A depicts at least partial ablation of the renal sympathetic nerves 4400 to the kidney using an imaging system such as an MRI machine or CT scanner 4000. The MRI/CT scan can be linked to a focused ultrasound (HIFU) machine to perform the ablations of the sympathetic nerves 4400 around the region of the renal artery 4500. The MRI/CT scan performs the imaging 4010 and transmits data (e.g. three dimensional representations of the regions of interest) to the ultrasound controller which then directs the ultrasound to target the region of interest with low intensity ultrasound (50-1000 mW/cm2), heat (>1000 mW/cm2), cavitation, or a combination of these modalities and/or including introduction of enhancing bioactive agent delivery locally or systemically (sonodynamic therapy). Optionally, a doppler ultrasound or other 3D/4D ultrasound is performed and the data pushed to the MRI system to assist with localization of the pathology; alternatively, the ultrasound data are utilized to directly control the direction of the energy being used to target the physiologic processes and CT/MRI is not obtained. Using this imaging and ablation system from a position external to a patient, many regions of the kidney can be treated such as the internal calyces 4350, the cortex 4300, the medulla 4320, the hilum 4330, and the region 4340 close to the aorta. Optionally, an intravascular catheter can be introduced into the patient to augment the procedure with intravascular energy, temperature measurement, acoustic energy detection, ionizing radiation detection, etc. For example, the catheter might be able to deliver radiofrequency energy to the wall of the blood vessel, or the catheter might be heated in response to the magnetic field being applied across the patient. For example, a balloon or other catheter tip with a metallic coating will be heated in the presence of a magnetic field. This heat, typically unwanted in the presence of an intravascular catheter, can be utilized to inhibit, or ablate the nerves leading to the kidney (as an example). The MRI system also has the advantage of being able to measure temperature and/or looking at tissue changes around the blood vessels treated, as described below. Similarly, the intravascular catheter can heat up in response to ultrasound in the case where the catheter contains elements Further parameters which can be measured include temperature via thermal spectroscopy using MRI or ultrasound thermometry/elastography; thermal imaging is a well-known feature of MRI scanners; the data for thermal spectroscopy exists within the MRI scan and can be extrapolated from the recorded data in real time by comparing regions of interest before and after or during treatment. Temperature data overlaid on the MRI scan enables the operator of the machine to visualize the increase in temperature and therefore the location of the heating to insure that the correct region has indeed been ablated and that excessive energy is not applied to the region. Having temperature data also enables control of the ablation field as far as applying the correct temperature for ablation to the nerves. For example, the temperature over time can be determined and fed back to the operator or in an automated system, to the energy delivery device itself. Furthermore, other spectroscopic parameters can be determined using the MRI scan such as oxygenation, blood flow, inflammation, or other physiologic and functional parameters. In one embodiment, an alternating magnetic field is used to stimulate and then overstimulate or inhibit an autonomic nerve (e.g. to or from the kidney).

Elastography is a technique in which the shear waves of the ultrasound beam and reflectance are detected. The tissue characteristics change as the tissue is heated and the tissue properties change. An approximate temperature can be assigned to the tissue based on elastography and the progress of the heating can be monitored.

MRI scanners 4000 generally consist of a magnet and an RF coil. The magnet might be an electromagnet or a permanent magnet. The coil is typically a copper coil which generates a radiofrequency field. Recently, permanent magnets have been utilized to create MRI scanners which are able to be used in almost any setting, for example a private office setting. Office based MRI scanners enable imaging to be performed quickly in the convenience of a physician's office as well as requiring less magnetic force (less than 0.5 Tesla) and as a consequence, less shielding. The lower tesla magnets also provides for special advantages as far as diversity of imaging and resolution of certain features. Importantly, the permanent magnet MRI scanners are open scanners and do not encapsulate the patient during the scan.

In one embodiment, a permanent magnet MRI is utilized to obtain an MRI image of the region of interest 4010. High intensity focused 4100 ultrasound is used to target the region of interest 4600 identified using the MRI. In one embodiment, the MRI is utilized to detect blood flow within one or more blood vessels such as the renal arteries, renal veins, superior mesenteric artery, veins, carotid arteries and veins, aortic arch coronary arteries, veins, to name a subset.

Image 4010 is or can be monitored by a health care professional to ensure that the region of interest is being treated and the treatment can be stopped if the assumed region is not being treated. Alternatively, an imaging algorithm can be initiated in which the region of interest is automatically (e.g. through image processing) identified and then subsequent images are compared to the initial demarcated region of interest.

Perhaps, most importantly, with MRI, the region around the renal arteries can be easily imaged as can any other region such as the eye, brain, prostate, breast, liver, colon, spleen, aorta, hip, knee, spine, venous tree, and pancreas. The imaging from the MRI can be utilized to precisely focus the ultrasound beam to the region of interest around the renal arteries or elsewhere in the body. With MRI, the actual nerves to be modified or modulated can be directly visualized and targeted with the energy delivered through the body from the ultrasound transducers. One disadvantage of MRI can be the frame acquisition (difficulty in tracking the target) rate as well as the cost of introducing an MRI machine into the treatment paradigm. In these regards, ultrasound imaging offers a much more practical solution. In some embodiments, the advantages of ultrasound and MRI are combined into a single system. In some embodiments, an intravascular catheter is further combined with the two imaging modalities to further enhance the treatment. In one embodiment, the intravascular catheter has a ferromagnetic tip which is moveable or heatable (or both) by the MRI scanner. The tip can be manipulated, manually or by the magnetic field (or both) to apply pressure to the wall of the blood vessel and subsequently heat the wall. In some embodiments, the tip can perform the above function(s) while measuring the temperature of the region around the blood vessel (the nerve region). In other embodiments, another device may be used to measure the temperature.

Figure 7D:
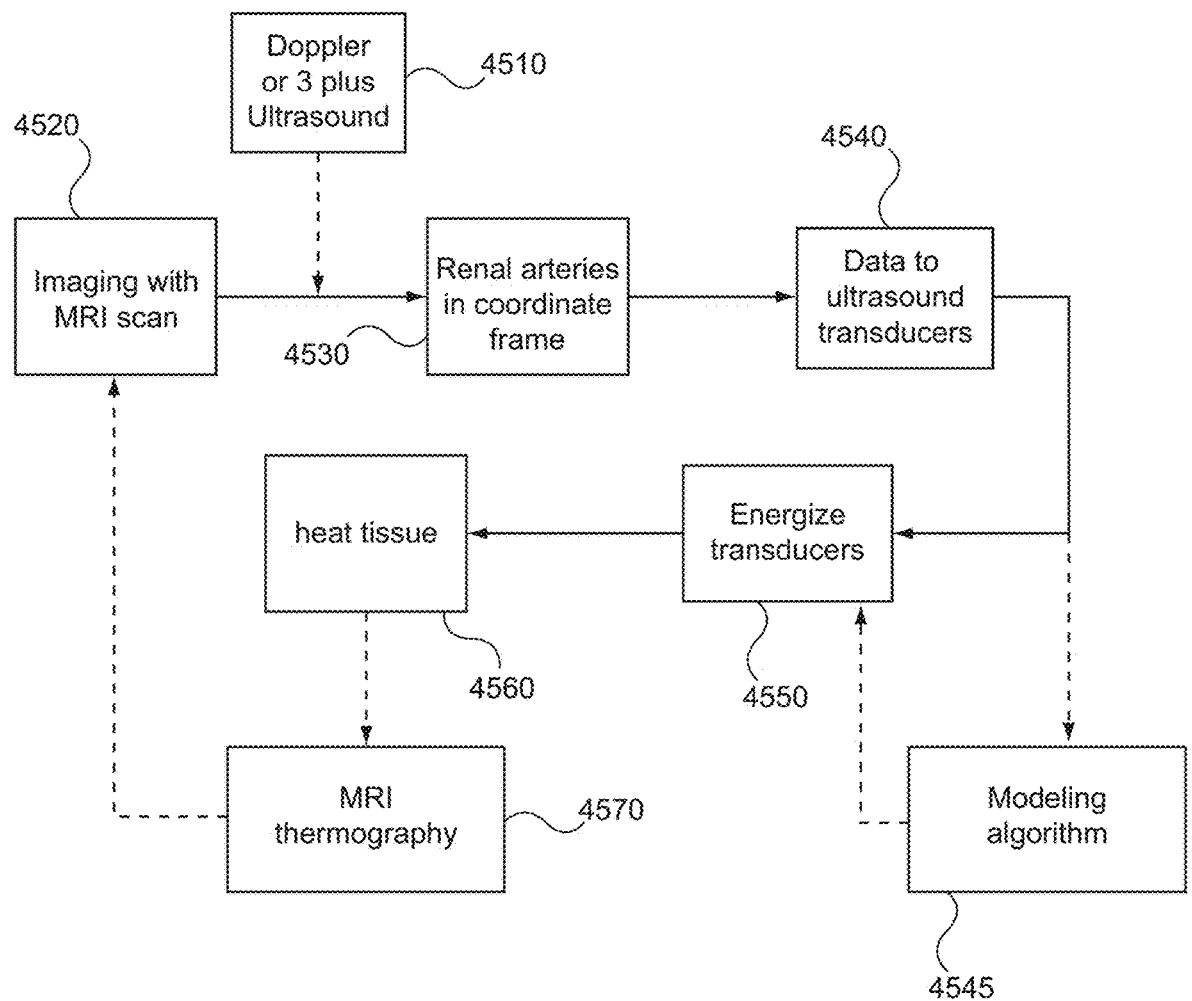
FIG. 7D depicts an algorithmic method to treat the autonomic nervous system using MRI and energy transducers.

FIG. 7D depicts a method of treating a region with high intensity focused ultrasound (HIFU). Imaging with an MRI 4520 or ultrasound 4510 (or preferably both) is performed. MRI can be used to directly or indirectly (e.g. using functional MRI or spectroscopy) to visualize the sympathetic nerves. T1 weighted or T2 weighted images can be obtained using the MRI scanner. In addition to anatomic imaging, the MRI scanner can also obtain temperature data regarding the effectiveness of the ablation zone as well as the degree to which the zone is being heated and which parts of the zones are being heated. Other spectroscopic parameters can be added as well such as blood flow and even nerve activity. Edema, inflammation, and necrosis can be detected as well with MRI. Ultrasound 4510 can be used to add blood flow to the images using Doppler imaging. The spectroscopic data can be augmented by imaging moieties such as particles, imaging agents, or particles coupled to imaging agents which are injected into the patient intravenously, or locally, and proximal to the region of the renal arteries; these imaging moieties may be visualized on MRI, ultrasound, or CT scan. Ultrasound can also be utilized to determine information regarding heating. The reflectance of the ultrasonic waves changes as the temperature of the tissue changes. By comparing the initial images with the subsequent images after heating, the temperature change which occurred after the institution of heating can be determined. Therefore, in one embodiment, information regarding heating at baseline is determined and incorporated into the treatment modeling during the ongoing treatment at time subsequent to t=0.

In one embodiment, the kidneys are detected by a cross-sectional imaging modality such as MRI, ultrasound, or CT scan. The renal arteries and veins are detected within the MRI image utilizing contrast or not utilizing contrast. Next, the imaging data is placed into a three dimensional coordinate system which is linked to one or more ultrasound (e.g. HIFU) transducers 4540 which focus ultrasound onto the region of the renal arteries in the coordinate frame 4530. The linking, or coupling, of the imaging to the therapeutic transducers is accomplished by determining the 3 dimensional position of the target by creating an anatomic model. The transducers are placed in a relative three dimensional coordinate frame as well. For example, the transducers can be placed in the imaging field 4520 during the MRI or CT scan such that the cross-sectional pictures include the transducers. Optionally, the transducers contain motion sensors, such as electromagnetic, optical, inertial, MEMS, and accelerometers, one or more of which allow for the transducer position to be monitored if for example the body moves relative to the transducer or the operator moves relative to the body. With the motion sensors, the position of the transducers can be determined with movement which might occur during the therapy. The updated information can then be fed back to the ultrasound therapy device so as to readjust the position of the therapy.

In one embodiment, a system is described in which the blood flow in the renal artery is detected by detecting the walls of the artery or renal vein or the blood flow in the renal artery or the renal vein. The coordinate reference of the blood vessels is then transmitted to the therapeutic transducer, for example, ultrasound. The therapeutic transducer is directed to the renal blood vessels using the information obtained by imaging. A model (FIG. 16M for example) of the vessels (including blood flow, movement, etc.) indicates the blood flow of the vessels and the walls of the vessels where the nerves reside. Energy is then applied to the model of the vessels to treat the nerves around the vessels.

Alternatively, in another embodiment, ultrasound is utilized and the ultrasound image 4510 can be directly correlated to the origin of the imaging transducer. In some embodiments the ultrasound is in two dimensions and in others, the ultrasound is presented in three dimensions. In some embodiments, the ultrasound is presented in a combination of two and three dimensions. For example, a two dimensional transducer may be quickly rotated at a specified speed and the integration of the pictures provides a three dimensional approximation. The therapeutic transducer 4540 in some embodiments is the same as the imaging transducer and therefore the therapeutic transducer is by definition coupled in a coordinate reference 4540 once the imaging transducer coordinates are known. If the therapeutic transducer and the imaging transducer are different devices, then they can be coupled by knowledge of the relative position of the two devices. The region of interest (ROI) is highlighted in a software algorithm; for example, the renal arteries, the calyces, the medullary region, the cortex, the renal hila, the celiac ganglia, the aorta, or any of the veins of the venous system as well. In another embodiment, the adrenal gland, the vessels traveling to the adrenal gland, or the autonomic nerves traveling to the adrenal gland are targeted with focused ultrasound and then either the medulla or the cortex of the adrenal gland or the nerves and arteries leading to the gland are partially or fully ablated with ultrasonic energy.

The targeting region or focus of the ultrasound is the point of maximal intensity. In some embodiments, targeting focus is placed in the center of the artery such that the walls on either side receive equivalent amounts of energy or power and can be heated more evenly than if one wall of the blood vessel is targeted. In some embodiments in which a blood vessel is targeted, the blood vessel being an artery and the artery having a closely surrounding vein (e.g. the renal artery/vein pedicle), the center of the focus might be placed at the boundary of the vein and the artery.

Once the transducers are energized 4550 after the region is targeted, the tissue is heated 4560 and a technique such as MRI thermography 4570 or ultrasound thermography is utilized to determine the tissue temperature. During the assessment of temperature, the anatomic data from the MRI scan or the Doppler ultrasound is then referenced to ensure the proper degree of positioning and the degree of energy transduction is again further assessed by the modeling algorithm 4545 to set the parameters for the energy transducers 4550. If there is movement of the target, the transducers may have to be turned off and the patient repositioned. Alternatively, the transducers can be redirected to a different position within the coordinate reference frame.

Ablation can also be augmented using agents such as magnetic nanoparticles or liposomal nanoparticles which are responsive to a radiofrequency field generated by a magnet. These particles can be selectively heated by the magnetic field. The particles can also be enhanced such that they will target specific organs and tissues using targeting moieties such as antibodies, peptides, etc. In addition to the delivery of heat, the particles can be activated to deliver drugs, bioactive agents, or imaging agents at the region at which action is desired (e.g. the renal artery). The particles can be introduced via an intravenous route, a subcutaneous route, a direct injection route through the blood vessel, or a percutaneous route. As an example, magnetic nanoparticles or microparticles respond to a magnetic field (e.g. by a MRI device) by generating heat in a local region around them. Similarly, liposomal particles might have a metallic particle within such that the magnetic particle heats up the region around the liposome but the liposome allows accurate targeting and biocompatibility.

The addition of Doppler ultrasound 4510 may be provided as well. The renal arteries are (if renal arteries or regions surrounding the arteries are the target) placed in a 3D coordinate reference frame 4530 using a software algorithm with or without the help of fiducial markers. Data is supplied to ultrasound transducers 4540 from a heat modeling algorithm 4545 and the transducers are energized with the appropriate phase and power to heat the region of the renal artery to between 40° C. and 90° C. within a time span of several minutes. The position within the 3D coordinate reference is also integrated into the treatment algorithm so that the ultrasound transducers can be moved into the appropriate position. The ultrasound transducers may have frequencies below 1 megahertz (MHz), from 1-20 MHz, or above 30 Mhz, or around 750 kHz, 500 kHz, or 250 kHz. The transducers may be in the form of a phased array, either annular, linear or curved, or the transducers may be mechanically moved so as to focus ultrasound to the target of interest. In addition, MRI thermography 4570 can be utilized so as to obtain the actual temperature of the tissue being heated. These data can be further fed into the system to slow down or speed up the process of ablation 4560 via the transducers 4550. For example, in the case where the temperature is not rising as fast as planned, the energy level can be increased. On the other hand, where the temperature is rising faster than originally planned, the energy density can be decreased.

Aside from focused ultrasound, ultrasonic waves can be utilized directly to either heat an area or to activate pharmaceuticals in the region of interest. There are several methodologies to enhance drug delivery using focused ultrasound. For example, particles can release pharmaceuticals when they are heated by the magnetic field. Liposomes can release a payload when they are activated with focused ultrasound. Ultrasound waves have a natural focusing ability if a transducer is placed in the vicinity of the target and the target contains an activateable moiety such as a bioactive drug or material (e.g. a nanoparticle sensitive to acoustic waves). Examples of sonodynamically activated moieties include some porphyrin derivatives.

So as to test the region of interest and the potential physiologic effect of ablation in that region, the region can be partially heated or vibrated with the focused ultrasound to stun or partially ablate the nerves. Next, a physiologic test such as the testing of blood pressure or measuring norepinephrine levels in the blood, kidney, blood vessels leading to or from the kidney, can be performed to ensure that the correct region was indeed targeted for ablation. Depending on the parameter, additional treatments may be performed.

Clinically, this technique might be called fractionation of therapy which underscores one of the major advantages of the technique to apply external energy versus applying internal energy to the renal arteries. An internal technique requires invasion through the skin and entry into the renal artery lumens which is costly and potentially damaging. Patients will likely not accept multiple treatments, as they are highly invasive and painful. An external technique allows for a less invasive treatment to be applied on multiple occasions, made feasible by the low cost and minimal invasion of the technology described herein.

In another embodiment, a fiducial is utilized to demarcate the region of interest. A fiducial can be intrinsic (e.g. part of the anatomy) or the fiducial can be extrinsic (e.g. placed in position). For example, the fiducial can be an implanted fiducial, an intrinsic fiducial, or device placed in the blood vessels, or a device placed percutaneously through a catheterization or other procedure. The fiducial can also be a bone, such as a rib, or another internal organ, for example, the liver. In one embodiment, the fiducial is a beacon or balloon or balloon with a beacon which is detectable via ultrasound. In another embodiment, the fiducial is a stent implanted in the renal artery, renal vein, vena cava, or aorta. The stent can be periodically heated by the MRI or ultrasound in the case where treatment is needed to be reapplied. In one embodiment, the blood flow in the renal arteries, detected via Doppler or B-mode imaging, is the fiducial and its relative direction is determined via Doppler analysis. Next, the renal arteries, and specifically, the region around the renal arteries are placed into a three dimensional coordinate frame utilizing the internal fiducials. A variant of global positioning system technology can be utilized to track the fiducials within the artery or around the arteries. In this embodiment, a position sensor is placed in the artery or vein through a puncture in the groin. The position of the sensor is monitored as the sensor is placed into the blood vessel and its position in physical space relative to the outside of the patient, relative to the operator and relative to the therapeutic transducer is therefore known. The three dimensional coordinate frame is transmitted to the therapeutic ultrasound transducers and then the transducers and anatomy are coupled to the same coordinate frame. At this point, the HIFU is delivered from the transducers, calculating the position of the transducers based on the position of the target in the reference frame. The fiducial may be active, in which electrical current is transmitted into the fiducial through a catheter or through induction of energy transmitted through the skin. The energy transmitted from the catheter back through the skin or down the catheter and out of the patient may be utilized to indicate the coordinates of treatment target(s) so that the externally directed energy may be applied at the correct location(s). The internal fiducials may be utilized to track motion of the region to which energy is being delivered. In some embodiments, there are multiple fiducials within the vessels being treated. For example, several fiducials are placed inside the renal artery so that the direction and/or shape of the vessel can be determined. Such information is important in the case of tortuosity of the blood vessel. Such redundancy can also be used to decrease the error and increase the accuracy of the targeting and tracking algorithms.

In one embodiment, a virtual fiducial is created via an imaging system. For example, in the case of a blood vessel such as the renal artery, an image of the blood vessel using B-mode ultrasound can be obtained which correlates to the blood vessel being viewed in direct cross section (1705; FIG. 17F). When the vessel is viewed in this type of view, the center of the vessel can be aligned with the center 1700 of an ultrasound array (e.g. HIFU array 1600) and the transducers can be focused and applied to the vessel, applying heat lesions 1680 to regions around the vessel 1705. With different positions of the transducers 1610 along a circumference or hemisphere 1650, varying focal points can be created 1620, 1630, 1640. The directionality of the transducers allows for a lesion(s) 1620, 1630, 1640 which run lengthwise along the vessel 1700. Thus, a longitudinal lesion 1620-1640 can be produced along the artery to insure maximal inhibition of nerve function. In some embodiments, the center of the therapeutic ultrasound transducer is off center relative to the center of the vessel so that the energy is applied across the vessel wall at an angle, oblique to the vessel. The transducer 1600 can also be aspheric in which the focus of the transducer is off center with respect to its central axis.

In this method of treatment, an artery such as a renal artery is viewed in cross-section or close to a cross-section under ultrasound guidance. In this position, the blood vessel is substantially parallel to the axis of the spherical transducer so as to facilitate lesion production. The setup of the ultrasound transducers 1600 has previously been calibrated to create multiple focal lesions 1620, 1630, 1640 along the artery if the artery is in cross-section 1680.

In one embodiment, the fiducial is an intravascular fiducial such as a balloon or a hermetically sealed transmitting device. The balloon is detectable via radiotransmitter within the balloon which is detectable by the external therapeutic transducers. The balloon can have three transducers, each capable of relaying its position so that the balloon can be placed in a three dimensional coordinate reference. Once the balloon is placed into the same coordinate frame as the external transducers using the transmitting beacon, the energy transducing devices can deliver energy (e.g. focused ultrasound) to the blood vessel (e.g. the renal arteries) or the region surrounding the blood vessels (e.g. the renal nerves). The balloon and transmitters also enable the ability to definitively track the vasculature in the case of movement (e.g. the renal arteries). In another embodiment, the balloon measures temperature or is a conduit for coolant applied during the heating of the artery or nerves. Multiple transducers might be set up outside the patient to detect the position of the internal fiducial from different directions (rather than three internal transducers, in this embodiment, there are three external transducers detecting the position of a single or multiple internal fiducials). Again, such redundancy in targeting position is beneficial because the exact position of the internal fiducial may be determined correctly. In another embodiment, multiple internal fiducials are placed inside the patient, in particular, within a blood vessel to determine the three dimensional orientation of the blood vessel.

Delivery of therapeutic ultrasound energy to the tissue inside the body is accomplished via the ultrasound transducers which are directed to deliver the energy to the target in the coordinate frame.

Once the target is placed in the coordinate frame and the energy delivery is begun, it is important to maintain targeting of the position, particularly when the target is a small region such as the sympathetic nerves. To this end, the position of the region of ablation is compared to its baseline position, both in a three dimensional coordinate reference frame. The ongoing positional monitoring and information is fed into an algorithm which determines the new targeting direction of the energy waves toward the target. In one embodiment, if the position is too far from the original position (e.g. the patient moves), then the energy delivery is stopped and the patient repositioned. If the position is not too far from the original position, then the energy transducers can be repositioned either mechanically (e.g. through physical movement) or electrically via phased array (e.g. by changing the relative phase of the waves emanating from the transducers). In another embodiment, multiple transducers are placed on the patient in different positions and each is turned on or off to result in the necessary energy delivery. With a multitude of transducers placed on the patient, a greater territory can be covered with the therapeutic ultrasound. The therapeutic positions can also serve as imaging positions for intrinsic and/or extrinsic fiducials.

In addition to heat delivery, ultrasound can be utilized to deliver cavitating energy which may enable drug delivery at certain frequencies. Cavitating energy can also lead to ablation of tissue at the area of the focus. A systemic dose of a drug can be delivered to the region of interest and the region targeted with the cavitating or other forms of ultrasonic energy. Other types of therapeutic delivery modalities include ultrasound sensitive bubbles or radiation sensitive nanoparticles, all of which enhance the effect of the energy at the target of interest. Therefore in one method, an ultrasonically sensitive bioactive material is administered to a patient, and focused ultrasound is applied through the skin of the patient to the region of the blood vessels leading to the kidney. The effect of the ultrasound on the region around the blood vessels is to release the bioactive material or otherwise heat the region surrounding the blood vessel. The ultrasonically sensitive bioactive material may be placed in a vessel, in which cases, ultrasound can be applied through the wall of the blood vessel to activate the material.

Figure 7E:
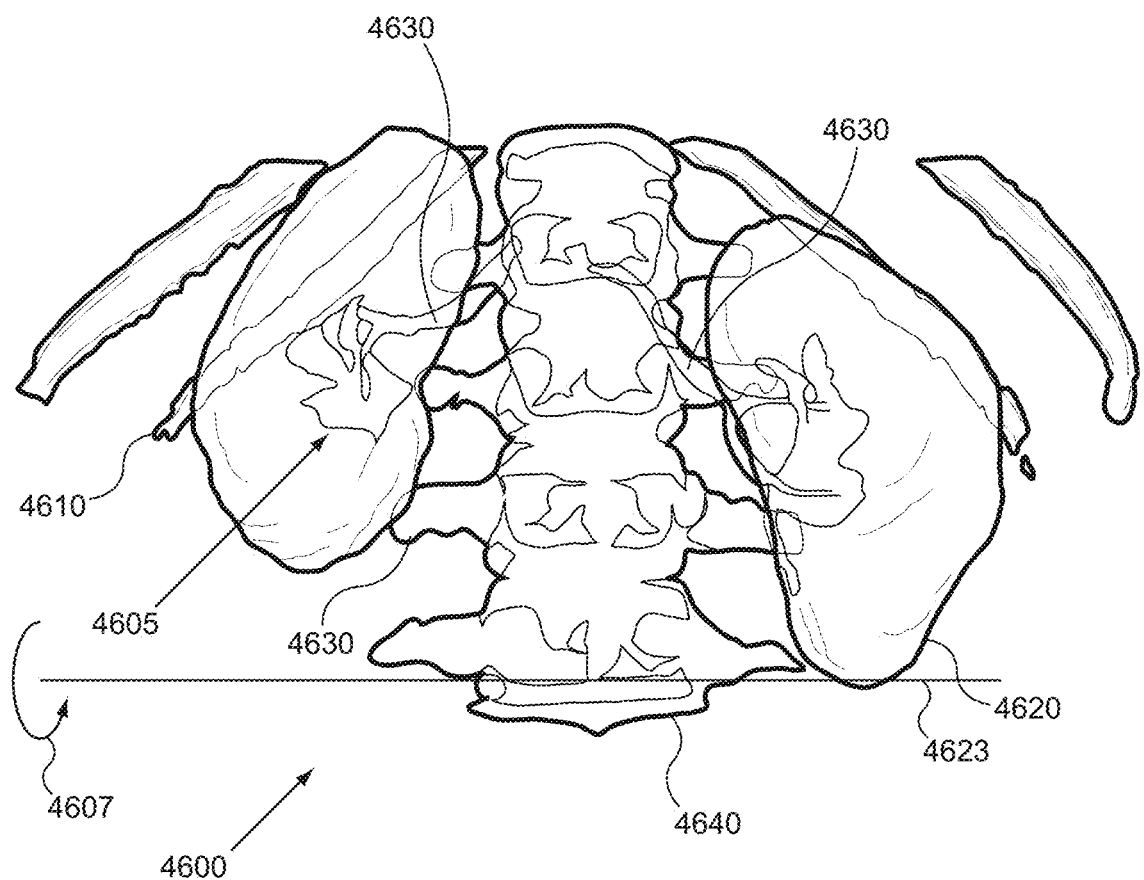
FIG. 7E depicts a geometric model obtained from cross-sectional images of the area of the aorta and kidneys along with angles of approach to the blood vessels and the kidney.

FIG. 7E depicts the anatomy of the region 4600, the kidneys 4620, renal arteries 4630, and bony structures 4610, 4640 as viewed from behind a human patient. FIG. 7E depicts the real world placement of the renal arteries into coordinate frame as outlined in FIG. 7D. Cross sectional CT scans from actual human patients were integrated to create a three-dimensional representation of the renal artery, kidney, and mid-torso region. Plane 4623 is a plane parallel to the transverse processes and angle 4607 is the angle one has to look up (toward the head of the patient) in order to "see" the renal artery under the rib. Such real world imaging and modeling allows for an optimal system to be developed so as to maximize efficacy and minimize risk of the treatment. Therefore with these parameters to consider, a system to treat the nerves surrounding the renal arteries is devised in which a transducer is positionable (e.g., to adjust a line of sight) with a negative angle with respect to a line connecting the spinal processes. Multiple transducers may be utilized to allow variations in the positioning associated with variations in anatomy or during respiratory motion, wherein the anatomy may be tracked during treatment.

Figure 7F:
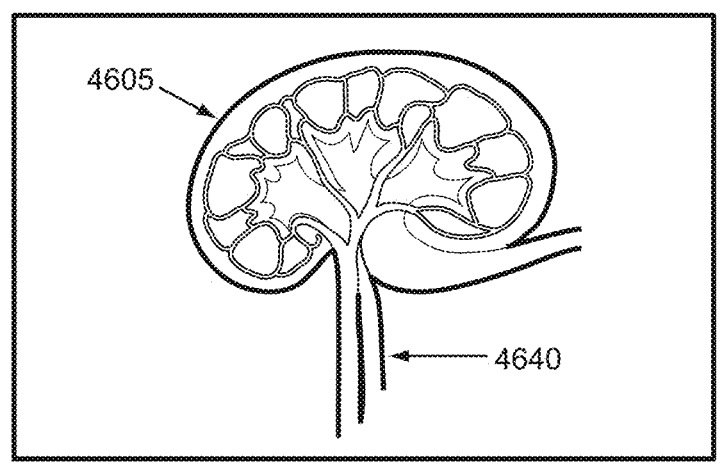
FIG. 7F depicts a close up image of the region of treatment.
Figure 71:
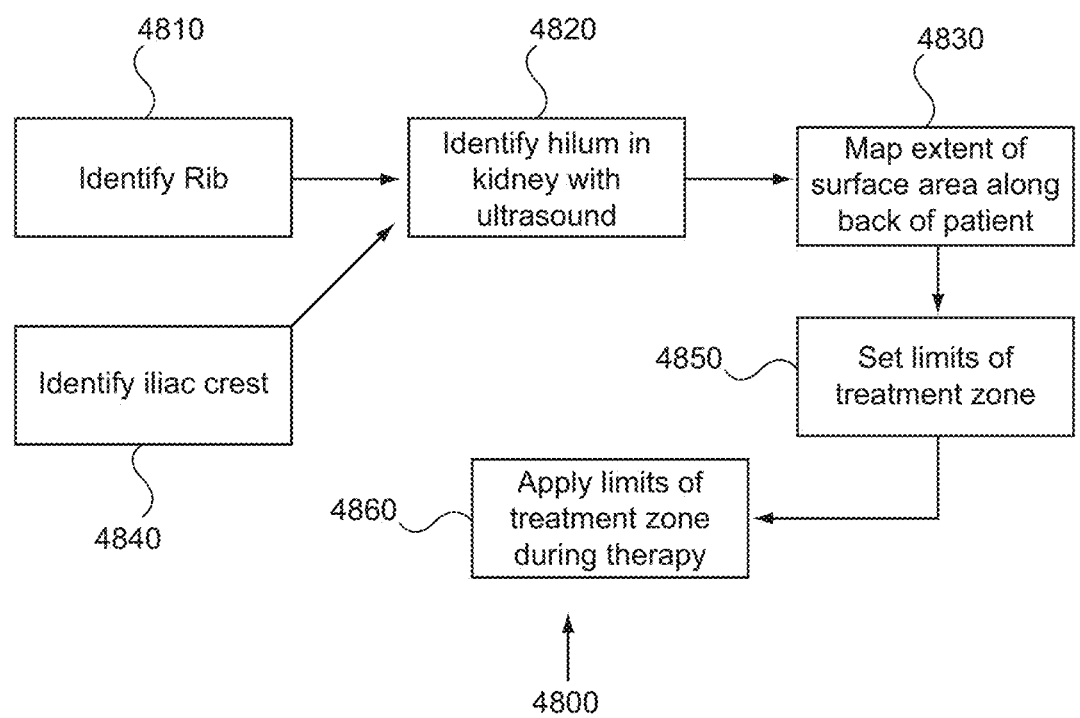

FIG. 7F depicts an image of the region of the renal arteries and kidney 4605 using ultrasound. The renal hilum containing the arteries and vein can be visualized using this imaging modality. This image is typical when looking at the kidney and renal artery from the direction and angle depicted in FIG. 7E. Importantly, at the angle 4607 in 7E, there is no rib in the ultrasound path and there no other important structures in the path either.

An ultrasound imaging trial was then performed to detect the available windows to deliver therapeutic ultrasound to the region of the renal arteries 4630 from the posterior region of the patient. It was discovered that the window depicted by arrow 4600 and depicted by arrow 4605 in the cross-sectional ultrasound image from ultrasound (FIG. 7F) provided optimal windows to visualize the anatomy of interest (renal pedicle).

FIG. 7G contains some of the important data from the trial 4700, the data in the "standard position 4730." These data 4720 can be used to determine the configuration of the clinical HIFU system to deliver ultrasound to the renal hilum. The renal artery 4635 was determined to be 7-17 cm from the skin in the patients on average. The flank to posterior approach was noted to be optimum to image the renal artery, typically through the parenchyma of the kidney as shown in FIG. 7F 4605. The hilum 4640 of the kidney is approximately 4-8 cm from the ultrasound transducer and the angle of approach 4637 (4607 in FIG. 7E) relative to an axis defined by the line connecting the two spinous processes and perpendicular to the spine . . . is approximately −10 to −48 degrees. It was also noted that the flank approach through the kidney was the safest approach in that it represents the smallest chances of applying ultrasound to other organs such as bowel.

Therefore, with these data, a system algorithm for treatment may been devised: b-mode ultrasound is utilized to visualize the kidney in cross-section; doppler ultrasound is utilized to identify the pedicle 4640 traveling to the kidney with the renal artery as the identifying anatomical structure via Doppler ultrasound; the distance to the pedical is determined via the b-mode imaging. With the kidney inside the b-mode image, safety can be attained as the kidney has been determined to be an excellent heat sink and absorber (that is HIFU has little effect on the kidney) of HIFU (see in-vivo data below); the distance is fed into the processing algorithm and the HIFU transducer is fed the position data of the HIFU transducer. Furthermore, small piezoelectric crystals may be located at (e.g., along) the therapeutic ultrasound transducer, and may be utilized to determine a safe path between a source of ultrasound from the crystal at the ultrasound transducer and the target blood vessel. An echo may be sent from the crystal to the target and the time for a return signal may be determined. With the information about the return signal (e.g. distance to target, speed of return), the safety of the path may be determined. If bowel with air inside (for example) were in the path, the return signal would deviate from an expected signal, and the transducer can then be repositioned. Similarly, if bone (e.g. rib) is in the path of the ultrasound beam, the expected return signal will significantly deviate from the expected return time, thereby indicating that the path cannot be utilized.

Upon further experimentation, it was discovered that by positioning the patient in the prone position (backside up, abdomen down), the structures under study 4750 . . . that is, the renal arteries 4770 and 4780, the kidney hilum were even closer to the skin and the respiratory motion of the artery and kidney was markedly decreased. FIG. 7H depicts these results 4750, 4760 showing the renal artery 4770 at 6-10 cm and the angle of approach 4790 relative to the spine 4607 shallower at −5 to −20 degrees. Similar results were obtained in the case where the patient remained flat and the legs were propped up using a wedge or bump under them.

Therefore, with these clinical data, in one embodiment, a method of treatment 4800 (FIG. 7I) of the renal nerves in a patient has been devised: 1) identify the rib 4810 and iliac crest 4840 of a patient on the left and right flank of the patient 4810; 2) identify the left or right sided kidney with ultrasound 4820; 3) identify the hilum of the kidney and the extent the renal hilum is visible along surface of patient 4820 using an imaging technology; 4) identify the blood vessels leading to the kidney from one or more angles, extracting the extent of visibility 4860 along the surface area of the patient's back; 5) determine the distance to the one or more of the renal artery, renal vein, kidney, and the renal hilum 4850; 6) optionally, position patient in the prone position with a substantive positioning device underneath the back of the patient or overtop the abdomen of the patient 4830, to optimize visibility; 7) optionally determine, through modeling, the required power to obtain a therapeutic dose at the renal hilum and region around the renal blood vessels; 8) apply therapeutic energy to renal blood vessels; 9) optionally track the region of the blood vessels to ensure the continued delivery of energy to the region as planned in the modeling; 10) optionally, turning off delivery of energy in the case the focus of the energy is outside of the planned region; 11) optionally, adapting the system through movement of the therapeutic and imaging ultrasound transducers so as to orient the ultrasound applicators in relation to the vessel target; 12) optionally placing a fiducial in one or more blood vessels to further enhance the device's ability to localize and track the vessel; 13) determining an algorithm for treatment based on one or more of: the distance to the vessel, the thickness of the skin, the thickness of the muscle, and the thickness of the kidney through which the ultrasound traverses; 14) applying the therapeutic ultrasound with pulses in less than 10 s to ramp up and apply at least 100 W/cm$^2$ for at least one second; 15) optionally, directing the therapeutic transducer at an angle anywhere from −5 to −25 degrees (i.e. pointing upward toward the cephalic region) relative to a line connecting the spinous process.

Figure 7J:
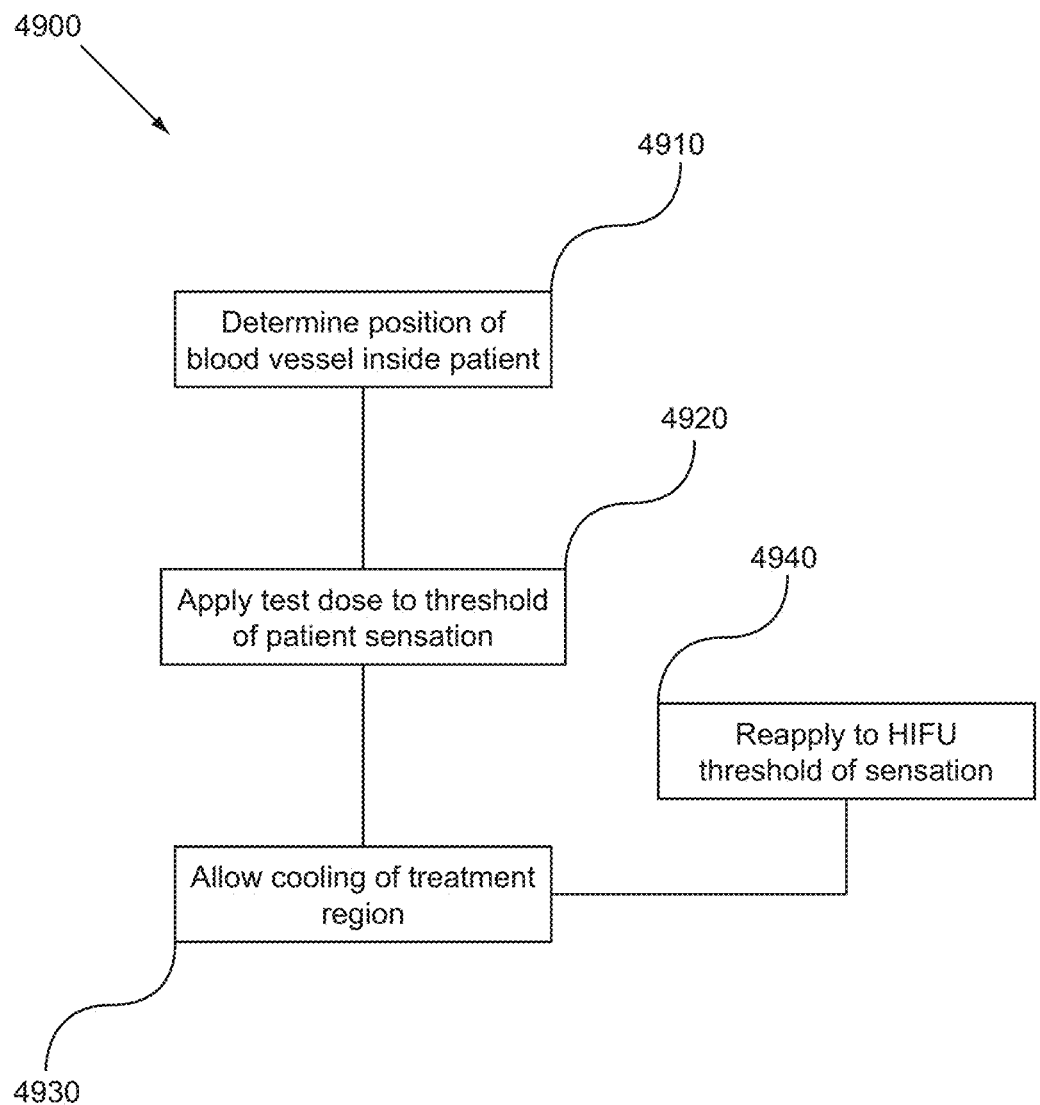
FIG. 7J depicts a clinical algorithm to apply energy to the blood vessel leading to the kidney.
Figure 7K:
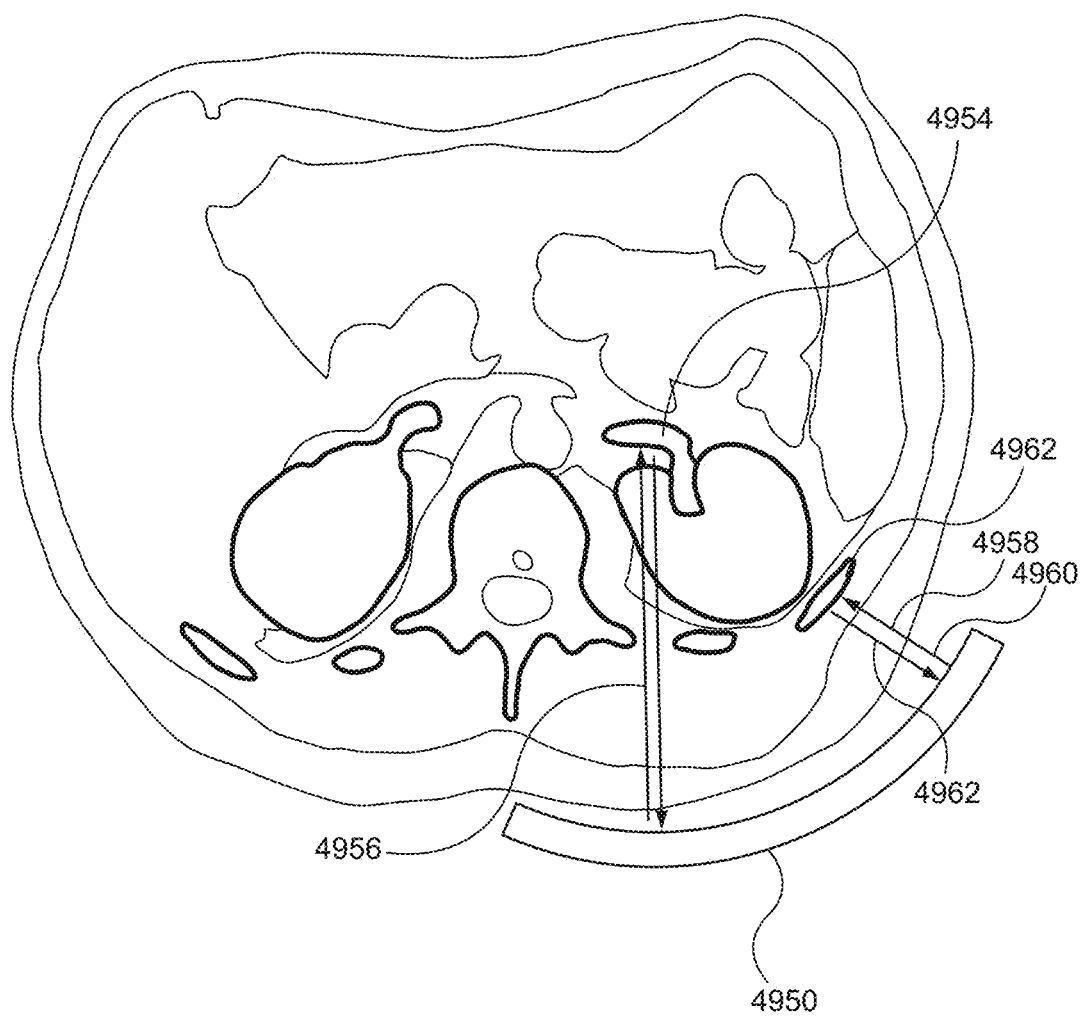
FIG. 7K depicts a device to diagnose proper directionality to apply energy to the region of the kidney.

In another embodiment, FIG. 7J, a clinical algorithm 4900 is depicted in which a position of a blood vessel is determined 4910. For example, the blood vessel may be adjacent a nerve region of interest (e.g. renal artery and nerve, aorta and sympathetic nerves, cerebral arteries and nerves, carotid artery and nerves). A test dose of energy is applied to the threshold of patient sensation 4920. In the case of a renal nerve, the sensation threshold might be a renal colic type of sensation. At the point of sensation 4920, the dose can be lowered and cooled and then an additional dose can be applied at a level just below the sensation threshold. Such a sequence 4900 can be repeated 4940 many times over until the desired effect is achieved. Intermittent off time allows for cooling 4930 of the region. In FIG. 7K, a transducer 4950 is depicted with both diagnostic and therapeutic ability. Wave 4960 is a diagnostic wave which in this example interferes with bone (rib). In some embodiments, the therapeutic wave which would otherwise emanate from this region of the transducer is switched off and therapeutic waves are not generated. On the other side of the transducer, waves 4956 do indeed allow a clear path to the renal blood vessels 4954 and indeed a therapeutic beam is permitted from this region. The diagnostic energy may be ultrasonic energy, radiofrequency energy, X-ray energy, or optical energy. For example, MRI, ultrasound, CT scan, or acoustic time of flight technology might be utilized to determine whether or not a clear path to the renal hilum exists.

In summary, in one technique, a diagnostic test energy is delivered through the skin to the region of the renal blood vessels. Next, an assessment of the visibility of the renal hilum in terms of distance and clearance is made and therapeutic transducers are switched on or off based on clearance to the renal hilum from a path through the skin. Such a technique might continue throughout treatment or prior to treatment.

Figure 7L:
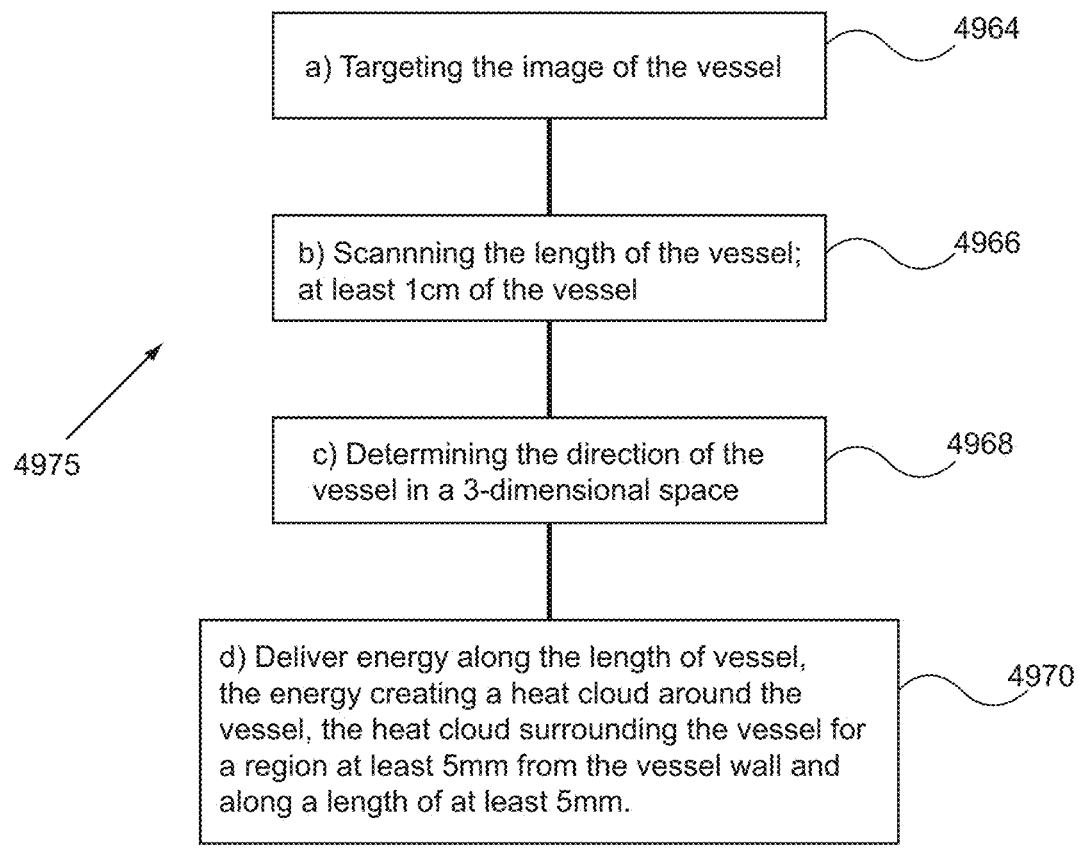
FIG. 7L depicts a methodology to ablate a nerve around an artery by applying a cloud of heat or neurolytic substance.

Combining the above data, FIG. 7L depicts a generalized system to inhibit nerves which surround a blood vessel 4975. In a first step, an image of the vessel is produced 4964; next a length of the vessel is scanned 4966; following this step, a direction of the vessel is determined in three dimensional space and delivery of a heat cloud is performed circumferentially around the vessel in which the heat cloud is produced at least 5 mm from the vessel wall in a radial direction and over a length of at least 5 mm. The cloud is a region of diffused heat without focal hot spots. The heat diffuses from the region and can be generated from inside the vessel or outside the vessel. The vessel itself is protected by convection and removal of heat from the vessel via the natural blood flow or through the addition of an additional convective device in or near the vessel.

The heat cloud can be generated by high intensity ultrasound (see modeling and data below), radiofrequency energy, and/or optical energy. For example, infrared energy can be delivered through the blood vessel wall to heat the region surrounding the blood vessel. The heating effect can be detected through MRI thermometry, infrared thermometry, laser thermometry, etc. The infrared light may be applied alone or in combination with phototherapeutic agents.

In some embodiments, a heat cloud is not generated but a cloud to inhibit or ablate nerves in the region may be provided. Such cloud may be gas (e.g. carbon dioxide), liquid (hot water), phototherapeutic agents, and other toxins such as ethanol, phenol, and neurotoxins.

In contrast to devices which deliver highly focused heat to the wall and rely on conduction or current fall from the vessel wall, a heatcloud or generalized cloud presents a potentially safer option in which the nerve ablating components are diffused around the vessel.

Figure 7M:
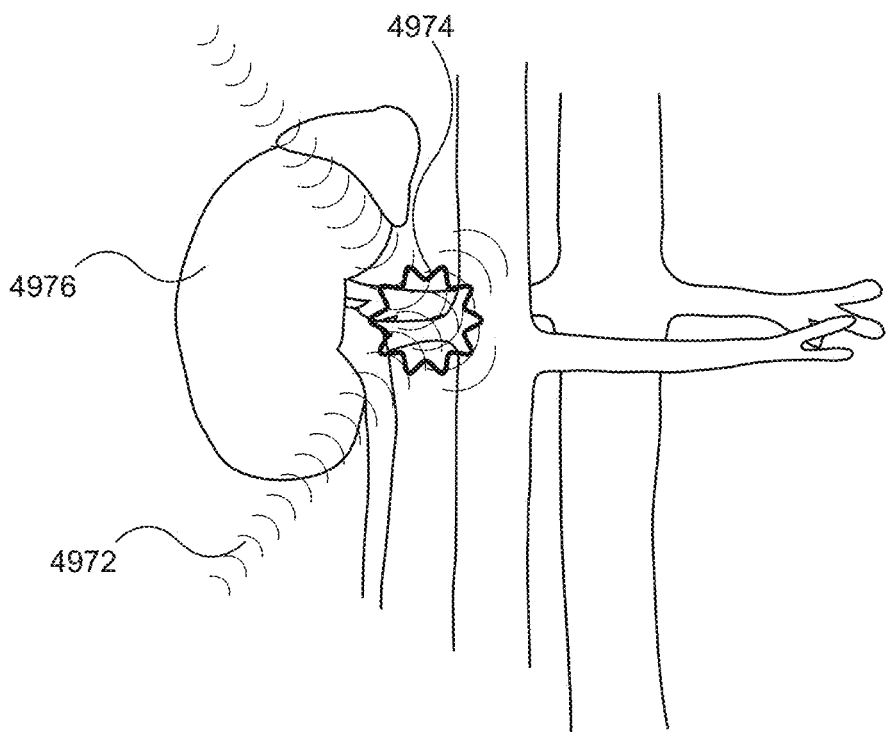
FIG. 7M depicts a clinical algorithm to apply energy along a renal blood vessel.

FIG. 7M depicts an example of delivering a heat cloud 4974 to a blood vessel from outside the patient 4972. The vessel is placed in a three dimensional coordinate reference. The vessel is targeted during treatment. The cloud surrounds the vessels and the entire hilum leading to the kidney.

Figure 7N:
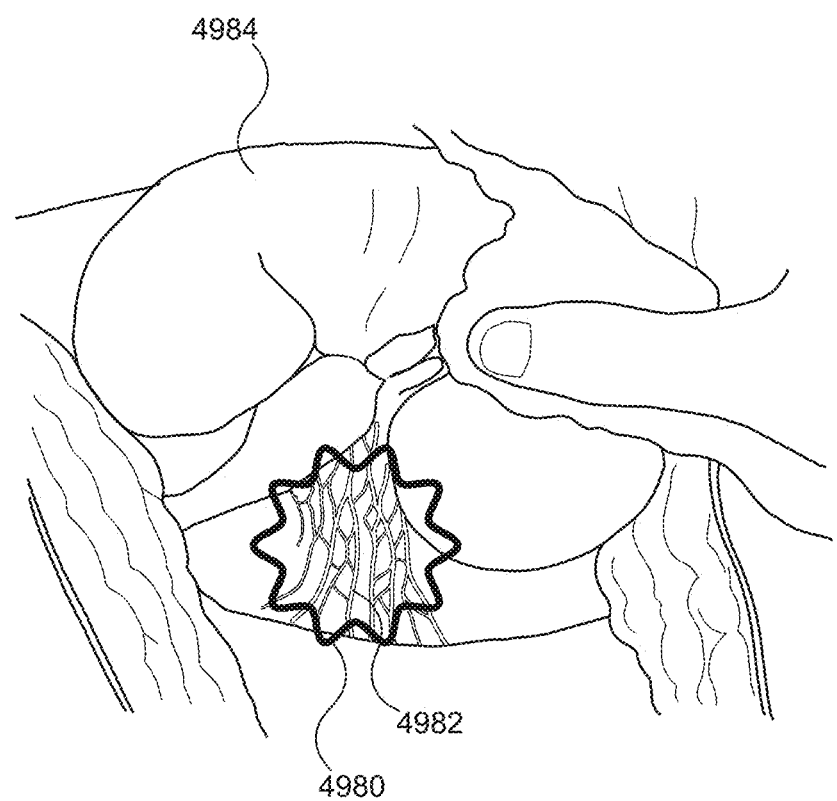
FIG. 7N depicts a cloud of heat to affect the nerves leading to the kidney.

FIG. 7N shows a depiction of the nerves leading to the kidney. This picture is from an actual dissection of the vessels from a human cadaver. As can be seen, the nerves 4982 surround the blood vessels leading to the kidney 4984. The heat cloud 4980 is shown surrounding the nerves 4982 leading to the kidney 4984. Importantly, limitation of previous catheter based approaches was that the heat cloud could not be generated around the vessels from a location inside the vessels. This heat cloud effectively allows for the target region to be overscanned during the treatment.

Figure 7O:
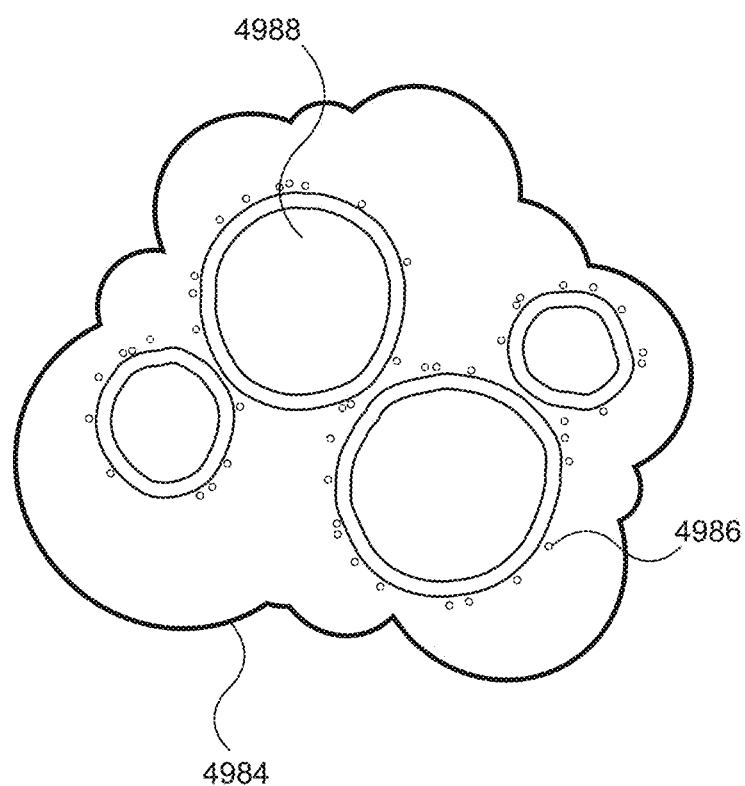
FIG. 7O depicts a close up of a heat cloud as well as nerves leading to the kidney.

FIG. 7O depicts a cross section of the cloud 4984 surrounding the nerves 4986 and vessels 4988. It can be seen that a focal method to heat the nerves through the vessel wall might be difficult to affect a large portion of the nerves because the nerves are so diffusely presented in the region in some cases. Therefore, in this embodiment, heat is applied diffusely to the region surrounding the blood vessel in the form of a cloud.

Figure 8A:
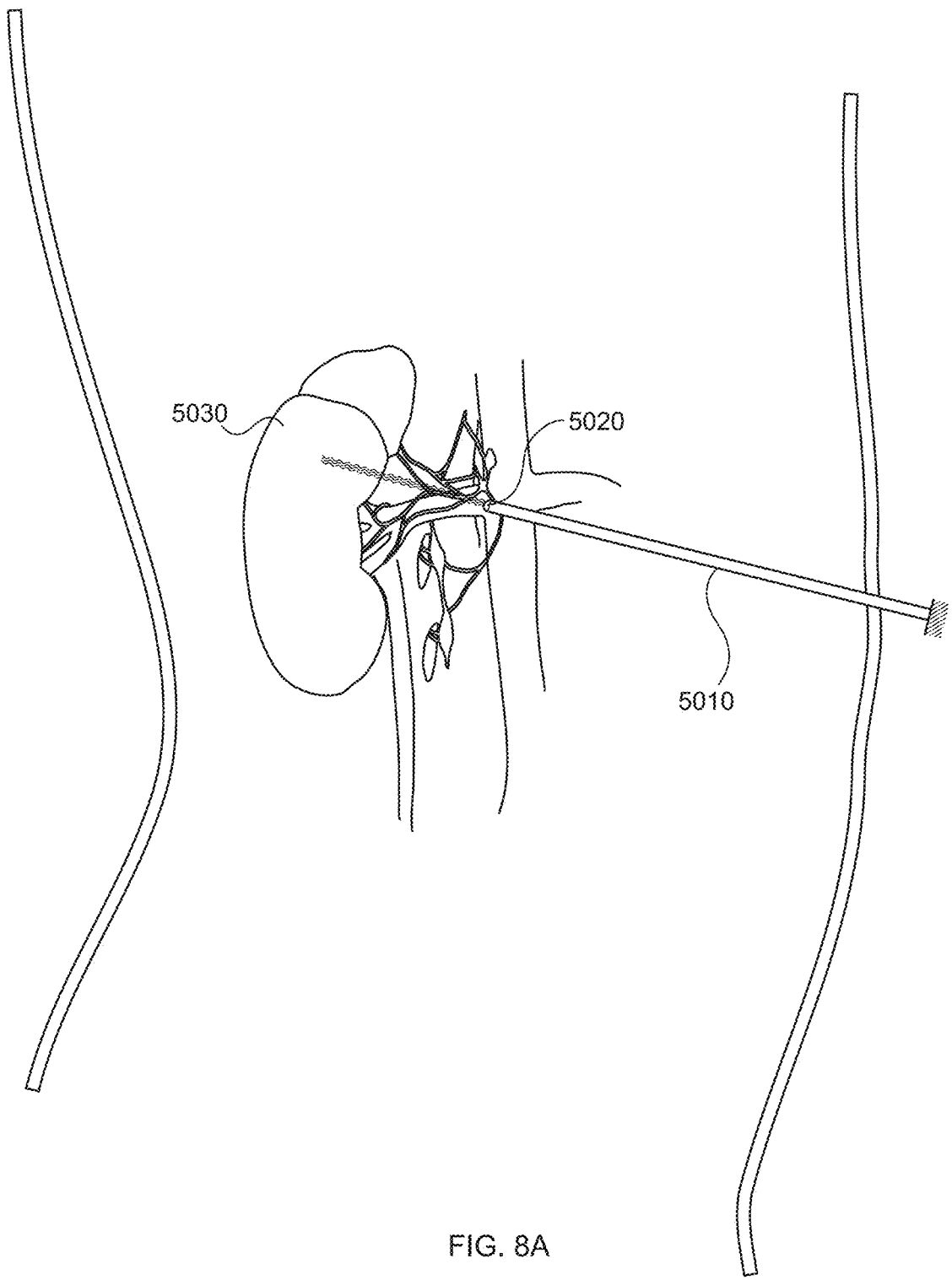
FIG. 8A depicts a percutaneous approach to treating the autonomic nervous system surrounding the kidneys.

FIG. 8A depicts a percutaneous procedure and device 5010 in which the region around the renal artery is directly approached through the skin from an external position. A combination of imaging and application of energy (e.g. ablation) may be performed to ablate the region around the renal artery to treat hypertension, end stage renal disease, diabetes, sleep apnea, and/or heart failure. Probe 5010 is positioned through the skin and in proximity to the kidney 5030. The probe may include sensors at its tip 5020 which detect heat or temperature or may enable augmentation of the therapeutic energy delivery. One or more imaging devices (e.g., CT device, ultrasound device, MRI device) may be utilized to ensure a clear path for the probe to reach the region of the renal hilum. Ablative, ionizing energy, heat, or light may be applied to the region to inhibit the sympathetic nerves around the renal artery using the probe 5010. Ultrasound, radiofrequency, microwave, direct heating elements, and balloons with heat or energy sources may be applied to the region of the sympathetic nerves. Imaging may be included on the probe or performed separately while the probe is being applied to the region of the renal blood vessels.

In one embodiment, the percutaneous procedure in FIG. 8A is performed under MRI, CT, or ultrasound guidance to obtain localization or information about the degree of heat being applied. In one embodiment, ultrasound is applied but at a sub-ablative dose. That is, the energy level is enough to damage or inhibit the nerves but the temperature is such that the nerves are not ablated but paralyzed or partially inhibited by the energy. A particularly preferred embodiment would be to perform the procedure under guidance from an MRI scanner because the region being heated can be determined anatomically in real time as well via temperature maps. As described above, the images after heating can be compared to those at baseline and the signals are compared at the different temperatures.

In one embodiment, selective regions of the kidney are ablated through the percutaneous access route; for example, regions which secrete hormones which are detrimental to a patient or to the kidneys or other organs. Using energy applied externally to the patient through the skin and from different angles affords the ability to target any region in or on the kidney or along the renal nerves or at the region of the adrenal gland, aorta, or sympathetic chain. This greater breadth in the number of regions to be targeted is enabled by the combination of external imaging and external delivery of the energy from a multitude of angles through the skin of the patient and to the target. The renal nerves can be targeted at their takeoff from the aorta onto the renal artery, at their synapses at the celiac ganglia, or at their bifurcation point along the renal artery.

Figure 8B:
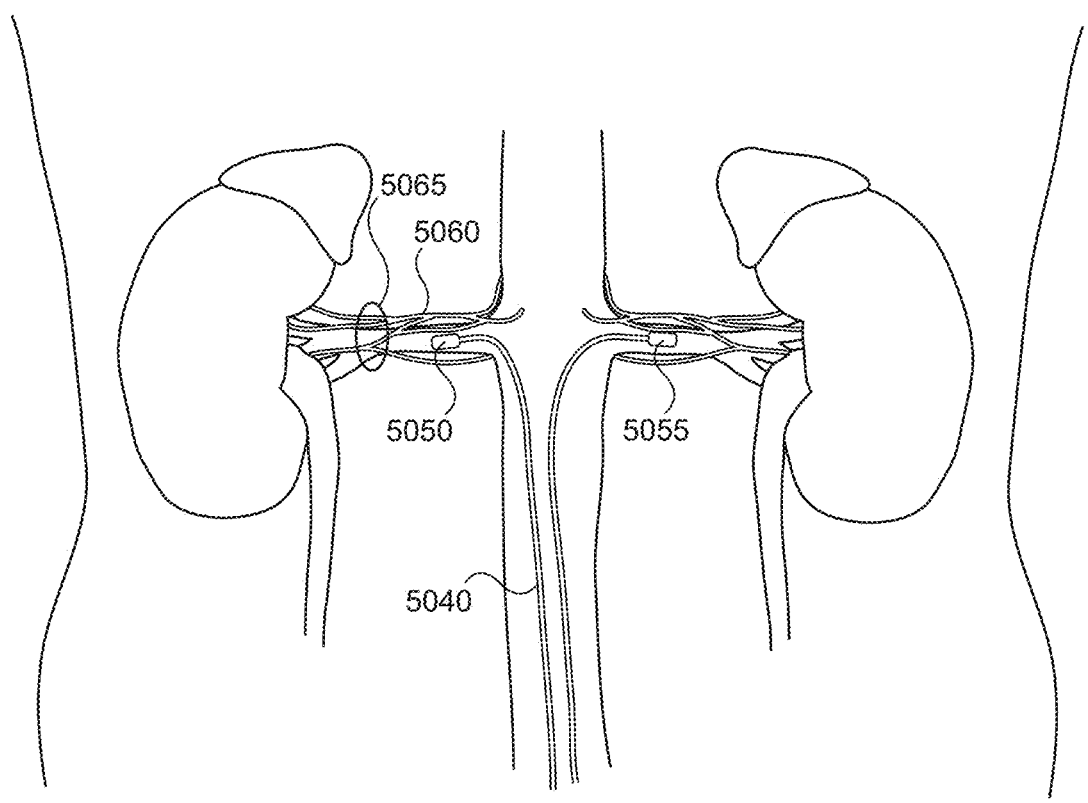
FIG. 8B depicts an intravascular approach to treating or targeting the autonomic nervous system.

In a further embodiment, probe 5010 can be utilized to detect temperature or motion of the region while the ultrasound transducers are applying the energy to the region. A motion sensor, position beacon, or accelerometer can be used to provide feedback for the HIFU transducers. In addition, an optional temperature or imaging modality may be placed on the probe 5010. The probe 5010 can also be used to locate the position within the laparoscopic field for the ablations to be performed. The dose delivered by this probe is approximately In FIG. 8B, intravascular devices 5050, 5055 are depicted which apply energy to the region around the renal arteries 5065 from within the renal arteries. The intravascular devices can be utilized to apply radiofrequency, ionizing radiation, and/or ultrasound (either focused or unfocused) energy to the renal artery and surrounding regions. MRI or ultrasound or direct thermometry can be further utilized to detect the region where the heat is being applied while the intravascular catheter is in place.

In one embodiment, devices 5050, 5055 (FIG. 8B) apply ultrasound energy which inhibits nerve function not by heating, but by mechanisms such as periodic pressure changes, radiation pressure, streaming or flow in viscous media, and pressures associated with cavitation, defined as the formation of holes in liquid media. Heat can selectively be added to these energies but not to create a temperature which ablates the nerves, thereby facilitating the mechanism of vibration and pressure. In this embodiment, the ultrasound is not focused but radiates outward from the source to essentially create a cylinder of ultrasonic waves that intersect with the wall of the blood vessel. An interfacial material between the ultrasound transducer and the wall of the artery may be provided such that the ultrasound is efficiently transduced through the arterial wall to the region of the nerves around the artery. In another embodiment, the ultrasound directly enters the blood and propagates through the ultrasound wall to affect the nerves. In some embodiments, cooling is provided around the ultrasound catheter which protects the inside of the vessel yet allows the ultrasound to penetrate through the wall to the regions outside the artery. A stabilization method for the ultrasound probe is also included in such a procedure. The stabilization method might include a stabilizing component added to the probe and may include a range finding element component of the ultrasound so that the operator knows where the ultrasound energy is being applied from outside the wall of the blood vessel.

In another embodiment, an ultrasound probe is applied directly to the wall of the blood vessel, utilizing heat and/or vibration to inhibit the nerves surrounding the blood vessel. In this embodiment, the temperature at the wall of the blood vessel can be measured directly at the catheter tip through laser thermometry or a thermistor. Alternatively, MRI or infrared thermometry can be used as well.

Imaging can be performed externally or internally in this embodiment in which a catheter is placed inside the renal arteries. For example, external imaging with MRI or Ultrasound may be utilized to visualize changes during the ultrasound modulation of the nerve bundles. Indeed, these imaging modalities may be utilized for the application of any type of energy within the wall of the artery. For example, radiofrequency delivery of energy through the wall of the renal artery may be monitored through similar techniques. Thus the monitoring of the procedural success of the technique is independent of the technique in most cases. In one method, a radiofrequency catheter is applied to the wall of the blood vessel and the temperature of the region around the blood vessel is measured. In another embodiment, heated water vapor is applied to the region of the blood vessel. In another embodiment, MRI induced heating of a metallic tipped catheter is detected using MRI thermometry. In another embodiment, focused ultrasound is detected using MRI thermometry.

Alternatively, in another embodiment, the devices 5050, 5055 can be utilized to direct externally applied energy (e.g. ultrasound) to the correct place around the artery as the HIFU transducers deliver the energy to the region. For example, the intravascular probe 5050 can be utilized as a homing beacon for the imaging/therapeutic technology utilized for the externally delivered HIFU.

Figure 8C:
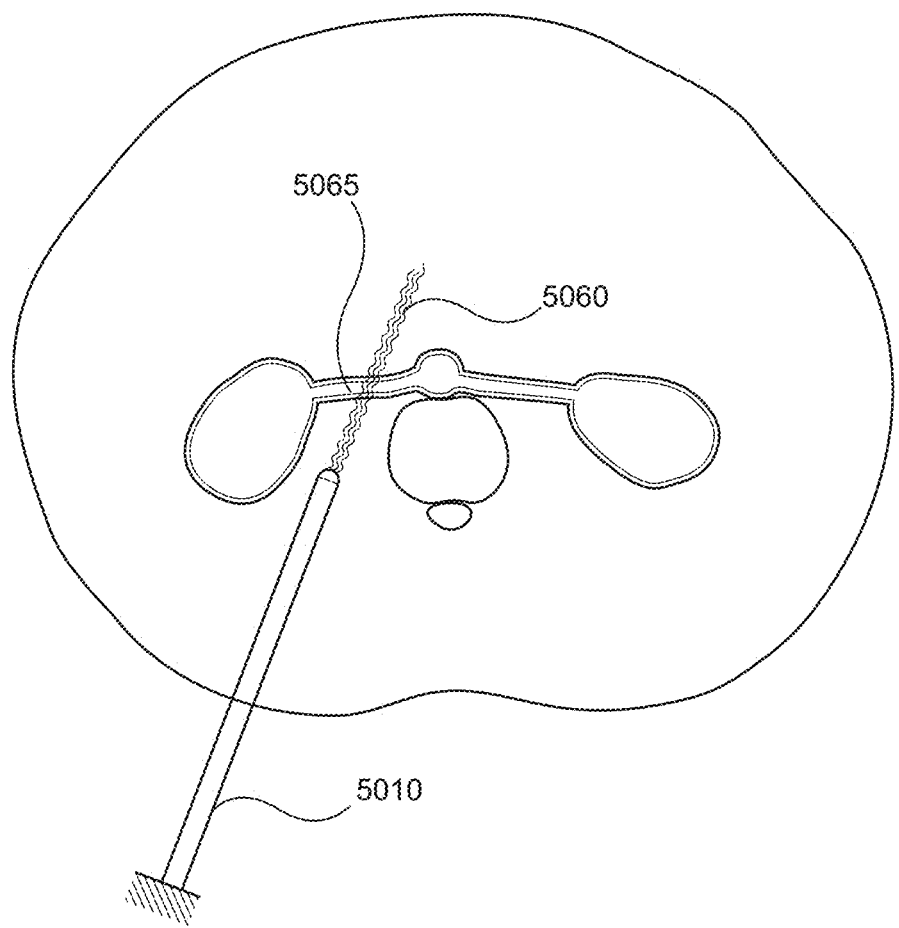
FIG. 8C depicts a percutaneous approach to the renal hila using a CT scan and a probe to reach the renal blood vessels.

FIG. 8C depicts a percutaneous procedure to inhibit the renal sympathetic nerves. Probe 5010 is utilized to approach the renal hilum 5060 region from posterior and renal artery 5065. With the data presented below, the probe can be armed with HIFU to denervate the region. The data presented below indicates the feasibility of this approach as far as ultrasound enabling denervation of the vessels quickly and easily. In another embodiment, a cloud of heat energy is produced near or around the blood vessel, for example, with warmed gas, with a neurotoxin, with a gas such as carbon dioxide which is known to anesthetize nerves at high concentrations, etc.

Figure 8D:
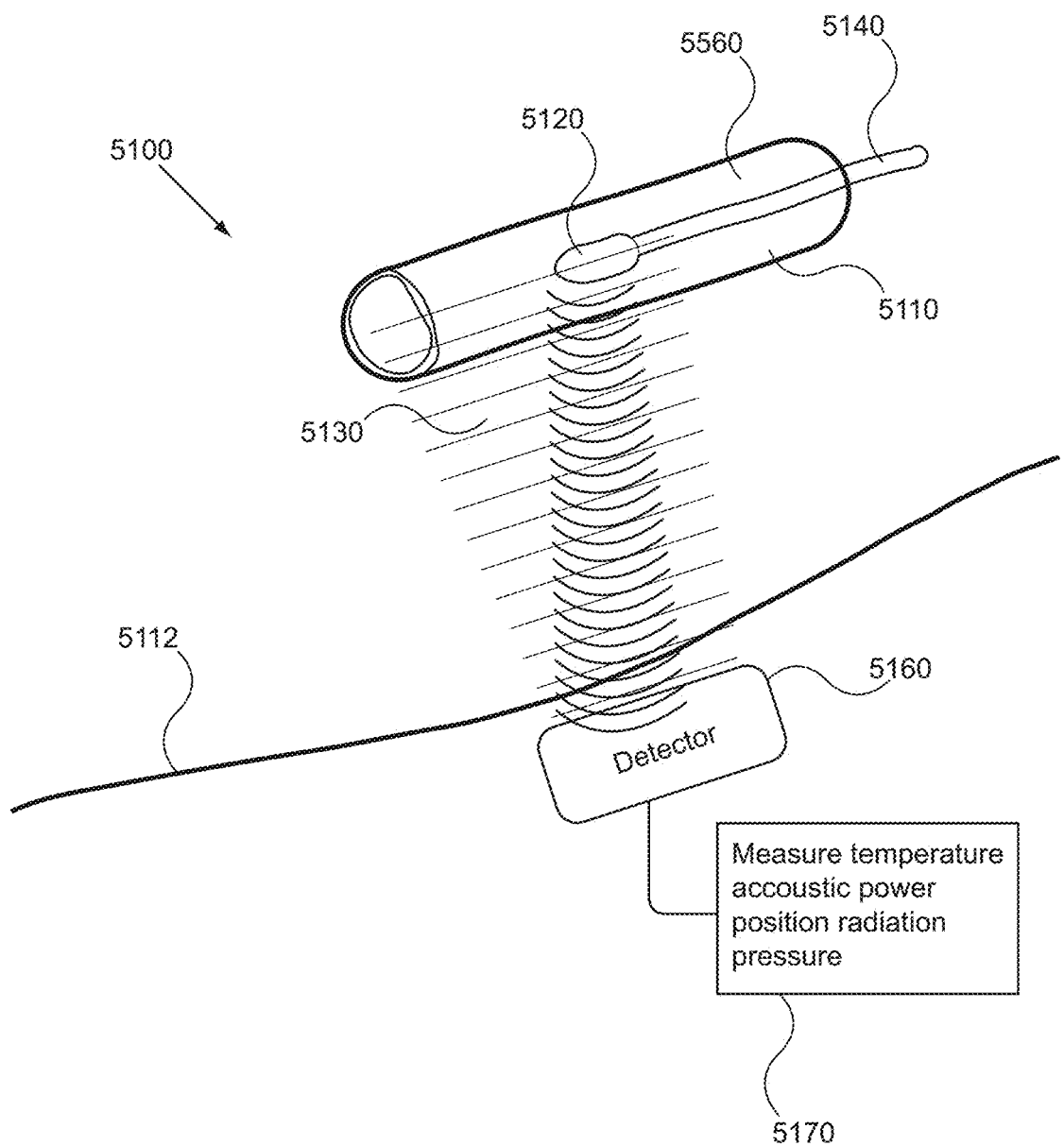
FIG. 8D depicts an intravascular detection technique to characterize the interpath between the blood vessel and the skin.

In FIG. 8D, a technique is shown in which ultrasound transmitted through the wall of a blood vessel 5560 from a catheter 5140 with a piezoelectric crystal 5120 at one end. A detector 5160 is placed outside the skin 5112 of the patient to detect the signal emitted from the piezoelectric. A number of parameters 5170 can be determined/detected with this method including position, temperature, acoustic power, radiation pressure, and cavitation threshold. The detection might be done inside the catheter in some embodiments or at the skin in other embodiments. In one embodiment, for example, the acoustic impedance from the blood vessel to the skin is determined through the detection of the time of flight of the ultrasound waves from the piezoelectric transducer on the end of the catheter. In another embodiment, structures which might block ultrasound are detected by sending a signal to the external detector form the internal detector.

FIGS. 8E and 8F depict cross sectional 5200 imaging of the abdomen. Energy waves 5230 are depicted traveling from a posterior direction through the skin to the region of the blood vessels 5210 leading to the kidney. Device 5240 can be placed outside the patient on the skin of the patient, which transmit the waves 5230 to a nerve region surrounding a blood vessel. CT or MRI imaging can be utilized during the procedure to help direct the waves. In addition, or alternatively, thermal imaging (e.g. with infrared or laser light) may be used.

Figure 9A:
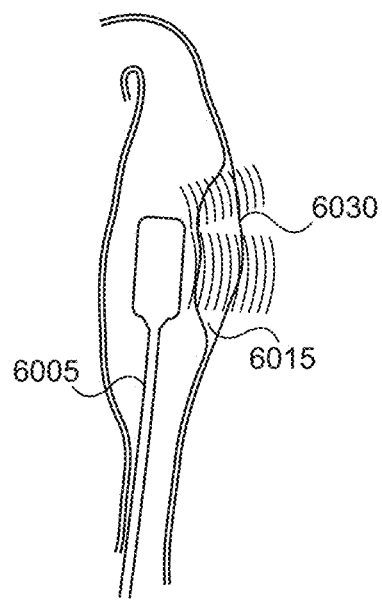
FIGS. 9A-9C depicts the application of energy from inside the aorta to regions outside the aorta to treat the autonomic nervous system.

In another embodiment, the physiologic process of arterial expansion (aneurysms) is targeted. In FIG. 9a, an ultrasound transducer is 6005 is placed near the wall of an aneurysm 6030. Ultrasonic energy 6015 is applied to the wall 6030 of the aneurysm to thicken the wall and prevent further expansion of the aneurysm. In some embodiments, clot within the aneurysm is targeted as well so that the clot is broken up or dissolved with the ultrasonic energy. Once the wall of the aneurysm is heated with ultrasonic energy to a temperature of between 40 and 70 degrees, the collagen, elastin, and other extracellular matrix in the wall will harden as it cools, thereby preventing the wall from further expansion.

In another embodiment, a material is placed in the aneurysm sac and the focused or non-focused ultrasound utilized to harden or otherwise induce the material in the sac to stick to the aorta or clot in the aneurysm and thus close the aneurysm permanently. In one embodiment therefore, an ultrasound catheter is placed in an aorta at the region of an aneurysm wall or close to a material in an aneurysmal wall. The material can be a man-made material placed by an operator or it can be material such as thrombus which is in the aneurysm naturally. Ultrasound is applied to the wall, or the material, resulting in hardening of the wall or of the material, strengthening the aneurysm wall and preventing expansion. The energy can also be applied from a position external to the patient or through a percutaneously positioned energy delivering catheter.

Figure 9B:
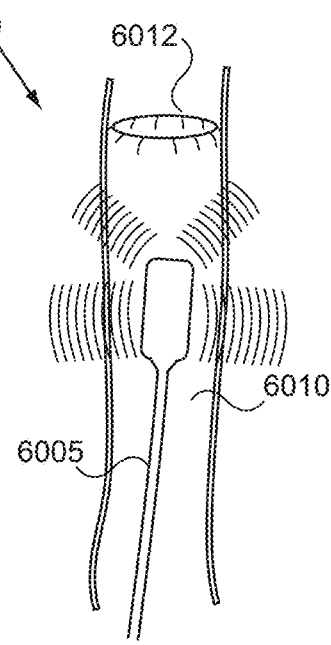

FIG. 9b 6000 depicts a clot prevention device 6012 (vena cava filter) within a blood vessel such as the aorta or vena cava 6010. The ultrasound catheter 6005 is applied to the clot prevention device (filter) 6012 so as to remove the clot from the device or to free the device 6012 from the wall of the blood vessel in order to remove it from the blood vessel 6000.

Figure 9C:
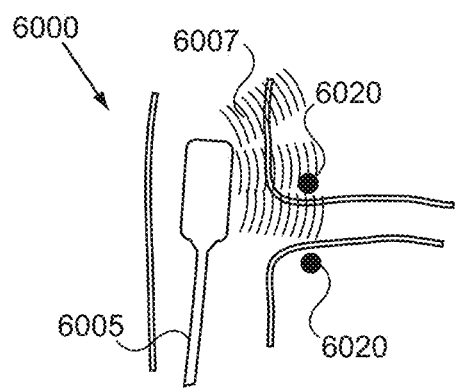

FIG. 9C depicts a device and method in which the celiac plexus 6020 close to the aorta 6000 is ablated or partially heated using heat or vibrational energy from an ultrasonic energy source 6005 which can apply focused or unfocused sound waves 6007 at frequencies ranging from 20 kilohertz to 5 Mhz and at powers ranging from 1 mW to over 100 kW in a focused or unfocused manner. Full, or partial ablation of the celiac plexus 6020 can result in a decrease in blood pressure via a similar mechanism as applying ultrasonic energy to the renal nerves; the ablation catheter is a focused ultrasound catheter but can also be a direct (unfocused) ultrasonic, a microwave transducer, or a resistive heating element. Energy can also be delivered from an external position through the skin to the aorta or celiac plexus region.

Figure 10:
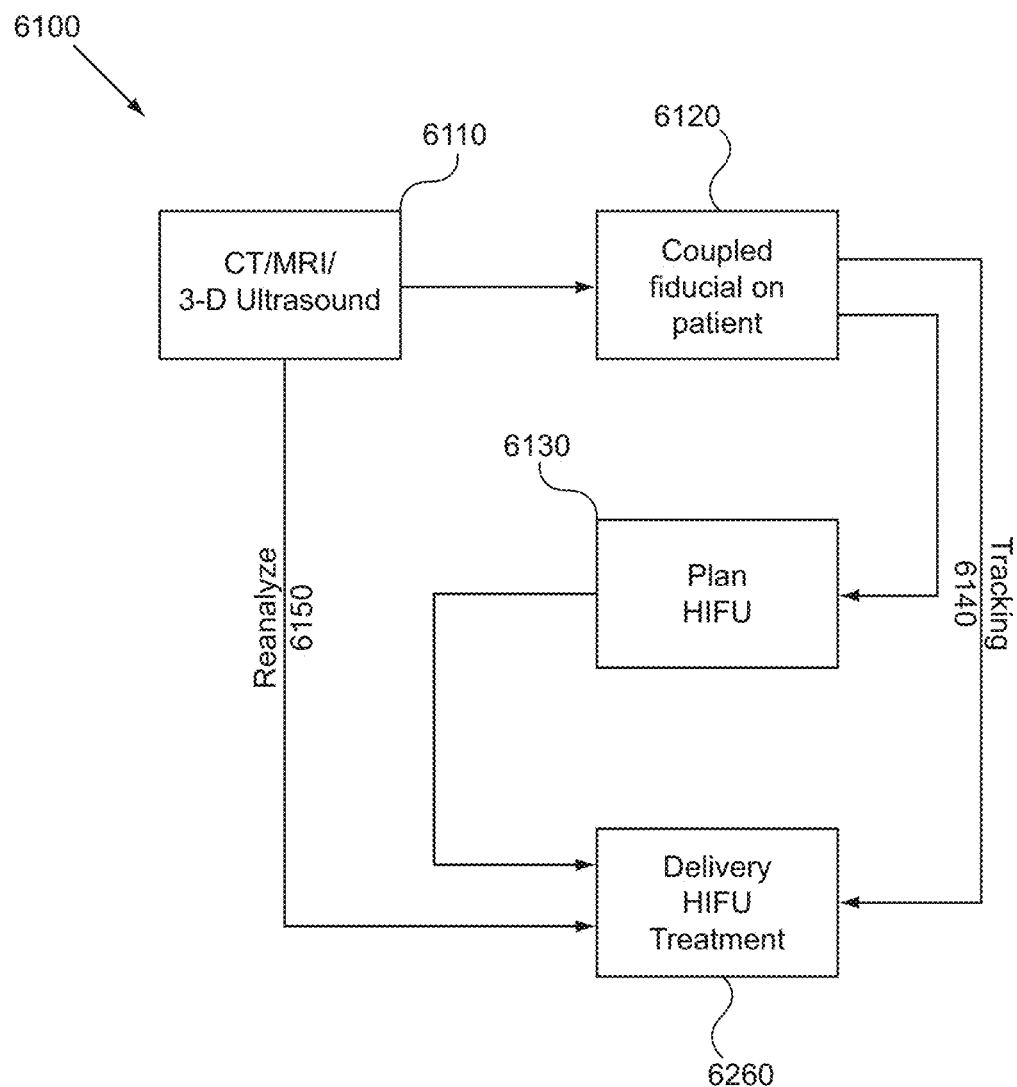
FIG. 10 depicts steps to treat a disease using HIFU while monitoring progress of the treatment as well as motion.

FIG. 10 depicts a method 6100 to treat a patient with high intensity or low intensity focused ultrasound (HIFU or LIFU) 6260. In a first step, a CT and/or MRI scan and/or thermography and/or ultrasound (1D,2D,3D) is performed 6110. A fiducial or other marking on or in the patient 6120 is optionally used to mark and track 6140 the patient. The fiducial can be an implanted fiducial, a temporary fiducial placed internally or externally in or on the patient, or a fiducial intrinsic to the patient (e.g. bone, blood vessel, arterial wall) which can be imaged using the CT/MRI/Ultrasound devices 6110. The fiducial can further be a temporary fiducial such as a catheter temporarily placed in an artery or vein of a patient or a percutaneously placed catheter. A planning step 6130 for the HIFU treatment is performed in which baseline readings such as position of the organ and temperature are determined; a HIFU treatment is then planned using a model (e.g. finite element model) to predict heat transfer, or pressure to heat transfer, from the ultrasound transducers 6130. The planning step incorporates the information on the location of the tissue or target from the imaging devices 6110 and allows placement of the anatomy into a three dimensional coordinate reference such that modeling 6130 can be performed.

The planning step 6130 includes determination of the positioning of the ultrasound transducers as far as position of the focus in the patient. X,Y,Z, and up to three angular coordinates are used to determine the position of the ultrasonic focus in the patient based on the cross sectional imaging 6110. The HIFU transducers might have their own position sensors built in so that the position relative to the target can be assessed. Alternatively, the HIFU transducers can be rigidly fixed to the table on which the patient rests so that the coordinates relative to the table and the patient are easily obtainable. The flow of heat is also modeled in the planning step 6130 so that the temperature at a specific position with the ultrasound can be planned and predicted. For example, the pressure wave from the transducer is modeled as it penetrates through the tissue to the target. For the most part, the tissue can be treated as water with a minimal loss due to interfaces. Modeling data predicts that this is the case. The relative power and phase of the ultrasonic wave at the target can be determined by the positional coupling between the probe and target. A convective heat transfer term is added to model heat transfer due to blood flow, particularly in the region of an artery. A conductive heat transfer term is also modeled in the equation for heat flow and temperature.

Another variable which is considered in the planning step is the size of the lesion and the error in its position. In the ablation of small regions such as nerves surrounding blood vessels, the temperature of the regions may need to be increased to a temperature of 60-90 degrees Celsius to permanently ablate nerves in the region. Temperatures of 40-60 degrees may temporarily inhibit or block the nerves in these regions and these temperatures can be used to determine that a patient will respond to a specific treatment without permanently ablating the nerve region. Subsequently, additional therapy can be applied at a later time so as to complete the job or perhaps, re-inhibit the nerve regions. In some embodiments, the temperature inside the blood vessel is measured and held to a temperature of less than 60 degrees Celsius, or less than 70 degrees Celsius, in which case the procedure might be stopped (e.g., when a desired temperature is reached).

An error analysis is also performed during the treatment contemplated in FIG. 10. Each element of temperature and position contains an error variable which propagates through the equation of the treatment. The errors are modeled to obtain a virtual representation of the temperature mapped to position. This map is correlated to the position of the ultrasound transducers in the treatment of the region of interest.

During the delivery of the treatment 6260, the patient may move, in which case the fiducials 6120 track the movement and the position of the treatment zone is re-analyzed 6150 and the treatment is restarted or the transducers are moved either mechanically or electrically to a new focus position.

In another embodiment, a cross-sectional technique of imaging is used in combination with a modality such as ultrasound to create a fusion type of image. The cross-sectional imaging is utilized to create a three dimensional data set of the anatomy. The ultrasound, providing two dimensional images, is linked to the three dimensional imaging provided by the cross-sectional machine through fiducial matches between the ultrasound and the MRI. As a body portion moves within the ultrasound field, the corresponding data is determined (coupled to) the cross-sectional (e.g. MRI image) and a viewing station can show the movement in the three dimensional dataset. The ultrasound provides real time images and the coupling to the MRI or other cross-sectional image depicts the ultrasound determined position in the three dimensional space.

Figure 11A:
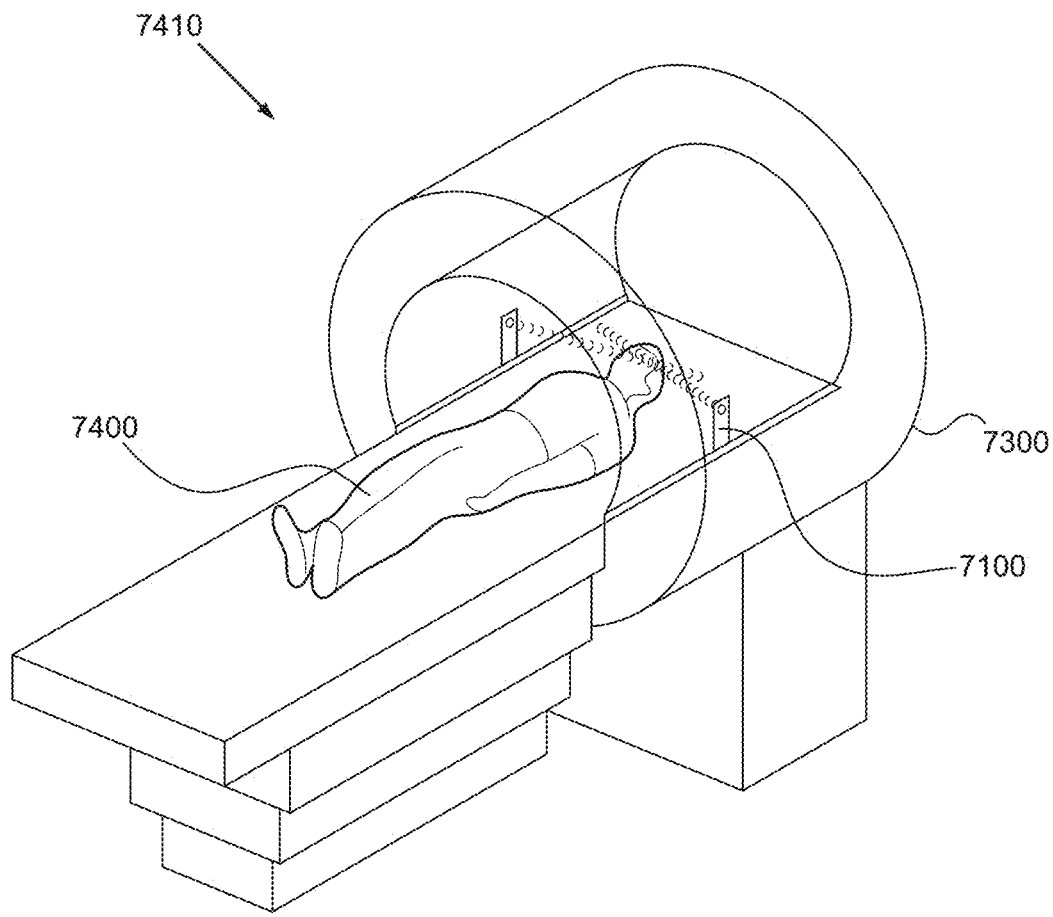
FIG. 11A depicts treatment of brain pathology using cross sectional imaging.
Figure 11B:
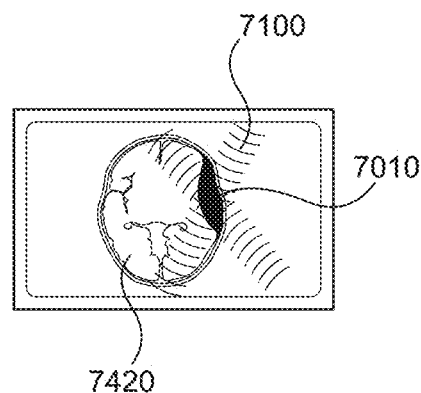
FIG. 11B depicts an image on a viewer showing therapy of the region of the brain being treated.
Figure 11C:
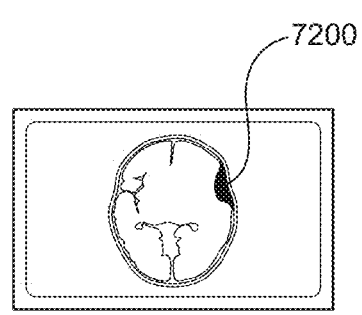
FIG. 11C depicts another view of a brain lesion as might be seen on an imaging device which assists in the treatment of the lesion.

FIG. 11 depicts the treatment 7410 of another disease in the body of a patient, this time in the head of a patient. Subdural and epidural hematomas occur as a result of bleeding of blood vessels in the dural or epidural spaces of the brain, spinal column, and scalp. FIG. 11 depicts a CT or MRI scanner 7300 and a patient 7400 therein. An image is obtained of the brain 7000 using a CT or MRI scan. The image is utilized to couple the treatment zone 7100 to the ultrasound array utilized to heat the region. In one embodiment 7100, a subdural hematoma, either acute or chronic, is treated. In another embodiment 7200, an epidural hematoma is treated. In both embodiments, the region of leaking capillaries and blood vessels are heated to stop the bleeding, or in the case of a chronic subdural hematoma, the oozing of the inflammatory capillaries.

In an exemplary embodiment of modulating physiologic processes, a patient 7400 with a subdural or epidural hematoma is chosen for treatment and a CT scan or MRI 7300 is obtained of the treatment region. Treatment planning ensues and the chronic region of the epidural 7200 or sub-dural 7010 hematoma is targeted for treatment with the focused ultrasound 7100 transducer technology. Next the target of interest is placed in a coordinate reference frame as are the ultrasound transducers. Therapy 7100 ensues once the two are coupled together. The focused ultrasound heats the region of the hematoma to dissolve the clot and/or stop the leakage from the capillaries which lead to the accumulation of fluid around the brain 7420. The technology can be used in place of or in addition to a burr hole, which is a hole placed through the scalp to evacuate the fluid.

Figure 12:
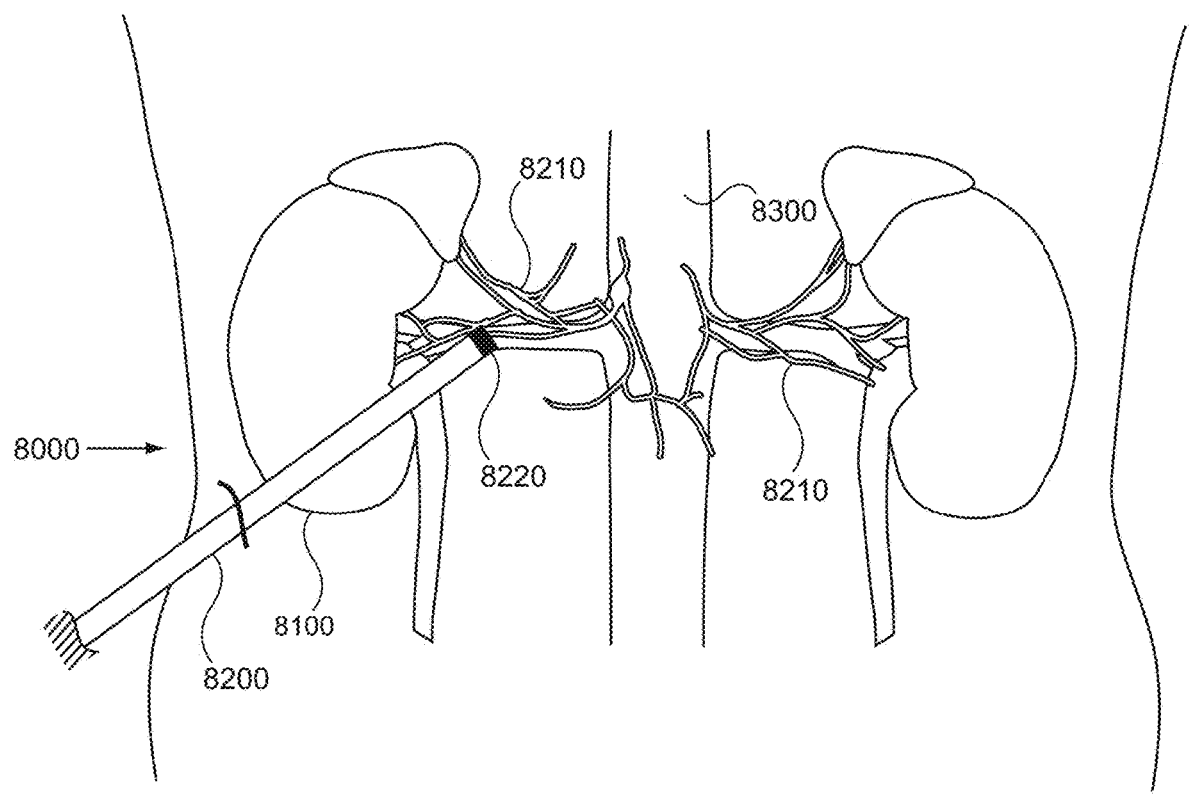
FIG. 12 depicts treatment of the renal nerve region using a laparoscopic approach.

FIG. 12 depicts a laparoscopic based approach 8000 to the renal artery region in which the sympathetic nerves 8210 can be ligated, interrupted, or otherwise modulated. In laparoscopy, the abdomen of a patient is insufflated and laparoscopic instruments introduced into the insufflated abdomen. The retroperitoneum is easily accessible through a flank approach or (less so) through a transabdominal (peritoneal)

approach. A laparoscopic instrument 8200 with a distal tip 8220 can apply heat or another form of energy or deliver a drug to the region of the sympathetic nerves 8210. The laparoscopic instrument can also be utilized to ablate or alter the region of the celiac plexus 8300 and surrounding ganglia. The laparoscope can have an ultrasound transducer 8220 attached, a temperature probe attached, a microwave transducer attached, or a radiofrequency transducer attached. The laparoscope can be utilized to directly ablate or stun the nerves (e.g. with a lower frequency/energy) surrounding vessels or can be used to ablate or stun nerve ganglia which travel with the blood vessels. Similar types of modeling and imaging can be utilized with the percutaneous approach as with the external approach to the renal nerves. With the discovery through animal experimentation (see below) that a wide area of nerve inhibition can be affected with a single ultrasound probe in a single direction (see above), the nerve region does not have to be directly contacted with the probe, the probe instead can be directed in the general direction of the nerve regions and the ultrasound delivered. For example, the probe can be placed on one side of the vessel and activated to deliver focused or semi-focused ultrasound over a generalized region which might not contain greater than 1 cm of longitudinal length of the artery but its effect is enough to completely inhibit nerve function along.

Figure 13:
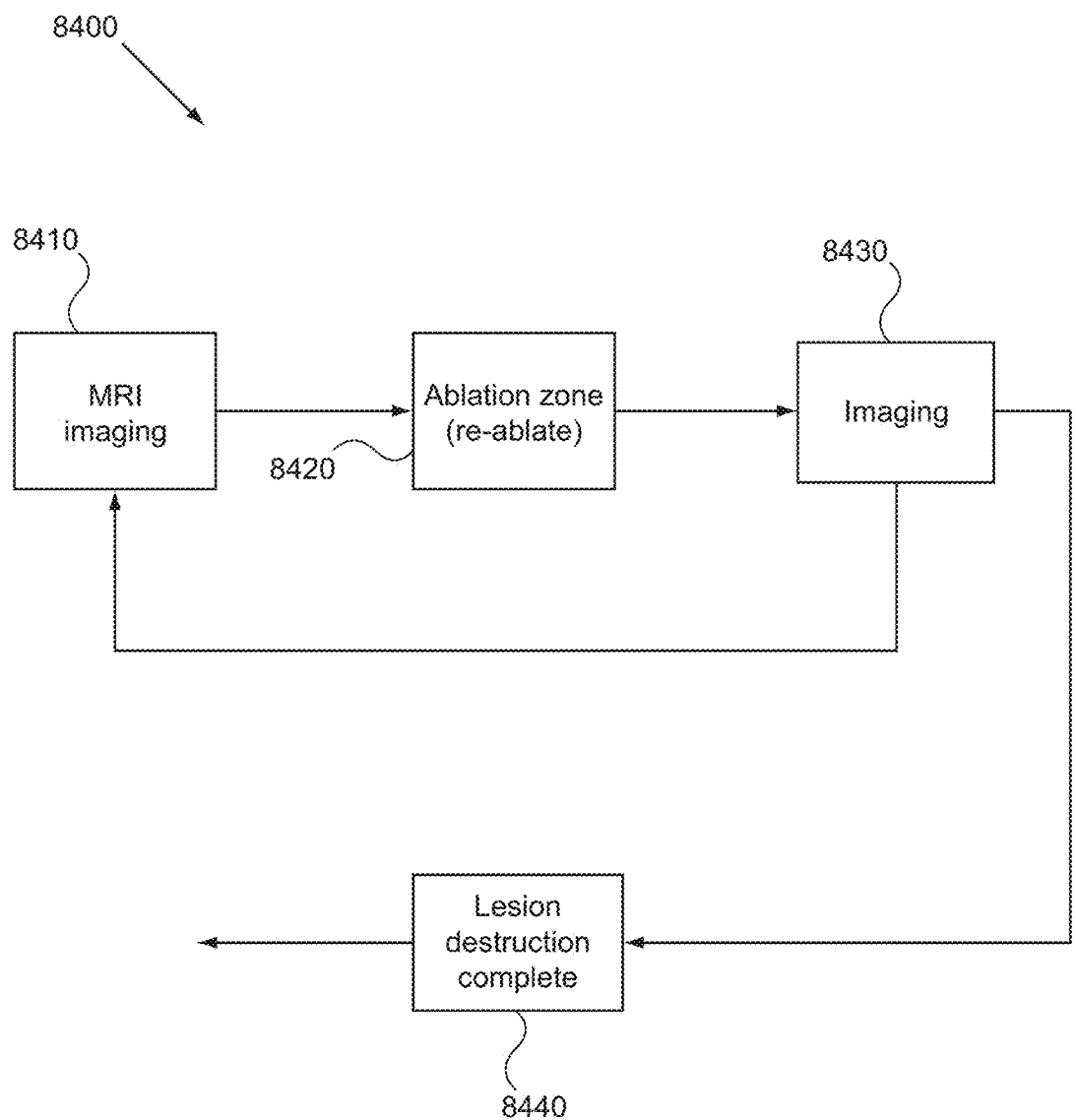
FIG. 13 depicts a methodology for destroying a region of tissue using imaging markers to monitor treatment progress.

FIG. 13 depicts an algorithm 8400 for the treatment of a region of interest using directed energy from a distance. MRI and/or CT with or without an imaging agent 8410 can be utilized to demarcate the region of interest (for example, the ablation zone) and then ablation 8420 can be performed around the zone identified by the agent using any of the modalities above. This algorithm is applicable to any of the therapeutic modalities described above including external HIFU, laparoscopic instruments, intravascular catheters, percutaneous catheters and instruments, as well as any of the treatment regions including the renal nerves, the eye, the kidneys, the aorta, or any of the other nerves surrounding peripheral arteries or veins. Imaging 8430 with CT, MRI, ultrasound, or PET can be utilized in real time to visualize the region being ablated. At such time when destruction of the lesion is complete 8440, imaging with an imaging (for example, a molecular imaging agent or a contrast agent such as gadolinium) agent 8410 can be performed again. The extent of ablation can also be monitored by monitoring the temperature or the appearance of the ablated zone under an imaging modality. Once lesion destruction is complete 8440, the procedure is finished. In some embodiments, ultrasonic diagnostic techniques such as elastography are utilized to determine the progress toward heating or ablation of a region.

Figure 14:
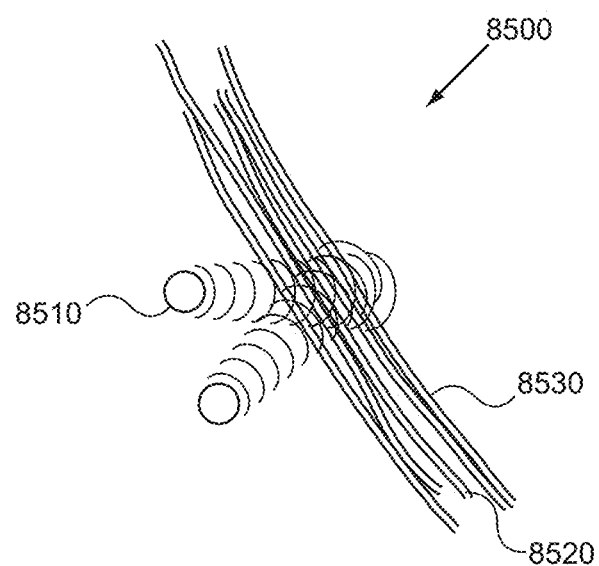
FIG. 14 depicts the partial treatment of portions of a nerve bundle using converging imaging and therapy wave.

FIG. 14 depicts ablation in which specific nerve fibers of a nerve are targeted using different temperature gradients, power gradients, or temperatures 8500. For example, if temperature is determined by MRI thermometry or with another technique such as ultrasound, infrared thermography, or a thermocouple, then the temperature can be kept at a temperature in which only certain nerve fibers are targeted for destruction or inhibition. Alternatively, part or all of the nerve can be turned off temporarily to then test the downstream effect of the nerve being turned off. For example, the sympathetic nerves around the renal artery can be turned off with a small amount of heat or other energy (e.g. vibrational energy) and then the effect can be determined. For example, norepinephrine levels in the systemic blood, kidney, or renal vein can be assayed; alternatively, the stimulation effect of the nerves can be tested after temporary cessation of activity (e.g. skin reactivity, blood pressure lability, cardiac activity, pulmonary activity, renal artery constriction in response to renal nerve stimulation). For example, in one embodiment, the sympathetic activity within a peripheral nerve is monitored; sympathetic activity typically manifests as spikes within a peripheral nerve electrical recording. The number of spikes correlates with the degree of sympathetic activity or over-activity. When the activity is decreased by (e.g. renal artery de-inervation), the concentration of spikes in the peripheral nerve train is decreased, indicating a successful therapy of the sympathetic or autonomic nervous system. Varying frequencies of vibration can be utilized to inhibit specific nerve fibers versus others. For example, in some embodiments, the efferent nerve fibers are inhibited and in other embodiments, the afferent nerve fibers are inhibited. In some embodiments, both types of nerve fibers are inhibited, temporarily or permanently. In some embodiments, the C fibers 8520 are selectively blocked at lower heat levels than the A nerve fibers. In other embodiment, the B fibers are selectively treated or blocked and in some embodiments, the A fibers 8530 are preferentially blocked. In some embodiments, all fibers are inhibited by severing the nerve with a high dose of ultrasound 8510. Based on the experimentation described above, the power density to achieve full blockage might be around 100-800 W/cm$^2$ or with some nerves from about 500 to 2500 W/cm$^2$. In some embodiments, a pulse train of 100 or more pulses each lasting 1-2 seconds (for example) and delivering powers from about 50 w/cm$^2$ to 500 W/cm$^2$. Indeed, prior literature has shown that energies at or about 100 W/Cm$^2$ is adequate to destroy or at least inhibit nerve function (Lele, P P. Effects of Focused Ultrasound Radiation on Peripheral Nerve, with Observations on Local Heating. Experimental Neurology 8, 47-83 1963). Based on data obtained in proof of concept, the ramp up to the correct power is desirable in some embodiments due to the nature of the region in which there is a tremendous amount of perfusion through the large blood vessels through the renal vein, artery, vena cava, etc. Modeling indicates that a slow increase in power ramp up allows the blood vessels to remove a greater amount of heat than when the rise in temperature is performed within a few seconds.

FIG. 15a depicts treatment 8600 of a vertebral body or intervertebral disk 8610 in which nerves within 8640 or around the vertebral column 8630 are targeted with energy 8625 waves. In one embodiment, nerves around the facet joints are targeted. In another embodiment, nerves leading to the disks or vertebral endplates are targeted. In another embodiment, nerves within the vertebral bone 8630 are targeted by heating the bone itself. Sensory nerves run through canals 8635 in the vertebral bone 8630 and can be inhibited or ablated by heating the bone 8630. In one method of treatment, focused ultrasound is applied from a position external to a patient and energy directed toward the vertebral bone; the bone is heated by the focused ultrasound and the nerve inside the bone is injured or paralyzed by the heat inside the bone. Such methodology can also be utilized to harden bone in the context of treating a vertebral body fracture to quell the pain response to the fracture.

FIG. 15B depicts a close-up of the region of the facet joint. Focused ultrasound to this region can inhibit nerves involved in back pain which originate at the dorsal root nerve and travel to the facet joint 8645. Ablation or inhibition of these nerves can limit or even cure back pain due to facet joint arthropathy. Focused ultrasound can be applied to the region of the facet joint from a position outside the patient to the facet joint using powers of between 100

W/cm² and 2500 W/cm² at the nerve from times ranging from 1 second to 10 minutes.

Figure 16A:
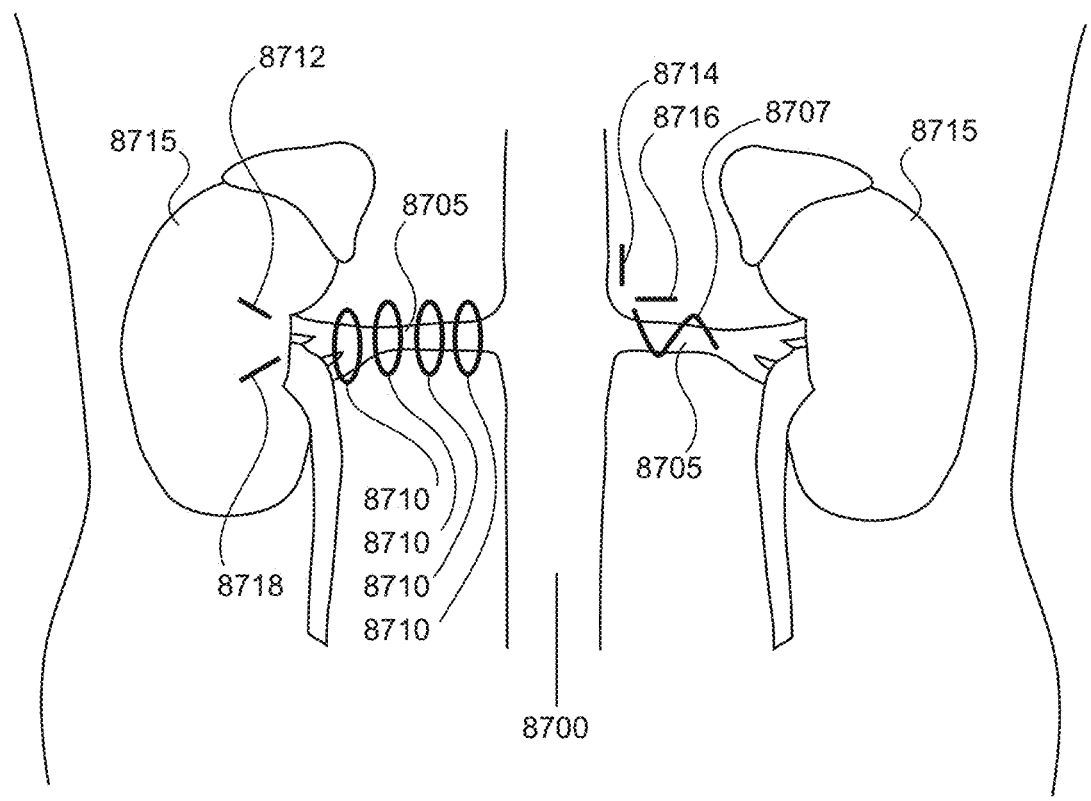
FIG. 16A depicts the types of lesions which are created around the renal arteries to affect a response.

FIG. 16A depicts a set of lesion types, sizes, and anatomies 8710*a-f* which lead to de-innervation of the different portions of the sympathetic nerve tree around the renal artery. For example, the lesions can be annular, cigar shaped, linear, doughnut and/or spherical; the lesions can be placed around the renal arteries 8705, inside the kidney 8710, and/or around the aorta 8700. For example, the renal arterial tree comprises a portion of the aorta 8700, the renal arteries 8705, and kidneys 8715. Lesions 8714 and 8716 are different types of lesions which are created around the aorta 8700 and vascular tree of the kidneys. Lesions 8712 and 8718 are applied to the pole branches from the renal artery leading to the kidney and inhibit nerve functioning at branches from the main renal artery. These lesions also can be applied from a position external to the patient. Lesions can be placed in a spiral shape 8707 along the length of the artery as well. These lesions can be produced using energy delivered from outside the blood vessels using a completely non-invasive approach in which the ultrasound is applied through the skin to the vessel region or the energy can be delivered via percutaneous approach. Either delivery method can be accomplished through the posterior approach to the blood vessels as discovered and described above.

In one method therefore, ultrasound energy can be applied to the blood vessel leading to a kidney in a pattern such that a circular pattern of heat and ultrasound is applied to the vessel. The energy is transmitted through the skin in one embodiment or through the artery in another embodiment. As described below, ultrasound is transmitted from a distance and is inherently easier to apply in a circular pattern because it doesn't only rely on conduction.

Figure 16B:
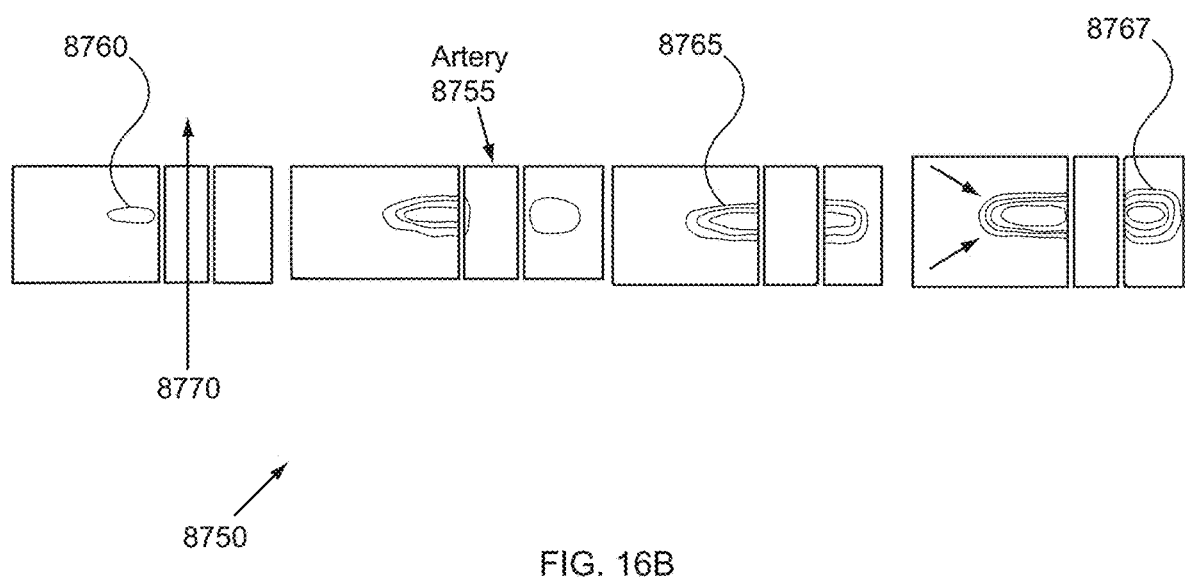
FIG. 16B depicts a simulation of ultrasound around a blood vessel I support of FIG. 16A.

Previously, it was unknown and undiscovered whether or not the annular shaped lesions as shown in FIG. 16*a* would have been sufficient to block nerve function of the autonomic nerves around the blood vessels. Applicant of the subject application discovered that the annular shaped ablations 8710 not only block function but indeed completely block nerve function around the renal artery and kidney and with very minimal damage (FIG. 16C), if any, to the arteries and veins themselves. In these experiments, focused ultrasound was used to block the nerves; the ultrasound was transmitted through and around the vessel from the top (that is, only one side of the vessel) at levels of 200-2500 W/cm². The energy travels through the flowing blood to affect the opposite side of the blood vessel. Simulations are shown in FIGS. 16B and 16D and described below. Norepinephrine levels in the kidney 8780, which are utilized to determine the degree of nerve inhibition, were determined before and after application of energy. The lower the levels of norepinephrine, the more nerves which have been inhibited or affected. In these experiments which were performed, the norepinephrine levels approached zero 8782 versus controls (same animal, opposite kidney) 8784 which remained high. In fact, the levels were equal to or lower than the surgically denuded blood vessels (surgical denudement involves directly cutting the nerves surgically and application of phenol to the vessel wall). It is important to note that the renal artery and vein walls remained substantially unharmed; this is likely due to the fact that the quick arterial blood flow removes heat from the vessel wall and the fact that the main renal artery is extremely resilient due to its large size, high blood flow, and thick wall; these findings are consistent with the modeling performed as shown in FIGS. 16B and 16D. To summarize, ultrasound (focused and relatively unfocused) was applied to one side of the renal artery and vein complex. The marker of nerve inhibition, norepinephrine levels inside the kidney, were determined to be approaching zero after application to the nerves from a single direction, transmitting the energy through the artery wall to reach nerves around the circumference of the artery. The level of zero norepinephrine 8782 indicates essentially complete abolition of nerve function proving that the annular lesions were in fact created as depicted in FIG. 16A and simulated in FIGS. 16B and 16D. Histological results also confirm the annular nature of the lesions and limited collateral damage as predicted by the modeling in 16B.

Therefore, in one embodiment, the ultrasound is applied from a position external to the artery in such a manner so as to create an annular or semi-annular rim of heat all the way around the artery to inhibit, ablate, or partially ablate the autonomic nerves surrounding the artery. The walls or the blood flow of the artery can be utilized to target the ultrasound to the nerves which, if not directly visualized, are visualized through use of a model to approximate the position of the nerves based on the position of the blood vessel.

FIG. 16B further supports the physics and physiology described herein, depicting a theoretical simulation 8750 of the physical and animal experimentation described above. That is, focused ultrasound was targeted to a blood vessel in a computer simulation 8750. The renal artery 8755 is depicted within the heating zone generated within a focused ultrasound field. Depicted in the figure is the temperature at <1 s 8760 and at approximately 5 s 8765 and longer time >10 s 8767. Flow direction 8770 is shown as well. The larger ovals depict higher temperatures with the central temperature >100° C. The ultrasound field is transmitted through the artery 8755, with heat building up around the artery as shown via the temperature maps 8765. Importantly, this theoretical simulation also reveals the ability of the ultrasound to travel through the artery or blood vessel 8767 and affect both walls of the blood vessel. These data are consistent with the animal experimentation described above, creating a unified physical and experimental dataset. In some cases, the ultrasonic energy may be applied to the blood vessel quickly to avoid removal of the heat by the blood flow. In the case where the ultrasound ramp up around the vessel is not applied quickly, a steady state is reached in which the heat applied is equal to the heat dissipated, and it may become difficult to heat the rim of the blood vessel.

FIG. 16C depicts the results of an experimental focused ultrasound treatment in which one kidney was treated with the ultrasound and the other served as a control. Norepinephrine 8780 is the marker of the effect of sympathetic nerve inhibition and its concentration was measured in the cortex of the kidney. The experimental result 8782 was very low compared to the control 8784 level indicating almost complete inhibition of the nerves which travel to the kidney. A circumferential effect of the heat is provided to obtain such a dramatic effect on norepinephrine levels leading to the kidney.

FIG. 16D is a depiction of a simulation with multiple beams being applied to the region of the blood vessel wall. The ultrasound might be scanned toward the blood vessel or otherwise located point by point within the treatment region. In one embodiment, the power to the blood vessel is delivered such that the temperature ramps over 60 degrees within 2 s or within 5 s or within 10 s. Subsequently, the energy is turned off and then reapplied after a period of 1, 2, 5, or 10 seconds. In some embodiments, the energy may be on for a prescribed duration, such as 1, 2, 5, 10 seconds, etc. In some embodiments, a technique such as infrared thermography or laser Doppler thermography is used to determine the temperature of the skin and subcutaneous tissue to decide when it is safe to deliver an additional dose of energy to the target zone. Such a treatment plan creates a cloud of heat centered on the inside of the wall of the blood vessel. In other embodiments, the energy may be on for 30, 60, or 90 seconds, but the power is lower than that for the shorter on-time periods of 1, 2, 5, 10 seconds.

Figure 5C:
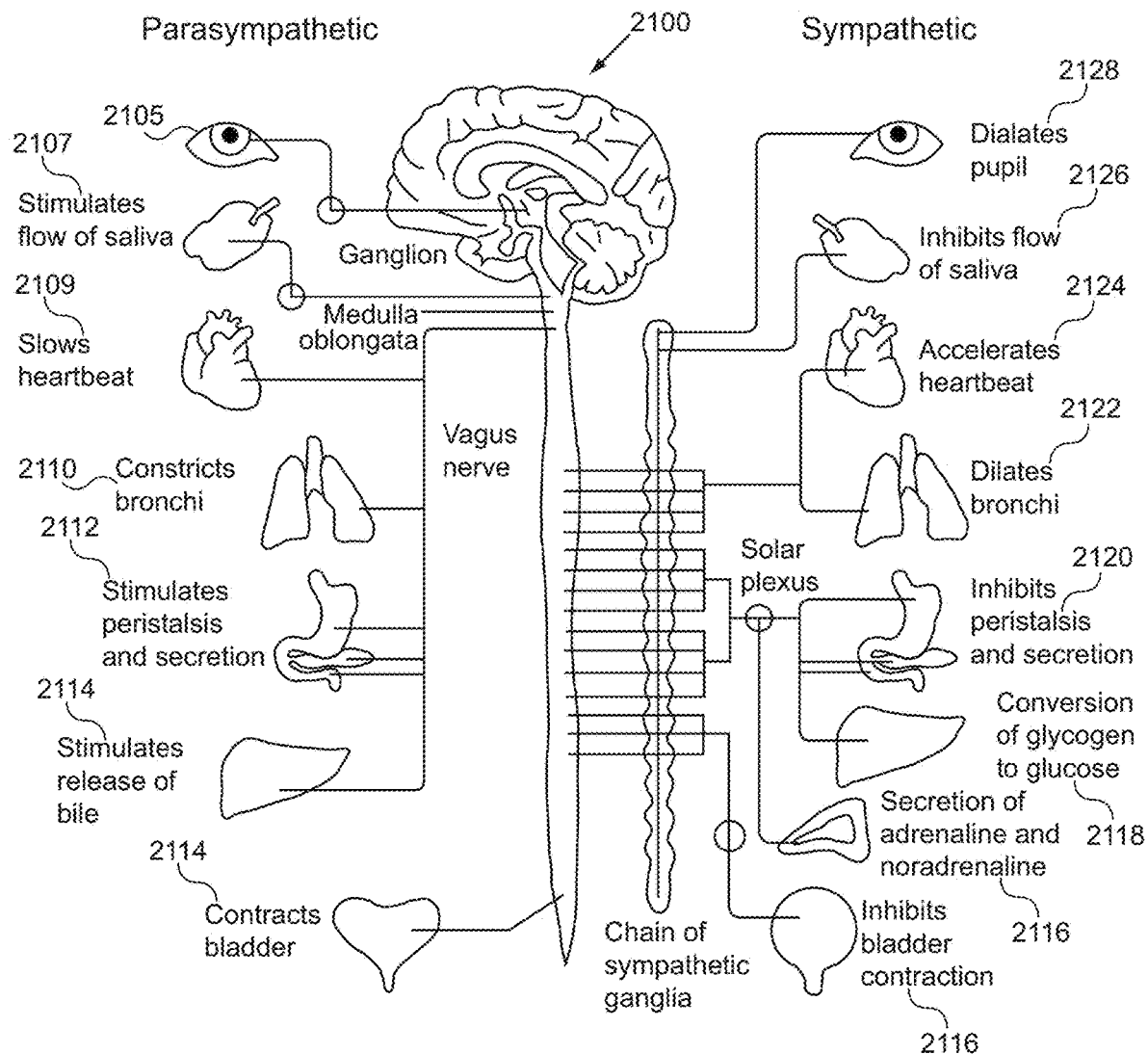
FIG. 5C depicts the application of energy to other autonomic nervous system structures.

Similarly, other vessels leading to other organs which rely on sympathetic, parasympathetic, and general autonomic innervation can be treated as well utilizing this technique. Referring to FIG. 5C, blood vessels which lead to the eye 2105 (carotid artery), the mouth (facial arteries) and saliva glands 2107, the heart 2109, the bronchi 2110, the stomach 2112, the gallbladder 2114 and liver 2118, the bladder 2114, the adrenal gland 2116, the pancreas can be stimulated or inhibited utilizing this technique of focused energy delivery targeting a blood vessel. In one example, an underactive pancreas is treated by denervation, which results in improved glucose tolerance. In another embodiment, the liver is denervated by ablated arteries surrounding portal veins or hepatic arteries leading to the liver. Any of the above organs may be denervated using a similar technique as that described with reference to the blood vessels leading to the kidney.

FIGS. 16D-H depict another simulation with multiple treatment performed over time (up to 132 s) in a pattern such as shown in FIG. 16D. FIG. 16H is a close up of FIG. 16D and depicts a blood vessel 8795 (with a flow rate of the renal artery and renal vein in a human being) and vessel wall 8796. In this simulation, the focused energy was applied in a 10 s on and 6 s off pattern to allow heat to surround 8793 the vessel 8795. The transducer 8790, subcutaneous tissue 8792, and muscle wall 8794 are depicted. This simulation reveals the ability of focused energy to create a cloud around the blood vessel particularly with high blood flow such as to the kidney.

Figure 16I:
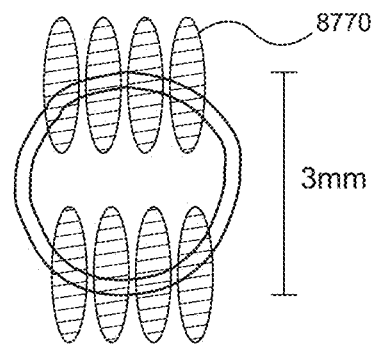
FIGS. 16I-16K depict various treatment plans of focused energy around a blood vessel.

FIGS. 16I,J,K depict some of the patterns which can be applied to a blood vessel. In FIG. 16D, application of the focused energy 8770 to the vessel is shown in a pattern created by the transducer mover. FIG. 16I depicts another type of pattern 8772 with a broader brush stroke around the vessel.

Figure 16J:
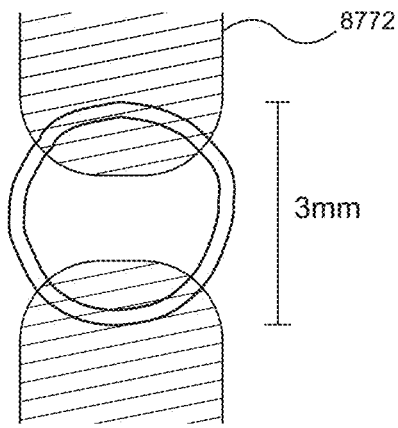
Figure 16K:
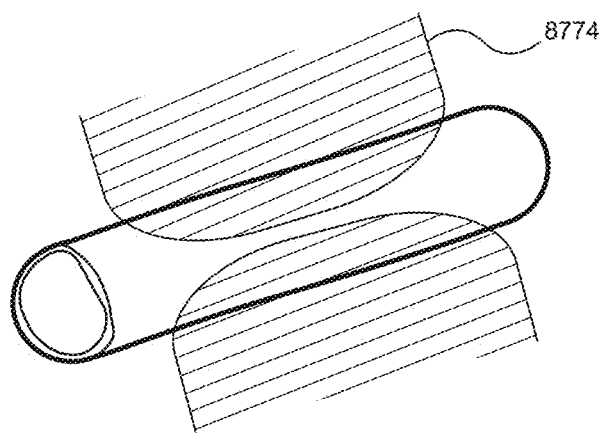

FIG. 16I and FIG. 16J depict cross sectional patterns across a blood vessel. FIG. 16K depicts a longitudinal pattern 8774 along the vessel.

Figure 16L:
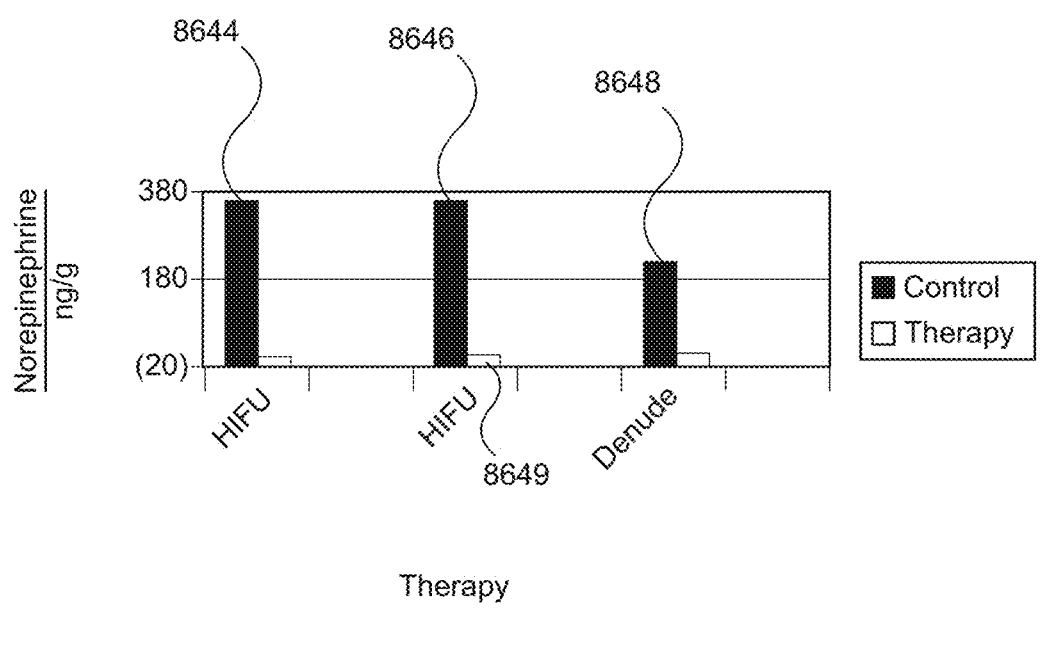
FIGS. 16L-16M depict data indicating that focused energy applied from the outside can affect sympathetic nerve supply to organs.
Figure 16M:
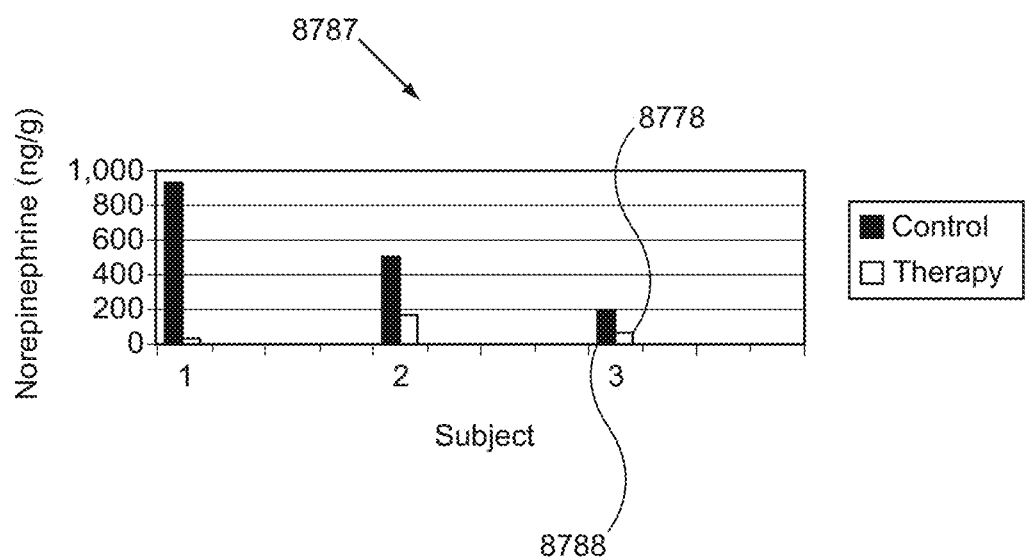

FIGS. 16L and 16M depict the results of an experiment 8787 in which nerves leading to the kidney are treated with heat from an externally applied source, and nerves inhibited from producing norepinephrine.

FIG. 16L depicts the results of an experiment in which the HIFU 8644 was compared to a surgical control 8648. HIFU was applied across the vessel so that the ultrasound passed through the blood and the vessel to affect both walls of the vessel. As can be seen in the FIG. 16L, the HIFU applied from outside the patient is as good as denervation with surgery revealing that focused ultrasound can indeed remove, inhibit, or ablate nerves surrounding blood vessels. To the extent nerves are contained within the walls of the blood vessel, focused ultrasound can be used to inhibit or ablate the nerves within the media of the blood vessel wall.

FIG. 16M depicts a similar experiment in which focused ultrasound is applied through the skin to the nerves surrounding the blood vessels traveling to the kidney. Bar 8788 is a control kidney and 8778 is a therapy kidney. A pattern of heat is applied to the blood vessel over a 2-3 minute period resulting in the observed changes in norepinephrine and indicating denervation of the sympathetic nerves around a blood vessel leading to an organ.

As can be seen, the control side 8788, 8644, 8646, 8648 reveal a high norepinephrine level and the therapy side 8778, 8649 reveals a low norepinephrine level, indicating treatment was successful. This experiment was performed utilizing an externally placed ultrasound system which focused the energy on the nerves in one of the patterns shown above.

Therefore, based on the animal and theoretical experimentation, there is proven feasibility of utilizing ultrasound to quickly and efficiently inhibit the nerves around the renal arteries from a position external to the blood vessels as well as from a position external to the skin of the patient.

The pattern of application may be different from systems to treat tumors and other pathologies in which it is desired that 100% of the region be treated. The nerve region surrounding the blood vessels is diffuse and it is not necessary to inhibit all nerves in order to have an effect on blood pressure. Therefore, the goal is to apply broad brush strokes of energy across the vessel to create an annular zone, or cloud of heat around the vessel. Subsequent to a first treatment, a second treatment may be applied in which additional nerves are affected. The second treatment may occur minutes, hours, days, or years after the treatment, and may depend on physiological changes or regrowth of the nerves. In some cases, a quality factor is calculated based on the degree of movement of the applicator. The quality factor relates to the degree of time the applicator actually was focused on the identified target. Although 100% is ideal, sometimes it may not be achieved. Therefore, in some cases, when the applicator focuses on the target for 90% of the time, the treatment may be considered successful. In other embodiments, the quality factor might be the amount of time the targeted region is actually within 90% of the target, for example, within 500 microns of the target, or within 1 mm of the target, or within 2 mm of the target, etc. The detection of the target is determined via imaging, internal fiducial, and/or external fiducial.

Utilizing the experimental simulations and animal experimentation described above, a clinical device can and has been devised and tested in human patients. FIG. 17A depicts a multi-transducer HIFU device 1100 which applies a finite lesion 1150 along an artery 1140 (e.g. a renal artery) leading to a kidney 1130. The lesion can be spherical in shape, cigar shaped 1150, annular shaped 8710 (FIG. 16A), or point shaped; however, in a preferred embodiment, the lesion runs along the length of the artery and has a cigar shape 1150. This lesion is generated by a spherical or semi-spherical type of ultrasound array in a preferred embodiment. Multiple cigar shaped lesions as shown in FIG. 17C lead to a ring type of lesion 1350.

FIG. 17B depicts an imaging apparatus display which monitors treatment. Lesion 1150 is depicted on the imaging apparatus as is the aorta 1160 and renal artery 1155. The image might depict heat, tissue elastography, vibrations, temperature or might be based on a simulation of the position of the lesion 1150. MRI, CT, infrared thermography, ultrasound, laser thermography, or thermistors may be used to determine temperature of the tissue region. FIG. 17C depicts another view of the treatment monitoring, with the renal artery in cross section 1340. Lesion 1350 is depicted in cross section in this image as well. The lesion 1350 might be considered to circumscribe the vessel 1340 in embodiments where multiple lesions are applied.

Figure 17D:
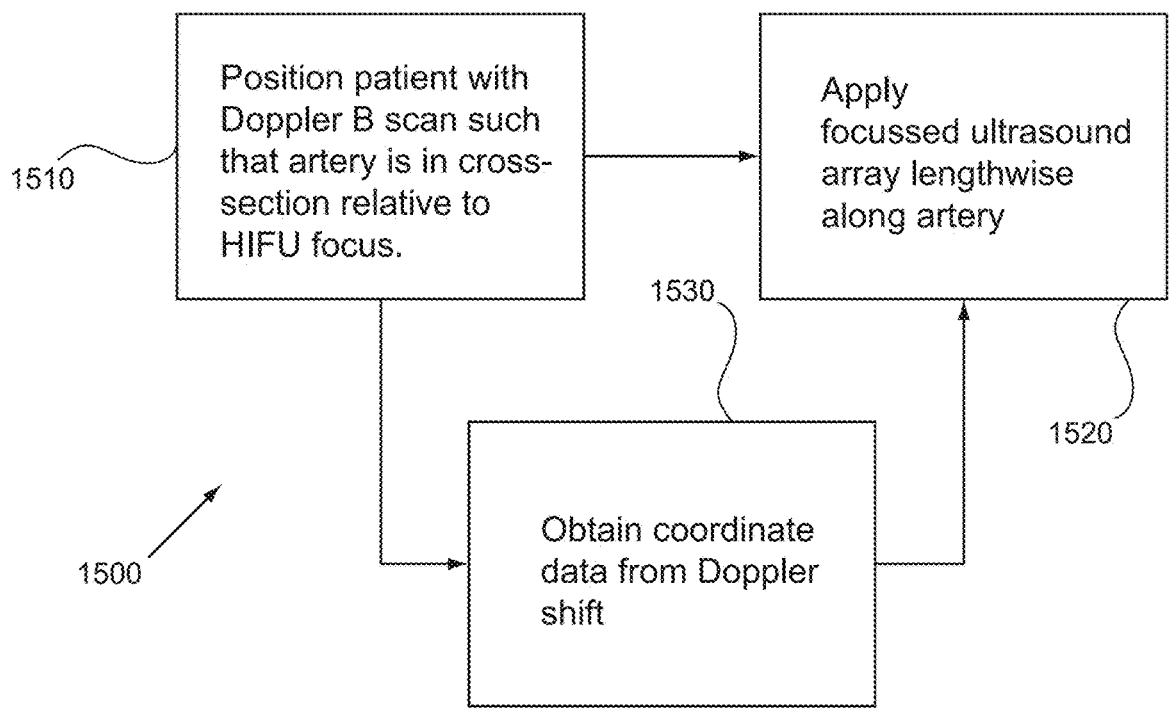
FIG. 17D depicts a method for localizing HIFU transducers relative to Doppler ultrasound signals.

FIG. 17D depicts a methodology 1500 to analyze and follow the delivery of therapeutic focused ultrasound to an arterial region. A key step is to first position 1510 the patient optimally to image the treatment region; the imaging of the patient might involve the use of Doppler imaging, M mode imaging, A scan imaging, or even MRI, fluoroscopy, or CT scan. The imaging unit is utilized to obtain coordinate data 1530 from the doppler shift pattern of the artery. Next, the focused ultrasound probe is positioned 1520 relative to the imaged treatment region 1510 and treatment can be planned or applied.

Figure 17E:
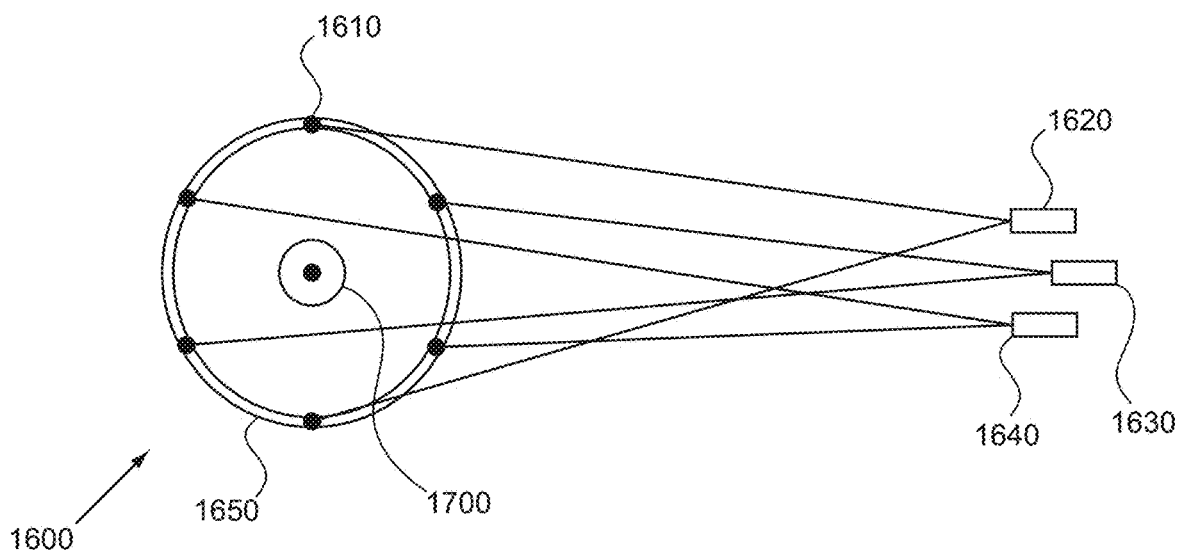
FIG. 17E depicts an arrangement of transducers relative to a target.
Figure 17F:
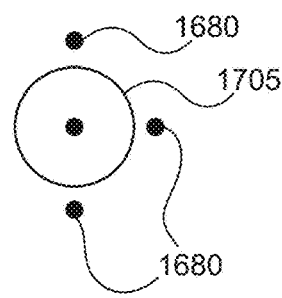
FIG. 17F depicts ablation zones in a multi-focal region in cross-section.

FIG. 17E depicts the pathway of the acoustic waves from a spherical or cylindrical type of ultrasound array 1600. In some embodiments, the transducer is aspherical such that a sharp focus does not exist but rather the focus is more diffuse in nature or off the central axis. Alternatively, the asphericity might allow for different pathlengths along the axis of the focusing. For example, one edge of the ultrasound transducer might be called upon for 15 cm of propagation while another edge of the transducer might be called upon to propagate only 10 cm, in which case a combination of different frequencies or angles might be required.

Ultrasound transducers 1610 are aligned along the edge of a cylinder 1650, aimed so that they intersect at one or more focal spots 1620, 1630, 1640 around the vessel (e.g. renal artery). The transducers 1610 are positioned along the cylinder or sphere or spherical approximation (e.g. aspherical) 1650 such that several of the transducers are closer to one focus or the other such that a range of distances 1620, 1630, 1640 to the artery is created. The patient and artery are positioned such that their centers 1700 co-localize with the center of the ultrasound array 1600. Once the centers are co-localized, the HIFU energy can be activated to create lesions along the length of the artery wall 1640, 1620, 1630 at different depths and positions around the artery. The natural focusing of the transducers positioned along a cylinder as in FIG. 17E is a lengthwise lesion, longer than in thickness or height, which will run along the length of an artery 1155 when the artery 1340 is placed along the center axis of the cylinder. When viewed along a cross section (FIG. 17F), the nerve ablations are positioned along a clock face 1680 around the blood vessel.

In another embodiment, a movement system for the transducers is utilized so that the transducers move along the rim of the sphere or cylinder to which they are attached. The transducers can be moved automatically or semi-automatically, based on imaging or based on external position markers. The transducers are independently controlled electrically but coupled mechanically through the rigid structure.

Importantly, during treatment, a treatment workstation 1300 (FIG. 17C) gives multiple views of the treatment zone with both physical appearance and anatomy 1350. Physical modeling is performed in order to predict lesion depth and the time to produce the lesion; this information is fed back to the ultrasound transducers 1100. The position of the lesion is also constantly monitored in a three dimensional coordinate frame and the transducer focus at lesions center 1150 in the context of monitoring 1300 continually updated.

In some embodiments, motion tracking prevents the lesion or patient from moving too far out of the treatment zone during the ablation. If the patient does move outside the treatment zone during the therapy, then the therapy can be stopped. Motion tracking can be performed using the ultrasound transducers, tracking frames and position or with transducers from multiple angles, creating a three dimensional image with the transducers. Alternatively, a video imaging system can be used to track patient movements, as can a series of accelerometers positioned on the patient which indicate movement. In some cases, this embodiment can include a quality factor used to change the dose delivered to the patient based on movement which tends to smear the delivered dose, as described herein.

Figure 18:
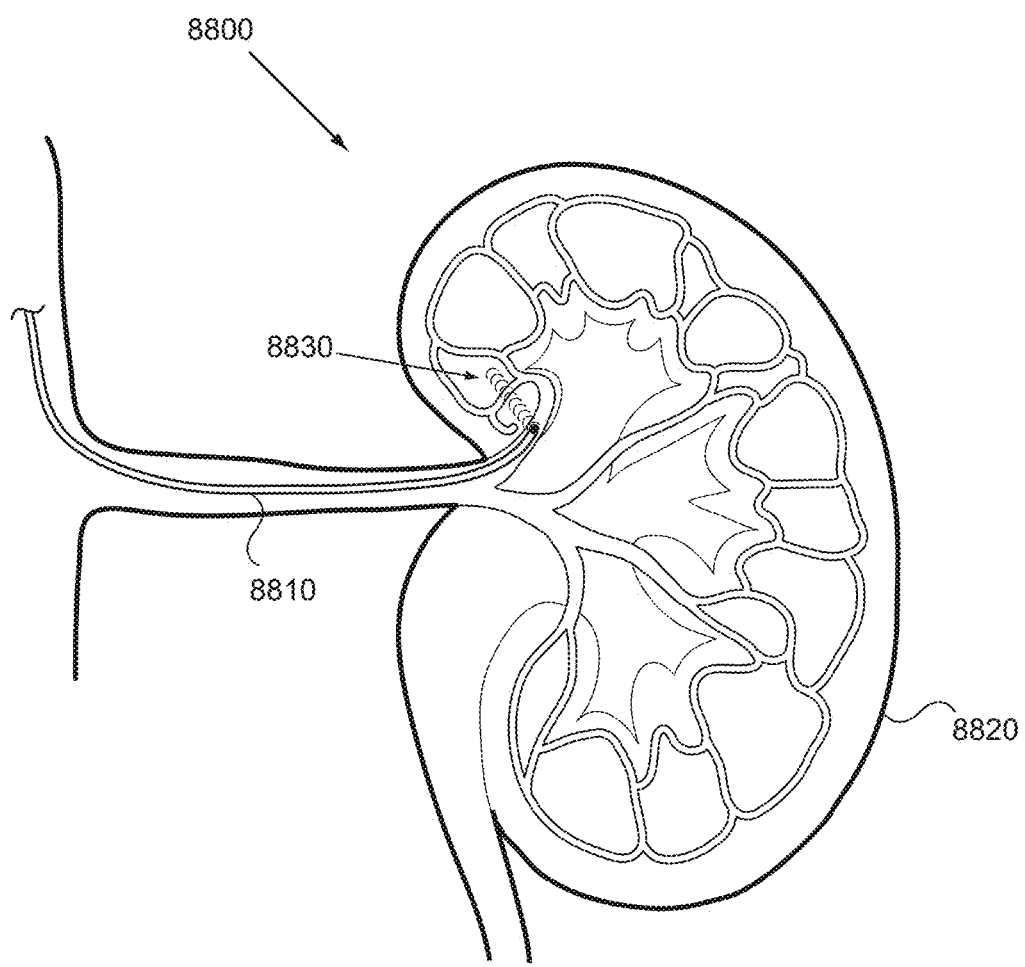
FIG. 18 depicts the application of energy internally within the kidney to affect specific functional changes at the regional level within the kidney.

FIG. 18 depicts a micro-catheter 8810 which can be placed into renal calyces 8820; this catheter allows the operator to specifically ablate or stimulate 8830 regions of the kidney 8800. The catheter can be used to further allow for targeting of the region around the renal arteries and kidneys by providing additional imaging capability or by assisting in movement tracking or reflection of the ultrasound waves to create or position the lesion. The catheter or device at or near the end of the catheter may transmit signals outside the patient to direct an energy delivery device which delivers energy through the skin. Signaling outside the patient may comprise energies such as radiofrequency transmission outside the patient or radiofrequency from outside to the inside to target the region surrounding the catheter.

The following patent and patent applications describe the delivery of ultrasound using a targeting catheter within a blood vessel, and are expressly incorporated by reference herein:

Ser. Nos. 11/583,569, 12/762,938, 11/583,656, 12/247, 969, 10/633,726, 09/721,526, 10/780,405, 09/747,310, 12/202,195, 11/619,996, 09/696,076

In one system 8800, a micro catheter 8810 is delivered to the renal arteries and into the branches of the renal arteries in the kidney 8820. A signal is generated from the catheter into the kidney and out of the patient to an energy delivery system. Based on the generated signal, the position of the catheter in a three dimensional coordinate reference is determined and the energy source is activated to deliver energy 8830 to the region indicated by the microcatheter 8810.

In an additional embodiment, station keeping is utilized. Station keeping enables the operator to maintain the position of the external energy delivery device with respect to the movement of the operator or movement of the patient. As an example, targeting can be achieved with the energy delivery system and tracking of movement of the energy delivery system relative to the target. As the energy delivery system moves from its initial state, the station keeping allows the focus to be moved with the target as the target moves from its original position. Such station keeping is described herein and illustrated in FIGS. 19C-D. A quality factor may be used by the device to increase or decrease dosing depending on the degree of movement. For example, if the quality factor deviation from a desired value by a certain amount, then the dose may be increased or decreased.

The microcatheter may be also be utilized to place a flow restrictor inside the kidney (e.g. inside a renal vein) to "trick" the kidney into thinking its internal pressure is higher than it might be. In this embodiment, the kidney generates signals to the central nervous system to lower sympathetic output to target organs in an attempt to decrease its perfusion pressure.

Alternatively, specific regions of the kidney might be responsible for hormone excretion or other factors which lead to hypertension or other detrimental effects to the cardiovascular system. The microcatheter can generate ultrasound, radiofrequency, microwave, or X-ray energy. The microcatheter can be utilized to ablate regions in the renal vein or intra-parenchymal venous portion as well. In some embodiments, ablation is not required but vibratory energy emanating from the probe is utilized to affect, on a permanent or temporary basis, the mechanoreceptors or chemoreceptors in the location of the hilum of the kidney.

Figure 19A:
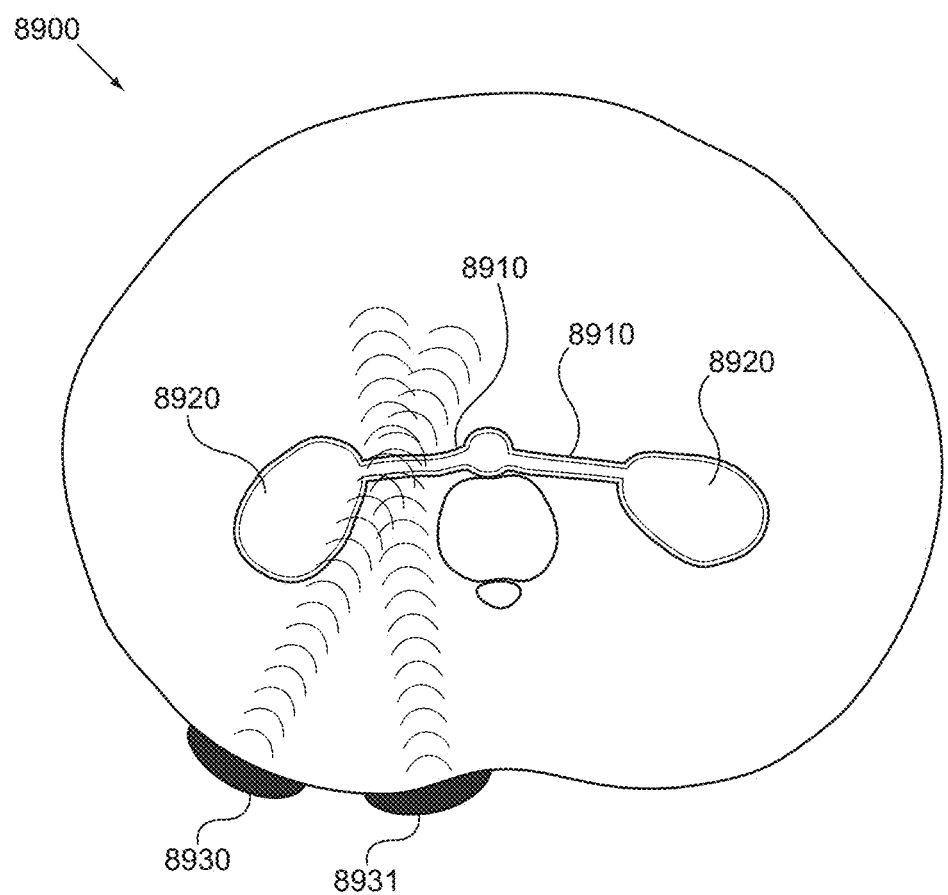
FIG. 19A depicts the direction of energy wave propagation to treat regions of the autonomic nervous system around the region of the kidney hilum.

FIG. 19A depicts the application 8900 of energy to the region of the renal artery 8910 and kidney 8920 using physically separated transducers 8930, 8931. Although two are shown, the transducer can be a single transducer which is connected all along an outer frame. The transducer(s) can be spherical (sharp focus) or aspherical (diffuse focus), they can be coupled to an imaging transducer directly or indirectly where the imaging unit might be separated at a distance. In contrast to the delivery method of FIG. 17, FIG. 19A depicts delivery of ultrasound transverse to the renal arteries and not longitudinal to the artery. The direction of energy delivery is the posterior of the patient because the renal artery is the first vessel "seen" when traveling from the skin toward the anterior direction facilitating delivery of the therapy. In one embodiment, the transducers 8930, 8931 are placed under, or inferior to the rib of the patient or between the ribs of a patient; next, the transducers apply an ultrasound wave propagating forward toward the anterior abdominal wall and image the region of the renal arteries and renal veins, separating them from one another. In some embodiments, such delivery might be advantageous, if for example, a longitudinal view of the artery is unobtainable or a faster treatment paradigm is desirable. The transducers 8930, 8931 communicate with one another and are connected to a computer model of the region of interest being imaged (ROI), the ROI based on an MRI scan performed just prior to the start of the procedure and throughout the procedure. Importantly, the transducers are placed posterior in the cross section of the patient, an area with more direct access to the kidney region. The angle between the imaging transducers can be as low as 3 degrees or as great as 180 degrees depending on the optimal position in the patient.

In another embodiment, an MRI is not performed but ultrasound is utilized to obtain all or part of the cross-sectional view in FIG. 19A. For example, 8930 might contain an imaging transducer as well as a therapeutic energy source (e.g. ionizing energy, HIFU, low energy focused ultrasound, etc.) In some embodiments, a CT scan is utilized, which can obtain two dimensional images and output three dimensional images. In other embodiments, a fluoroscopy unit may be used.

Figure 19B:
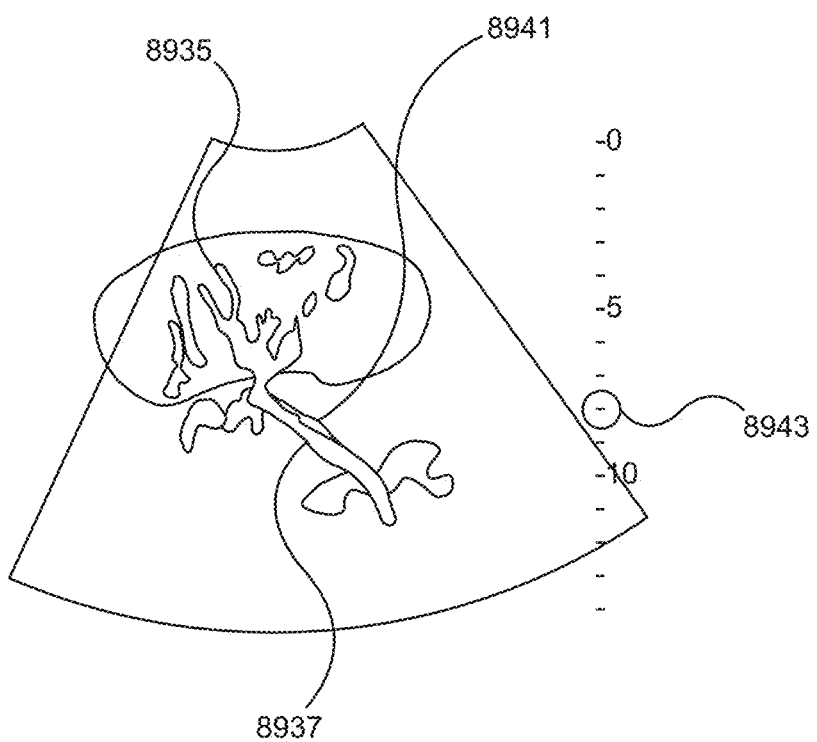
FIG. 19B depicts a schematic of a B mode ultrasound from a direction determined through experimentation to provide access to the renal hilum with HIFU.

FIG. 19B depicts an ultrasound image from a patient illustrating imaging of the region with patient properly positioned as described below. It is this cross section that can be treated with image guided HIFU of the renal hilum region. The kidney 8935 is visualized in cross section and ultrasound then travels through to the renal artery 8937 and vein 8941. The distance can be accurately measure 8943 with ultrasound (in this case 8 cm 8943). This information is useful to help model the delivery of energy to the renal blood vessels. The blood vessels (vein and/or artery) are utilized as fiducials for the targeting of the ultrasound, and the kidney is used to verify that the vessels indeed are leading to the correct organ. The kidney is further utilized to conduct the ultrasound to the blood vessels.

Figure 19C:
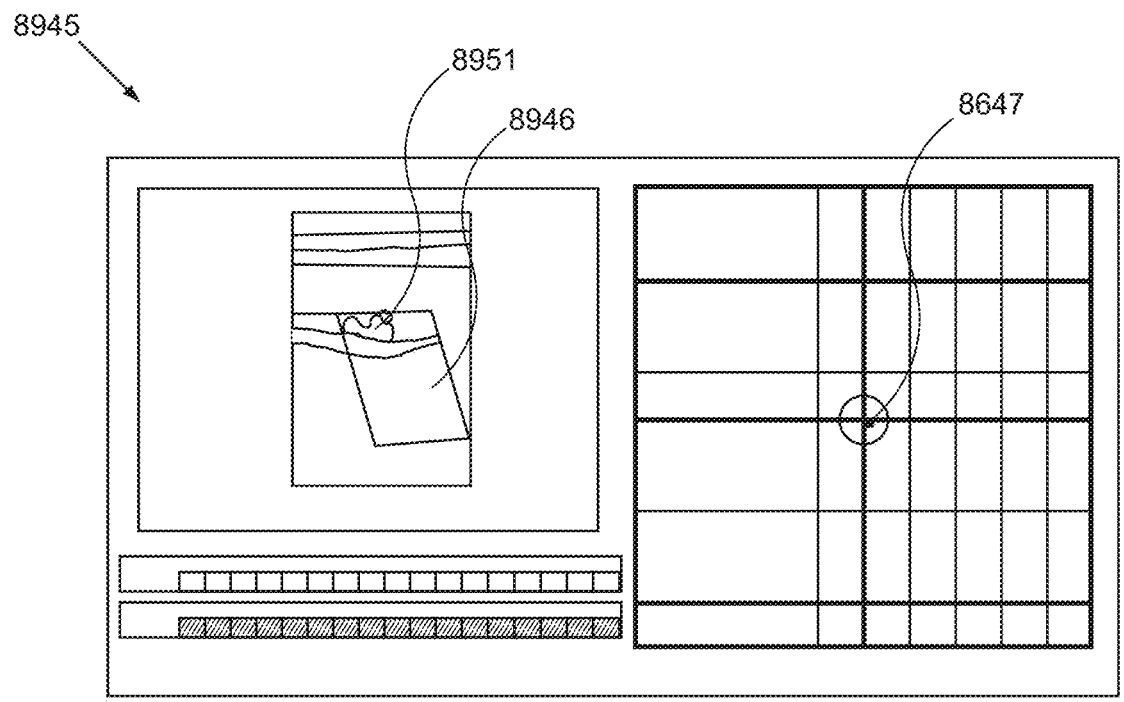
FIGS. 19C-19D depict a setup for the treatment of the renal blood vessels along with actual treatment of the renal blood vessels.
Figure 19D:
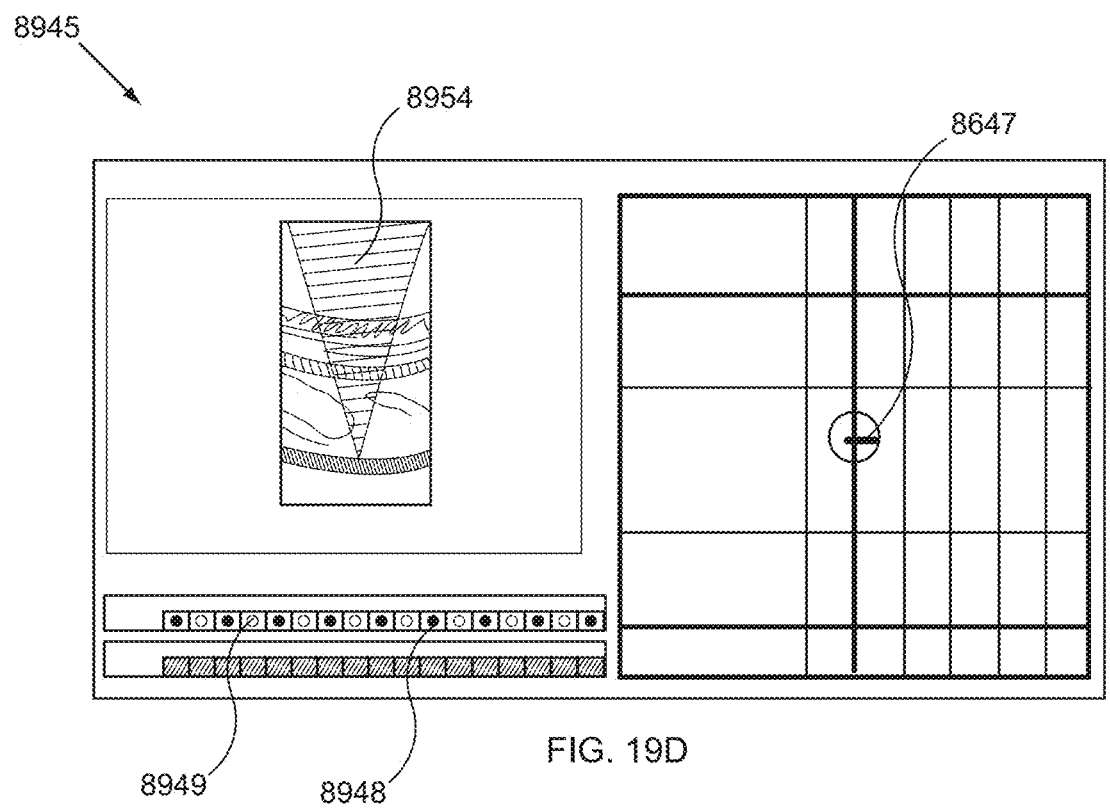

FIGS. 19C-D depicts an actual treatment of the renal hilum 8945. A targeting region 8946 is shown in which movement of the transducer and hilum is tracked and analyzed 8949 and 8948. The accuracy of the tracking is recorded and displayed 8948 over time. In this figure, the cool off period is shown and in FIG. 19D treatment 8954 is shown. In some embodiments, energy is delivered in the manner described herein through the kidney, which has been shown to be resilient to heat. In some cases, movement of the renal hilum and the transducer are recorded in real time, and therapy of the blood vessels is depicted in real time during the treatment. Success of tracking may, as well as progress of the therapy at the time of treatment, may be presented on a screen for viewing by the user as shown in the tracking bar below the ultrasound image. Success may be considered when the targeting is maintained within the target circle 8647 at least 90% of the time of each treatment. This targeting accuracy is generally attributed to success in the pre-clinical studies described below. A motion tracking system is built into the system to ensure that a proper dose is delivered to the region of the renal nerves leading to the kidney. The motion tracking system relates the coordinates in three dimensions to the treatment, and allows for the quality of the treatment to be determined. Therefore, in one embodiment, focused energy is applied to the region of the blood vessels to the kidney; hardware and software is utilized to quantify the degree of movement between the treatment device and the treatment region; a quality factor is utilized to ascertain whether additional time needs to be added to the treatment if the quality factor is too low to yield an effective treatment.

FIGS. 19C-D depict the setup 8645 for the treatment of the renal blood vessels along with actual treatment 8654 of the renal blood vessels 8651. Window 8653 is the target window for the treatment. Although renal blood vessels are depicted, any blood vessel with a surrounding nerve can be targeted. Success factor 8648 is based on motion of the target and/or operator. If the treatment fails to remain within the target 8647 for a set period of time, then a failure indicator 8648 is shown on the screen 8646 rather than a success indicator.

Figure 19E:
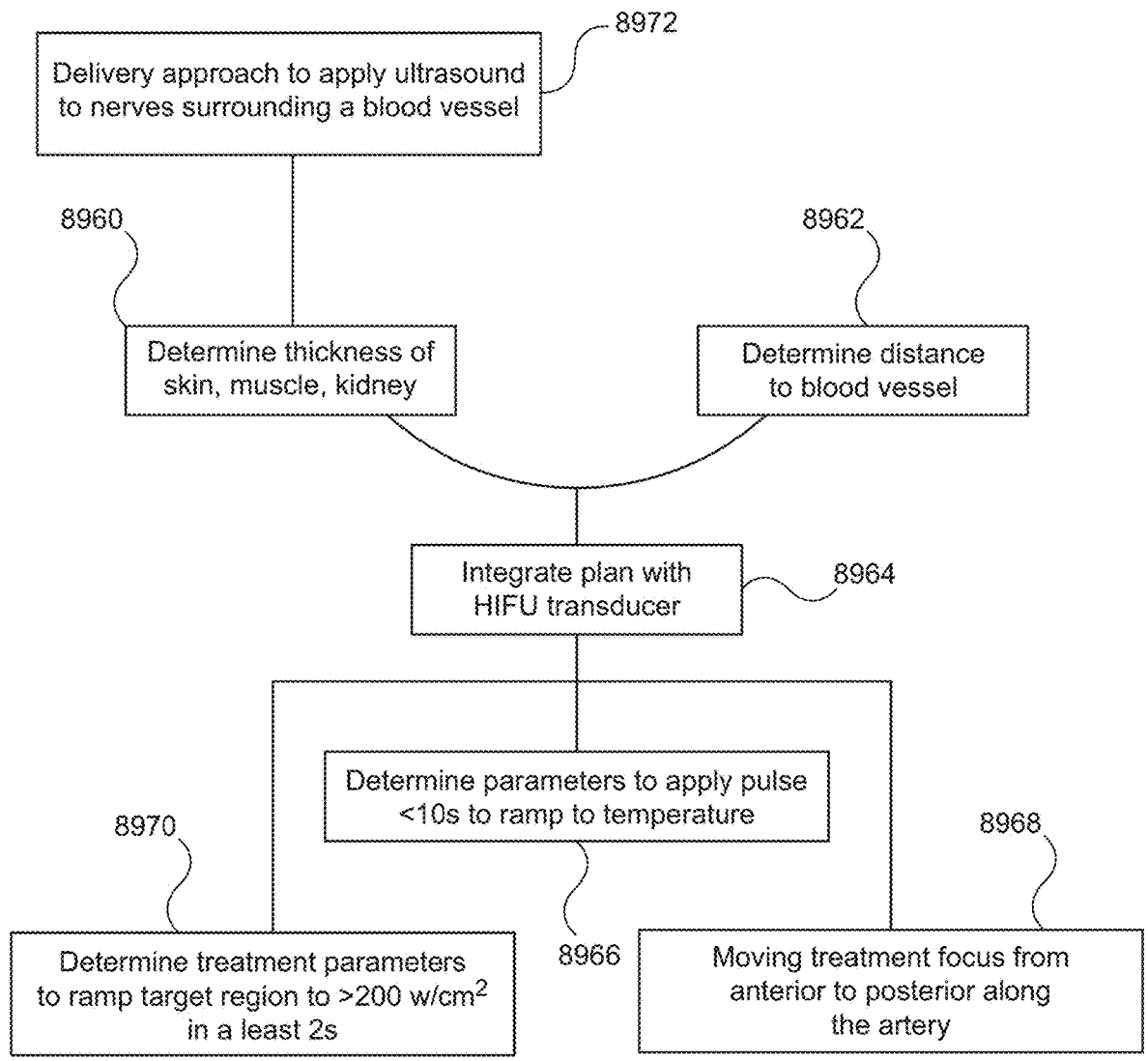
FIG. 19E is a schematic algorithm of the treatment plan for treatment shown in FIG. 19C-D.

FIG. 19E depicts a clinical method based on the treatment shown in FIGS. 19C-D above. The first step 8972 is to consider a delivery approach to apply ultrasound to nerves surrounding a blood vessel. The next step is to generate an ultrasound image of the region 8960 and the subsequent step is to determine the distance 8962 to the blood vessel and then integrate the plan with the HIFU transducer 8964. Based on data generated above, parameters are determined to apply pulses, generally less than 10 s of "on" time, to ramp the temperature of the region around the blood vessel to approximately 200 W/cm$^2$ in at least 2 seconds 8970. The focus is then moved along the artery or blood vessel 8968 from anterior to posterior and/or from side to side.

Figure 20:
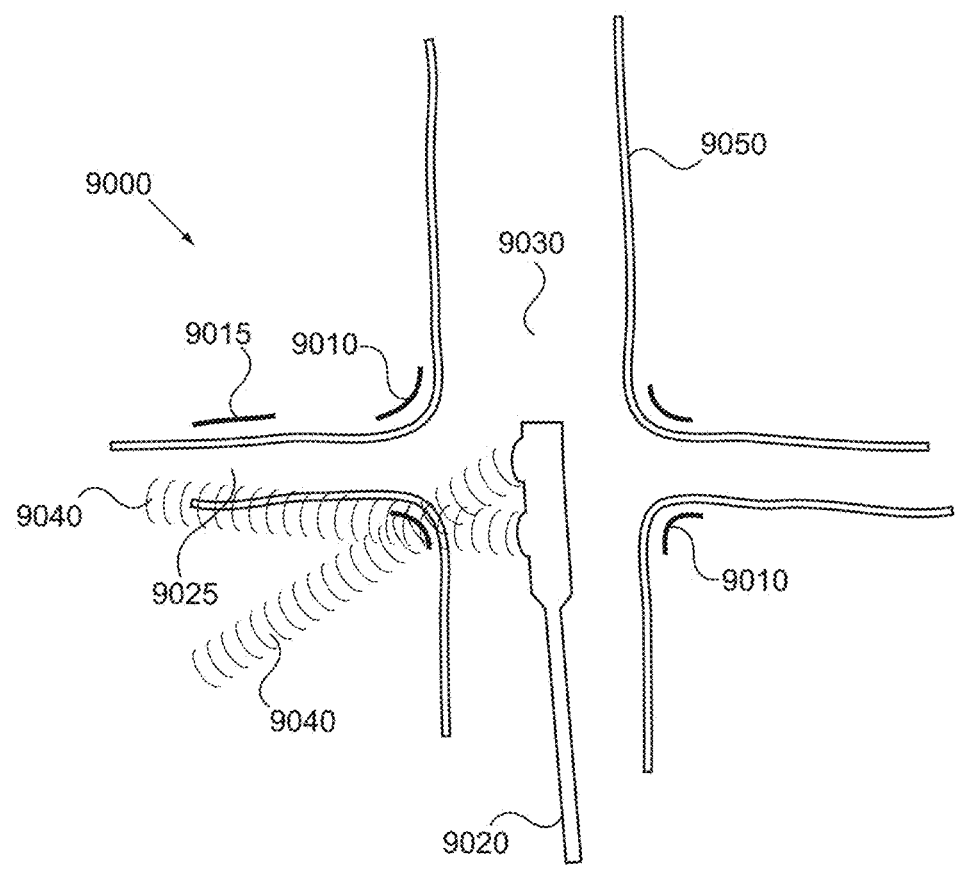
FIG. 20 depicts the application of ultrasound waves through the wall of the aorta to apply a therapy to the autonomic nervous system.

FIG. 20 depicts an alternative method, system 9000 and device to ablate the renal nerves 9015 or the nerves leading to the renal nerves at the aorta-renal artery ostium 9010. The intravascular device 9020 is placed into the aorta 9050 and advanced to the region of the renal arteries 9025. Energy is applied from the transducer 9020 and focused 9040 (in the case of HIFU, LIFU, ionizing radiation) to the region of the takeoff of the renal arteries 9025 from the aorta 9050. This intravascular 9030 procedure can be guided using MRI and/or MRI thermometry or it can be guided using fluoroscopy, ultrasound, or MRI. Because the aorta is larger than the renal arteries, the HIFU catheter can be placed into the aorta directly and cooling catheters can be included as well. In addition, in other embodiments, non-focused ultrasound can be applied to the region around the renal ostium or higher in the aorta. Non-focused ultrasound in some embodiments may require cooling of the tissues surrounding the probe using one or more coolants but in some embodiments, the blood of the aorta will take the place of the coolant, by its high flow rate; HIFU, or focused ultrasound, may not need the cooling because the waves are by definition focused from different angles to the region around the aorta. The vena cava and renal veins can also be used as a conduit for the focused ultrasound transducer to deliver energy to the region as well. In one embodiment, the vena cava is accessed and vibratory energy is passed through the walls of the vena cava and renal vein to the renal arteries, around which the nerves to the kidney travel. The veins, having thinner walls, allow energy to pass through more readily.

Figure 21A:
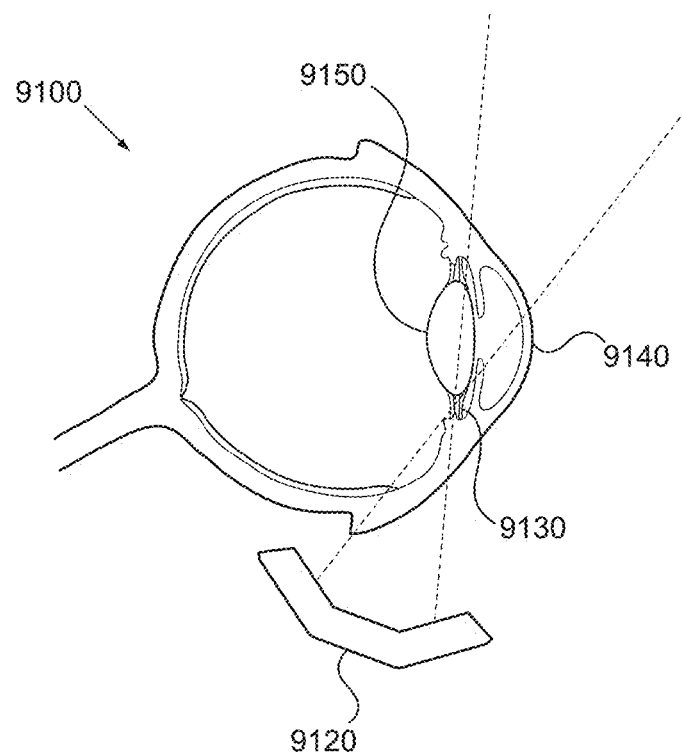
FIG. 21A depicts application of focused energy to the ciliary muscles and processes of the anterior region of the eye.
Figure 21B:
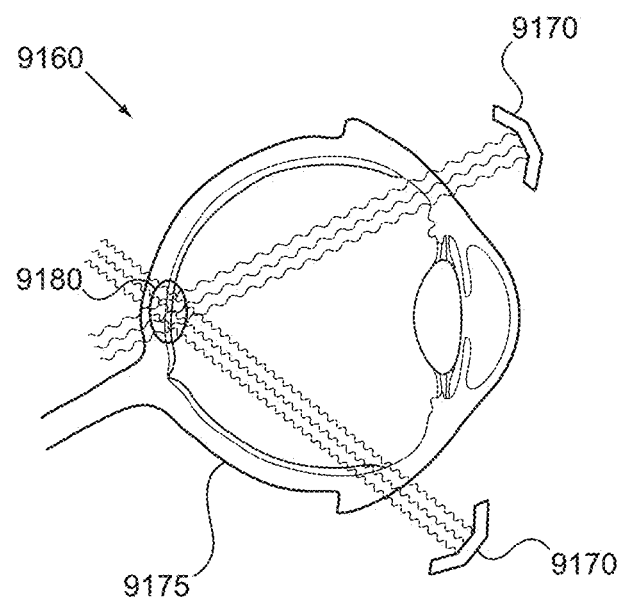
FIG. 21B depicts the application of focused non-ablative energy to the back of the eye to enhance drug or gene delivery or another therapy such as ionizing radiation.

FIG. 21a-b depicts an eyeball 9100. Also depicted are the zonules of the eye 9130 (the muscles which control lens shape) and ultrasound transducer 9120. The transducer 9120 applies focused ultrasound energy to the region surrounding the zonules, or the zonules themselves, in order to tighten them such that a presbyopic patient can accommodate and visualize object up close. Similarly, heat or vibration applied to the ciliary muscles, which then increases the outflow of aqueous humor at the region of interest so that the pressure within the eye cannot build up to a high level. The ultrasound transducer 9120 can also be utilized to deliver drug therapy to the region of the lens 9150, ciliary body, zonules, intra-vitreal cavity, anterior cavity 9140, posterior cavity, etc.

In some embodiments (FIG. 21b), multiple transducers 9160 are utilized to treat tissues deep within the eye; the ultrasonic transducers 9170 are focused on the particular region of the eye from multiple directions so that tissues along the path of the ultrasound are not damaged by the ultrasound and the focus region and region of effect 9180 is the position where the waves meet in the eye. In one embodiment, the transducers are directed through the pars plana region of the eye to target the macula 9180 at the posterior pole 9175 of the eye. This configuration might allow for heat, vibratory stimulation, drug delivery, gene delivery, augmentation of laser or ionizing radiation therapy, etc. In certain embodiments, focused ultrasound is not required and generic vibratory waves are transmitted through the eye at frequencies from 20 kHz to 10 MHz. Such energy may be utilized to break up clots in, for example, retinal venous or arterial occlusions which are creating ischemia in the retina. This energy can be utilized in combination with drugs utilized specifically for breaking up clots in the veins of the retina.

Figure 22:
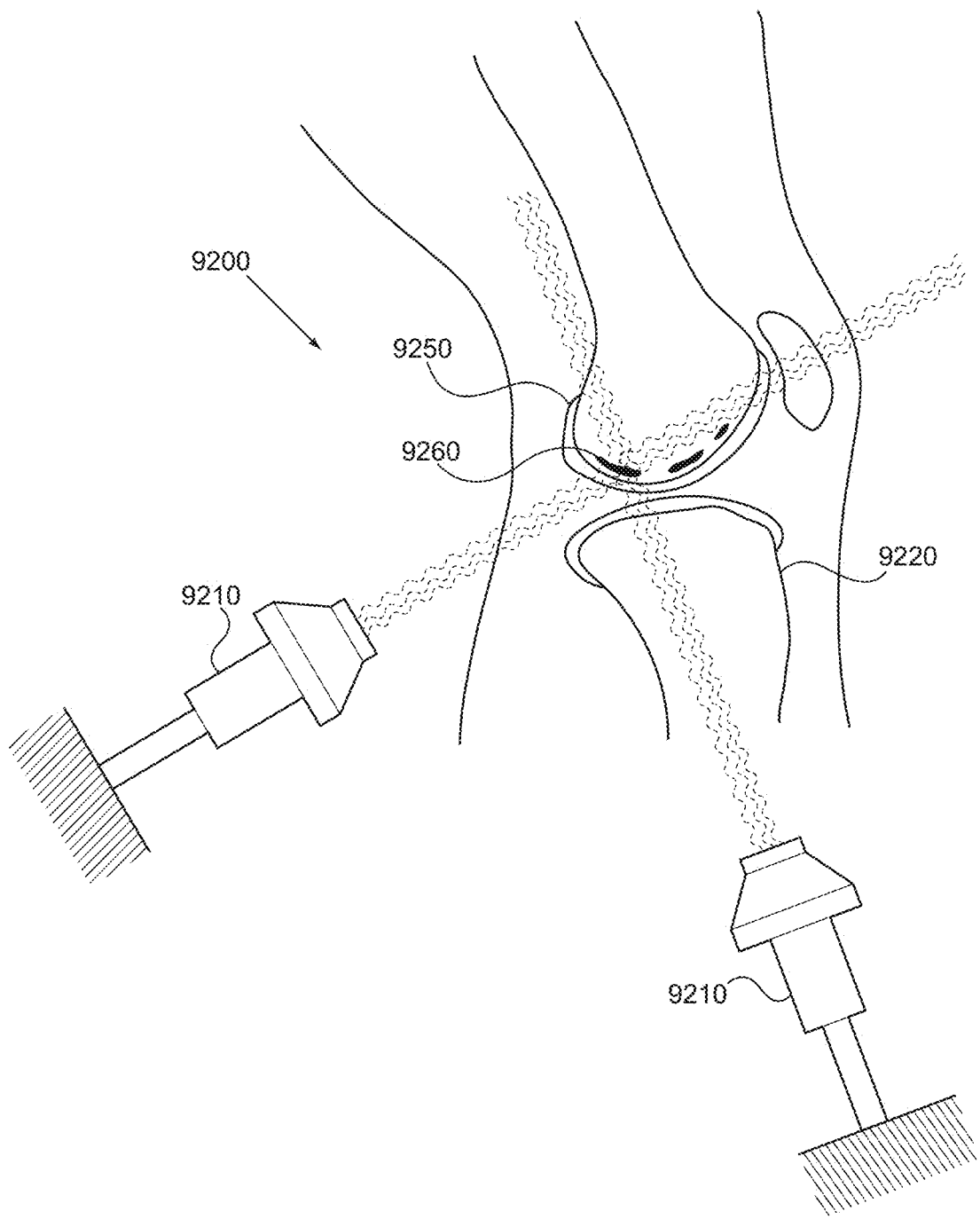
FIG. 22 depicts the application of focused energy to nerves surrounding the knee joint to affect nerve function in the joint.

FIG. 22 depicts a peripheral joint 9200 being treated with heat and/or vibrational energy. Ultrasound transducer 9210 emits waves toward the knee joint to block nerves 9260 just underneath the bone periostium 92209250 or underneath the cartilage. Although a knee joint is depicted, it should be understood that many joints can be treated including small joints in the hand, intervertebral joints, the hip, the ankle, the wrist, and the shoulder. Unfocused or focused ultrasonic energy can be applied to the joint region to inhibit nerve function reversibly or irreversibly. Such inhibition of nerve function can be utilized to treat arthritis, post-operative pain, tendonitis, tumor pain, etc. In one preferred embodiment, vibratory energy can be utilized rather than heat. Vibratory energy applied to the joint nerves can inhibit their functioning such that the pain fibers are inhibited.

Figure 23A:
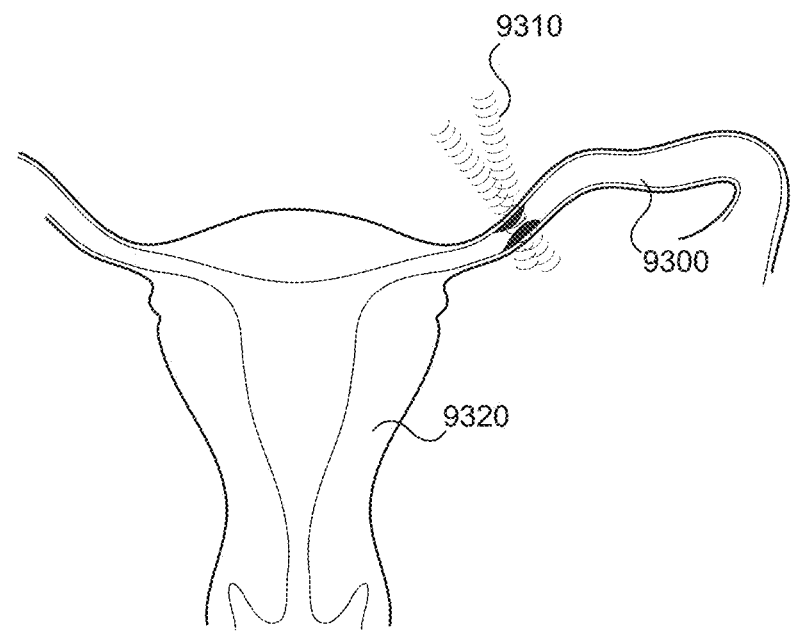
FIGS. 23A-23B depict the application of energy to the fallopian tube to sterilize a patient.
Figure 23B:
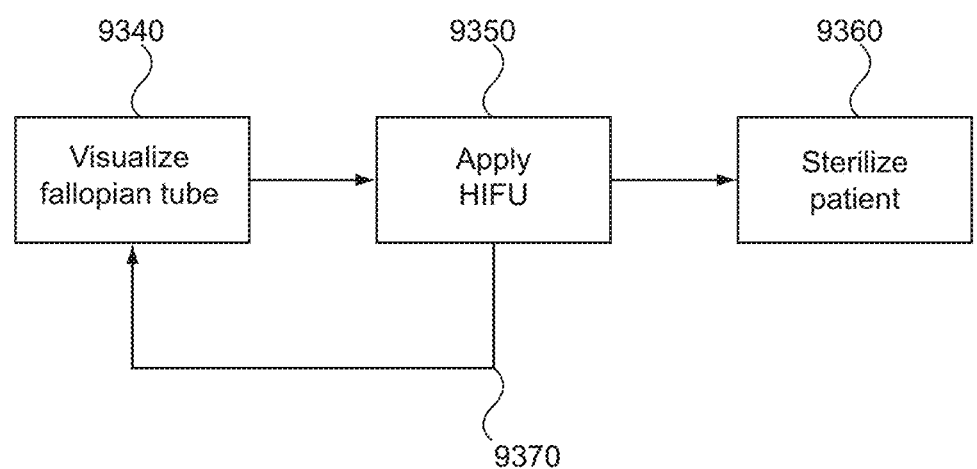

FIG. 23a-b depicts closure of a fallopian tube 9300 of a uterus 9320 using externally applied ultrasound 9310 so as to prevent pregnancy.

MRI or preferably ultrasound can be utilized for the imaging modality. Thermometry can be utilized as well so as to see the true ablation zone in real time. The fallopian tube 9300 can be visualized using ultrasound, MRI, CT scan or a laparoscope. Once the fallopian tube is targeted, external energy 9310, for example, ultrasound, can be utilized to close the fallopian tube to prevent pregnancy. When heat is applied to the fallopian tube, the collagen in the walls are heated and will swell, the walls then contacting one another and closing the fallopian preventing full ovulation and therefore preventing pregnancy. Although there is no doppler signal in the fallopian tube, the technology for visualization and treatment is similar to that for an artery or other duct. That is, the walls of the tube are identified and modeled, then focused ultrasound is applied through the skin to the fallopian tube to apply heat to the walls of the lumen of the fallopian tube.

In FIG. 23b, a method is depicted in which the fallopian tubes are visualized 9340 using MRI, CT, or ultrasound. HIFU 9350 is applied under visualization with MRI or ultrasound. As the fallopian tubes are heated, the collagen in the wall is heated until the walls of the fallopian tube close off. At this point the patient is sterilized 9360. During the treating time, it may be required to determine how effective the heating is progressing. If additional heat is required, then additional HIFU may be added to the fallopian tubes until there is closure of the tube and the patient is sterilized 9360. Such is one of the advantages of the external approach in which multiple treatments can be applied to the patient, each treatment closing the fallopian tubes further, the degree of success then assessed after each treatment. A further treatment can then be applied 9370.

In other embodiments, ultrasound is applied to the uterus or fallopian tubes to aid in pregnancy by improving the receptivity of the sperm and/or egg for one another. This augmentation of conception can be applied to the sperm and egg outside of the womb as well, for example, in a test tube in the case of extra-uterine fertilization.

Figure 24:
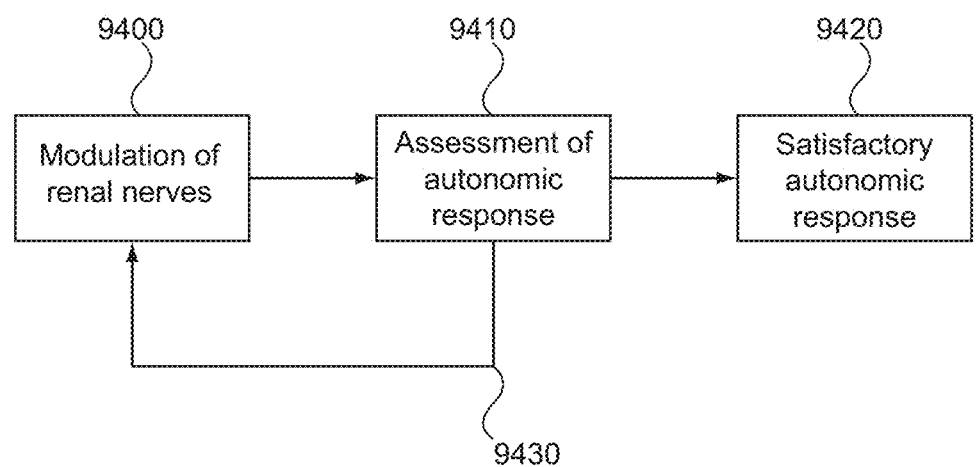
FIG. 24 depicts an algorithm to assess the effect of the neural modulation procedure on the autonomic nervous system. After a procedure is performed on the renal nerves, assessment of the autonomic response is performed by, for example, simulating the autonomic nervous system in one or more places.

FIG. 24 depicts a feedback algorithm to treat the nerves of the autonomic nervous system. It is important that there be an assessment of the response to the treatment afterward. Therefore, in a first step, modulation of the renal nerves 9400 is accomplished by any or several of the embodiments discussed above. An assessment 9410 then ensues, the assessment determining the degree of treatment effect engendered; if a complete or satisfactory response is determined 9420, then treatment is completed. For example, the assessment 9410 might include determination through microneurography, assessment of the carotid sinus reactivity (described above), heart rate variability, measurement of norepinephrine levels, tilt test, blood pressure, ambulatory blood pressure measurements, etc. With a satisfactory autonomic response, further treatment might not ensue or depending on the degree of response, additional treatments of the nerves 9430 may ensue.

Figure 25:
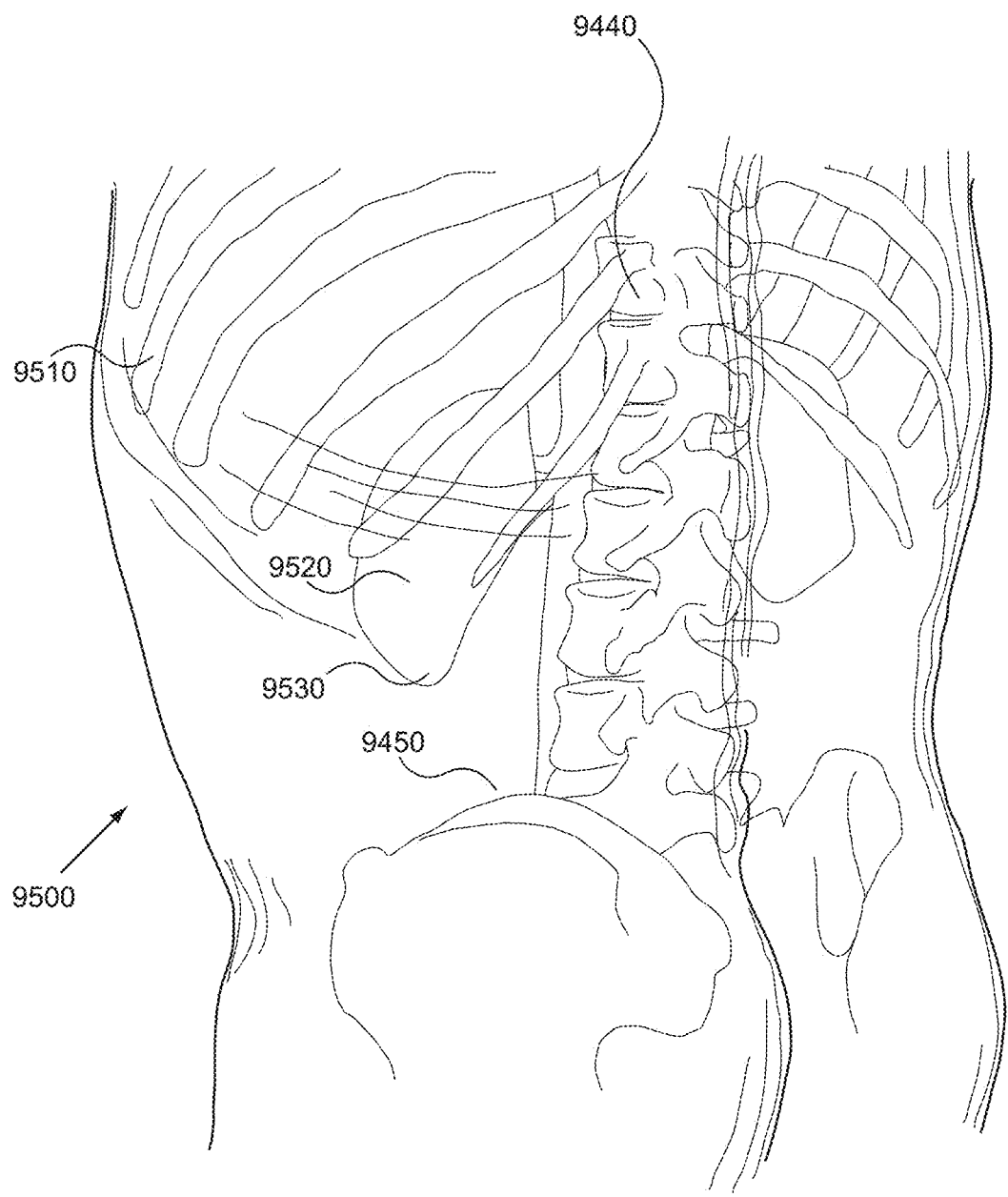
FIG. 25 depicts an optimized position of a device to apply therapy to internal nerves.

FIG. 25 depicts a reconstruction of a patient from CT scan images showing the position of the kidneys 9520 looking through the skin of a patient 9500. The ribs 9510 partially cover the kidney but do reveal a window at the inferior pole 9530 of the kidney 9520. Analysis of many of these reconstructions has lead to clinical paradigm in which the ribs 9510, pelvis 9420, and the vertebra 9440 are identified on a patient, the kidneys are identified via ultrasound and then renal arteries are identified via Doppler ultrasound. A relevant clinical window may have an access angle of between 40 and 60 degrees.

Figure 26A:
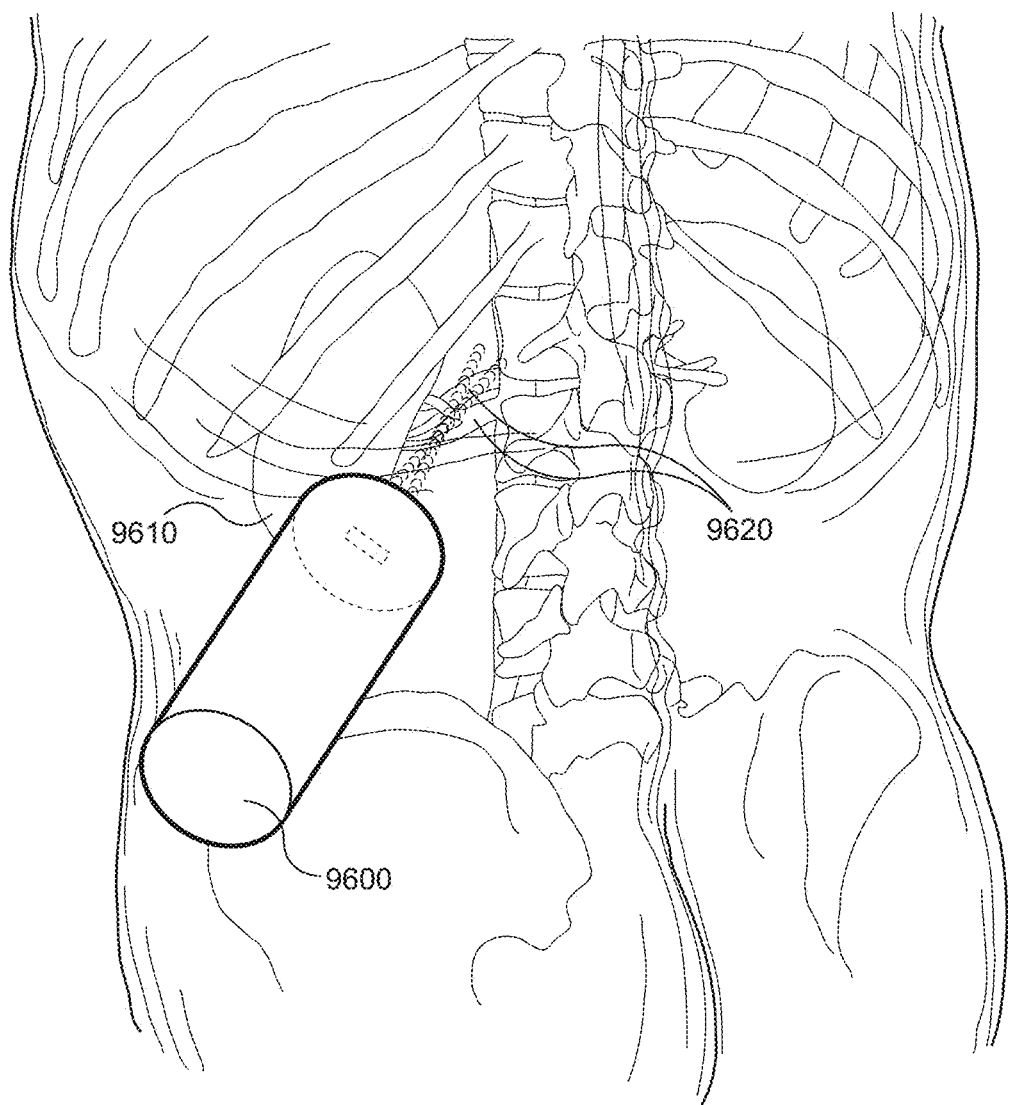
FIG. 26A depicts positioning of a patient to obtain parameters for system design.

As shown in FIG. 26a, once the ribs and vertebra are identified with the Doppler ultrasound, an external energy source 9600 can be applied to the region. Specifically, focused ultrasound (HIFU or LIFU) can be applied to the region once these structures are identified and a lesion applied to the blood vessels (renal artery and renal nerve) 9620 leading to the kidney 9610. As described herein, the position of the ultrasound transducer 9600 is optimized on the posterior of the patient as shown in FIG. 26A. That is, with the vertebra, the ribs, and the iliac crest bordering the region where ultrasound is applied.

Figure 26B:
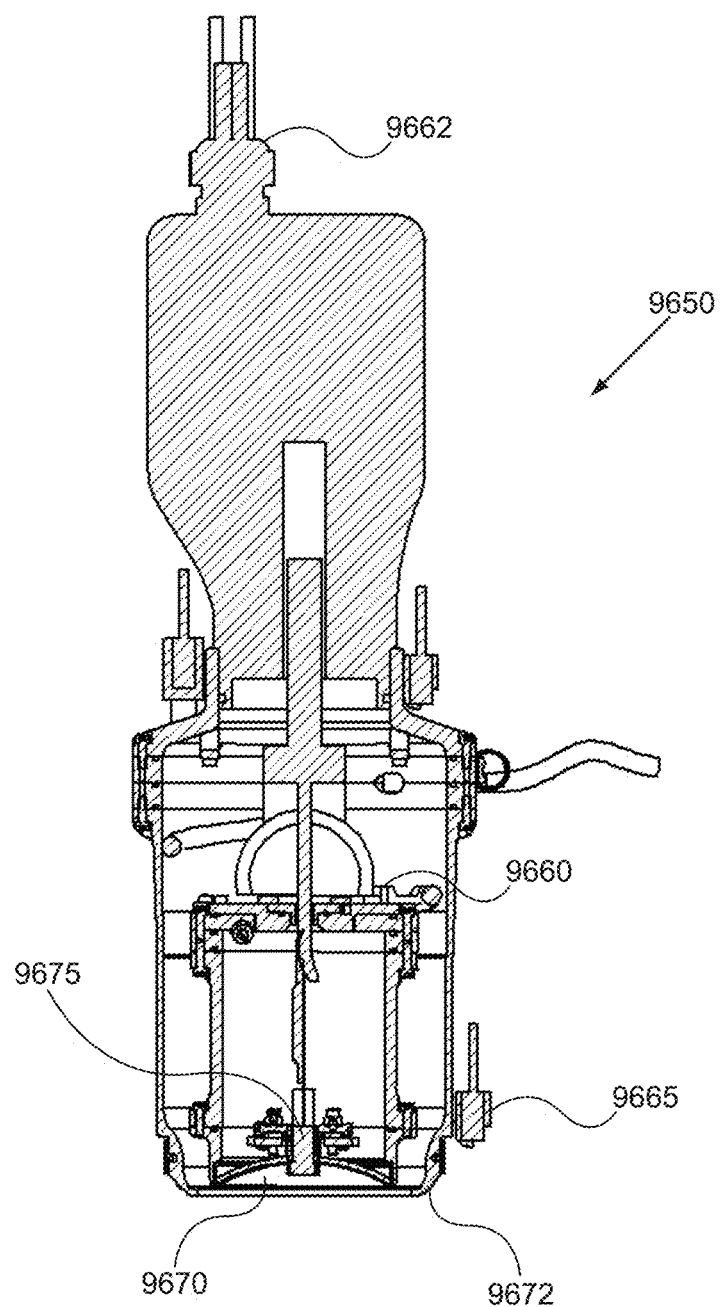
FIG. 26B depicts a device design based on the information learned from feasibility studies.

Based on the data above and specifically the CT scan anatomic information in FIG. 26A, FIG. 26B depicts a device and system 9650 designed for treatment of this region (blood vessels in the hilum of the kidney) in a patient. It contains a 0.5-3 Mhz ultrasound imaging transducer 9675 in its center and a cutout or attachment location of the ultrasound ceramic (e.g. PZT) for the diagnostic ultrasound placement. It also contains a movement mechanism 9660 to control the therapeutic transducer 9670. The diagnostic ultrasound device 9675 is coupled to the therapeutic device in a well-defined, known relationship. The relationship can be defined through rigid or semi-rigid coupling or it can be defined by electrical coupling such as through infrared, optical-mechanical coupling and/or electromechanical coupling. Along the edges of the outer rim of the device, smaller transducers 9670 can be placed which roughly identify tissues through which the ultrasound travels. For example, simple and inexpensive one or two-dimensional transducers might be used so as to determine the tissues through which the ultrasound passes on its way to the target can be used for the targeting and safety. From a safety perspective, such data is important so that the ultrasound does not hit bone or bowel and that the transducer is properly placed to target the region around the renal blood vessels. Also included in the system is a cooling system to transfer heat from the transducer to fluid 9662 running through the system. Cooling via this mechanism allows for cooling of the ultrasound transducer as well as the skin beneath the system. A further feature of the system is a sensor mechanism 9665 which is coupled to the system 9650 and records movement of the system 9650 relative to a baseline or a coordinate nearby. In one embodiment, a magnetic sensor is utilized in which the sensor can determine the orientation of the system relative to a magnetic sensor on the system. The sensor 9665 is rigidly coupled to the movement mechanism 9660 and the imaging transducer 9675. In addition to magnetic, the sensor might be optoelectric, acoustic, imaging (e.g. camera), or radiofrequency based.

Furthermore, the face 9672 of the transducer 9670 is shaped such that is fits within the bony region described and depicted in FIG. 26A. For example, in some embodiments, the shape might be elliptical or aspheric; in other embodiments, the shape may be triangular or pie shaped. In addition, in some embodiments, the ultrasound imaging engine might not be directly in the center of the device and in fact might be superior to the center and closer to the superior border of the face and closer to the ribs, wherein the renal artery is visualized better with the imaging probe 9675.

Figure 27:
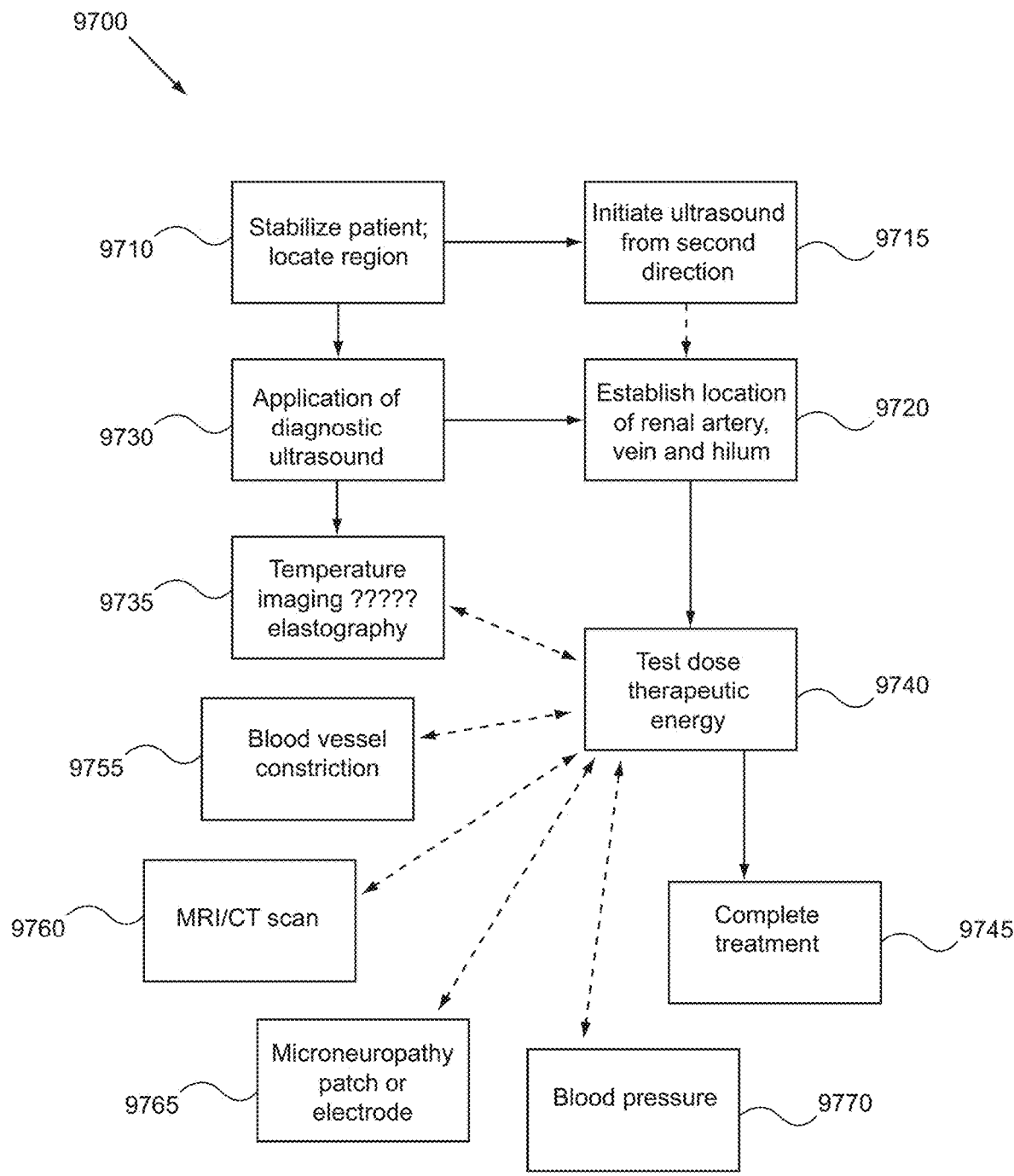
FIG. 27 depicts a clinical paradigm for treating the renal nerves of the autonomic nervous system based on feasibility studies.

Given the clinical data as well as the devised technologies described above (e.g. FIG. 26A-B), FIG. 27 illustrates the novel treatment plan 9700 to apply energy to the nerves around the renal artery with energy delivered from a position external to the patient.

In one embodiment, the patient is stabilized and/or positioned such that the renal artery and kidneys are optimally located 9710. Diagnostic ultrasound 9730 is applied to the region and optionally, ultrasound is applied from a second direction 9715. The positioning and imaging maneuvers allow the establishment of the location of the renal artery, the hilum, and the vein 9720. A test dose of therapeutic energy 9740 can be applied to the renal hilum region. In some embodiments, temperature 9735 can be measured. This test dose can be considered a full dose if the treatment is in fact effective by one or more measures. These measures might be blood pressure 9770, decrease in sympathetic outflow (as measured by microneurography 9765), increase in parasympathetic outflow, change in the caliber of the blood vessel 9755 or a decrease in the number of spontaneous spikes in a microneurographic analysis in a peripheral nerve (e.g. peroneal nerve) 9765, or an MRI or CT scan which reveals a change in the nervous anatomy 9760. In some embodiments, indices within the kidney are utilized for feedback. For example, the resistive index, a measure of the vasoconstriction in the kidney measured by doppler ultrasound is a useful index related to the renal nerve activity; for example, when there is greater autonomic activity, the resistive index increases, and vice versa.

Completion of the treatment 9745 might occur when the blood pressure reaches a target value 9770. In fact, this might never occur or it may occur only after several years of treatment. The blood pressure might continually be too high and multiple treatments may be applied over a period of years . . . the concept of dose fractionation. Fractionation is a major advantage of applying energy from a region external to a region around the renal arteries in the patient as it is more convenient and less expensive when compared to invasive treatments such as stimulator implantation and interventional procedures such as catheterization of the renal artery.

Figure 29A:
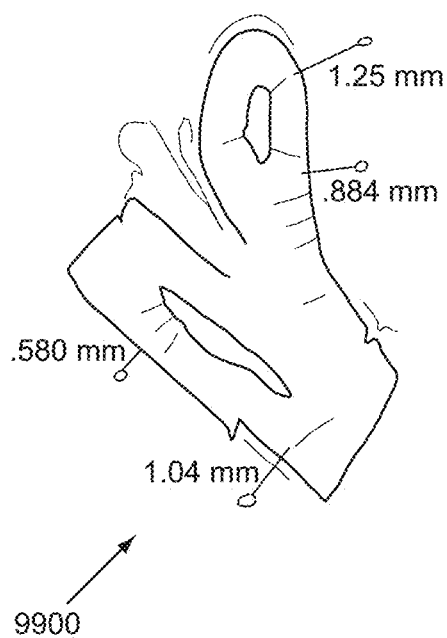
FIGS. 29A-D depict results of studies applying focused energy to nerves surrounding arteries and of ultrasound studies to visualize the blood vessels around which the nerves travel.
Figure 29B:
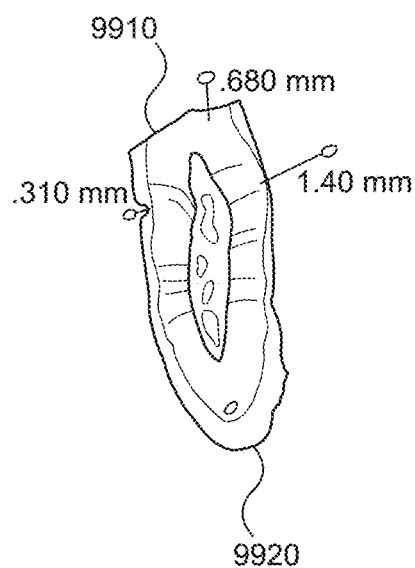
Figure 29C:
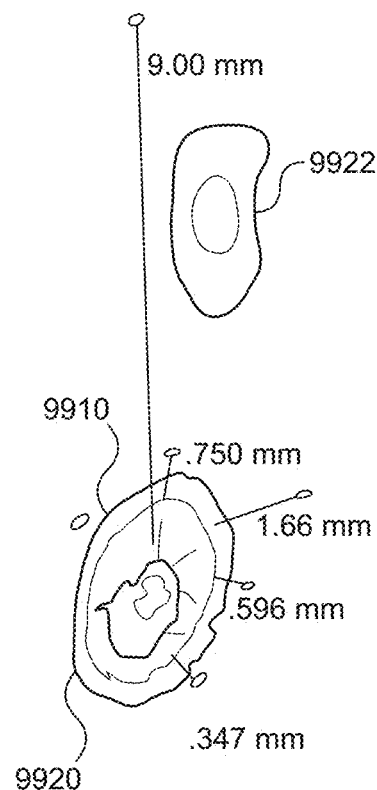

Another important component is the establishment of the location and position of the renal artery, renal vein, and hilum of the kidney 9720. As discussed above, the utilization of Doppler ultrasound signaling allows for the position of the nerves to be well approximated such that the ultrasound can be applied to the general region of the nerves. The region of the nerves can be seen in FIGS. 29A-D. FIGS. 29A-C are sketches from actual histologic slices. The distances from the arterial wall can be seen at different locations and generally range from 0.3 mm to 10 mm. Nonetheless, these images are from actual renal arteries and nerves and are used so as to develop the treatment plan for the system. For example, once the arterial wall is localized 9730 using the Doppler or other ultrasound signal, a model of the position of the nerves can be established and the energy then targeted to that region to inhibit the activity of the nerves 9720. Notably, the distance of many of these nerves from the wall of the blood vessel indicate that a therapy which applies radiofrequency to the wall of the vessel from the inside of the vessel likely has great difficulty in reaching a majority of the nerves around the blood vessel wall.

Figure 29D:
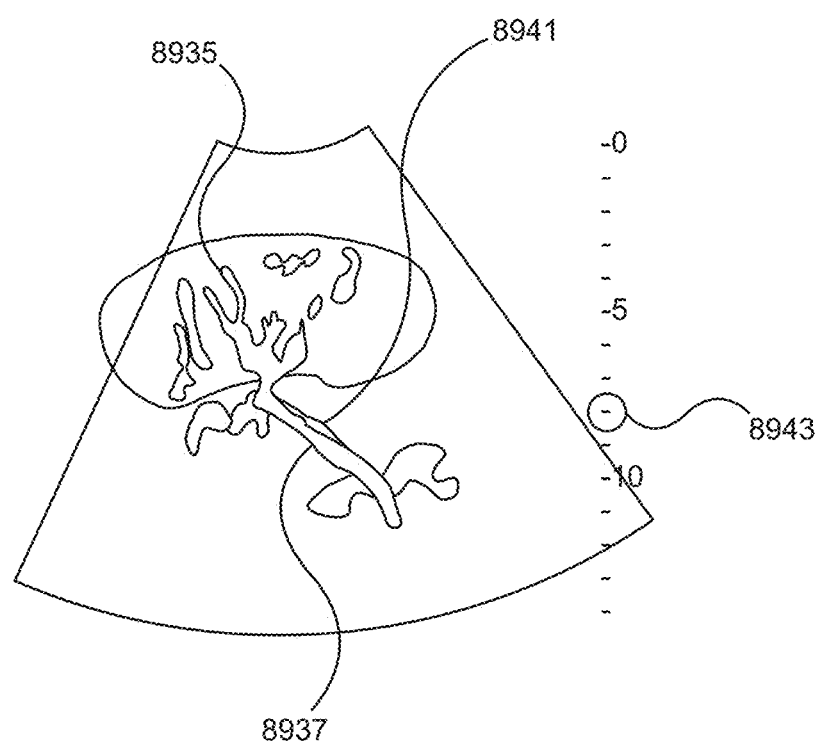

For example, FIG. 29D depicts a schematic from a live human ultrasound. As can be seen, the ultrasound travels through skin, through the subcutaneous fat, through the muscle and at least partially through the kidney 8935 to reach the hilum 8941 of the kidney and the renal blood vessels 8937. This direction was optimized through clinical experimentation so as to not include structures which tend to scatter ultrasound such as bone and lung. Experimentation lead to the optimization of this position for the imaging and therapy of the renal nerves. The position of the ultrasound is between the palpable bony landmarks on the posterior of the patient as described above and below. The vertebrae are medial, the ribs superior and the iliac crest inferior. Importantly, the distance of these structures 8943 is approximately 8-12 cm and not prohibitive from a technical standpoint. These images from the ultrasound are therefore consistent with the results from the CT scans described above as well.

FIG. 29E depicts the surface area 8760 available to an ultrasound transducer for two patients out of a clinical study. One patient was obese and the other thinner. Quantification of this surface area 8762 was obtained by the following methodology: 1) obtain CT scan; 2) mark off boundary of organs such as the vertebrae, iliac crest, and ribs; 3) draw line from renal blood vessels to the point along the edge of the bone; 4) draw perpendicular from edge bone to the surface of the skin; 5) map the collection of points obtained along the border of the bone. The surface area is the surface area between the points and the maximum diameter is the greatest distance between the bony borders. The collection of points obtained with this method delimits the area on the posterior of the patient which is available to the ultrasound transducer to either visualize or treat the region of the focal spot. By studying a series of patients, the range of surface areas was determined so as to assist in the design which will serve the majority of patients. The transducers modeled in FIG. 30 have surface areas of approximately 11×8 cm or 88 cm$^2$ which is well within the surface area 8762 shown in FIG. 29E, which is representative of a patient series. Furthermore the length, or distance, from the renal artery to the skin was quantified in shortest ray 8764 and longest ray 8766. Along with the angular data presented above, these data enable design of an appropriate transducer to achieve autonomic modulation and control of blood pressure.

In a separate study, it was shown that these nerves could be inhibited using ultrasound applied externally with the parameters and devices described herein. Pathologic analysis revealed that the nerves around the artery were completely inhibited and degenerated, confirming the ability of the treatment plan to inhibit these nerves and ultimately to treat diseases such as hypertension. Furthermore, utilizing these parameters, did not cause any damage within the path of the ultrasound through the kidney and to the renal hilum.

Importantly, it has also been discovered via clinical trials that when ultrasound is used as the energy applied externally, that centering the diagnostic ultrasound probe such that a cross section of the kidney is visualized and the vessels are visualized, is an important component of delivering the therapy to the correct position along the blood vessels. One of the first steps in the algorithm 9700 is to stabilize the patient in a patient stabilizer custom built to deliver energy to the region of the renal arteries. After stabilization of the patient, diagnostic ultrasound is applied to the region 9730 to establish the extent of the ribs, vertebrae, and pelvis location. Palpation of the bony landmarks also allows for the demarcation of the treatment zone of interest. The external ultrasound system is then placed within these regions so as to avoid bone. Then, by ensuring that a portion of the external energy is delivered across the kidney (for example, using ultrasound for visualization), the possibility of hitting bowel is all but eliminated. The ultrasound image in FIG. 29D depicts a soft tissue path from outside the patient to the renal hilum inside the patient. The distance is approximately 8-16 cm. Once the patient is positioned, a cushion 9815 is placed under the patient. In one embodiment, the cushion 9815 is simply a way to prop up the back of the patient. In another embodiment, the cushion 9815 is an expandable device in which expansion of the device is adjustable for the individual patient. The expandable component 9815 allows for compression of the retroperitoneum (where the kidney resides) to slow down or dampen movement of the kidney and maintain its position for treatment with the energy source or ultrasound.

A test dose of energy 9740 can be given to the region of the kidney hilum or renal artery and temperature imaging 9735, constriction of blood vessels 9755, CT scans 9760, microneurography 9765 patch or electrode, and even blood pressure 9770. Thereafter, the treatment can be completed 9745. Completion might occur minutes, hours, days, or years later depending on the parameter being measured.

Through experimentation, it has been determined that the region of the renal hilum and kidneys can be stabilized utilizing gravity with local application of force to the region of the abdomen below the ribs and above the renal pelvis.

Figure 28A:
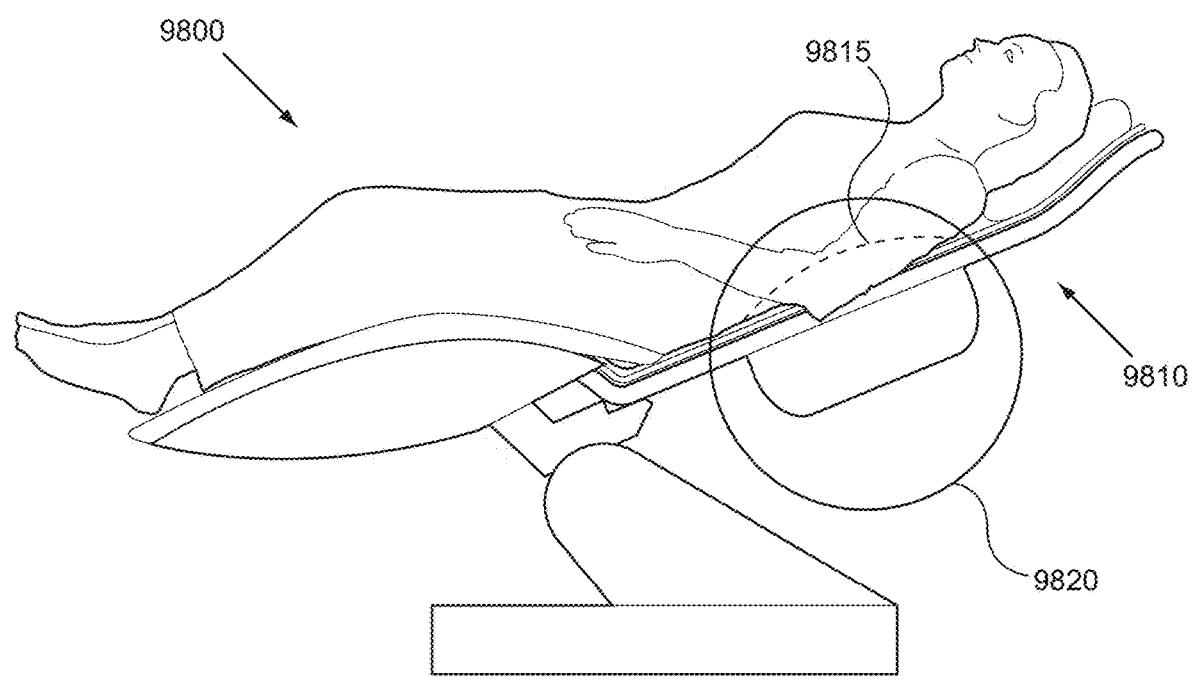
FIGS. 28A-28C depict a treatment positioning system for a patient incorporating a focused ultrasound system.
Figure 28B:
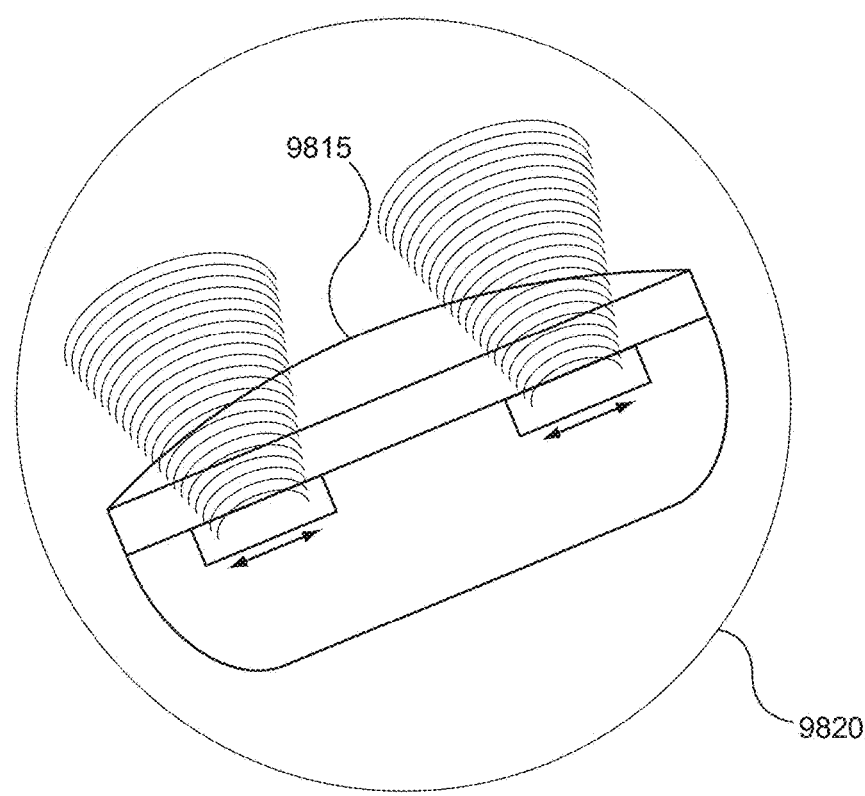
Figure 28C:
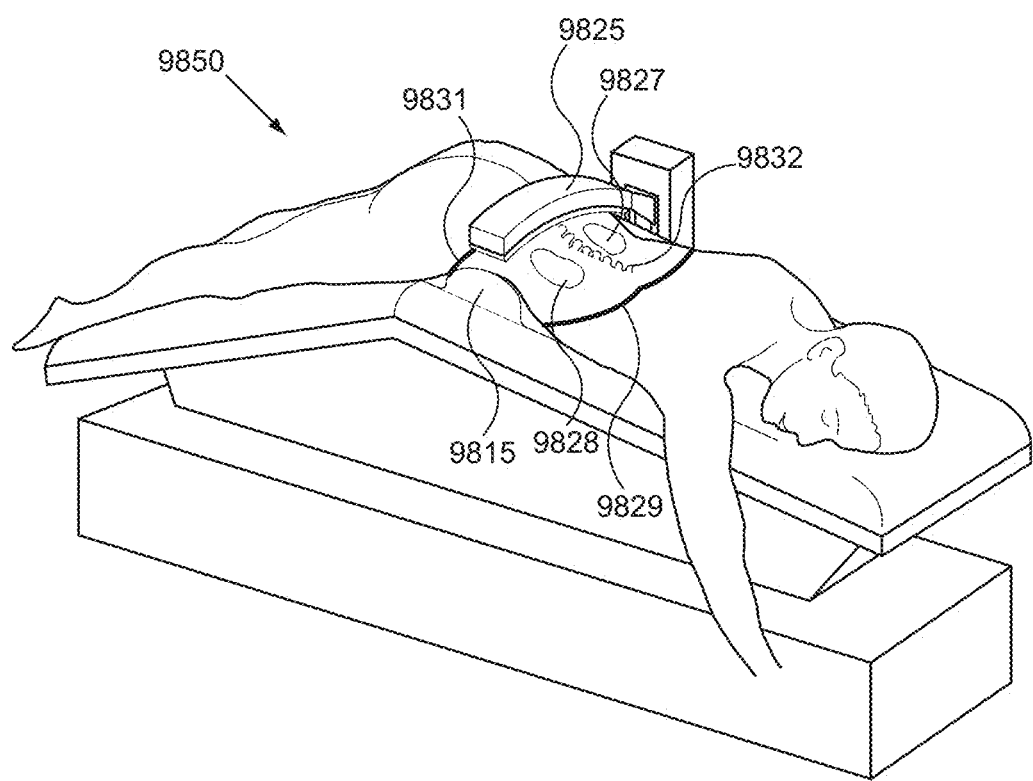

For example, FIGS. 28A-C depict examples of patient positioners intended to treat the region of the renal blood vessels.

FIG. 28A is one example of a patient positioned in which the ultrasound diagnostic and therapeutic 9820 is placed underneath the patient. The positioner 9810 is in the form of a tiltable bed. A patient elevator 9815 placed under the patient pushes the renal hilum closer to the skin and can be pushed forward in this manner; as determined in clinical trials, the renal artery is approximately 2-3 cm more superficial in this type of arrangement with a range of approximately 7-15 cm in the patients studied within the clinical trial. The weight of the patient allows for some stabilization of the respiratory motion which would otherwise occur; the patient elevator can be localized to one side or another depending on the region to be treated. Alternative approaches (in the case where the physician wants to maintain the patient in a flat position) are to place a positioning device under the patient's legs and maintain the upper torso substantially flat.

FIG. 28B detects a more detailed configuration of the ultrasound imaging and therapy engine 9820 inset. A patient interface 9815 is utilized to create a smooth transition for the ultrasound waves to travel through the skin and to the kidneys for treatment. The interface is adjustable such that it is customizable for each patient.

FIG. 28C depicts another embodiment of a positioner device 9850, this time meant for the patient to be face down. In this embodiment, the patient is positioned in the prone position lying over the patient elevator 9815. Again, through clinical experimentation, it was determined that the prone position with the positioner under the patient pushes the renal hilum posterior and stretches out the renal artery and vein allowing them to be more visible to ultrasound and accessible to energy deposition in the region. The positioner underneath the patient might be an expandable bladder with one or more compartments which allows for adjustability in the amount of pressure applied to the underside of the patient. The positioner might also have a back side which is expandable 9825 and can push against the posterior side of the patient toward the expandable front side of the positioner thereby compressing the stretched out renal blood vessels to allow for a more superficial and easier application of the energy device. These data can be seen in FIGS. 7G and 7H where the renal artery is quite a bit closer to the skin (7-17 cm down to 6-10 cm). The position of the energy devices for the left side 9827 of the patient and right side 9828 of the patient are depicted in FIG. 28C. The ribs 9829 delimit the upper region of the device placement and the iliac crest 9831 delimits the lower region of the device placement. The spinous processes 9832 delimit the medial edge of the region where the device can be placed and the region between 9828 is the location where the therapeutic transducer is placed.

Figure 28D:
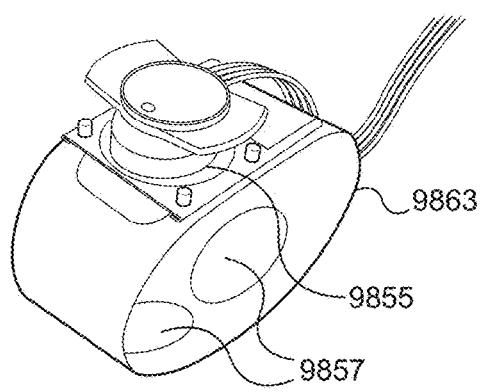
FIGS. 28D-28I illustrate system configurations for a system to treat nerves inside a patient using focused energy.
Figure 28E:
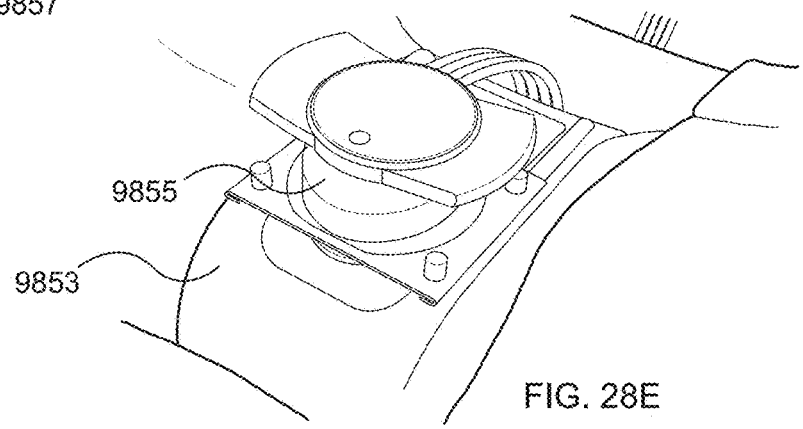

FIGS. 28D-28E depict a system implementation of the description above. Belt 9853 is fixed to the transducer 9855. Bladder 9857 is an adaptable and fillable cavity which can be used to help stabilize the flank region of the patient by pressing the posterior skin against the belt and transducer 9855. The transducer incorporates many of the embodiments described herein. For example, in the illustrated embodiments, the transducer is designed and manufactured with such a specification that it applies energy directed to the region of the renal artery and nerves. The transducer may be shaped like a pizza slice with annular components, or multiple elements forming into a global shape, like a pizza slice (as described herein). The transducer may also provide imaging and motion tracking capability such as with a pulse-echo detection system or with integral ultrasound imaging. The imaging aid might detect an indwelling vascular catheter or an implant. Nonetheless, the imaging aid can both detect the target track its motion. The therapeutic aspect of the transducer 9855 may generate focused ultrasound at a frequency of 0.5 MHz to 3 MHz depending on the specific configuration or pattern desired. Monitor 9862 is utilized to monitor the progress of the therapy throughout the treatment regimen.

Thus, in one embodiment of the system, as depicted in FIGS. 28D and 28E, the system comprises a belt which circumscribes the patient and applies a bladder (optionally) on one side of the patient to limit excursion of the abdominal organs and at least partially stabilize the abdominal organs, such as the kidney. Additionally, imaging and tracking may be utilized to maintain the positioning of the therapeutic energy focus. The stabilized focused energy system can then be automatically directed (e.g., by a processor) to track and follow the blood vessels and carry out a treatment according to a treatment plan, e.g., to treat tissue (nerves) surround the vessels leading to the kidney. The bladders may be filled automatically. In some cases, motion controllers may be utilized to direct the therapeutic energy focus to regions close to or within the hilum of the kidney.

Figure 28F:
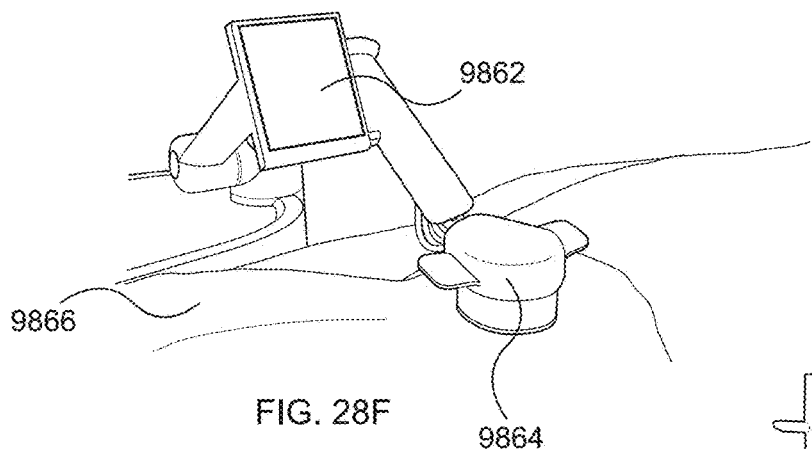
Figure 28G:
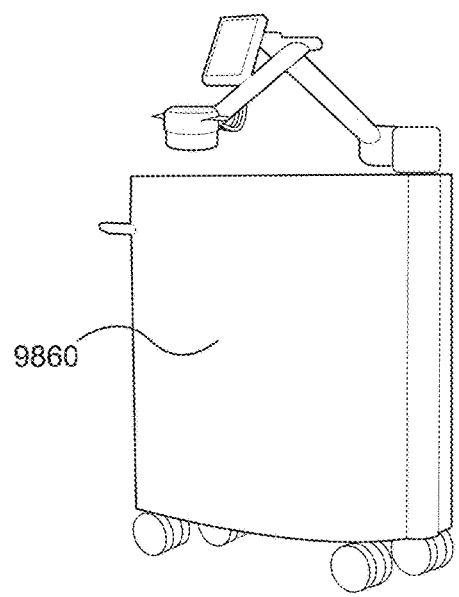

FIGS. 28E-G depict a more complete picture of the transducer to be applied to the back of the patient 9855 within the belt 9853 FIG. 28F depicts a 6 dimensional movement mechanism for the transducer platform with a positionable arm and its fit into the system configuration 9860. Six degrees of freedom are available for movement, which includes rotation and translation of the transducer. The platform is able to move in 6 degrees of freedom and the bottom mover allows for the transducer to be pressed against the skin of the patient.

Figure 28H:
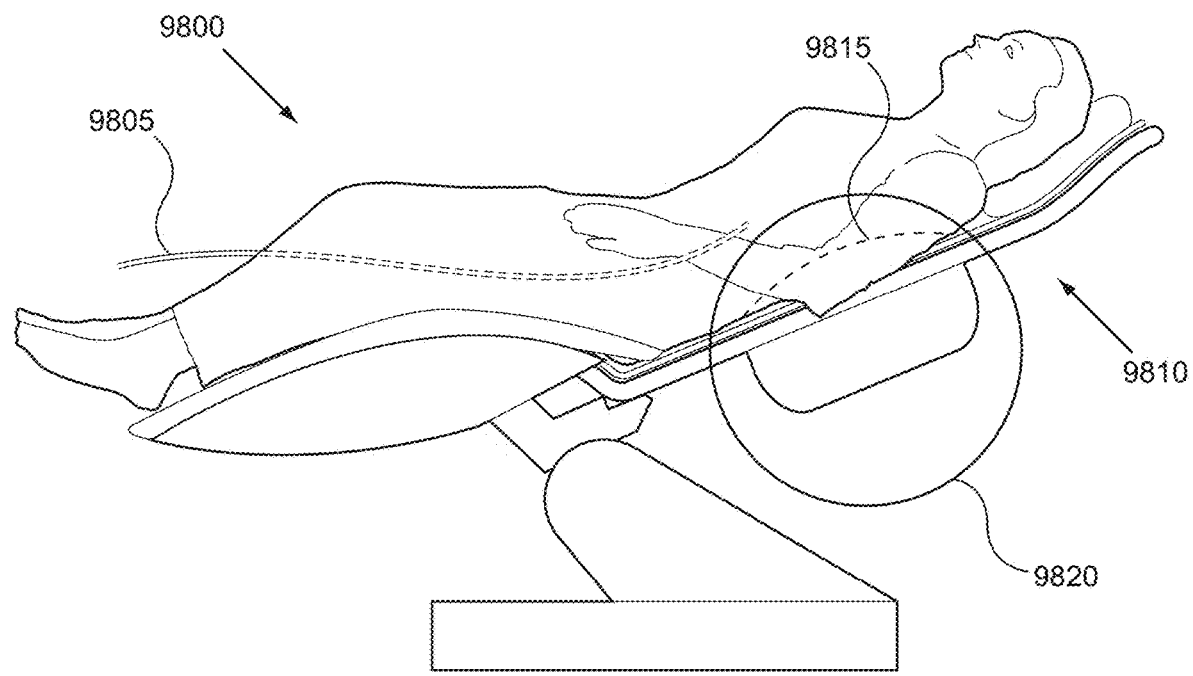

FIG. 28H depicts a patient treatment system 9800 in which a catheter 9805 is inserted into the patient 9810 and the system 9820 is placed behind the patient. Coupling applicator 9815 is pressed against the patient to maintain coupling contact between the therapeutic system 9820 and the patient. Catheter 9805 can be utilized to assist in targeting of the blood vessels and nerves being treated by the therapeutic system. Maintaining the therapeutic system behind the patient 9820 allows the patient's weight to be utilized in maintaining coupling between the system 9820 and patient 9810.

Figure 28I:
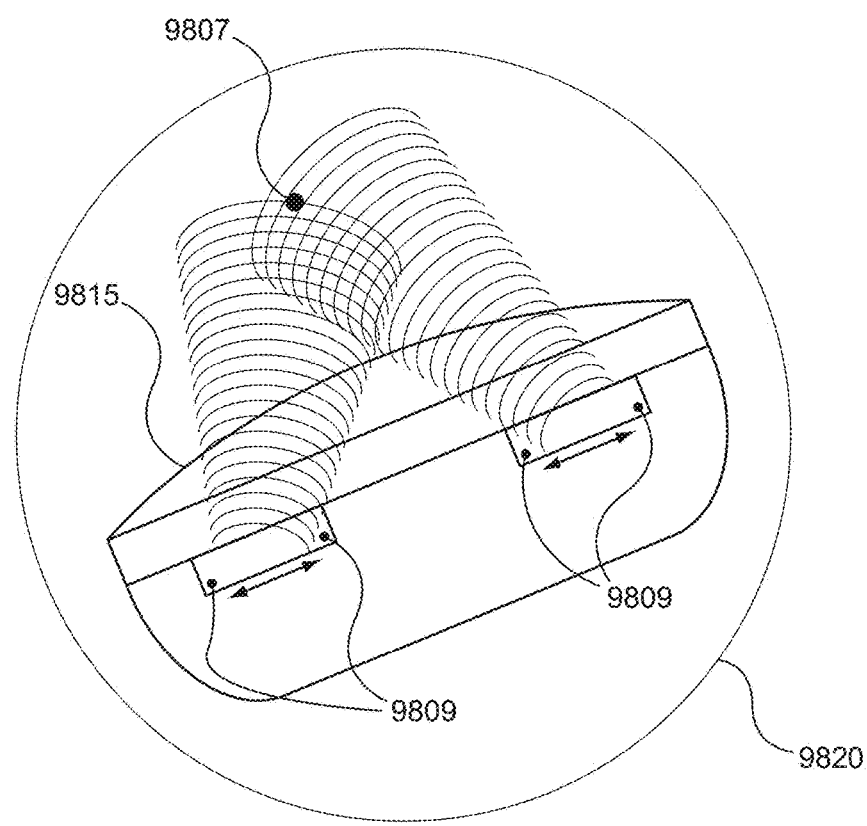

FIG. 28I is a close up picture of the transducer 9820. Elements 9809 are depicted with different phasings patterns to meet at the intersection 9807. Elements 9809 can also translate or rotate within the transducer allowing for a multi-modality.

Figure 28J:
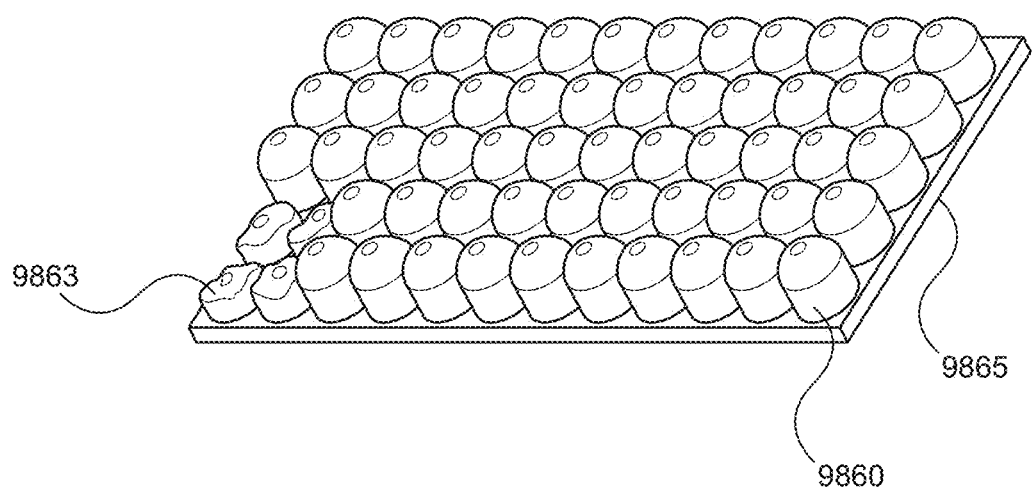
FIG. 28J is a depiction of an underlining for the patient with partial or fully inflated elements.
Figure 28K:
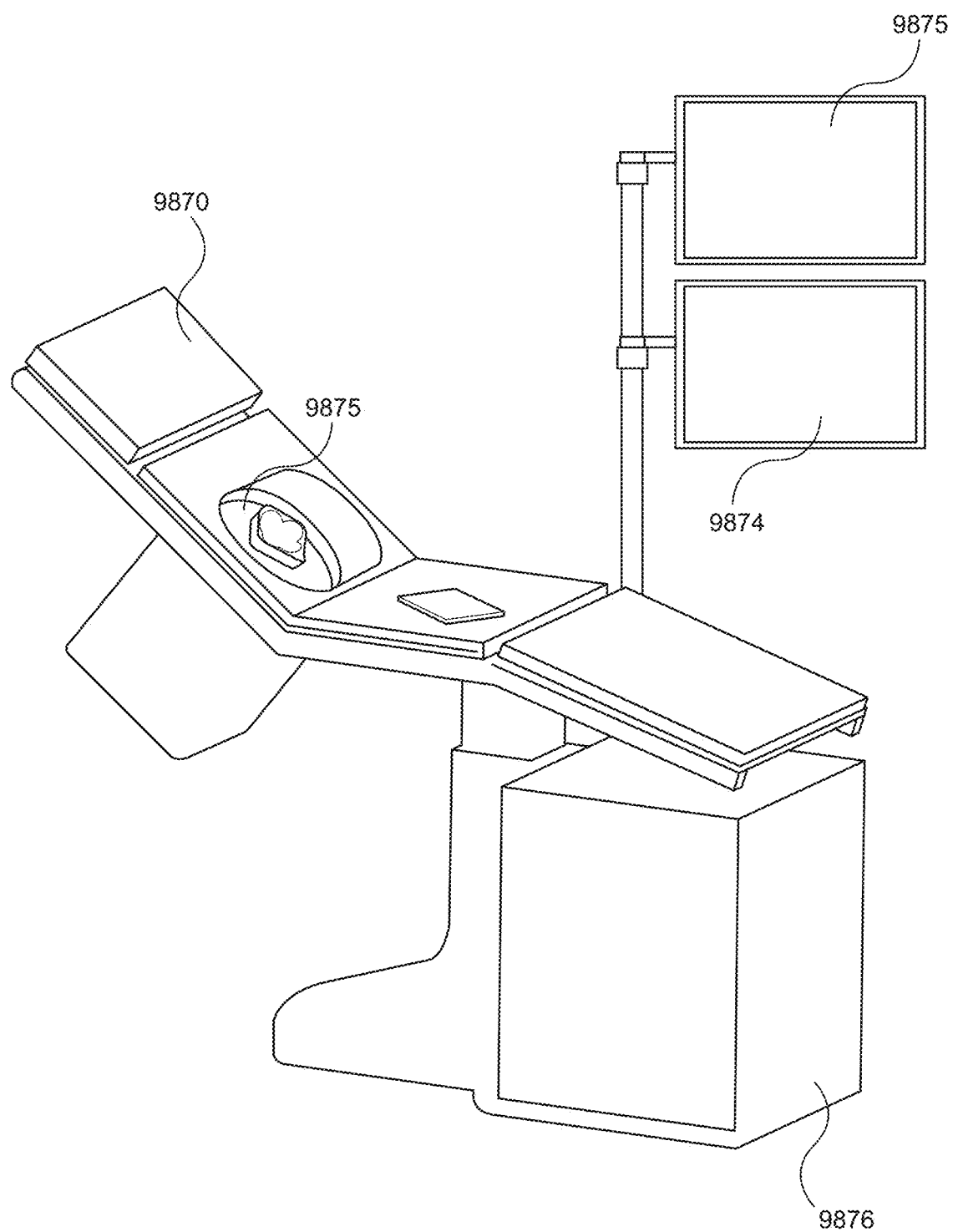
FIG. 28K is a configuration of a system built into a table for a patient.

FIG. 28J depicts a component 9865 to apply pressure to specific anatomic regions of the patient. Individual bladders 9860 can be inflated 9860 or deflated 9863 depending on the region of the patient for which pressure is applied. Such a system aids with conforming the applicator to the patient. In FIG. 28K, another configuration of a system to apply therapeutic energy to the region of the renal hilum is depicted. Transducer 9875 is depicted on the portion of the table which is positioned under the patient to be treated. Angiogram 9874 is visible in the case where a catheter is utilized for targeting. Therefore in one embodiment, the system to apply energy to the renal artery region is described in which a typical OR or cath lab table is retrofitted for a therapeutic ultrasound underneath the patient. The therapeutic ultrasound array contains a movement mechanism to maintain the array in contact with the skin of the patient, wherein the mechanism is able to translate to the left side of the patient or the right side of the patient. The movement mechanism can operate (e.g., to track a target) based on an image (e.g., a doppler image) of a blood vessel.

FIG. 28K depicts the movement mechanism 9875 within a table 9870 to treat a patient who is positioned in the supine position. The table elevation is on the front side of the patient, pushing upward toward the renal hilum and kidneys. The head of the table may be dropped or elevated so as to allow specific positioning positions. The elevated portion may contain an inflatable structure which controllably applies pressure to one side or another of the torso, head, or pelvis of the patient.

FIG. 29A-C depicts the anatomical basis 9900 of the targeting approach described herein. These figures are derived directly from histologic slides. Nerves 9910 can be seen in a position around renal artery 9920 and vein 9922. The range of radial distance from the artery is out to 2 mm and even out to 10 mm. Anatomic correlation with the modeling in FIG. 16B reveals the feasibility of the targeting and validates the approach based on actual pathology; that is, the approach of applying therapy to the renal nerves by targeting the adventitia of the artery, and using the kidney as both a conduit and fiducial for the focused energy (e.g., focused ultrasound energy). This is important because the methodology used to target the nerves is one of detecting the Doppler signal from the artery and then targeting the vessel wall around the doppler signal. Nerves 9910 can be seen surrounding the renal artery 9920 which puts them squarely into the temperature field shown in 16B indicating the feasibility of the outlined targeting approach in FIG. 27 and the lesion configuration in FIG. 16A. Further experimentation (utilizing similar types of pathology as well as levels of norepinephrine in the kidney) reveals that the required dose of ultrasound to the region to affect changes in the nerves is on the order of 100 $W/cm^2$ for partial inhibition of the nerves and 1-2 $kW/cm^2$ for complete inhibition and necrosis of the nerves. These doses or doses in between them might be chosen depending on the degree of nerve inhibition desired in the treatment plan. Importantly, it was further discovered through the experimentation that an acoustic plane through the blood vessels was adequate to partially or completely inhibit the nerves in the region. That is to say, that a plane through which the blood vessels travels perpendicularly is adequate to ablate the nerves around the artery as illustrated in FIG. 16B. Until this experimentation, there had been no evidence that ultrasound would be able to inhibit nerves surrounding an artery by applying a plane of ultrasound through the blood vessel. Indeed, it was proven that a plane of ultrasound essentially could circumferentially inhibit the nerves around the blood vessel.

FIG. 29D depicts a treatment combining the technical factors described herein. An ultrasound image with a doppler is shown with a blood vessel 8941 leading to a kidney 8935. The blood vessel (doppler signal and image) is targeted 8937 in three dimensions and the kidney 8935 is used as a conduit to conduct the focused energy (in this case ultrasound) toward the blood vessel. The kidney is further used as a fiducial, which indicates the direction, and indicates that the correct vessel is indeed targeted. A treatment paradigm is created in which a program is generated to move the focal plane around the target in three dimensions. Data generated, both theoretically and in pre-clinical models, reveals that the kidney indeed can be used as a conduit to conduct HIFU energy because the ability of the kidney to transmit ultrasound without heating is outstanding due to its high blood flow. Therefore, one preferred embodiment is that the kidney is utilized as a fiducial to direct the focused ultrasound, as well as allowing transmission through to the blood vessels of the kidney.

FIGS. 30A-I depict three dimensional simulations from a set of CT scans from the patient model shown in FIG. 26A. Numerical simulations were performed in three dimensions with actual human anatomy from the CT scans. The same CT scans utilized to produce FIGS. 7E, 19, and 25 were utilized to simulate a theoretical treatment of the renal artery region considering the anatomy of a real patient. Utilizing the doses shown in the experimentation above (FIGS. 29A-D) combined with the human anatomy from the CT scans, it is shown with these simulations that the ability exists to apply therapeutic ultrasound to the renal hilum from a position outside the patient. In combination with FIG. 29, which as discussed, depicts the position of the nerves around the blood vessels as well as the position of the vessels in an ultrasound, FIG. 30A-I depicts the feasibility of an ultrasound transducer which is configured to apply the required energy to the region of the hilum of the kidney without damaging intervening structures. These simulations are in fact confirmation for the proof of concept for this therapy and incorporate the knowledge obtained from the pathology, human CT scans, human ultrasound scans, and the system designs presented previously above.

Figure 30B:
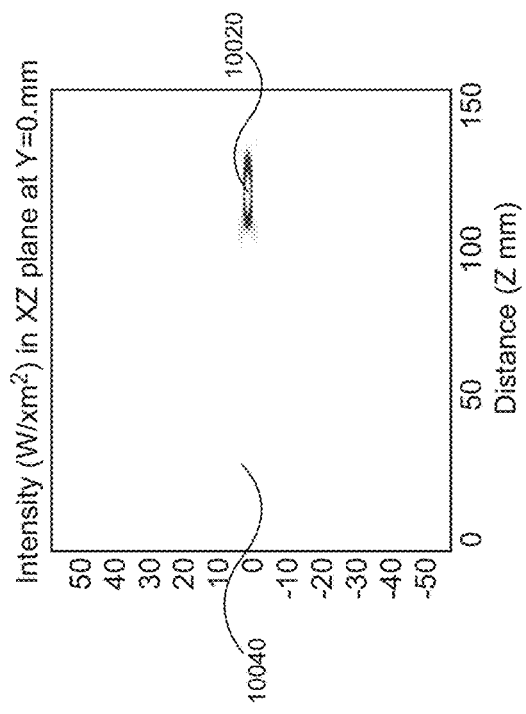
Figure 30C:
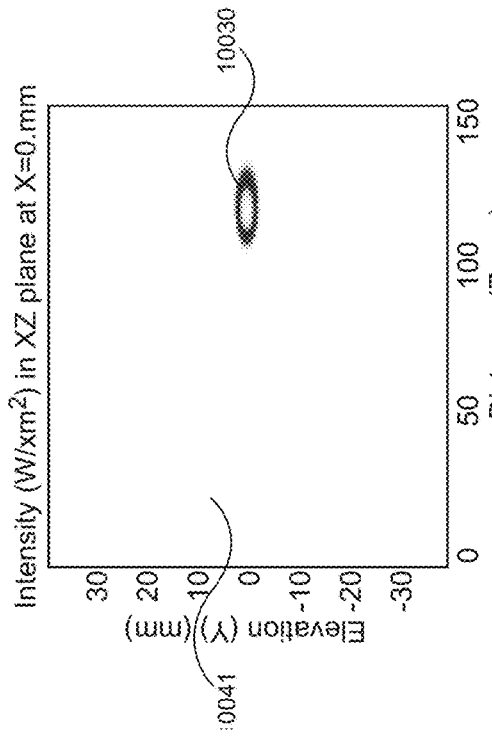
Figure 30A:
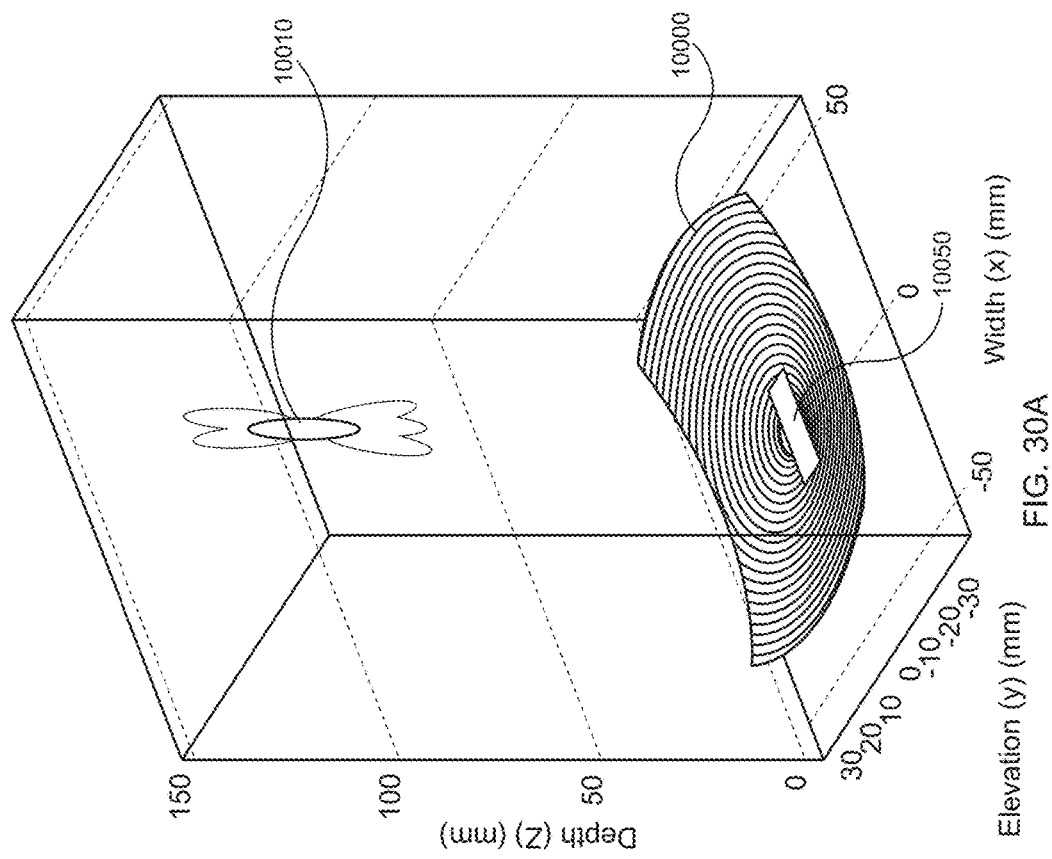

In one embodiment, FIG. 30A, the maximum intensity is reached at the focus 10010 is approximately 186 W/cm$^2$ with a transducer 10000 design at 750 MHz; the transducer is approximately 11×8 cm with a central portion 10050 for an ultrasound imaging engine. The input wattage to the transducer is approximately 120 W-150 W depending on the specific patient anatomy. The input voltage might be as high as 1000 W depending on the desired peak intensity at the focus. For example, for a peak intensity of 2 kW/cm$^2$, it may be desirable to have an input wattage of approximately 600-800 W.

FIGS. 30B and 30C depict the acoustic focus 10020, 10030 at a depth of approximately 9-11 cm and in two dimensions. Importantly, the region (tissues such as kidney, ureter, skin, muscle) proximal (10040 and 10041) to the focus 10020, 10030 do not have any significant acoustic power absorption indicating that the treatment can be applied safely to the renal artery region through these tissues as described above. Importantly, the intervening tissues are not injured in this simulation indicating the feasibility of this treatment paradigm.

Figure 30E:
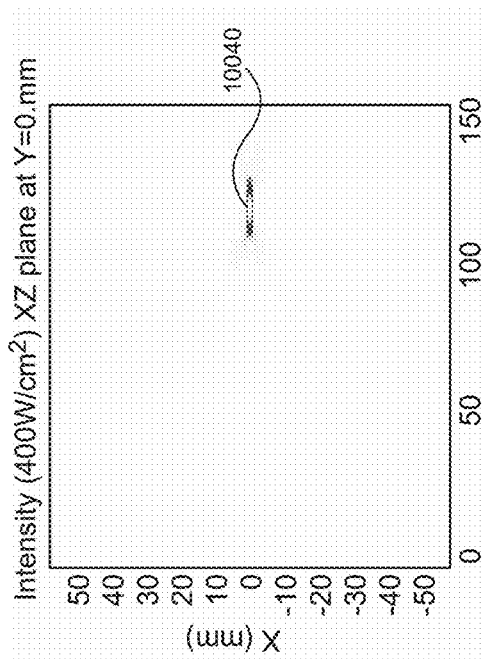
Figure 30F:
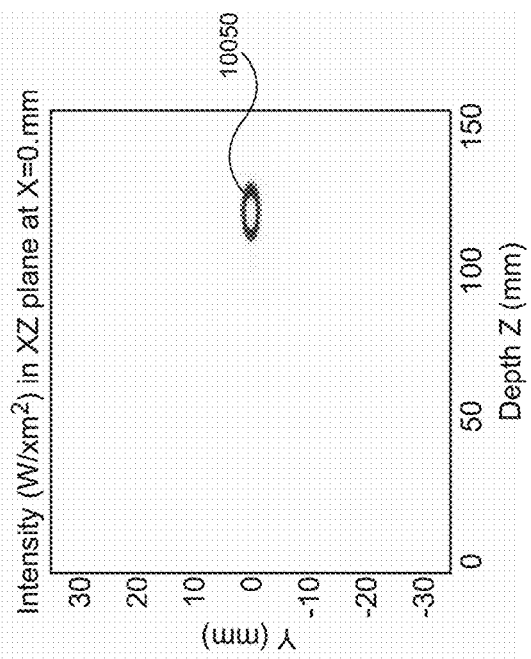
Figure 30D:
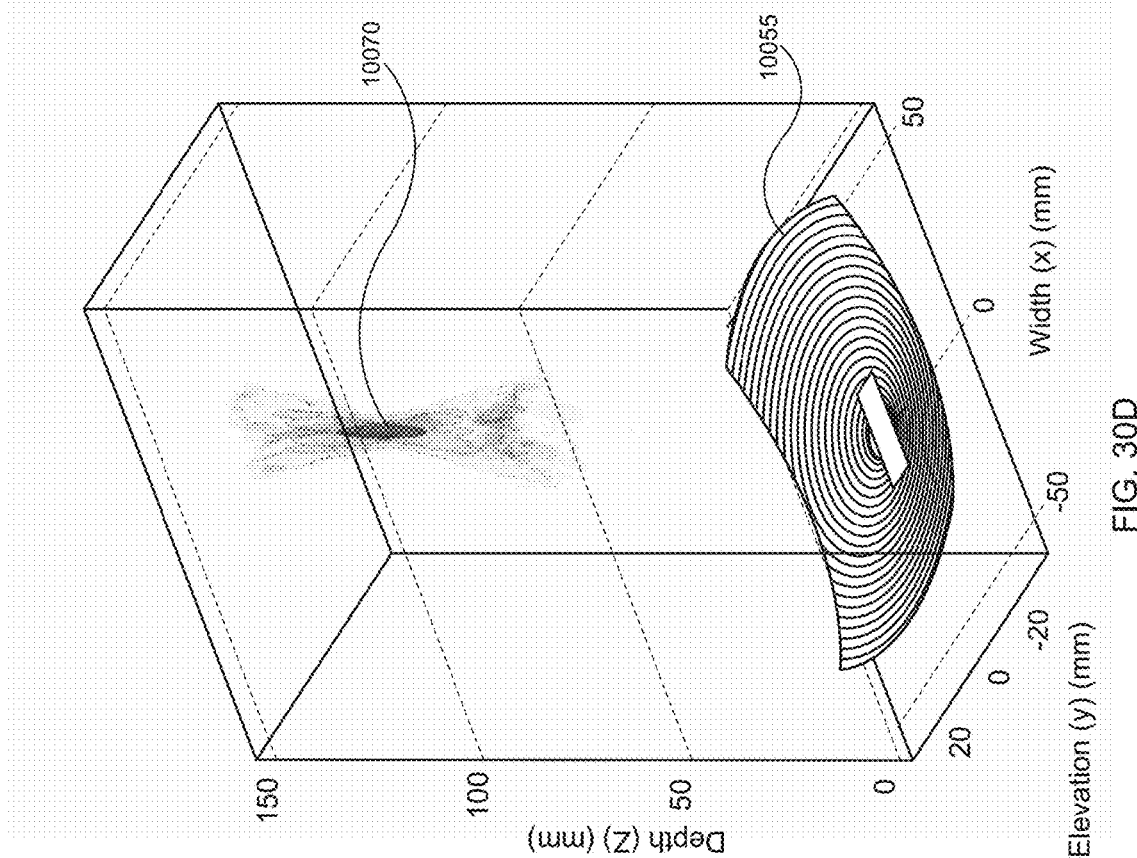

FIGS. 30D-F depict a simulation with a transducer 10055 having a frequency of approximately 1 MHz. With this frequency, the focal spot 10070, 10040, 10050 size is a bit smaller (approximately 2 cm by 0.5 cm) and the maximum power higher at the focus, approximately 400 W/cm$^2$ than shown in FIGS. 30A-C. In the human simulation, this is close to an optimal response and dictates the design parameters for the externally placed devices. The transducer in this design is a rectangular type of design (spherical with the edges shaved off) so as to optimize the working space in between the posterior ribs of the patient and the superior portion of the iliac crest of the patient. Its size is approximately 11 cm×8 cm which as described above and below is well within the space between the bony landmarks of the back of the patient.

FIGS. 30G-I depict a simulation with similar ultrasound variables as seen in FIGS. 30D-F. The difference is that the transducer 10090 was left as spherical with a central cutout rather than rectangular with a central cutout. The spherical transducer setup 10090 allows for a greater concentration of energy at the focus 1075 due to the increased surface area of vibratory energy. Indeed, the maximum energy from this transducer (FIG. 30G) is approximately 744 W/cm$^2$ whereas for the transducer in FIG. 30d, the maximum intensity is approximately 370 W/cm$^2$. FIG. 30H depicts one plane of the model and 30I another plane. Focus 10080, 10085 is depicted with intervening regions 10082 and 10083 free from acoustic power and heat generation, similar to FIG. 30A-F.

These simulations confirm the feasibility of a therapeutic treatment of the renal sympathetic nerves from the outside without damage to intervening tissues or structures such as bone, bowel, and lung. Hypertension is one clinical application of this therapy. A transducer with an imaging unit within is utilized to apply focused ultrasound to a renal nerve surrounding a renal artery. Both the afferent nerves and efferent nerves are affected by this therapy.

Other transducer configurations are possible. Although a single therapeutic transducer is shown in FIG. 30A-I, configurations such as phased array therapy transducers (more than one independently controlled therapeutic transducer) are possible. Such transducers allow more specific tailoring to the individual patient. For example, a larger transducer might be utilized with 2, 3, 4 or greater than 4 transducers. Individual transducers might be turned on or off depending on the patients anatomy. For example, a transducer which would cover a rib in an individual patient might be turned off during the therapy.

Although the central space is shown in the center of the transducer in FIGS. 30A-I, the imaging transducer might be placed anywhere within the field as long as its position is well known relative to the therapy transducers. For example, insofar as the transducer for therapy is coupled to the imaging transducer spatially in three dimensional space and this relationship is always known, the imaging transducer can be in any orientation relative to the therapeutic transducer.

Figure 30J:
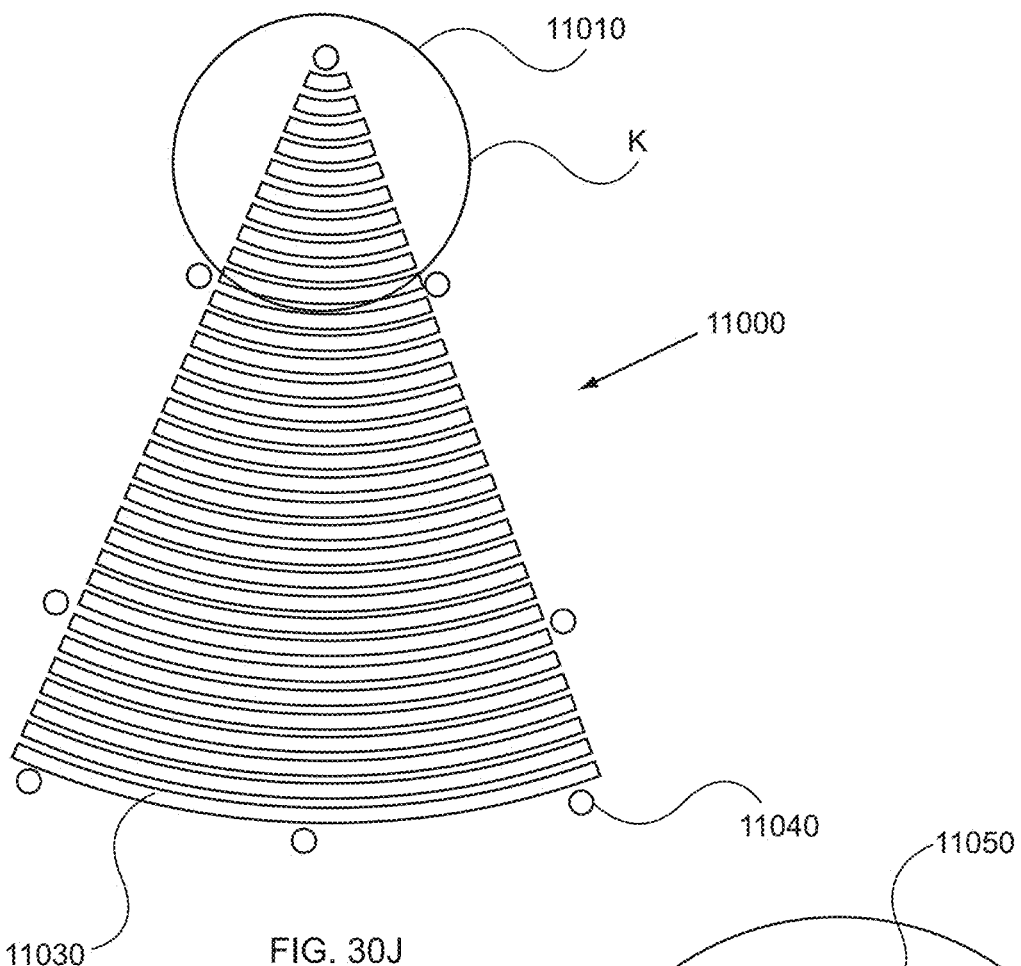
FIG. 30J depicts an annular array customized to treat the anatomy shown for the kidney and renal blood vessels above.
Figure 30K:
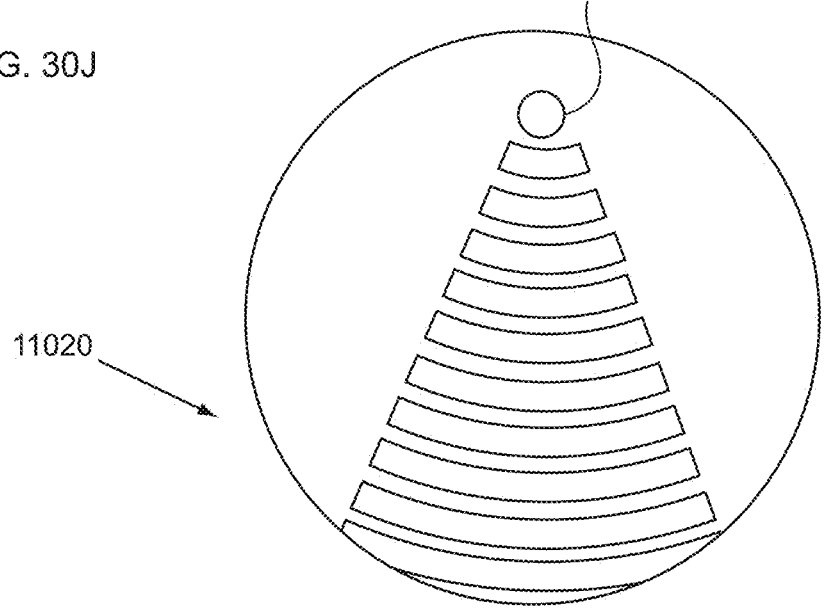
FIG. 30K highlights the annular array and depicts the imaging component at the apex.

Another embodiment of a customized transducer 11030 is depicted in FIGS. 30J-30K. Importantly, this transducer is specifically designed to accommodate the anatomy shown above for the kidney anatomy. The pizza slice shape 11000 is unique to treat the anatomy in which the ribs, spine and pelvis are considered. Sensors 11040 are located along the edges of the transducer and allow for imaging or otherwise to detect the direction of the ultrasound system as it travels through the patient toward its target. At the tip of the target, 11050, an ultrasound imaging probe is included where the probe is coupled to the therapeutic ultrasound array 11030 and 11020. The number of elements 11030 determines the spatial resolution of the array and the degree to which the focus can be electronically controlled.

The sensors around the side 11040 may be small 1D imaging transducers or contain a single plane. Alternatively, they may be acoustic time of flight sensors for measuring the distance to the target or a combination of the two different techniques.

Figure 30L:
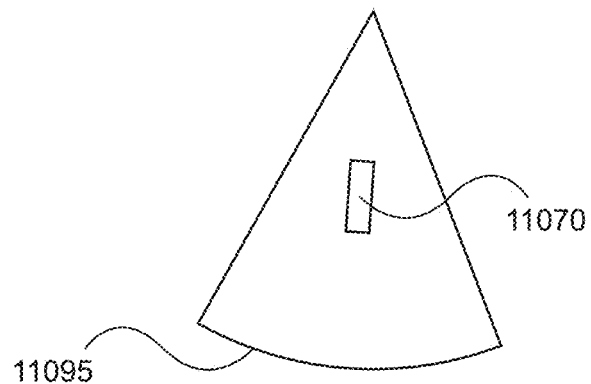
FIGS. 30L-N depict various cutouts for ultrasound imaging probes.
Figure 30M:
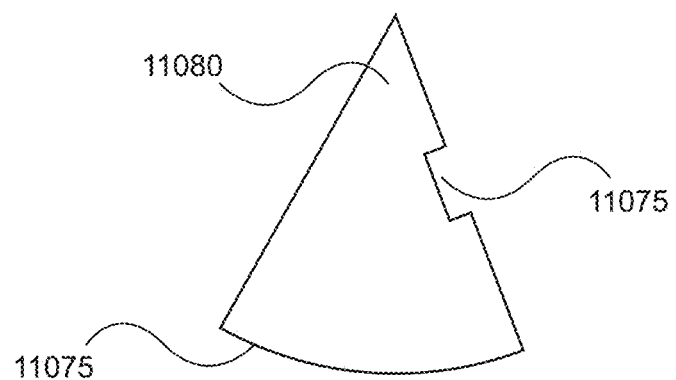
Figure 30N:
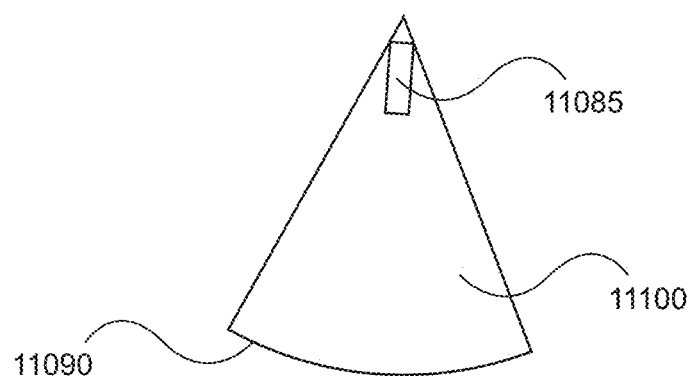

FIGS. 30L-N depicts additional views of the transducer in which the imaging component is in the center 11070, side cutout 11075, and within the pie slice shape 11085. The pizza slice shape does not necessarily have to be shaped as a slice but might be a larger array in which a slice shape is produced by turning on or off any number of transducers. The transducers in such an embodiment can have square, annular, or rectangular elements each of which has its own controller for imaging or therapeutic uses.

Figure 30O:
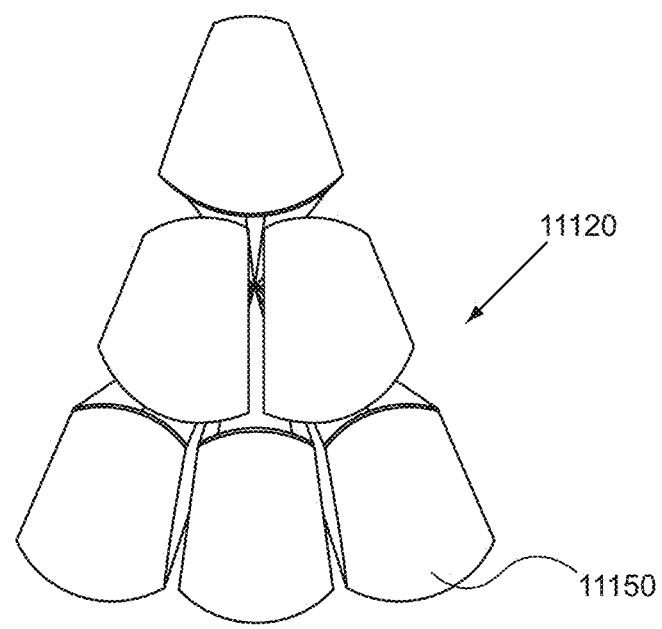
FIGS. 30O-P depict projection from the proposed transducer designs.
Figure 30P:
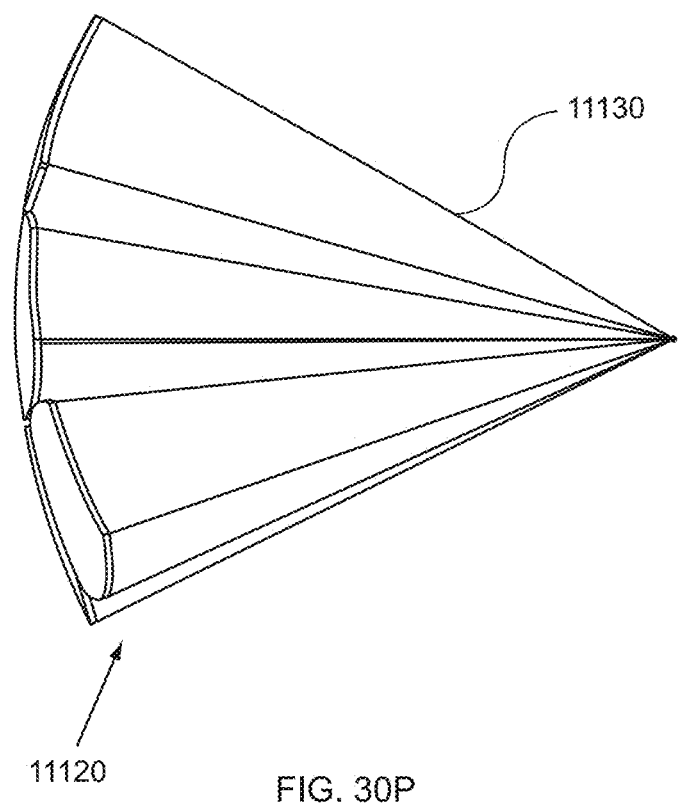
Figure 30Q:
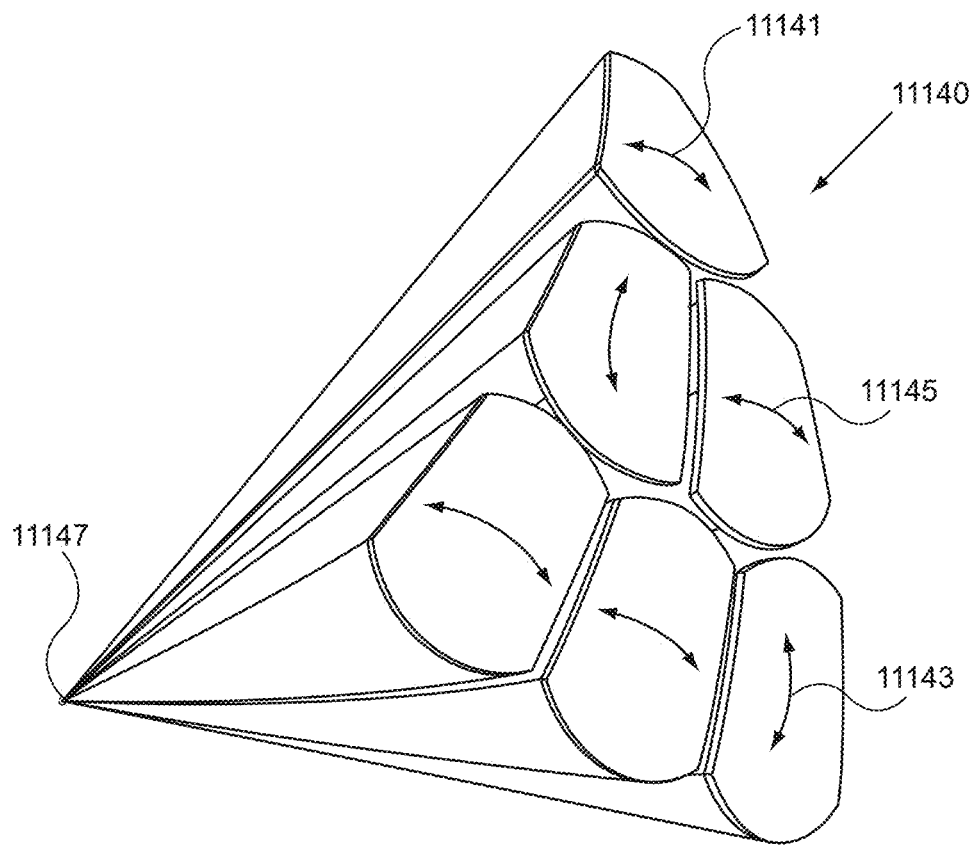
FIG. 30Q is a depiction of a focal zone created by the therapeutic transducer(s) to focus a single region.

FIG. 30O-Q depicts a transducer with several elements arranged into a fixed focus 11130. Each of the 6 elements 11150 can be tuned to focus on a spot a given focal length from the transducer. The pizza slice shape can be fit into the region between the ribs and spine and the pelvis to apply therapy to a blood vessel such as the renal artery or the renal vein. FIG. 30Q depicts discreet movers 11141, 11143, 11145 which dictate the degree of overlap at the focus 11147.

Figures 30R, 30S:
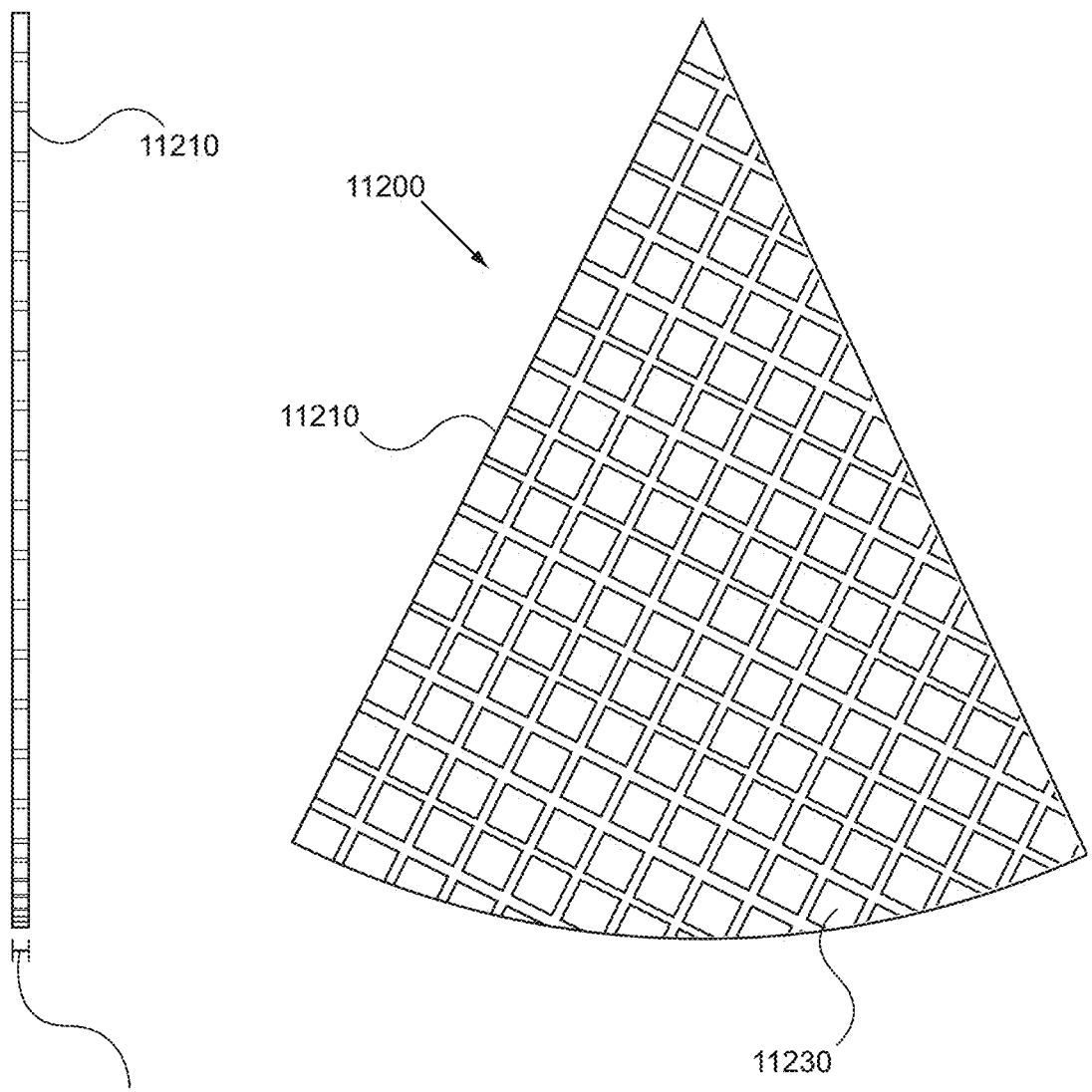
FIGS. 30R-30S depict a multi-element array in a pizza slice shape yet with many square elements.

FIG. 30R-S depicts a transducer 11200 with many elements 11230. Again, although shaped like a slice of a pie 11220, the shape can be created by turning on transducers from a larger cutout. A cross section 11210 is shown as well (FIG. 30R) revealing a thickness of the array which can range from several mm to a few cm. The profile is produced such that the transducer can be adapted to fit into the acoustic window of a human patient with anatomy described herein.

Figure 30T:
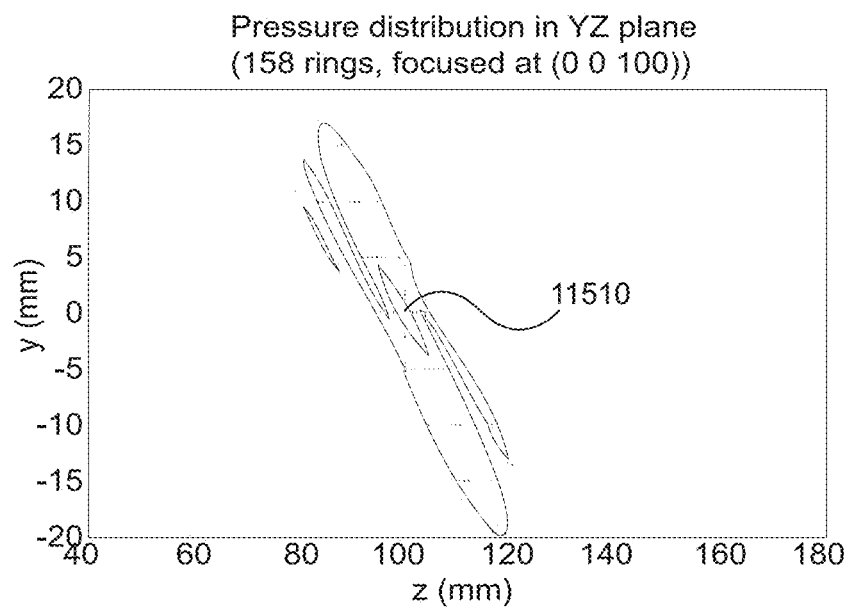
FIGS. 30T-30U depict simulations of the annular array specific for the anatomy to be treated around a kidney of a patient.
Figure 30U:
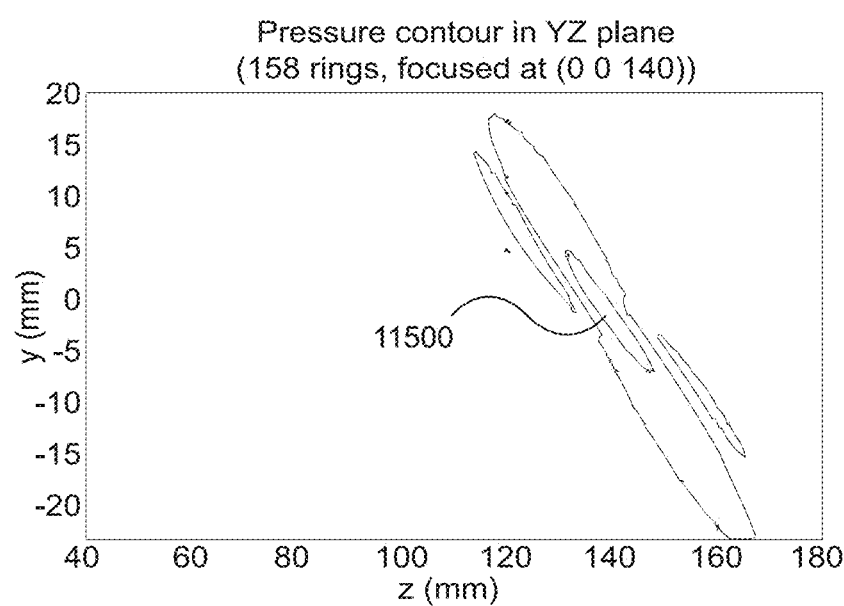
Figure 30V:
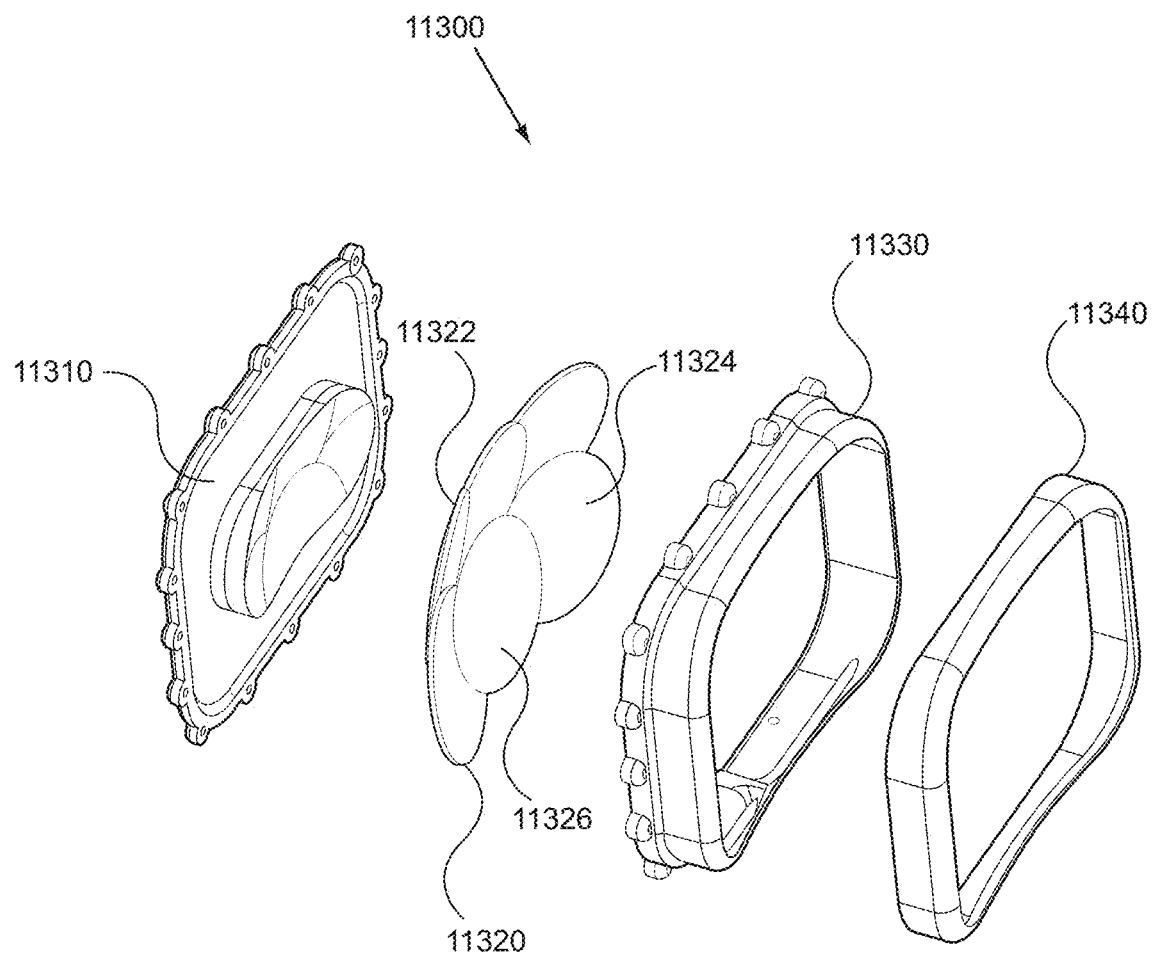
FIG. 30V depicts a housing for the custom array.

FIG. 30V is an expanded version of a transducer 11300 in which discrete bowls are fit together to simulate a larger bowl 11310 approximation. In this arrangement, the individual bowls 11324, 11324, 11326 each provide a piece of the curvature of a larger bowl, which would otherwise be very difficult to manufacture.

Figure 30W:
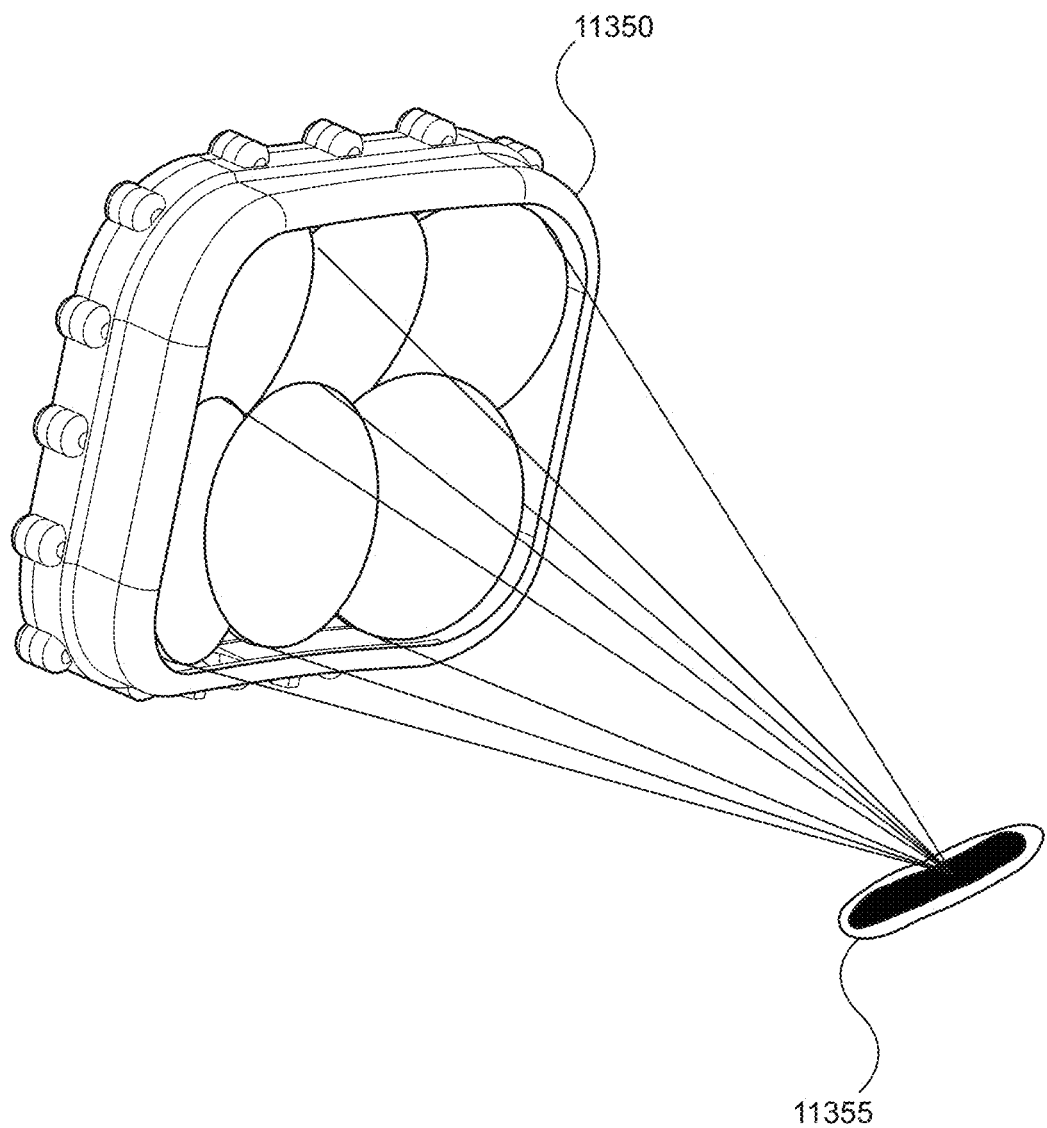
FIG. 30W depicts focusing of energy from the custom array along a blood vessel.

FIG. 30W depicts the assembly of the configuration 11350 with the bowls in combination which when powered, creates a single focus 11355. By moving each individual bowl slightly, the focus can be made to be elongate or circular.

FIGS. 30T-U depict simulations of the annular array transducers shown in FIGS. 30J-K. The simulation reveals that the focus can be electronically controlled between less than 10 cm distance 11510 to greater than 14 cm 11500. These distances are compatible with the blood vessels leading to the kidney and are delivered from within the envelope of the window on the posterior portion of the patient's back.

FIG. 30V depicts an exploded view of an assembly of a transducer 11300. A base 11310 might contain a motion control system for x-y-z motion, and optionally a pivot for rotation of the ultrasound array. Array 11322 is comprised of one or more ultrasound emanating crystals 11324 with different curvatures 11326, 11320 to focus energy. Housing 11330 might contain a nosecone or other directional structure to direct the ultrasound energy to a focus. Covering 11340 is a coupling structure with an integral membrane to couple the ultrasound energy to the patient. The transducer 11322 might provide a combination of phasing and mechanical movement for its operation.

Figure 31A:
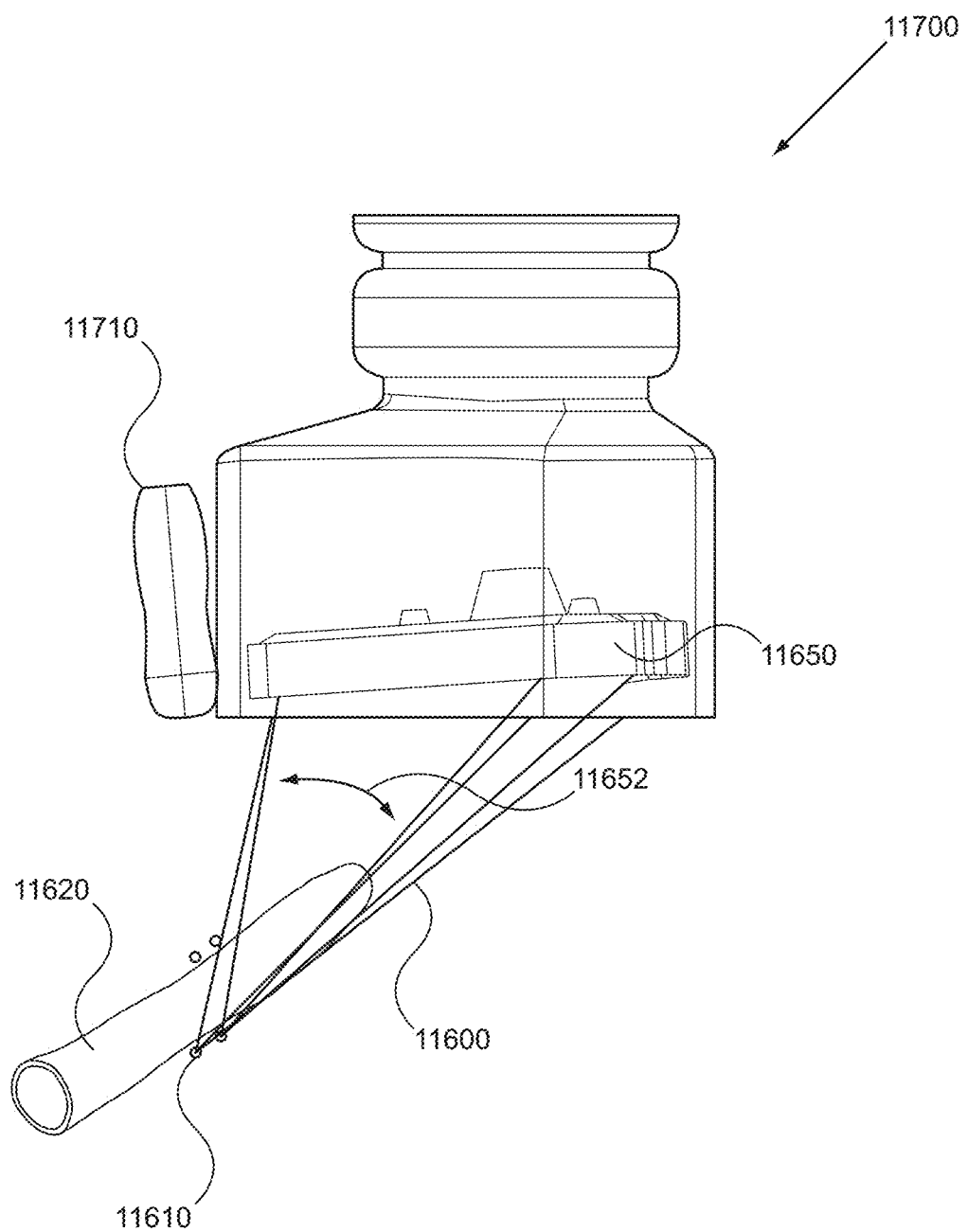
FIG. 31A depicts an off center focus from an alternative arrangement of the annular array transducer.

FIG. 31A depicts a perspective view of a transducer device customized for the anatomy of the blood vessels leading to the kidney. This design is based on the anatomic, biologic, and technical issues discovered and described above specific for the clinical treatment of nerves surrounding the blood vessels which go to the kidney. Transducer 11650 has multiple elements and is also able to be pivoted and translated. The individual elements of the array can be phased so that different depths of foci can be achieved 11600, 11610 to treat regions around a blood vessel 11620. An imaging transducer 11710 is attached to, or integrated with, the device 11700. Although the ultrasound imaging transducer has been described, in other embodiments, MRI, CT, or fluoroscopy can also be linked to the system 11700. The device further contains elements described above such as a mover to move the entire device as a complete unit, motion tracking to track its global motion in three dimensional space, and a water circulation system to maintain the temperature of the skin and the transducer to acceptable levels.

Angle 11652 is important to the anatomy which is being treated. It represents the envelope of the therapeutic beam and is incorporated into the design of the system. It is represented in one plane in this figure and would cover approximately 40 to 70 degrees in this figure which allows for a treatment depth of between 6 cm and 15 cm. For the short dimension (into the drawing), the angle (not shown) would be 35 to 65 degrees. The treatment depth may be desirably adjusted with different phasing from the transducer; however, the shape of the focus is not substantially affected. The position in X and Y may be adjusted using mechanical manipulation but can also be adjusted via phasing elements. Therefore, in one embodiment, an ultrasound transducer is described within which a multi-element array is disposed, the transducer devised to allow for electrical focusing of a focused ultrasound beam at an angle 11652 to the central axis of the transducer to move the beam focus in the direction perpendicular to the plane of the transducer but at an angle to the central axis of the transducer. The angle is customized for the anatomy being treated. For example, when treating a region such as the renal artery and nerve going to the kidney, the blood vessels are located at an angle from a plane of the skin when the transducer is place between the ribs, iliac crest, and spine (for example, see FIG. 31A, angle 11652, transducer 11650 is placed on the skin underneath the ribs, lateral to the spine and superior to the iliac crest). A mover may also be provided, which moves the transducer in the plane of the transducer and perpendicular to the central axis of the transducer.

Figure 31B:
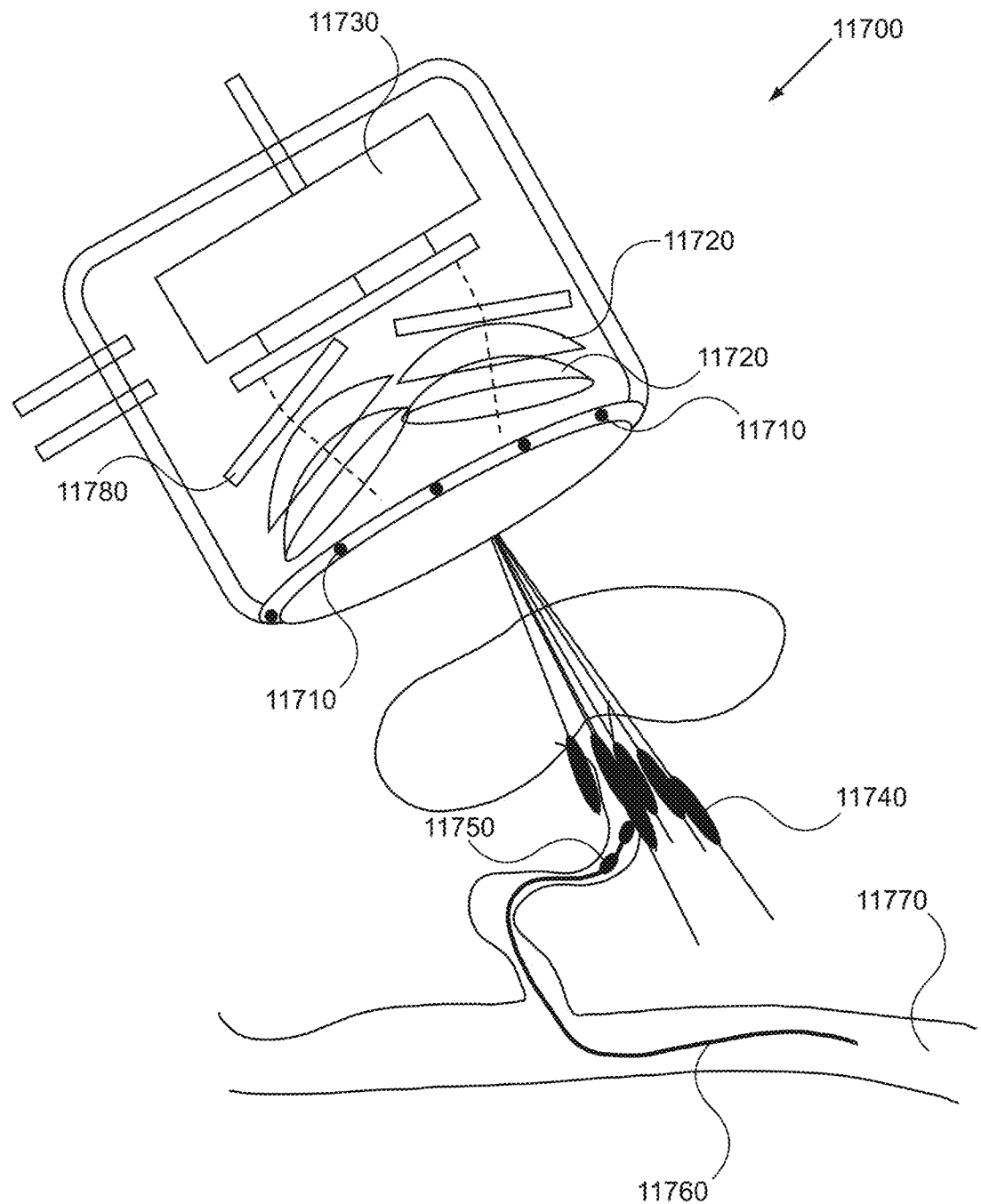
FIG. 31B depicts focusing of energy from an alternative embodiment of the customized transducer array in the clinical embodiment in which a catheter is placed within the patient.

FIG. 31B depicts another embodiment of a transducer 11700 designed to deliver focused ultrasound specifically to the region of the kidney and associated blood vessels 11770. The transducer has multiple small bowl shaped transducers 11720 fitted together for a deep focus 11740 of the ultrasound. The smaller bowl transducers 11720 are each movable utilizing a mechanical manipulator 11780 so as to create foci with different sizes at the target. A water cooling system is present as well 11730, which ensures that the skin and the transducers are maintained at a predetermined temperature. The variations in foci include elongated, spiral, and annular, each with different depths 11740. In this embodiment, imaging is a component of the transducers 11720. ATOF (acoustic time of flight) receivers 11710 can optionally receive signals from transducers 11750 on an indwelling vascular catheter 11760, which contains piezoelectric transducers capable of transmitting information through the patient to receivers 11710.

Figure 31C:
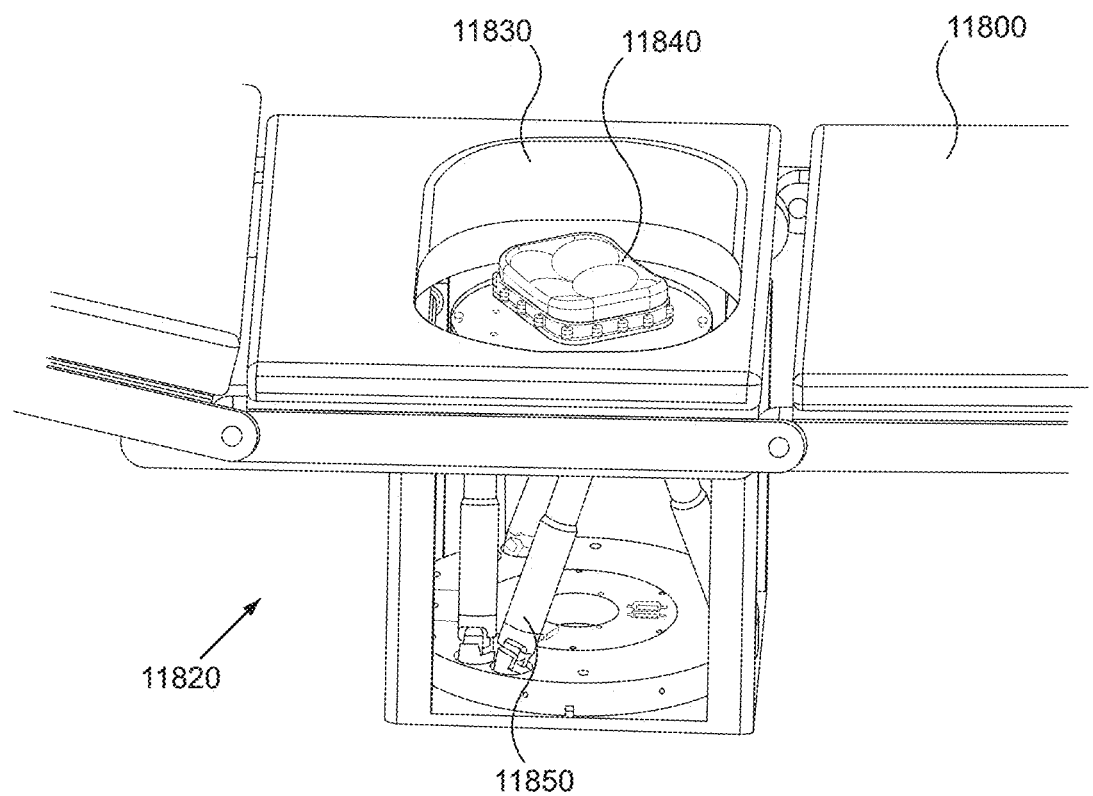
FIG. 31C is a depiction of a movement mechanism within a patient table.
Figure 31D:
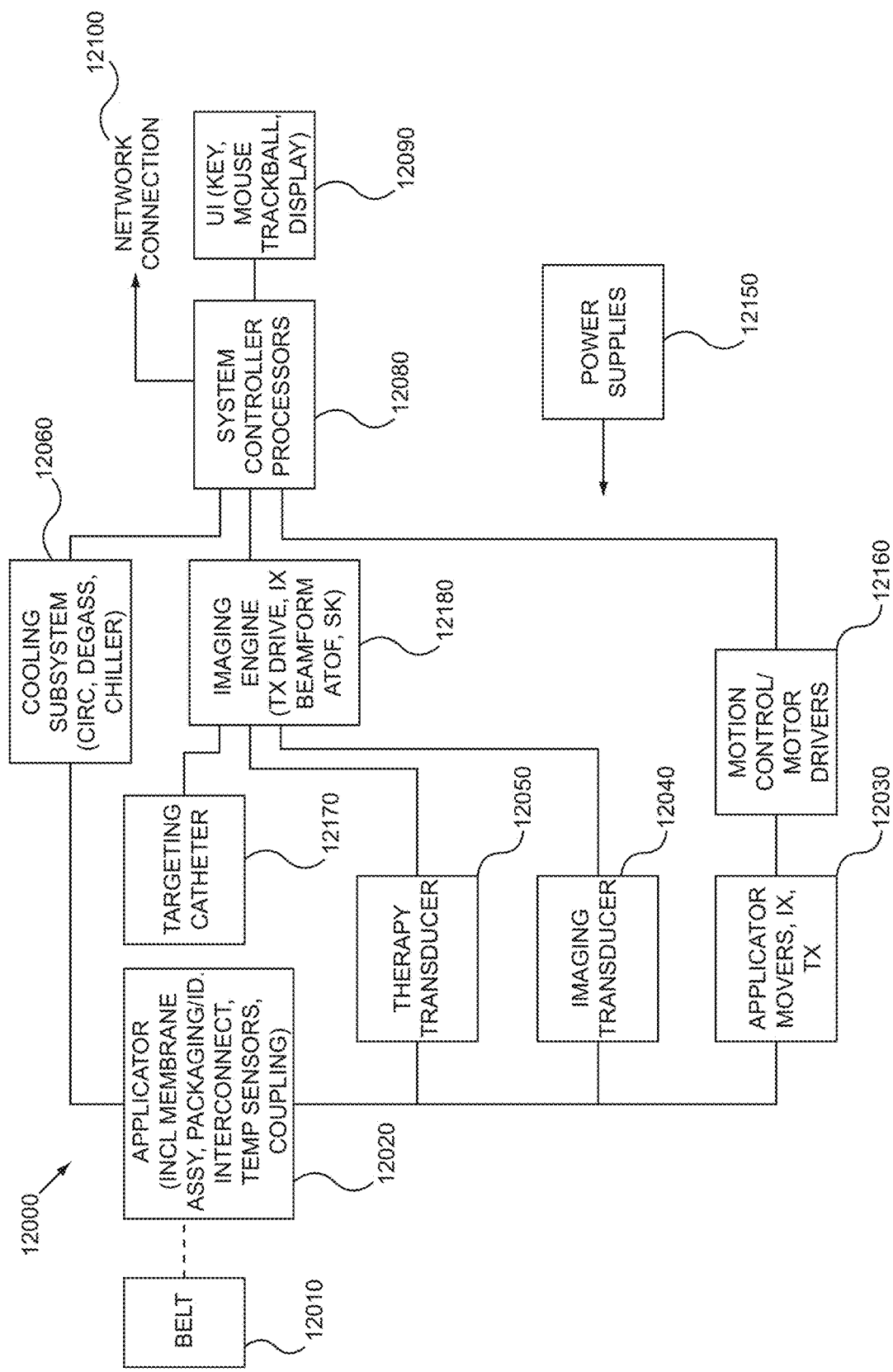
FIG. 31D is an overall block diagram of the system subsystems.

FIG. 31C depicts a two component mover mechanism (termed upper and lower movers) 11820 with a patient table 11800 to house the transducer arrangement and hold a patient. A mover 11850 is responsible for placing the transducer 11840 against the skin of the patient inside of the cutout 11830 in the table; clinical studies have shown that up to 50 pounds of pressure can be applied by the lower transducer to the skin of the patient to maintain coupling. The mover 11850 is also responsible for lowering the upper transducer 11840. The upper transducer 11840 is positioned at the angle and position required to treat a region such as the renal nerves around a renal blood vessel. Electronic focusing might be utilized for some components of the system, including the z direction which is the vertical direction through the central axis of the transducer and would generally be pointing in the direction in and out of the patient being treated. With electronic focusing, the distance can be automatically determined and calibrated relative to the transducer. In some embodiments, X and Y motions are altered electronically with various phasing patterns created through the transducer. In some embodiments, a combination of electronic phasing and mechanical movement is utilized to achieve the proper focusing and positioning of the system on the patient. The transducers being used for the therapeutic application of energy to the patient might also be utilized for detection of ultrasound signals which can be used for imaging detection. A separate imaging transducer can be utilized to augment the therapy transducer. For example, acoustic time of flight can be utilized or B mode or Doppler imaging can be utilized. Therefore, in one embodiment, the transducer is positioned at the proper angle to reach the renal blood vessels FIG. 31D depicts a system and subsystem overview of one configuration. A transducer belt 12010 can be applied to a patient, wherein the belt includes an applicator 12020 with transducer containing a membrane assembly, packaging, temperature sensors, and coupling attachments for coupling to the skin of the patient. Within the transducer assembly is a carveout for an imaging engine 12180, which can be an annular array for imaging in the same package as the therapy transducer, or it can be a separate array 12040 tuned for a different frequency specific for imaging. Within the transducer belt is a mover for the applicator, for example, a mover 12030 which can translate in X-Y-Z and rotate around a pivot to deliver an ultrasound focus to any position within a space around a blood vessel. Alternatively, in another embodiment, phased array transducers may be utilized in for treatment, imaging, or both. A cooling subsystem 12060 is a component of the system, wherein the cooling subsystem is configured to maintain the transducer and membrane temperature at a pre-specified level. An optional targeting catheter 12170 is included in the system, wherein the targeting catheter may be used in characterizing the energy being delivered from the focused ultrasound as well as in assisting and verifying the targeting accuracy of the imaging and the coupling of the imaging to the motion control 12030. The targeting catheter can also include sensors to determine the amount of energy applied to the vessel, the temperature of the vessel and surroundings, the acoustic power flux, and the degree of motion of the vessel during, before, or after treatment. A user interface is also included, the user interface comprising a track ball, a mouse, a touch screen, or a keyboard to allow user interaction with the system. The system is powered using power supplies 12150 which can be switched or non-switched depending on which subsystem is being activated at any given time.

FIGS. 30R and 30S depict the active shape of the transducer, and 30T and 30U depict the simulation of the focused ultrasound at the depth of treatment. The perspective view of the focus 11600 is shown in FIG. 31A and the annular transducer 11650 which delivers the ultrasound to a blood vessel 11620 and surrounding nerves 11610 is shown as well. An imaging array 11710 is included in the system 11700 as well.

The invention claimed is:

1. A method of affecting one or more nerves located outside a blood vessel in a patient comprising:
   placing a part of an intravascular catheter inside the blood vessel in the patient, the catheter comprising a piezoelectric component; and
   energizing the piezoelectric component to deliver unfocused ultrasound energy in an approximately spherical or ellipsoidal configuration towards at least a majority portion of a circumference of the blood vessel to thereby reach the one or more nerves outside the blood vessel;
   wherein the unfocused ultrasound energy is delivered to create a heated region at the one or more nerves outside the blood vessel.

2. The method of claim 1, further comprising delivering cooling to protect a wall of the blood vessel while the ultrasound energy is delivered to penetrate through the wall of the blood vessel to the one or more nerves outside the blood vessel.

3. The method of claim 1, wherein the catheter further comprises a stabilizing component configured to stabilize at least a part of the catheter with respect to the blood vessel.

4. The method of claim 1, further comprising detecting a position of the catheter using a component located outside the patient.

5. The method of claim 1, further comprising detecting the heated region using an energy source from outside the patient.

6. The method of claim 5, wherein the energy source is a part of an ultrasound imaging machine.

7. The method of claim 5, wherein the energy source is a part of an MRI device.

8. The method of claim 1, wherein the heated region comprises one or more heated areas that are circumferentially disposed outside the blood vessel.

9. The method of claim 1, wherein the unfocused ultrasound energy is delivered to treat hypertension.

10. The method of claim 1, wherein the unfocused ultrasound energy is delivered to affect the one or more nerve(s) sufficient enough to reduce hypertension.

11. A method of affecting autonomic nerve(s) outside a renal artery in a patient comprising:
    placing a part of an intravascular catheter inside the renal artery, the catheter comprising a piezoelectric component and an expandable member, the expandable member configured to occlude blood flow and to center the piezoelectric component in the renal artery when the expandable member is expanded; and
    energizing the piezoelectric component to deliver unfocused ultrasound energy in an approximately spherical or ellipsoidal configuration towards at least a majority portion of a circumference of the renal artery to thereby heat the autonomic nerve(s) outside the renal artery.

12. The method of claim 11, wherein the autonomic nerve(s) is heated inside a kidney.

13. The method of claim 11, wherein the unfocused ultrasound energy is delivered to treat hypertension.

14. The method of claim 11, wherein the unfocused ultrasound energy is delivered to selectively block A fibers, B fibers, or C fibers.

15. The method of claim 11, wherein the unfocused ultrasound energy is delivered to affect the renal nerve(s) sufficient enough to reduce hypertension.

16. The method of claim 11, wherein the unfocused ultrasound energy comprises cavitating energy.

17. The method of claim 11, further comprising delivering a drug.

18. The method of claim 11, further comprising guiding the catheter to the renal artery using ultrasound imaging performed outside the patient.

19. The method of claim 11, further comprising guiding the catheter to the renal artery using acoustic time-of-flight localization.

20. A method to affect nerve(s) outside a renal blood vessel of a patient, comprising:
    placing an ultrasound probe against a wall of a renal blood vessel; and
    energizing the ultrasound probe to deliver unfocused ultrasound energy in an approximately spherical or ellipsoidal configuration to apply heat or vibration to the wall of the renal blood vessel;

wherein the heat or the vibration travels to the nerve(s) outside the renal blood vessel to create a temporary or permanent change in a function of the nerve(s).

21. The method of claim 20, further comprising delivering cooling to protect the wall of the renal blood vessel.

22. The method of claim 20, wherein the ultrasound probe comprises a stabilizing component configured to stabilize at least a part of the ultrasound probe with respect to the renal blood vessel.

23. The method of claim 20, further comprising detecting a position of the ultrasound probe using a component located outside the patient.

24. The method of claim 20, wherein the heat or the vibration is applied to treat hypertension.

25. The method of claim 20, wherein the heat or the vibration is applied to affect the nerve(s) to reduce hypertension.

26. A method to affect a change in a blood pressure of a patient comprising:
    placing a part of a catheter into a hilum of a kidney; and
    delivering unfocused ultrasound energy in an approximately spherical or ellipsoidal configuration from the catheter to inhibit a function of mechanoreceptors or chemoreceptors in the hilum of the kidney temporarily or permanently.

27. The method of claim 26, further comprising detecting a position of the catheter using a component located outside the patient.

28. The method of claim 26, wherein the energy is delivered to treat hypertension.

29. A method to inhibit a nerve function of a patient comprising:
    placing a part of a catheter inside a blood vessel in the patient; and
    delivering unfocused ultrasound energy in an approximately spherical or ellipsoidal configuration from the catheter to inhibit the nerve function of a nerve outside the blood vessel,
    wherein delivering the unfocused ultrasound energy creates a pressure change, radiation pressure, pressure associated with cavitation, or media flow, inside the patient.

30. The method of claim 29, wherein the act of delivering energy comprises delivering ultrasound energy through a wall of the blood vessel.

31. The method of claim 29, wherein the act of delivering energy comprises delivering ultrasound energy into blood inside the blood vessel.

32. The method of claim 29, further comprising delivering cooling to protect an inside wall of the blood vessel.

33. The method of claim 29, further comprising stabilizing the part of the catheter relative to the blood vessel.

* * * * *